(12) United States Patent
Bayly et al.

(10) Patent No.: US 8,063,105 B2
(45) Date of Patent: Nov. 22, 2011

(54) RENIN INHIBITORS

(75) Inventors: Christopher I. Bayly, Beaconsfield (CA); Austin C. Chen, Pierrefonds (CA); Daniel Dube, Saint-Lazare-de-Vaudreuil (CA); Laurence Dube, Laval (CA); Michel Gallant, Kirkland (CA); Patrick Lacombe, Montreal (CA); Dwight MacDonald, Ile Bizard (CA); Daniel McKay, Chute a Blondeau (CA); David A. Powell, Montreal (CA); Erich L. Grimm, Baie d'Urfe (CA)

(73) Assignee: Merck Canada Inc., Kirkland, Quebec (CA)

( * ) Notice: Subject to any disclaimer, the term of this patent is extended or adjusted under 35 U.S.C. 154(b) by 691 days.

(21) Appl. No.: 11/988,437

(22) PCT Filed: Jul. 20, 2006

(86) PCT No.: PCT/CA2006/001196
§ 371 (c)(1),
(2), (4) Date: Jan. 7, 2008

(87) PCT Pub. No.: WO2007/009250
PCT Pub. Date: Jan. 25, 2007

(65) Prior Publication Data
US 2009/0281103 A1 Nov. 12, 2009

Related U.S. Application Data

(60) Provisional application No. 60/702,026, filed on Jul. 22, 2005.

(51) Int. Cl.
*A61K 31/165* (2006.01)
*C07C 229/00* (2006.01)
*C07C 233/00* (2006.01)

(52) U.S. Cl. .............. 514/620; 560/39; 564/165
(58) Field of Classification Search ............ 514/531, 514/620; 560/39; 564/165
See application file for complete search history.

(56) References Cited

FOREIGN PATENT DOCUMENTS

| | | |
|---|---|---|
| CA | 2147056 | 10/1995 |
| CA | 2251381 | 10/1997 |
| EP | 364804 | 4/1990 |
| EP | 432974 | 6/1991 |
| EP | WO2005040120 | 5/2005 |
| WO | WO 2005/054244 | 6/2005 |
| WO | WO 2005/061457 | 7/2005 |

*Primary Examiner* — Taylor Victor Oh
(74) *Attorney, Agent, or Firm* — Anna L. Cocuzzo; Richard S. Parr; Catherine D. Fitch

(57) ABSTRACT

The present invention relates to novel renin inhibitors of the general Formula (I), and their use as active ingredients in the preparation of pharmaceutical compositions. The invention also concerns related aspects including processes for the preparation of the compounds. These novel renin inhibitors are used in treating cardiovascular events and renal insufficiency.

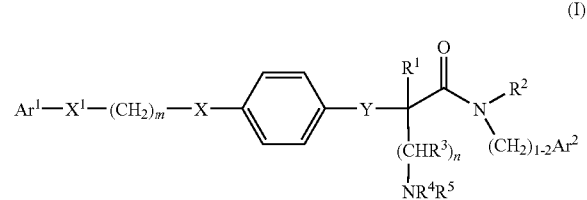

8 Claims, No Drawings

RENIN INHIBITORS

CROSS REFERENCE TO RELATED APPLICATION

This application is a U.S. National Phase application under 35 U.S.C. §371 of PCT Application No. PCT/CA2006/001196, filed Jul. 20, 2006, which claims priority under 35 U.S.C. §119(e) from U.S. Provisional Application Ser. No. 60/702,026, filed Jul. 22, 2005.

The claimed invention was made as a result of activities undertaken within the scope of a joint research agreement between Merck & Co., Inc. and Actelion Pharmaceuticals Ltd. The agreement was executed on Dec. 4, 2003. The field of the invention is described below.

FIELD OF THE INVENTION

The invention relates to novel renin inhibitors of the general formula (I). The invention also concerns related aspects including processes for the preparation of the compounds, pharmaceutical compositions containing one or more compounds of formula (I) and especially their use as renin inhibitors in cardiovascular events and renal insufficiency.

BACKGROUND OF THE INVENTION

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol.*, 1999, 6, 127; Patent Application WO97/09311; Marki H. P. et al., *Il Farmaco*, 2001, 56, 21). However, the development status of these compounds is not known.

The present invention relates to the identification of renin inhibitors of a non-peptidic nature and of low molecular weight. Described are orally active renin inhibitors of long duration of action which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors.

The compounds described in this invention represent a novel structural class of renin inhibitors.

SUMMARY OF THE INVENTION

The present invention is directed to certain compounds and their use in the inhibition of the renin enzyme, including treatment of conditions known to be associated with the renin system. The invention includes compounds of Formula I and pharmaceutically acceptable salts thereof, or an optical isomer thereof:

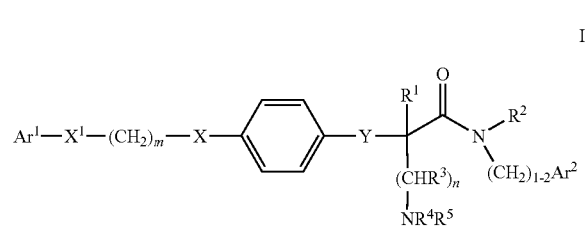

I wherein, m is 1 or 2;

n, in each instance in which it occurs, is independently 0, 1 or 2;

p, in each instance in which it occurs, is independently 0, 1 or 2;

X and $X^1$ are each independently selected from the group consisting of $CH_2$, O, and $S(O)_p$, provided that when both X and $X^1$ are each independently O or $S(O)_p$, m is 2;

Y is selected from the group consisting of $N(R^a)$, $CH(R^a)$, O, and $S(O)_p$;

$R^1$, $R^3$, and $R^a$ are each independently selected from the group consisting of H, $C_1$-$C_6$alkyl and $C_2$-$C_6$alkenyl, wherein the alkyl and alkenyl group is unsubstituted or substituted with one, two, three or four substituents independently selected from:
1) OH,
2) CN,
3) $CF_3$,
4) COOH,
5) $C_1$-$C_6$alkoxy,
6) $C(O)R^b$,
7) $C(O)N(R^c)_2$,
8) $S(O)_p C_1$-$C_6$alkyl,
9) $SO_2 N(R^c)_2$,
10) $N(R^c)_2$,
11) $NHC(O)R^b$,
12) $NHC(O)NHR^d$,
13) $NHC(S)NHR^d$,
14) $NH(NR^c)NHR^c$,
15) tetrazolyl, and
16) —$(CH_2)_{1-2}R^e$;

$R^4$ is selected from the group consisting of H, $C_1$-$C_6$alkyl and $C_2$-$C_6$alkenyl, wherein the alkyl and alkenyl group is unsubstituted or substituted with one, two, three or four substituents independently selected from:
1) OH,
2) CN,
3) $CF_3$,
4) COOH,
5) $C_1$-$C_6$alkoxy,
6) $C(O)R^b$,
7) $C(O)N(R^c)_2$,
8) $S(O)_p C_1$-$C_6$alkyl,
9) $SO_2 N(R^c)_2$,
10) $N(R^c)_2$,
11) $NHC(O)R^b$,
12) $NHC(O)NHR^d$,
13) $NHC(S)NHR^d$,
14) $NH(NR^c)NHR^c$, and
15) tetrazolyl,
or $R^4$, together with $R^5$, forms a 5- or 6-membered heterocyclic ring which is unsubstituted or mono- or di-substituted with a substituent selected from the group consisting of =O and $C_1$-$C_6$ alkyl;

$R^5$ is selected from the group consisting of hydrogen and —$C(NH(NH_2)$, or $R^5$ together with $R^4$, forms a 5- or 6-membered heterocyclic ring which is unsubstituted or mono- or di-substituted with a substituent selected from the group consisting of =O and $C_1$-$C_6$ alkyl;

$R^2$ and $R^b$ are independently selected from the group consisting of H, $C_1$-$C_6$alkyl, $C_2$-$C_6$alkenyl, $C_1$-$C_6$alkoxy, $CF_3$ and $CH_2CF_3$;

$R^c$ is selected from the group consisting of H, $C_1$-$C_6$alkyl and $CH_2CF_3$;

$R^d$ is selected from the group consisting of H and $C_1$-$C_6$alkyl, wherein the alkyl group is unsubstituted or substituted with one, two, three or four substituents selected from the group consisting of:
1) OH,
2) CN,
3) $CF_3$,
4) COOH, and
5) $C(O)NHR^c$, and
6) tetrazolyl;

$R^4$ is a 5- or 6-membered heteroaryl ring having 1 or 2 nitrogen atoms;

$Ar^1$ is an unsubstituted or substituted aryl ring or an unsubstituted or substituted 5- or 6-membered heteroaryl ring containing 1 to 3 heteroatoms selected from O, S and N, wherein the substituted aryl ring and substituted heteroaryl ring are substituted with one, two three or four substituents independently selected from the group consisting of:
1) OH,
2) CN,
3) halogen,
4) $N_3$,
5) $NO_2$,
6) COOH,
7) $OCF_2H$,
8) $CF_3$,
9) $C_1$-$C_6$alkyl,
10) $C_2$-$C_6$alkenyl,
11) $C_1$-$C_6$alkoxy,
12) $C(O)C_1$-$C_6$alkyl, and
13) $S(O)_p C_1$-$C_6$alkyl,
wherein substituents (9)-(13) are unsubstituted or substituted with one, two three or four substituents independently selected from the group consisting of:
a) OH,
b) COOH,
c) CN,
d) $CF_3$,
e) $C_1$-$C_6$alkoxy,
f) $S(O)_p C_1$-$C_6$alkyl;

$Ar^2$ is independently selected from the group consisting of $Ar^1$ and a 9- or 10 membered fused bicyclic aryl or heteroaryl ring, wherein the fused bicyclic heteroaryl contains 1 to 4 heteroatoms selected from O, S and N, wherein the fused bicyclic aryl and heteroaryl are each unsubstituted or substituted with one, two, three or four substituents independently selected from the group consisting of:
1) OH,
2) CN,
3) halogen,
4) $N_3$,
5) $NO_2$,
6) COOH,
7) $OCF_2H$,
8) $CF_3$,
9) $C_1$-$C_6$alkyl, unsubstituted or substituted with $Ar^3$,
10) $C_1$-$C_6$alkyl,
11) $C_2$-$C_6$alkenyl,
12) $C_1$-$C_6$alkoxy,
13) $C(O)C_1$-$C_6$alkyl,
14) $S(O)_p C_1$-$C_6$alkyl,
15) —$O(CH_2)_{1-2}Ar^3$,
16) —$O(CH_2)_{1-2}D$,
17) —$OC(O)D$,
18) —$OC(O)NH(C_1$-$C_6$alkylene)$C(O)NH_2$, and
19) —$OC(O)NH(C_1$-$C_6$alkylene)$(OH)R^d$;
wherein substituents (10)-(14) are unsubstituted or substituted with one, two three or four substituents independently selected from the group consisting of:
a) OH,
b) $COOR^d$,
c) CN,
d) $CF_3$,
e) $C_1$-$C_6$alkoxy,
f) $S(O)_p C_1$-$C_6$alkyl,
g) tetrazolyl
h) —$C(O)NH_2$,
i) —COONa,
j) —$NR^d R^d$, and
k) —$NR^d C(O)R^d$;

$Ar^3$ is an unsubstituted or substituted aryl ring or an unsubstituted or substituted 5- or 6-membered heteroaryl ring containing 1 to 3 heteroatoms selected from O, S and N, wherein the substituted aryl ring and substituted heteroaryl ring are substituted with one, two three or four substituents independently selected from the group consisting of:
1) OH,
2) CN,
3) $OCF_2H$,
4) $CF_3$,
5) $C_1$-$C_3$alkyl,
6) $C_1$-$C_3$alkoxy, and
7) —$SO_2R^a$; and D is a 5- or 6-membered saturated heterocyclic ring having 1 or 2 nitrogen atoms and 0 or 1 oxygen atoms, wherein the ring may be unsubstituted or substituted with $C_1$-$C_6$alkyl.

DETAILED DESCRIPTION OF THE DISCLOSURE

The compounds of Formula I above, and pharmaceutically acceptable salts thereof, are renin inhibitors. The compounds are useful for inhibiting renin and treating conditions such as hypertension.

One embodiment of the invention relates to compounds of Formula I, or a pharmaceutically acceptable salt thereof, wherein Y is $CH(R^a)$, wherein $R^a$ is as originally defined. Within this subset, all other variables are as originally defined.

Another embodiment of the invention relates to compounds of Formula I, or a pharmaceutically acceptable salt thereof, wherein $R^1$ is H. Within this subset, all other variables are as originally defined. Within another subset of this embodiment Y is $CH(R^a)$, wherein $R^a$ is as originally defined and all other variables are as originally defined.

Another embodiment of the invention relates to compounds of Formula I, or a pharmaceutically acceptable salt thereof, wherein n is 1. Within this subset, all other variables are as originally defined. Within another subset of this embodiment Y is $CH(R^a)$, wherein $R^a$ is as originally defined and all other variables are as originally defined. Within another subset of this embodiment Y is $CH(R^a)$, wherein $R^a$ is as originally defined, $R^1$ is H and all other variables are as originally defined. Within another subset of this embodiment $R^1$ is H, Y is $CH_2$ or —$CH(CH_2Ar^3)$, $R^2$ is $C_1$-$C_6$ alkyl or $C_1$-$C_6$ alkenyl, and all other variables are as originally defined.

Another embodiment of the invention relates to compounds of Formula I, or a pharmaceutically acceptable salt thereof, wherein $R^2$ is $C_1$-$C_6$alkyl. Within this subset, all other variables are as originally defined.

Another embodiment of the invention relates to compounds of Formula I, or a pharmaceutically acceptable salt thereof, wherein $R^2$ is $C_3$-$C_6$cycloalkyl. Within this subset, all other variables are as originally defined.

Specific examples of compounds of formula I, and pharmaceutically acceptable salts thereof, include The compounds represented by the structures shown above have the following names:
(i) N-{3-[(Acetyl-methyl-amino)-methyl]-benzyl}-2-aminomethyl-N-cyclopropyl-3-{4-[2-(2,6-dichloro-4-methyl-phenoxy)-ethoxy]-phenyl}-propionamide,
(ii) 2-Aminomethyl-N-cyclopropyl-3-{4-[2-(2,6-dichloro-4-methyl-phenoxy)-ethoxy]-phenyl}-N-(1,2,3,4-tetrahydro-quinolin-8-ylmethyl)-propionamide,
(iii) 2-Aminomethyl-N-cyclopropyl-3-{4-[2-(2,6-dichloro-4-methyl-phenoxy)-ethoxy]-phenyl}-N-quinolin-4-ylmethyl-propionamide,
(iv) 3-Amino-N-cyclopropyl-2-{4-[2-(2,6-dichloro-4-methyl-phenoxy)-ethoxy]-benzyl}-N-(2,3-dimethyl-benzyl)-propionamide,
(v) 2-Aminomethyl-N-cyclopropyl-3-{4-[2-(2,6-dichloro-4-methyl-phenoxy)-ethoxy]-phenyl}-N-[3-(2-methanesulfonyl-ethyl)-benzyl]-propionamide,
(vi) 5-(2-[Cyclopropyl-(2,3-dichloro-benzyl)-carbamoyl]-3-{4-[2-(2,6-dichloro-4-methyl-phenoxy)-ethoxy]-phenyl}-propylamino)-pentanoic acid methyl ester,
(vii) 6-(2-[Cyclopropyl-(2,3-dichloro-benzyl)-carbamoyl]-3-{4-[2-(2,6-dichloro-4-methyl-phenoxy)-ethoxy]-phenyl}-propylamino)-hexanoic acid,
(viii) 6-(2-[Cyclopropyl-(2,3-dichloro-benzyl)-carbamoyl]-3-{4-[2-(2,6-dichloro-4-methyl-phenoxy)-ethoxy]-phenyl}-propylamino)-hexanoic acid methyl ester,
(ix) N-Cyclopropyl-N-(2,3-dichloro-benzyl)-3-{4-[2-(2,6-dichloro-4-methyl-phenoxy)-ethoxy]-phenyl}-2-[(2,2,2-trifluoro-ethylamino)-methyl]-propionamide,
(x) 2-Aminomethyl-N-cyclopropyl-3-{4-[2-(2,6-dichloro-4-methyl-phenoxy)-ethoxy]-phenyl}-N-[3-(3-methoxy-propyl)-benzyl]-propionamide,
(xi) 2-Aminomethyl-N-[2-chloro-5-(3-methoxy-propyl)-benzyl]-N-cyclopropyl-3-{4-[2-(2,6-dichloro-4-methyl-phenoxy)-ethoxy]-phenyl}-propionamide,
(xii) 2-[(2-[Cyclopropyl-(2,3-dichloro-benzyl)-carbamoyl]-3-{4-[2-(2,6-dichloro-4-methyl-phenoxy)-ethoxy]-phenyl}-propylamino)-methyl]-cyclopropanecarboxylic acid,
(xiii) 2-[(2-[Cyclopropyl-(2,3-dichloro-benzyl)-carbamoyl]-3-{4-[2-(2,6-dichloro-4-methyl-phenoxy)-ethoxy]-phenyl}-propylamino)-methyl]-cyclopropanecarboxylic acid ethyl ester,
(xiv) 2-Aminomethyl-3-{4-[3-(2-chloro-3,6-difluoro-phenoxy)-propyl]-phenyl}-N-cyclopropyl-N-[3-(3-methoxy-propyl)-benzyl]-propionamide,
(xv) 2-Aminomethyl-3-{4-[3-(2-chloro-3,6-difluoro-phenoxy)-propyl]-phenyl}-N-[2-chloro-5-(3-methoxy-propyl)-benzyl]-N-cyclopropyl-propionamide,
(xvi) 3-Amino-N-cyclopropyl-N-(2,3-dichloro-benzyl)-2-{4-[2-(2,6-dichloro-4-methyl-phenoxy)-ethyl]-benzyl}-propionamide,
(xvii) 2-Aminomethyl-3-{4-[3-(2-chloro-3,6-difluoro-phenoxy)-propyl]-phenyl}-N-cyclopropyl-N-(2,3-dichloro-benzyl)-2-methyl-propionamide,
(xviii) 3-Amino-N-cyclopropyl-N-(2,3-dichloro-benzyl)-2-{4-[2-(2,6-dichloro-4-methyl-phenoxy)-ethoxy]-benzyl}-propionamide,
(ixx) 2-Aminomethyl-N-cyclopropyl-N-(2,3-dichloro-benzyl)-3-{4-[3-(2,6-dichloro-4-methyl-phenoxy)-propyl]-phenyl}-propionamide,
(xx) 3-{4-[3-(2-Chloro-3,6-difluoro-phenoxy)-propyl]-phenyl}-N-cyclopropyl-N-(2,3-dichloro-benzyl)-2-methylaminomethyl-propionamide,
(xxi) 2-(Benzylamino-methyl)-3-{4-[3-(2-chloro-3,6-difluoro-phenoxy)-propyl]-phenyl}-N-cyclopropyl-N-(2,3-dichloro-benzyl)-propionamide,
(xxii) 2-Aminomethyl-3-{4-[3-(2-chloro-3,6-difluoro-phenoxy)-propyl]-phenyl}-N-cyclopropyl-N-(2,3-dichloro-benzyl)-propionamide, and
(xxiii) 2-Aminomethyl-N-[2-chloro-5-(2-methoxy-ethyl)-benzyl]-N-cyclopropyl-3-{4-[2-(2,6-dichloro-4-methyl-phenoxy)-ethoxy]-phenyl}-propionamide.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —$CH_2C(O)$— groups (keto forms) may undergo tautomerism to form hydroxyl —CH═C(OH)— groups (enol forms). Both keto and enol forms are included within the scope of the present invention.

In addition compounds with carbon-carbon double bonds may occur in Z- and E-forms with all isomeric forms of the compounds being included in the present invention.

List of Abbreviations:
ABTS 2,2'-Azino-bis(3-ethylbenzthiazoline-6-sulfonic Acid) $2NH_3$
Ac acetyl
ADDP 1,1'-(azodicarbonyl)-dipiperidine
AIBN 2,2'-azobis(2-methylpropionitrile)
Boc t-butyloxycarbonyl
BSA bovine serum albumin
DIBAL diisobutylaluminum hydride
DME dimethoxyethane
DMF dimethylformamide
DMP Dess-Martin periodinane
DMSO dimethylsulfoxide
EDTA ethylenediaminetetraacetic acid
EIA enzyme immunoassay
HATU O-(7-azabenzotriazol-1-yl)-N,N,N',N'-tetramethyluronium hexafluorophosphate
LAH lithium aluminum hydride
PBS phosphate-buffered saline
TBAF tetra-n-butylammonium fluoride
TBS tert-butyldimethylsilyl
THF tetrahydrofuran
TBSO tert-butyldimethylsilyloxy Embodiments of the method of the present invention include those in which the compound of Formula I administered to the subject is as defined in the compound embodiments, classes and sub-classes set forth above.

As used herein except where noted, "alkyl" is intended to include both branched- and straight-chain saturated aliphatic hydrocarbon groups, and is intended to include the cyclic group cycloalkyl, including all isomers, having the specified number of carbon atoms. The term "cycloalkyl" means carbocycles containing no heteroatoms. Examples of cycloalkyl include cyclopropyl, cyclobutyl, cyclopentyl, cyclohexyl. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkenyl" includes both branched and straight chain unsaturated hydrocarbon groups containing at least two carbon atoms joined by a double bond. The alkene ethylene is represented, for example, by "$CH_2CH_2$" or alternatively, by "$H_2C$═$CH_2$". "$C_{2-5}$ alkenyl" (or "$C_2$-$C_5$ alkenyl") for example, means linear or branched chain alkenyl groups having from 2 to 5 carbon atoms and includes all of the pentenyl isomers as well as 1-butenyl, 2-butenyl, 3-butenyl, 1-propenyl, 2-propenyl, and ethenyl (or ethylenyl). Similar terms such as "$C_{2-3}$ alkenyl" have an analogous meaning.

Unless otherwise specifically noted as only "unsubstituted" or only "substituted", alkyl, cycloalkyl, alkylene, alkoxy, and alkenyl groups are unsubstituted or substituted with 1 to 3 substituents on each carbon atom, with halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)S(O)$_{0-2}$—, ($C_0$-$C_6$ alkyl)S(O)$_{0-2}$ ($C_0$-$C_6$ alkyl)-, ($C_0$-$C_6$ alkyl)C(O)NH—, $H_2N$—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, —NH($C_1$-$C_6$ alkyl)NHC(O)NH($C_1$-$C_6$ alkyl), —$NHSO_2NH_2$, —NH($C_1$-$C_6$ alkyl)$NHSO_2$($C_1$-$C_6$ alkyl), —($C_0$-$C_6$ alkyl)$NHSO_2$($C_1$-$C_6$ alkyl), tetrazolyl, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

The term "$C_0$" as employed in expressions such as "$C_{0-6}$ alkyl" means a direct covalent bond. Similarly, when an integer defining the presence of a certain number of atoms in a group is equal to zero, it means that the atoms adjacent thereto are connected directly by a bond. For example, in the structure

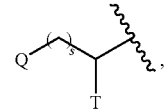

wherein s is an integer equal to zero, 1 or 2, the structure is

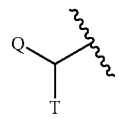

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

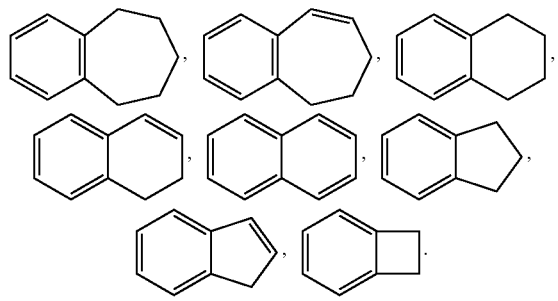

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, and biphenylenyl.

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Unless otherwise specifically noted as only "unsubstituted" or only "substituted", cycloalkyl, aryl and heterocycle groups are unsubstituted or substituted. As used herein, the terms "substituted $C_{3-8}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)$S(O)_{0-2}$—, aryl-$S(O)_{0-2}$—, ($C_0$-$C_6$ alkyl)$S(O)_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahy droisoquinolinyl, isoquinolinyl, 2,3-dihydrobenzofuranyl, 2,3-dihydrobenzo-1,4-dioxinyl (i.e., 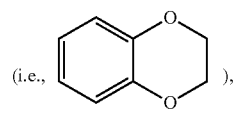 ), imidazo(2,1-b)(1,3)thiazole, (i.e., 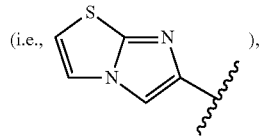 ), and benzo-1,3-dioxolyl (i.e., 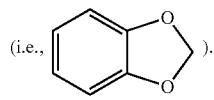 ).

In certain contexts herein,

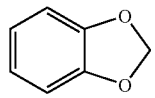

is alternatively referred to as phenyl having as a substituent methylenedioxy attached to two adjacent carbon atoms.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed. The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g., a solvent or water) trapped within.

In compounds of the invention having pyridyl N-oxide moieties, the pyridyl-N-oxide portion is structurally depicted using conventional representations such as

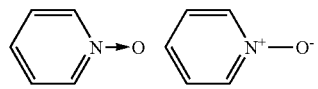

which have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

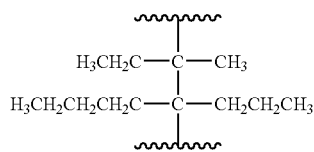

Pharmaceutically acceptable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

The compounds of Formula I can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain of the compounds employed in the present invention carry an acidic moiety (e.g., —COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In another embodiment, the invention relates to a method for the treatment and/or prophylaxis of diseases, which are associated with a dysregulation of the renin-angiotensin system as well as for the treatment of the above-mentioned diseases.

The invention also relates to the use of compounds of formula (I) for the preparation of a medicament for the treatment and/or prophylaxis of the above-mentioned diseases.

Compounds of formula (I) or the above-mentioned pharmaceutical compositions are also of use in combination with other pharmacologically active compounds comprising ACE-inhibitors, neutral endopeptidase inhibitors, angiotensin II receptor antagonists, endothelin receptors antagonists, vasodilators, calcium antagonists, potassium activators, diuretics, sympatholitics, beta-adrenergic antagonists, alpha-adrenergic antagonists or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as anangiotensin II receptor antagonist, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound.

In a preferred embodiment, this amount is comprised between 1 mg and 1000 mg per day. In a particularly preferred embodiment, this amount is comprised between 1 mg and 500 mg per day. In a more particularly preferred embodiment, this amount is comprised between 1 mg and 200 mg per day.

In the method of the present invention (i.e., inhibiting renin), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990.

Assays Demonstrating Biological Activity

Inhibition of Human Recombinant Renin

The enzymatic in vitro assay was performed in 384-well polypropylene plates (Nunc). The assay buffer consisted of PBS (Gibco BRL) including 1 mM EDTA and 0.1% BSA. The reaction mixture were composed of 47.5 µL per well of an enzyme mix and 2.5 µL of renin inhibitors in DMSO. The enzyme mix was premixed at 4° C. and consists of the following components:
  human recombinant renin (40 pM)
  synthetic human angiotensin(1-14) (0.5 µM)
  hydroxyquinoline sulfate (1 mM)

The mixtures were then incubated at 37° C. for 3 h. The enzyme reaction was stopped by placing the reaction plate on wet ice.

To determine the enzymatic activity and its inhibition, the accumulated Ang I was detected by an enzyme immunoassay (EIA) in 384-well plates (Nunc). 5 µL of the reaction mixture or standards were transferred to immuno plates which were previously coated with a covalent complex of Ang I and bovine serum albumin (Ang I-BSA). 75 µL of Ang I-antibodies in assay buffer above including 0.01% Tween 20 were added and the plates were incubated at 4° C. overnight.

An alternative protocol could be used by stopping the enzymatic reaction with 0.02N final concentration of HCl. 5 µL of the reaction mixture or standards were transferred to immuno plates and 75 µL of Ang I-antibodies in assay buffer above including 0.01% Tween 20 were added and the plates were incubate at RT for 4 h.

The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid) $2NH_3$) was added and the plates incubated for 60 min at RT. The plate was evaluated in a microplate reader at 405 nm. The percentage of inhibition was calculated for each concentration point and the concentration of renin inhibition was determined that inhibited the enzyme activity by 50% ($IC_{50}$). The $IC_{50}$-values of all compounds tested were below 1 µM.

Inhibition of Renin in Human Plasma

The enzymatic in vitro assay was performed in 384-well polypropylene plates (Nunc). The assay buffer consisted of PBS (Gibco BRL) including 1 mM EDTA and 0.1% BSA. The reaction mixture was composed of 80 µL per well of human plasma, enzyme, Ang I-antibodies mix and 5 µL of renin inhibitors in DMSO. The human plasma mix was premixed at 4° C. and consists of
  human plasma from 10 normal donors
  human recombinant renin (3 µM)
  Ang I-antibodies.

The mixtures were then incubated at 37° C. for 2 h.

To determine the enzymatic activity and its inhibition, the accumulated Ang I was detected by an enzyme immunoassay (EIA) in 384-well plates (Nunc). 10 µL of the reaction mixture or standards were transferred to immuno plates which were previously coated with a covalent complex of Ang I and bovine serum albumin (Ang I-BSA). 70 µL assay buffer were added and the plates were incubated at 4° C. overnight. The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid) $2NH_3$) was added and the plates incubated for 60 min at RT. The plate was evaluated in a microplate reader at 405 nm. The percentage of inhibition was calculated of each concentration point and the concentration of renin inhibition was determined that inhibited the enzyme activity by 50% ($IC_{50}$). The $IC_{50}$-values of all compounds tested were below 10 M.

In vivo animal model—Female double transgenic rats were purchased from RCC Ltd, Fullingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial blood pressures in the range of 160-170 mmHg.

Transmitter implantation—The rats were anaesthetised with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements—Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

Methods of Synthesis

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, $Et_2O$, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, $^1H$ NMR and high-pressure liquid chromatography (HPLC). Chemical symbols have their usual meanings. The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Compounds of the present invention can be prepared according to the following general methods as exemplified in Scheme 1-11. For example a Knoevenagel type condensation between cyanoacetate II and appropriately substituted aldehyde III can provide α,β-unsaturated ester IV. Concomitant reduction of the alkene and the cyano groups in IV can be accomplished stepwise or in one step using hydrogenation or with reducing agents such as $CoCl_2$—$NaBH_4$. The resulting saturated amine can be better isolated after protection with for example an N—BOC to give derivative V. Saponification of ester V and coupling of the resulting acid with amine VI will provide protected aminoamide VII. Finally, removal of the protecting group can provide the desired aminoamide VIII. (Scheme 1).

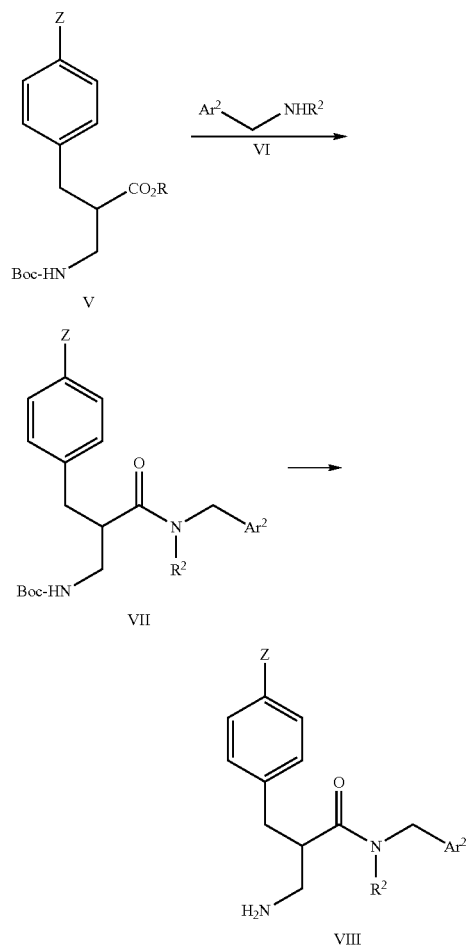

Alternatively, the sequence can be modified with the initial coupling of amine VI with cyanoacetic acid IX to give amide precursor X (Scheme 2). Subsequent Knoevenagel condensation with substituted aldehyde III can deliver the α,β-unsaturated amide XI. Reduction of the double bond and nitrile group can be accomplished using for example the $CoCl_2$—$NaBH_4$ reagent. The resulting saturated amine is most conveniently isolated as the N—BOC derivative VII. Finally, removal of the BOC protecting group under acidic conditions furnishes the desired aminoamide VIII

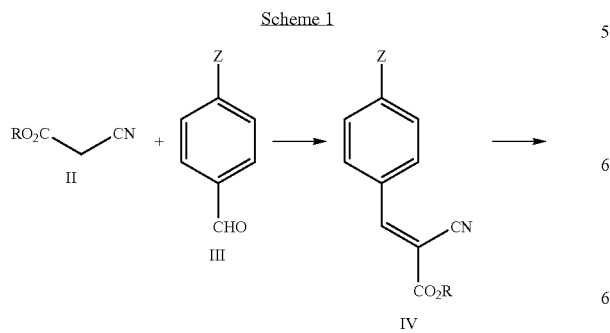

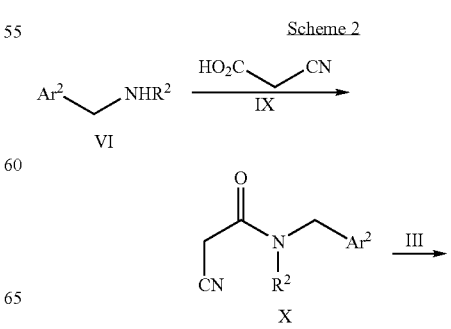

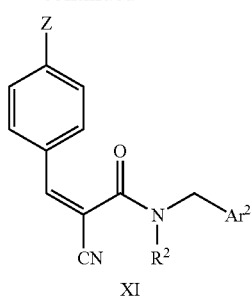

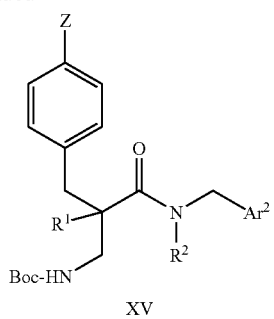

Z = Ar¹—X¹—(CH₂)ₘ—X—, TBSO(CH₂)ₘ—X—

Z = Ar¹—X¹—(CH₂)ₘ—X—, TBSO(CH₂)ₘ—X—

It is also possible to obtain the title compounds by alkylation of cyanoamide X using a base such as potassium hexamethyldisilazide with an appropriately substituted benzyl halide XII (Scheme 3). The resulting cyanoamide can be further alkylated with, for example, an alkyl halide to give the corresponding disubstituted analog XIV.

The 3-amino amide XXI can be built from the corresponding 3-pentenoate XVI by alkylation using a strong base and an appropriate benzyl halide XII as described in Scheme 4. After the amide formation, the double bond in XVIII can be cleaved by ozonolysis followed by reduction to the primary alcohol XIX. The latter could be transformed to the azide XX by, for example, displacement of the corresponding mesylate. Reduction of azide group to amine will then provide the desired product XXI.

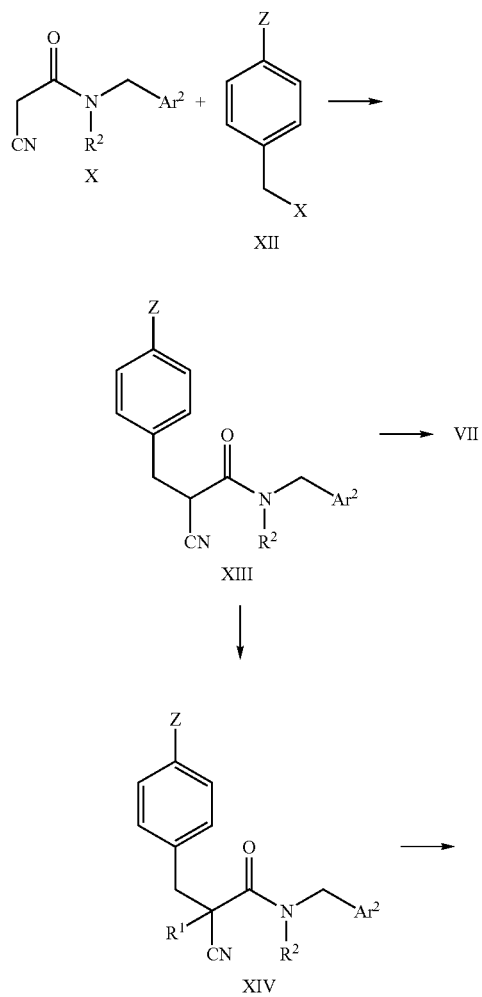

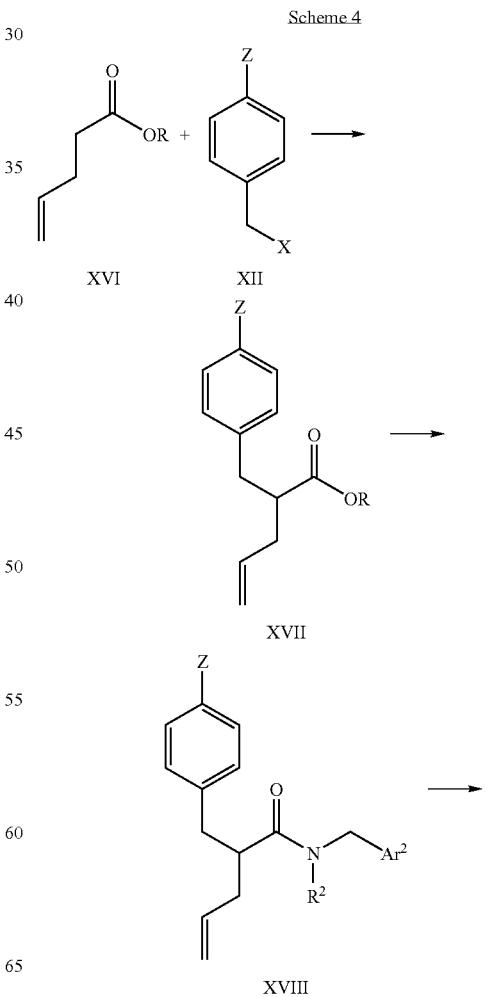

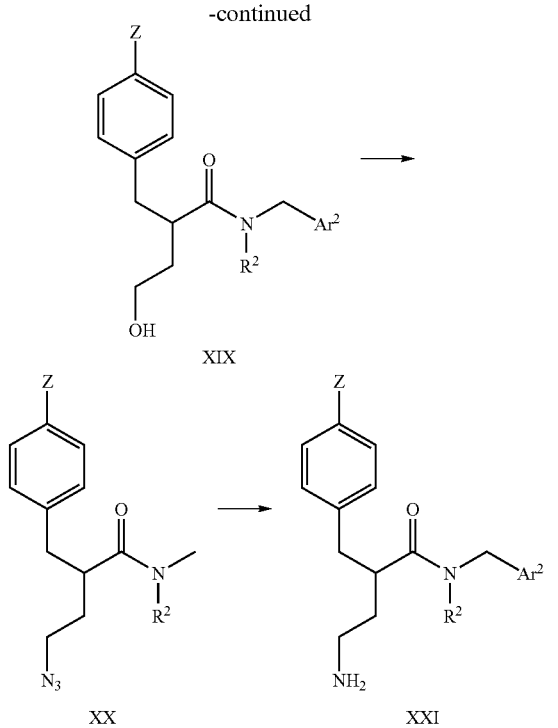
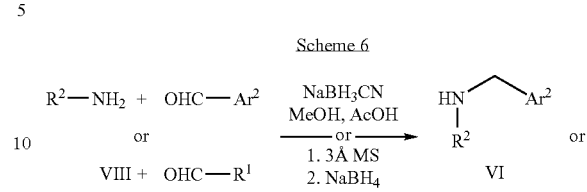
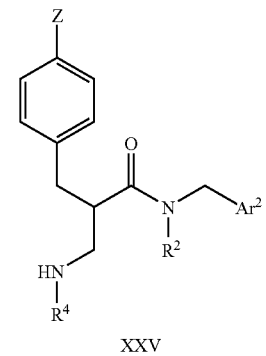

the amide formation could be readily achieved via the reductive amination of the corresponding aldehydes (Scheme 6).

3A MS refers to 3 Angstrom molecular sieves

Conversion of the amine such as VIII into its corresponding guanidine analogue XXVII could be affected through the use of diimidothiotricarbonate XXVI (Scheme 7) followed by acid-promoted deprotection.

The alpha-amino amide homologue XXIV can be built from commercially available amino acid derivatives using standard chemistry for alkylation of phenol and amide formation as exemplified in Scheme 5.

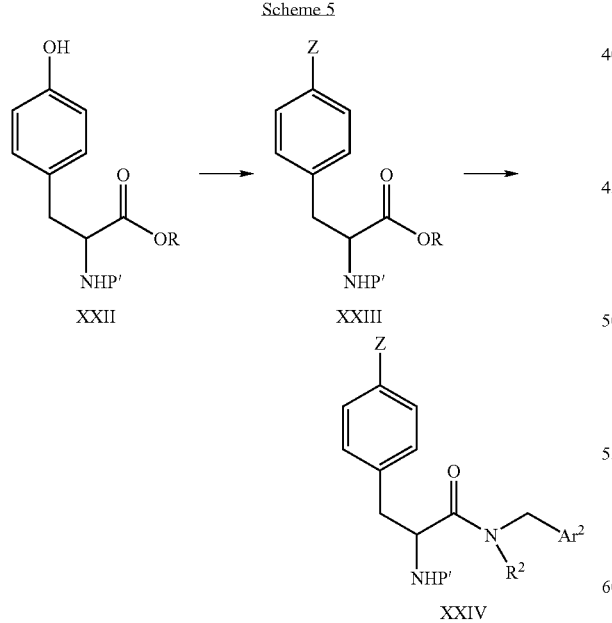
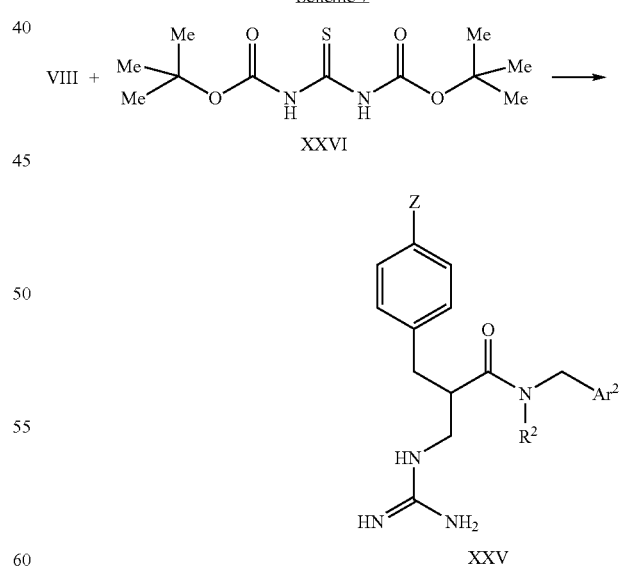

N-alkylation of aminoamide VIII, to afford the secondary amine XXV, and the secondary amine precursors VI used in Introduction of a β-substituent (i.e. XXIX) can be readily accomplished, for example, via reaction of an organocuprate with α,β-unsaturated amide XI (Scheme 8). Subsequent reduction of XXVIII using, for example the $CoCl_2$—$NaBH_2$ reagent, would afford the desired product XXIX.

Scheme 8

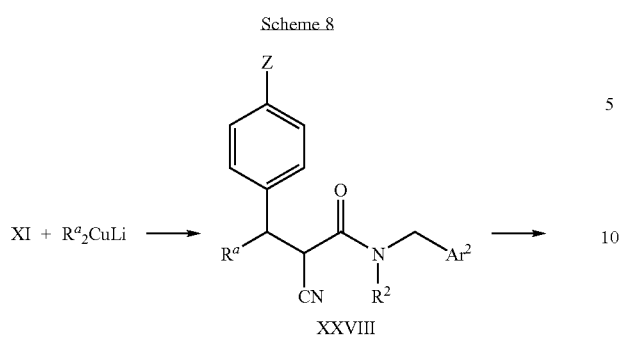

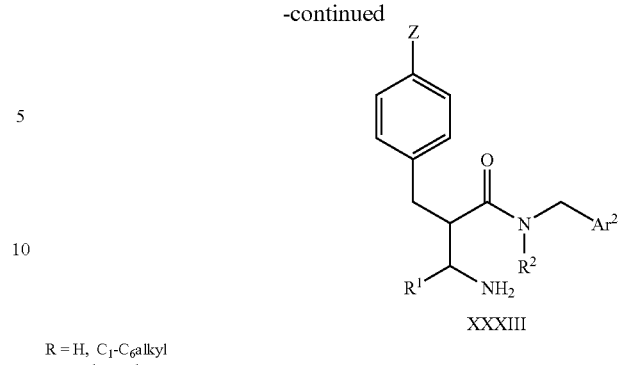

R = H, C$_1$-C$_6$alkyl
Z = Ar$^1$—X$^1$—(CH$_2$)$_m$—X—, TBSO(CH$_2$)$_m$—X—

Inhibitors possessing a substituent α to the amino group (i.e. XXXIII) can be accessed by alkylation of β-ketoester XXX (Scheme 9) with an appropriately substituted benzyl halide XII in the presence of a base such as potassium hexamethyldisilazide. Conversion of the resulting ester XXXI into β-ketoamide XXXII and its subsequent reductive amination with ammonium acetate is one way of synthesizing the desired aminoamide XXXIII.

Scheme 9

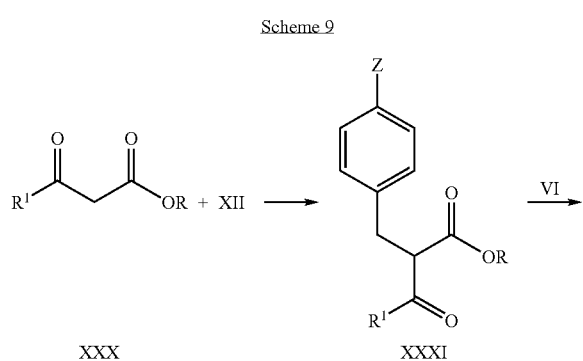

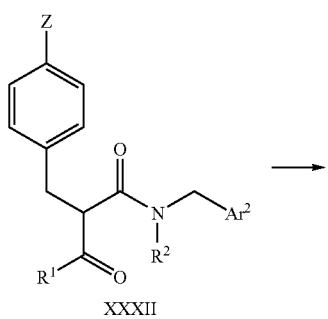

The aldehydes used in the preparation of VI can be obtained from the corresponding bromobenzoate XXXV (Scheme 10). Suzuki type coupling of XXXV with for example borane XXXIV can afford ester XXXVI. The desired aldehydes XXXVII can be obtained by direct reduction of the ester using DIBAL or via a two-step sequence, for example a reduction with LAH followed by oxidation with Dess-Martin periodinane (DMP).

Scheme 10

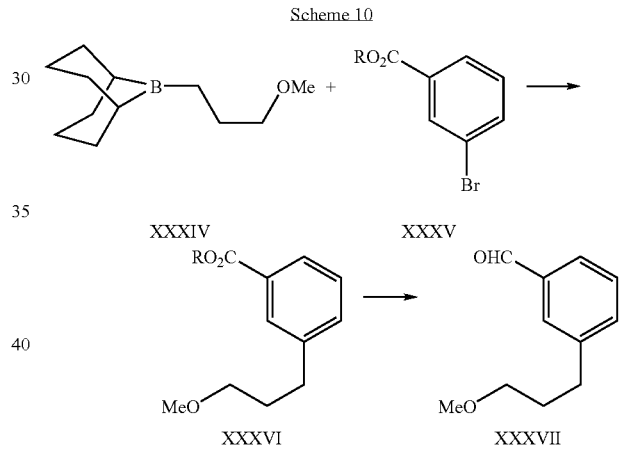

R = H, C$_1$-C$_6$alkyl

Aldehyde of type XL with a methoxyethyl chain can also be prepared from the corresponding bromobenzoate XXXV (Scheme 11). For example, a copper mediated Grignard displacement with allylbromide can furnish alkene XXXVIII. Its ozonolysis followed by a reductive workup can provide alcohol XXXIX. Subsequent methylation with iodomethane and reduction of the ester with LAH and then oxidation can deliver the desired aldehyde XL.

Scheme 11

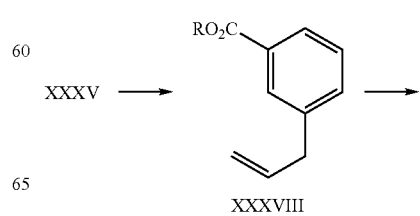

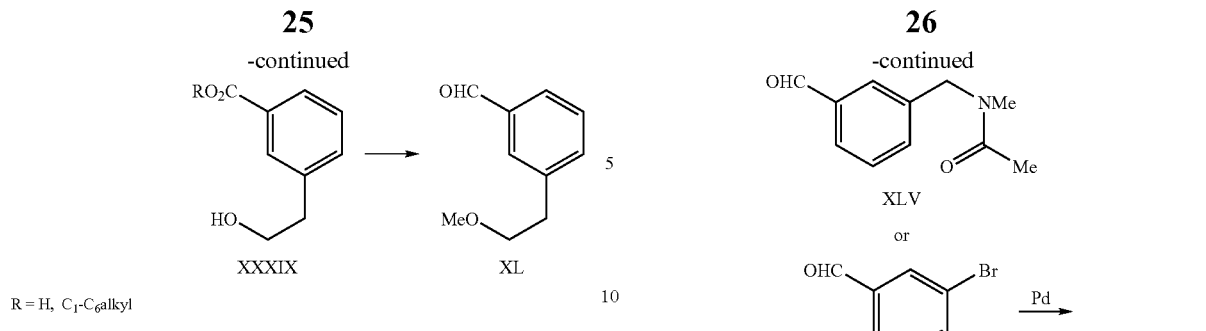

R = H, $C_1$-$C_6$alkyl

Alternatively, the aldehydes like XLIII can be prepared from the corresponding iodo or bromo phenyl using palladium-catalyzed carbonylation (Scheme 12). In this example, the nucleophilic displacement of iodobenzyl bromide XLI by methylsulfone salt provides the methylsulfone XLII. Subsequent reductive palladium-catalyzed carbonylation with carbon monoxide affords the desired aldehyde XLIII.

Formylation using DMF from lithium halogen exchange of a bromo or iodo phenyl analog is another strategy for the synthesis of, for example, aldehyde XLV or XLVII (Scheme 13). Starting with dibromophenyl analogue such as XLVI would allow for palladium-mediated elaboration of the aryl bromide obtained following formylation to give, for example, XLVIII.

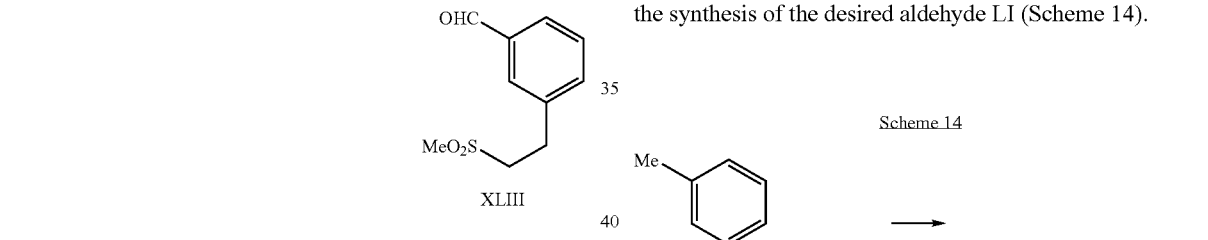

Radical bromination of a benzyl analog such as XLIX followed by oxidation would constitute another approach to the synthesis of the desired aldehyde LI (Scheme 14).

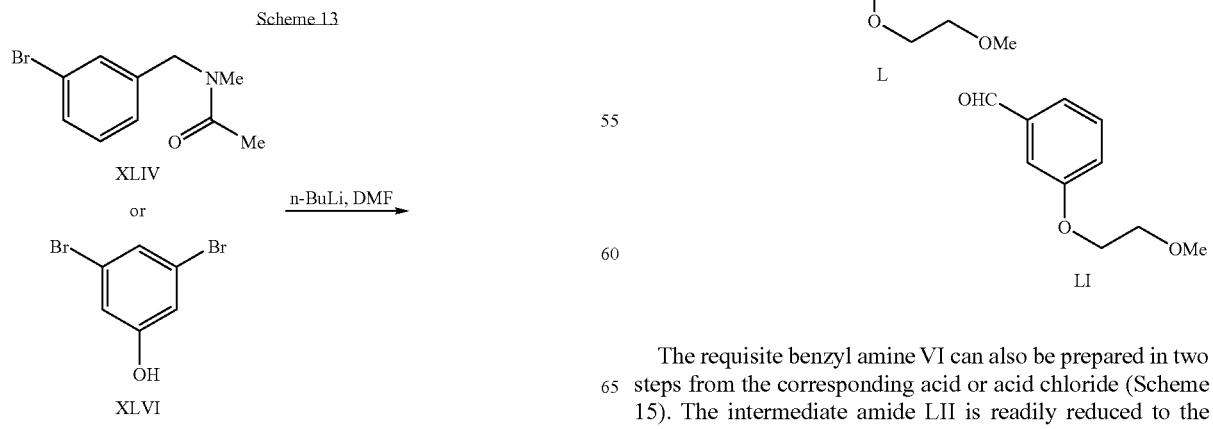

The requisite benzyl amine VI can also be prepared in two steps from the corresponding acid or acid chloride (Scheme 15). The intermediate amide LII is readily reduced to the amine using for example, a reagent such as borane.

Scheme 15

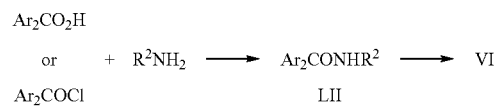

The aryl aldehydes LV, can be assembled as depicted in Scheme 16. The substituted phenol can be heated neat at 150° C. with ethylene carbonate and imidazole to deliver the alcohol LIII. Subsequent coupling with 4-hydroxybenzaldehyde under typical Mitsunobu type conditions then can afford aldehyde LV. Alternatively, the requisite aldehydes can be obtained via sequential etherification and palladium-catalyzed reductive carbonylation of alcohol LIV.

Scheme 16

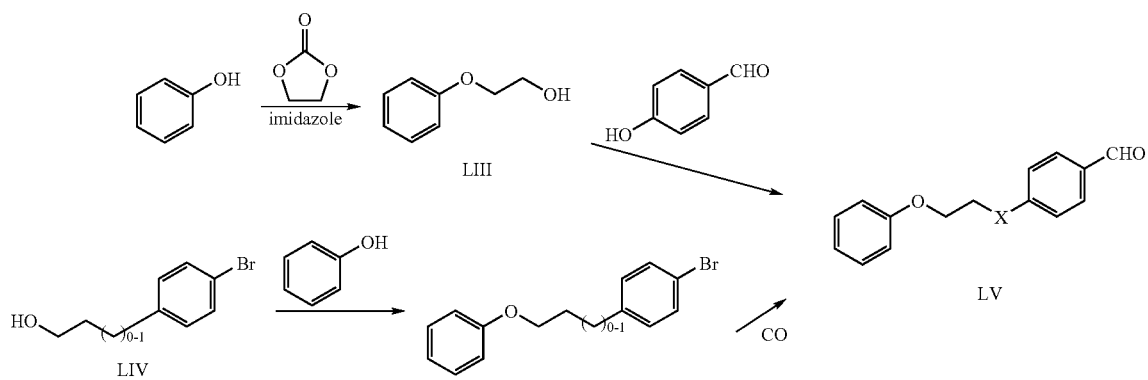

The cyclopropylamine building blocks in Table 1 were synthesized as follows.

TABLE 1

| Compound | Structure |
|---|---|
| Amine 1 | cyclopropyl-NH-CH2-(2,3-dimethylphenyl) |
| Amine 2 | cyclopropyl-NH-CH2-(2,3-dichlorophenyl) |
| Amine 3 | cyclopropyl-NH-CH2-(quinolin-4-yl) |
| Amine 4 | cyclopropyl-NH-CH2-(quinolin-8-yl) |
| Amine 5 | cyclopropyl-NH-CH2-(3-(3-methoxypropyl)phenyl) |
| Amine 6 | cyclopropyl-NH-CH2-(2-chloro-5-(3-methoxypropyl)phenyl) |
| Amine 7 | cyclopropyl-NH-CH2-(2-chloro-5-(2-methoxyethyl)phenyl) |
| Amine 8 | cyclopropyl-NH-CH2-(3-(2-(methylsulfonyl)ethyl)phenyl) |

TABLE 1-continued

| Compound | Structure |
|---|---|
| Amine 9 | *N-methyl-N-(3-((cyclopropylamino)methyl)benzyl)acetamide* |
| Amine 10 | *N-methyl-N-(3-((cyclopropylamino)methyl)-4-chlorobenzyl)acetamide* |
| Amine 11 | *3-(3-((cyclopropylamino)methyl)-4-chlorophenyl)propan-1-ol* |
| Amine 12 | *2-(3-((cyclopropylamino)methyl)-4-chlorophenoxy)-1-methoxyethane* |
| Amine 13 | *N-cyclopropyl-1-(6-(pyridin-4-ylmethyl)quinolin-8-yl)methanamine* |
| Amine 14 | *N,N-dimethyl-3-(3-((cyclopropylamino)methyl)-4-chlorophenyl)propan-1-amine* |
| Amine 15 | *N-cyclopropyl-(2,3-dichloro-5-(3-methoxypropyl)benzyl)amine* |
| Amine 16 | *2-(8-((cyclopropylamino)methyl)quinolin-6-yl)acetonitrile* |
| Amine 17 | *N-cyclopropyl-(2-(3-methoxypropyl)quinolin-4-yl)methanamine* |
| Amine 18 | *3-(3-((cyclopropylamino)methyl)-4-chlorophenyl)propanenitrile* |
| Amine 19 | *N-cyclopropyl-(2-methyl-5-(3-methoxypropyl)benzyl)amine* |
| Amine 20 | *2-(3-((cyclopropylamino)methyl)-4-chlorophenyl)acetonitrile* |

TABLE 1-continued
| Compound | Structure |
|---|---|
| Amine 21 | 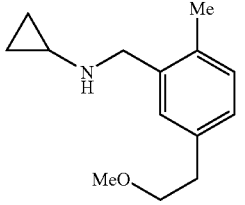 |
| Amine 22 | 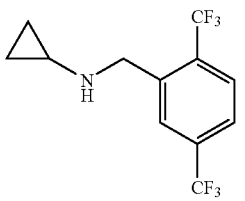 |
| Amine 23 | 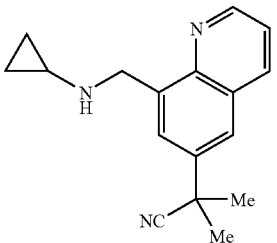 |
| Amine 24 | 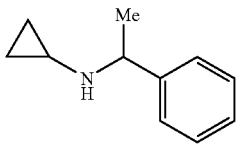 |
| Amine 25 | 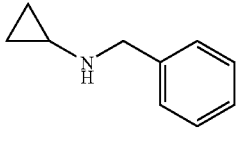 |
| Amine 26 | 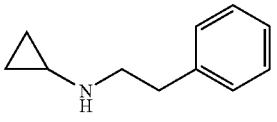 |
| Amine 27 | 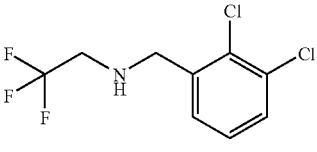 |
| Amine 28 | 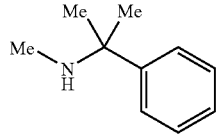 |
| Amine 29 | 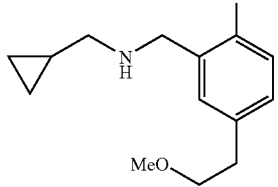 |
| Amine 30 | 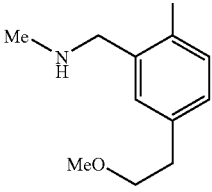 |
| Amine 31 | 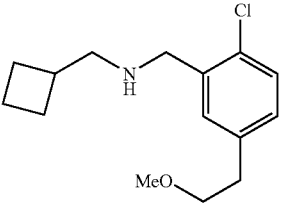 |
| Amine 32 | 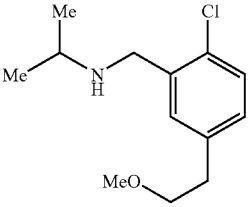 |
| Amine 33 | 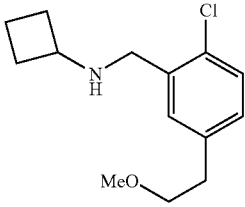 |
| Amine 34 | 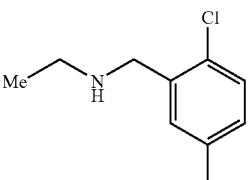 |
| Amine 35 | |

TABLE 1-continued
| Compound | Structure |
|---|---|
| Amine 36 | 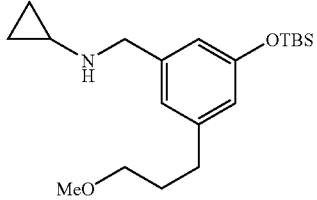 |
| Amine 37 | 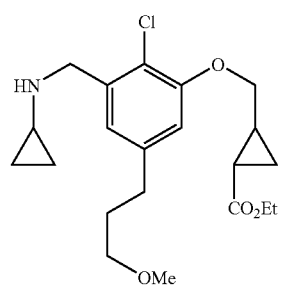 |
| Amine 38 | 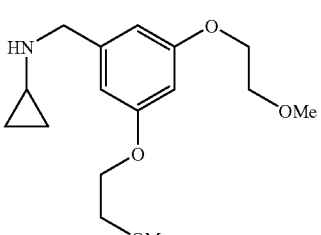 |
| Amine 39 | 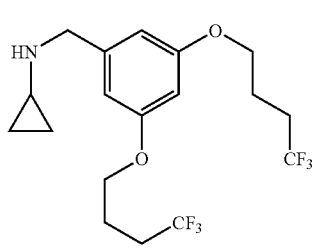 |
| Amine 40 | 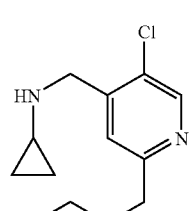 |
| Amine 41 | 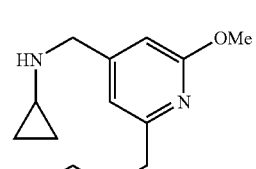 |
| Amine 42 | 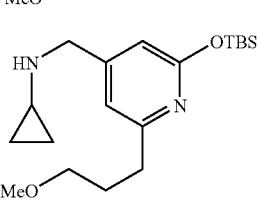 |
| Amine 43 | 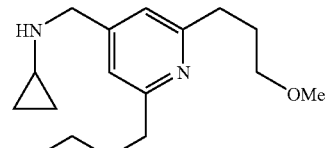 |
| Amine 44 | 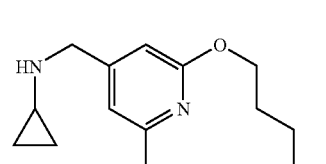 |
| Amine 45 | 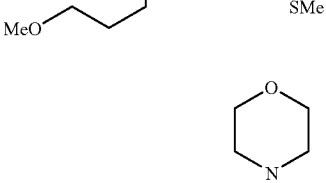 |
| Amine 46 | 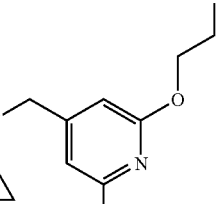 |
| Amine 47 | 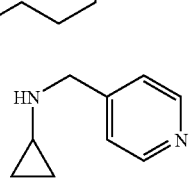 |
| Amine 48 | 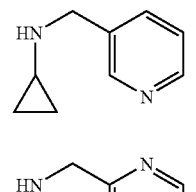 |
| Amine 49 | 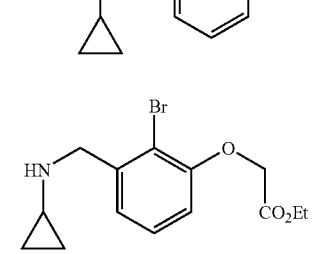 |
| Amine 50 | 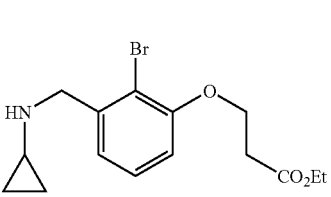 |

TABLE 1-continued

| Compound | Structure |
| --- | --- |
| Amine 51 | (structure: 2-bromo-3-(ethoxycarbonylbutoxy)benzyl cyclopropylamine) |

Amine 1

N-(2,3-Dimethylbenzyl)cyclopropanamine

A mixture of 2,3-dimethylbenzaldehyde (1 eq.), cyclopropylamine (1.2 eq.) and sodium bicarbonate (1.5 eq.) were heated at reflux in MeOH (0.5 M) for 1 h. The reaction mixture was then cooled in ice and sodium borohydride (1.2 eq.) was introduced portionwise. Following the completion of addition, the reaction mixture was warmed to RT and stirred at RT for 1 h. The volatiles were then removed in vacuo and the resulting residue was partitioned between $H_2O$ and $CH_2Cl_2$. The organic layer was separated, washed with brine, dried over $MgSO_4$ and filtered. Concentration of the filtrate in vacuo afforded the title compound as a light yellow oil.

Amine 2

N-(2,3-Dichlorobenzyl)cyclopropanamine

Amine 2 was prepared according to the procedure described in Amine 1, but using instead 2,3-dichlorobenzaldehyde as the starting aldehyde. Purification of the crude product by way of flash chromatography ($SiO_2$, 98:2→1:1 (v/v) Hex:EtOAc) afforded the title compound as a colorless oil.

Amine 3

N-(Quinolin-4-ylmethyl)cyclopropanamine

A mixture of 4-quinolinecarboxaldehyde (1 eq.), cyclopropylamine (1 eq.) and sodium cyanoborohydride (1.5 eq.) were combined in MeOH (0.2 M). At 0° C., acetic acid (3 eq.) was added dropwise and the reaction mixture was slowly warmed to RT over 16 h. The reaction mixture was then diluted with ether and quenched with 1N aq. NaOH. The aqueous layer was separated and back-extracted with ether. The combined organic extracts were then washed with water and brine, dried over $MgSO_4$ and filtered. Concentration of the filtrate in vacuo afforded a purple residue. Purification of the crude product thus obtained by way of flash chromatography ($SiO_2$, 98:2 (v/v) $CH_2Cl_2$:2 M $NH_3$ in MeOH) afforded the title compound as a viscous, yellow oil.

Amine 4

N-(Quinolin-8-ylmethyl)cyclopropanamine

Amine 4 was prepared according to the procedure described in Amine 3, but using instead 8-quinolinecarboxaldehyde as the starting material. The title compound was isolated as a viscous, yellow oil.

Amine 5

N-[3-(3-Methoxypropyl)benzyl]cyclopropanamine

Step 1: Ethyl 3-(3-methoxypropyl)benzoate

To a THF solution (0.1 M) of allyl methyl ether (1.4 eq.) was added, at 0° C., 9-borabicyclo[3.3.1]nonane (2.4 eq.) over a period of 30 min. The solution was stirred at 0° C. for 1 h and then warmed slowly to RT over 16 h. To the resulting clear solution was then added sodium methoxide (2.4 eq.), $Cl_2Pd(dppf)$-dichloromethane complex (5% loading) and ethyl 3-bromobenzoate (1 eq.). The now brown suspension was heated to reflux for 16 h. The reaction mixture was cooled to RT, quenched with sat. aq. $NH_4Cl$ and extracted with ether. The combined organic extracts were washed with brine, dried over $MgSO_4$ and filtered. Concentration of the filtrate in vacuo afforded a brown oil. Purification of the crude product thus obtained by way of flash chromatography ($SiO_2$, Hex→4:1 (v/v) Hex:EtOAc) afforded the title compound as a light yellow oil.

Step 2: [3-(3-Methoxypropyl)phenyl]methanol

To a THF solution (0.2 M) of ethyl 3-(3-methoxypropyl)benzoate from the previous step (1 eq.) was added lithium aluminum hydride (1.0 M THF solution, 5 eq.) at 0° C. over a period of 20 min. The resulting suspension was stirred at 0° C. for 1 h and then at RT for 1 h. The reaction was quenched, at 0° C., with the dropwise addition of $H_2O$ and then 1 N aq. NaOH. The biphasic mixture was allowed to stir at RT for 10 min, poured into $H_2O$ and extracted with ether. The combined organic extracts were washed with brine, dried over $MgSO_4$ and filtered. Concentration of the filtrate in vacuo afforded a cloudy oil. Purification of the crude product thus obtained by way of flash chromatography ($SiO_2$, 7:3 (v/v) Hex:EtOAc) afforded the title compound as a colorless oil.

Step 3: 3-(3-Methoxypropyl)benzaldehyde

To a $CH_2Cl_2$ solution (0.3 M) of [3-(3-methoxypropyl)phenyl]methanol from the previous step (1 eq.) was added Dess-Martin periodinane (1.2 eq.). The resulting suspension was stirred at RT for 2 h. The reaction was quenched with sat. aq. $NaHCO_3$ and 2 N aq. $Na_2S_2O_3$. The biphasic mixture was allowed to stir at RT for 20 min, poured into sat. aq. $NaHCO_3$ and extracted with $CH_2Cl_2$. The combined organic extracts were washed with brine, dried over $MgSO_4$ and filtered. Concentration of the filtrate in vacuo afforded a cloudy oil. Purification of the crude product thus obtained by way of flash chromatography ($SiO_2$, Hex→7:3 (v/v) Hex:EtOAc) afforded the title compound as a colorless oil.

Step 4: Amine 5

Amine 5 was prepared according to the procedure described in Amine 3, but using instead 3-(methoxypropyl)benzaldehyde from the previous step as the starting material. The title compound was isolated as a colorless oil.

Amine 6

N-[2-Chloro-5-(3-methoxypropyl)benzyl]cyclopropanamine

Amine 6 was prepared according to the reaction sequence described for Amine 5, but using instead ethyl 5-bromo-2- chlorobenzoate as the starting material. The title compound was isolated as a colorless oil.

Amine 7

N-[2-Chloro-5-(2-methoxyethyl)benzyl]cyclopropanamine

Step 1: tert-Butyl 5-bromo-2-chlorobenzoate 5-bromo-2-chlorobenzoic acid (1 eq.) and anhydrous DMF (1.2 eq.) was taken up in toluene (0.9 M). To this was then added, dropwise over 5 min, oxalyl chloride (1.2 eq.) and the reaction mixture was stirred at RT for 1 h. The volatiles were then removed in vacuo and the resulting residue was taken up in toluene (0.9 M). At 0° C., potassium tert-butoxide (2.5 eq.) was added and the reaction mixture was stirred at RT for 1 h. The reaction mixture was poured into $H_2O$ and extracted with ether. The combined organic extracts were washed with brine, dried over $MgSO_4$ and filtered. Concentration of the filtrate in vacuo afforded a pale yellow oil. Purification of the crude product thus obtained by way of flash chromatography ($SiO_2$, Hex→85:15 (v/v) Hex:EtOAc) afforded the title compound as a light yellow oil.

Step 2: tert-Butyl 5-allyl-2-chlorobenzoate

At 0° C., isobutylmagnesium bromide (2.0 M ether solution, 1.2 eq.) and n-butyl lithium (2.5 M hexane solution, 2.4 eq.) were added to anhydrous THF (0.3 M). After stirring at 0° C. for 30 min, the reaction mixture was cooled to −40° C. and tert-butyl 5-bromo-2-chlorobenzoate from the previous step (1 eq.) was added over 15 min. The now red solution was stirred at −40° C. for 1 h before copper (I) cyanide (30% loading) was added. The resulting suspension was stirred at −40° C. for 15 min and then added allyl bromide (3 eq.). After stirring at −40° C. for another 2 h, the reaction mixture was quenched with sat. aq. $NH_4Cl$ and warmed to RT. The biphasic mixture was poured into more sat. aq. $NH_4Cl$ and extracted with ether. The combined organic extracts were washed with brine, dried over $MgSO_4$ and filtered. Concentration of the filtrate in vacuo afforded a brown oil. Purification of the crude product thus obtained by way of flash chromatography ($SiO_2$, Hex→19:1 (v/v) Hex:ether) afforded the title compound as a light yellow oil.

Step 3: tert-Butyl 2-chloro-5-(2-hydroxyethyl)benzoate

To a solution of tert-butyl 5-allyl-2-chlorobenzoate from the previous step (1 eq.) in $CH_2Cl_2$ (0.4 M) was bubbled, at −78° C., freshly generated ozone until a persistent blue color was obtained. The reaction solution was stirred at −78° C. for a further 1 h before sodium borohydride (2 eq.) in (0.4 M) MeOH was added. The resulting mixture was warmed to RT and stirred at RT for 1 h. The reaction mixture was diluted with sat. aq. $NaHCO_3$ and extracted with ether. The combined organic extracts were washed with brine, dried over $MgSO_4$ and filtered. Concentration of the filtrate in vacuo afforded a colorless oil. Purification of the crude product thus obtained by way of flash chromatography ($SiO_2$, 4:1→1:1 (v/v) Hex:EtOAc) afforded the title compound as a colorless oil.

Step 4: tert-Butyl 2-chloro-5-(2-methoxyethyl)benzoate

To a suspension of sodium hydride (60% w/w dispersion in oil, 2 eq.) in anhydrous THF (0.23 M) was added tert-butyl 2-chloro-5-(2-hydroxyethyl)benzoate from the previous step (1 eq.). The reaction mixture was heated at reflux for 30 min before iodomethane (7.9 eq.) was added. After carefully quenching with sat. aq. $NaHCO_3$, the resulting mixture was extracted with ether. The combined organic extracts were washed with brine, dried over $MgSO_4$ and filtered. Concentration of the filtrate in vacuo afforded a cloudy oil. Purification of the crude product thus obtained by way of flash chromatography ($SiO_2$, Hex→85:15 (v/v) Hex:EtOAc) afforded the title compound as a colorless oil.

Step 5: [2-Chloro-5-(2-methoxyethyl)phenyl]methanol

To a solution of tert-butyl 2-chloro-5-(2-methoxyethyl)benzoate from the previous step (1 eq.) in anhydrous THF (0.26 M) was added, at 0° C., lithium aluminum hydride (1.0 M THF solution, 3 eq.). The resulting suspension was stirred at 0° C. for 1 h and then at RT for 1 h. After carefully quenching with EtOAc and $H_2O$, sat. aq. sodium potassium tartrate was added. The resulting biphasic mixture was vigorously stirred at RT for 30 min and then extracted with ether. The combined organic extracts were washed with brine, dried over $MgSO_4$ and filtered. Concentration of the filtrate in vacuo afforded a cloudy oil. Purification of the crude product thus obtained by way of flash chromatography ($SiO_2$, 90:10→70:30 (v/v) Hex:EtOAc) afforded the title compound as a colorless oil.

Step 6: 2-Chloro-5-(2-methoxyethyl)benzaldehyde

To a solution of [2-chloro-5-(2-methoxyethyl)phenyl]methanol from the previous step (1 eq.) in $CH_2Cl_2$ (0.4 M) was added Dess-Martin periodinane (1.2 eq.) portionwise. The resulting suspension was stirred at RT for 2 h. The reaction was quenched with sat. aq. $NaHCO_3$ and sat. aq. $NaHSO_3$. The biphasic mixture was allowed to stir at RT for 20 min before it was extracted with $CH_2Cl_2$. The combined organic extracts were washed with brine, dried over $MgSO_4$ and filtered. Concentration of the filtrate in vacuo afforded a colorless oil. Purification of the crude product thus obtained by way of flash chromatography ($SiO_2$, Hex→9:1 (v/v) Hex:EtOAc) afforded the title compound as a colorless oil.

Step 7: Amine 7

Amine 7 was prepared according to the procedure described in Amine 3, but using instead 2-chloro-5-(2-methoxyethyl)benzaldehyde from the previous step as the starting material. The title compound was isolated as a colorless oil.

Amine 8

N-{3-[2-(Methylsulfonyl)ethyl]benzyl}cyclopropanamine

Step 1: 2-(3-Iodophenyl)ethyl methyl sulfone

To a solution of dimethyl sulfone (1 eq.) in 60 mL of anhydrous THF (0.2 M) was added, at −78° C., n-butyl lithium (1.6 M hexane solution, 1.2 eq.) over a period of 10 min. The resulting mixture was stirred at −78° C. for 1 h. To the now yellow solution was added, at −78° C., 3-iodobenzyl bromide (1 eq.). The reaction mixture was then slowly warmed to RT over 16 h. The reaction was carefully quenched with 10% aq. HCl and extracted with ether. The combined organic extracts were washed with brine, dried over $MgSO_4$ and filtered. Concentration of the filtrate in vacuo afforded a viscous oil. Purification of the crude product thus obtained by way of flash chromatography (SiO$_2$, Hex→1:1 (v/v) Hex:EtOAc) followed by trituration with hexanes afforded the title compound as a white crystalline solid.

Step 2: 3-[2-(Methylsulfonyl)ethyl]benzaldehyde

To a solution of 2-(3-iodophenyl)ethyl methyl sulfone from the previous step (1 eq.) in anhydrous, deoxygenated DMF (0.5 M) was added freshly-dried sodium formate (1.5 eq.) and Pd(PPh$_3$)Cl$_2$ (2% loading). Through the resulting yellow suspension, was bubbled CO and then reaction was heated to 95° C. for 6 h. The now black reaction suspension was cooled to RT, diluted with water, and extracted with ether. The combined organic extracts were washed with brine, dried over MgSO$_4$ and filtered. Concentration of the filtrate in vacuo afforded an orange semi-solid. Purification of the crude product thus obtained by way of flash chromatography (SiO$_2$, 1:1 (v/v) Hex:EtOAc) afforded the title compound as a colorless oil.

Step 3: Amine 8

Amine 8 was prepared according to the procedure described in Amine 3, but using instead 3-[2-(methylsulfonyl)ethyl]benzaldehyde from the previous step as the starting material. The title compound was isolated as a colorless oil.

Amine 9

N-{3-[(Cyclopropylamino)methyl]benzyl}-N-methylacetamide

Step 1: N-(3-Bromobenzyl)-N-methylacetamide

To a DMF (0.1 M) solution of 3-bromo-N-methylbenzylamine (1 eq.), Hunig's base (3 eq) and 4-(dimethylamino)pyridine (5% loading) was added acetyl chloride (1.5 eq). The resulting reaction mixture was stirred at RT for 16 h. After quenching the reaction with sat. aq. NaHCO$_3$, the mixture was extracted with EtOAc. The organic extract was washed with 10% aq. HCl, sat. aq. NaHCO$_3$, and brine. Drying over Na$_2$SO$_4$, filtration and concentration of the filtrate in vacuo afforded the crude product as a yellow oil. Purification by way of flash chromatography (SiO$_2$, 4:1 (v/v) Hex:EtOAc→EtOAc) afforded the title compound as a yellow oil.

Step 2: N-(3-Formylbenzyl)-N-methylacetamide

To a solution of N-(3-bromobenzyl)-N-methylacetamide from the previous step (1 eq.) in anhydrous, deoxygenated DMF (0.5 M) was added freshly-dried sodium formate (1.5 eq.) and Pd(PPh$_3$)Cl$_2$ (5% loading). Through the resulting yellow suspension was bubbled CO and then the reaction was heated to 80° C. for 16 h. The now black reaction suspension was cooled to RT, diluted with water and extracted with ether. The combined organic extracts were washed with brine, dried over Na$_2$SO$_4$ and filtered. Concentration of the filtrate in vacuo afforded an orange semi-solid. Purification of the crude product thus obtained by way of flash chromatography (SiO$_2$, 7:3 (v/v) Hex:EtOAc) afforded the title compound as a light yellow oil.

Step 3: Amine 9

Amine 9 was prepared according to the procedure described in Amine 3, but using instead N-(3-formylbenzyl)-N-methylacetamide from the previous step as the starting material. The title compound was isolated as a colorless oil.

Amine 10

N-{4-Chloro-3-[(cyclopropylamino)methyl]benzyl}-N-methylacetamide

Step 1: (5-Bromo-2-chlorophenyl)methanol

To a solution of ethyl 5-bromo-2-chlorobenzoate (1 eq.) in THF (0.03 M) was added, at −78° C., DIBAL (2.5 eq). The reaction was stirred at −78° C. for 1 h and then warmed slowly to RT over 1 h. The reaction mixture was then diluted with ether and carefully quenched with aq. 6 M HCl. The organic layer was separated and the aqueous layer was back extracted with ether. The combined organic extracts were washed with sat. aq. NaHCO$_3$ and brine, dried over MgSO$_4$ and filtered. Concentration of the filtrate in vacuo afforded a white semi-solid. Purification of the crude product thus obtained by way of flash chromatography (SiO$_2$, 3:1 (v/v) Hex:EtOAc) afforded the title compound as a light yellow oil.

Step 2: [(5-Bromo-2-chlorobenzyl)oxy](tert-butyl)dimethylsilane

To a solution of (5-bromo-2-chlorophenyl)methanol from the previous step (1 eq.) in DMF (0.25 M) was added imidazole (1.2 eq.) and tert-butyldimethylsilyl chloride (1.1 eq.). The resulting solution was stirred at RT for 3 h. The reaction mixture was quenched with sat. aq. NH$_4$Cl and extracted with ether. The combined organic extracts were washed further with aq. 10% HCl, sat. aq. NaHCO$_3$, and brine. Concentration of the organic extracts in vacuo afforded an orange oil. Purification of the crude product thus obtained by way of flash chromatography (SiO$_2$, 9:1 (v/v) Hex:EtOAc) afforded the title compound as a light yellow oil.

Step 3: 3-({[tert-Butyl(dimethyl)silyl]oxy}methyl)-4-chlorobenzaldehyde

To a solution of [(5-bromo-2-chlorobenzyl)oxy](tert-butyl)dimethylsilane from the previous step (1 eq.) in THF (0.08 M) was added, at −78° C., n-butyl lithium (2.5 M hexane solution, 1.1 eq) dropwise over 15 min. The reaction mixture was stirred at −78° C. for a further 30 min before DMF (2 eq.) was slowly added. The resulting solution was allowed to warm to RT over 3 h and then quenched with H$_2$O. The organic layer was separated and the aqueous layer was back-extracted with EtOAc. The combined organic extracts were washed with sat. aq. NaHCO$_3$ and brine, dried over Na$_2$SO$_4$ and filtered. Concentration of the filtrate in vacuo afforded an orange oil. Purification of the crude product thus obtained by way of flash chromatography (SiO$_2$, 9:1 (v/v) Hex:EtOAc) afforded the title compound as a yellow oil.

Step 4: [3-({[tert-Butyl(dimethyl)silyl]oxy}methyl)-4-chlorobenzyl]methylamine

To a solution of 3-({[tert-butyl(dimethyl)silyl]oxy}methyl)-4-chlorobenzaldehyde from the previous step (1 eq.) in THF (0.3 M) was added methylamine (2.0 M THF solution, 5 eq.) and freshly-activated 3A molecular sieves. The resulting mixture was stirred at RT for 16 h. The molecular sieves were then filtered off and the filtrate was evaporated in vacuo. The resulting residue was taken up in ethanol (0.25 M) and added sodium borohydride (3 eq.). After 3 h of stirring at RT, the reaction was quenched by the addition of 1 N aq. HCl and then basified with 1 N aq. NaOH. This was extracted with EtOAc. The combined organic extracts were washed with brine, dried over $Na_2SO_4$ and filtered. Concentration of the filtrate in vacuo afforded a cloudy oil. Purification of the crude product thus obtained by way of flash chromatography ($SiO_2$, 19:1 (v/v) $CH_2Cl_2$: 2 M $NH_3$ in MeOH) afforded the title compound as a pale yellow oil.

Step 5: N-[3-({[tert-Butyl(dimethyl)silyl] oxy}methyl)-4-chlorobenzyl]-N-methylacetamide To a solution of [3-({[tert-butyl(dimethyl)silyl] oxy}methyl)-4-chlorobenzyl]methylamine from the previous step (1 eq.) in pyridine (0.09 M) was added acetic anhydride (1.1 eq.) The resulting reaction mixture was stirred at RT for 3 h. After quenching the reaction with $H_2O$, the mixture was extracted with EtOAc. The combined organic extracts were washed with 10% aq. HCl, sat. aq. $NaHCO_3$, and brine. Drying over $Na_2SO_4$, filtration and concentration of the filtrate in vacuo afforded the crude product as a brown oil. Purification by way of flash chromatography ($SiO_2$, 7:3 (v/v) Hex:EtOAc→EtOAc) afforded the title compound as a pale yellow oil.

Step 6: N-[4-Chloro-3-(hydroxymethyl)benzyl]-N-methylacetamide

To a solution of N-[3-({[tert-butyl(dimethyl)silyl] oxy}methyl)-4-chlorobenzyl]-N-methylacetamide from the previous step (1 eq.) in THF (0.8M) was added tetrabutylammonium fluoride (1.0 M THF solution, 1.5 eq.). The resulting reaction mixture was stirred at RT for 1 h. After quenching the reaction with 10% aq. HCl, the mixture was extracted with EtOAc. The combined organic extracts were washed with sat. aq. $NaHCO_3$ and brine, dried over $Na_2SO_4$ and filtered. Concentration of the filtrate in vacuo afforded a pale yellow oil. Purification of the crude product thus obtained by way of flash chromatography ($SiO_2$, 9:1 (v/v) $CH_2Cl_2$:MeOH) afforded the title compound as a light yellow oil.

Step 7: N-(4-Chloro-3-formylbenzyl)-N-methylacetamide

To a solution of N-[4-chloro-3-(hydroxymethyl)benzyl]-N-methylacetamide from the previous step (1 eq.) in $CH_2Cl_2$ (0.8 M) was added Dess-Martin periodinane (1.2 eq.) portionwise. The resulting suspension was stirred at RT for 3 h. The reaction was quenched with MeOH and $H_2O$. The organic layer was separated and the aqueous layer was back-extracted with EtOAc. The combined organic extracts were washed sat. aq. $NaHCO_3$ and brine, dried over $Na_2SO_4$ and filtered. Concentration of the filtrate in vacuo afforded a pale yellow oil. Purification of the crude product thus obtained by way of flash chromatography ($SiO_2$, EtOAc) afforded the title compound as a pale yellow oil.

Step 8: Amine 10

To a solution of N-(4-chloro-3-formylbenzyl)-N-methylacetamide from the previous step (1 eq.) in THF (0.08 M) was added cyclopropylamine (2 eq.) and freshly activated 3A molecular sieves. The resulting mixture was stirred at RT for 48 h. The molecular sieves were then filtered off and the filtrate was evaporated in vacuo. The resulting residue was taken up in methanol (0.07 M) and added sodium borohydride (2 eq.). After 2 h of stirring at RT, the reaction was quenched by the addition of 1 N aq. HCl. The volatiles were removed in vacuo and the resulting residue was partitioned between EtOAc and $H_2O$. The organic layer was separated and the aqueous layer was back extracted with EtOAc. The combined organic extracts were washed with brine, dried over $Na_2SO_4$ and filtered. Concentration of the filtrate in vacuo afforded the title compound as a colorless oil.

Amine 11

3-{4-Chloro-3-[(cyclopropylamino)methyl] phenyl}propan-1-ol

Amine 6 (1 eq.) in chloroform (0.3 M) was added iodotrimethylsilane (9 eq.). The resulting solution was stirred at RT for 8 h. The reaction was then quenched with MeOH before the volatiles were removed in vacuo. The resulting reddish-orange oil was taken up in dichloromethane and washed sequentially with 1 N aq. NaOH, water and brine. The organic layer was separated, dried over $MgSO_4$, filtered and the filtrate concentrated in vacuo to afford a pale yellow oil. Purification of the crude product thus obtained by way of flash chromatography ($SiO_2$, 95:5 (v/v) $CH_2Cl_2$: 2 M $NH_3$ in MeOH) afforded the title compound as a viscous, pale yellow oil.

Amine 12

N-[2-Chloro-5-(2-methoxyethoxy)benzyl]cyclopropanamine

Step 1: 1-Chloro-4-(2-methoxyethoxy)-2-methylbenzene

To a solution of ethyl 4-chloro-3-methylphenol (1 eq.) in acetone (0.2 M) was added potassium carbonate (5 eq.) and 1-bromo-2-methoxyethane (1.3 eq.). The resulting suspension was refluxed for 25 h. The insolubles were removed via filtration and the filtrate was concentrated in vacuo to furnish the title compound.

Step 2: 2-(Bromomethyl)-1-chloro-4-(2-methoxyethoxy)benzene

To a solution of 1-chloro-4-(2-methoxyethoxy)-2-methylbenzene from the previous step (1 eq.) in carbon tetrachloride (0.02 M) was added N-bromosuccinimide (1 eq.) and a few crystals of AIBN (1.1 eq.). The resulting mixture was irradiated with sunlamp at reflux for 1 h. The insolubles were removed via filtration and the filtrate was concentrated in vacuo to furnish the title compound.

Step 3: 2-Chloro-5-(2-methoxyethoxy)benzaldehyde

To a solution of 2-(bromomethyl)-1-chloro-4-(2-methoxyethoxy)benzene from the previous step (1 eq.) in dioxane (0.2 M) was added 4-methylmorpholine N-oxide (3 eq.). The reaction mixture was heated at 80° C. The resulting solution was allowed to cool to RT, poured into brine and then extracted with EtOAc. The combined organic extracts were dried over $MgSO_4$, filtered and the filtrate concentrated in vacuo. Purification of the crude product thus obtained by way of flash chromatography ($SiO_2$, Hex→2:1 (v/v) Hex:EtOAc) afforded the title compound as a pale yellow oil.

Step 4: Amine 12

Amine 7 was prepared according to the procedure described in Amine 3, but using instead 2-chloro-5-(2-methoxyethoxy)benzaldehyde from the previous step as the starting material. The title compound was isolated as a colorless oil.

Amine 13

N-{[6-(pyridine-4-ylmethyl)quinoline-8-yl]methyl}cyclopropanamine

Step 1:
6-(Pyridine-4-ylmethyl)quinoline-8-carbaldehyde

To a solution of 8-bromo-6-(pyridine-4-ylmethyl)quinoline (1 eq.) in THF (0.13 M) was added, at −78° C., n-butyl lithium (2.5 M hexane solution, 1.1 eq) dropwise over 15 min. The reaction mixture was stirred at −78° C. for a further 30 min before DMF (1.5 eq.) was slowly added. The resulting solution was allowed to warm to RT over 3 h and then quenched with $H_2O$. The organic layer was separated and the aqueous layer was back-extracted with EtOAc. The combined organic extracts were washed with sat. aq. $NaHCO_3$ and brine, dried over $Na_2SO_4$ and filtered. Concentration of the filtrate in vacuo afforded a brown oil. Purification of the crude product thus obtained by way of flash chromatography ($SiO_2$, 7:3 (v/v) Hex:EtOAc→EtOAc) afforded the title compound.

Step 2: Amine 13

To a solution of 6-(pyridine-4-ylmethyl)quinoline-8-carbaldehyde from the previous step (1 eq.) in THF (0.07 M) was added cyclopropylamine (2 eq.) and freshly activated 3 Å molecular sieves. The resulting mixture was stirred at RT for 18 h. The molecular sieves were then filtered off and the filtrate was evaporated in vacuo. The resulting residue was taken up in methanol (0.07 M) and added sodium borohydride (1 eq.). After 2 h of stirring at RT, the reaction was quenched by the addition of water. The volatiles were removed in vacuo and the resulting residue was partitioned between EtOAc and $H_2O$. The organic layer was separated and the aqueous layer was back extracted with EtOAc. The combined organic extracts were washed with sat. aq. $NaHCO_3$, dried over $Na_2SO_4$ and filtered. The filtrate was concentrated in vacuo to afford the title compound as a pale yellow oil.

Amine 14

{2-Chloro-5-[3-(dimethylamino)propyl]benzyl}cyclopropanamine

Step 1: 5-Bromo-2-chloro-N-cyclopropylbenzamide

To a toluene solution (1 M) of 5-bromo-2-chlorobenzoic acid (1 eq.) and DMF (1.2 eq.) was added at 0° C. oxalyl chloride (1.2 eq.) dropwise over 1 h. The resulting solution was stirred at 0° C. for 2 h before the volatiles were removed in vacuo. The resulting residue was taken up in dichloromethane (1 M), cooled to 0° C. and added sequentially cyclopropylamine (1.5 eq.) and Hunig's base (2 eq.) dropwise over 1 h. The resulting suspension was stirred at RT for 18 h. The reaction was quenched with 1 N HCl and extracted with dichloromethane. The combined organic extracts were dried over $MgSO_4$, filtered and the filtrate concentrated in vacuo to ~⅓ in volume. The resulting white suspension was added an equivalent volume of hexanes and the title compound was isolated via vacuum filtration.

Step 2:
N-(5-Bromo-2-chlorobenzyl)cyclopropanamine

At 0° C., a suspension of 5-bromo-2-chloro-N-cyclopropylbenzamide from the previous step (1 eq.) in THF (0.4 M) was added borane (1 M THF solution, 3 eq.). The resulting suspension was warmed to RT over 1 h and then heated at reflux for 1 h. The now pale yellow solution was re-cooled to 0° C. and carefully quenched with 1 N aq. HCl. The resulting mixture was heated at reflux for 1 h to ensure complete breakdown of the amine-borane complex. Following careful neutralization with 1 N aq. NaOH, the aqueous layer was separated and back extracted with EtOAc. The combined organic extracts were washed with brine, dried over $MgSO_4$ and filtered. The filtrate was concentrated in vacuo and the crude product thus obtained was purified further by way of column chromatography ($SiO_2$, Hex→80:20 (v/v) Hex:$Et_2O$) to reveal the title compound as a colorless oil.

Step 3: tert-Butyl (5-bromo-2-chlorobenzyl)cyclopropylcarbamate

A THF solution (0.3 M) of N-(5-bromo-2-chlorobenzyl)cyclopropanamine from the previous step (1 eq.) was added at −78° C. potassium hexamethyldisilazide (0.5 M in toluene, 1.2 eq.). After 1 h of stirring at −78° C., di-tert-butyl dicarbonate was added and the resulting mixture was slowly warmed to RT over 2 h. The reaction was quenched with sat. aq. $NH_4Cl$ and then extracted with ether. The combined organic extracts were washed with brine, dried over $MgSO_4$, filtered and the filtrate concentrated in vacuo. Further purification by way of column chromatography ($SiO_2$, Hex→80:20 (v/v) Hex:$Et_2O$) to reveal the title compound as a pale yellow oil.

Step 4: tert-Butyl (5-allyl-2-chlorobenzyl)cyclopropylcarbamate

A THF solution (0.13 M) of tert-butyl (5-bromo-2-chlorobenzyl)cyclopropylcarbamate from the previous step (1 eq.), $Pd(PCy_3)_2$ (0.05 eq.) and cesium fluoride (2.0 eq.) was added allyl tributylstannane (1.2 eq.). The resulting brown solution was heated at reflux for 8 h and then filtered through a pad of $SiO_2$. The insolubles were rinsed further with ether and the filtrate was concentrated in vacuo to afford a brown semisolid. Purification of the crude product thus obtained by way of column chromatography ($SiO_2$, Hex→90:10 (v/v) Hex:$Et_2O$) afforded the title compound as a colorless oil.

Step 5: tert-Butyl [2-chloro-5-(3-(hydroxypropyl)benzyl]cyclopropylcarbamate To a solution of tert-butyl (5-allyl-2-chlorobenzyl)cyclopropylcarbamate from the previous step (1 eq.) in THF (0.3 M) was added dropwise at 0° C. $BH_3.SMe_2$ complex (1.1 eq.) over 20 min. The resulting solution was stirred at 0° C. for 1 h and then at RT for another 2 h. The reaction was then quenched at 0° C. with NaOH (1 N aqueous solution, 4 eq.) and $H_2O_2$ (30% w/w aqueous solution, 4 eq.). The biphasic mixture was slowly warmed to RT and stirred at RT for 2 h. The aqueous layer then was separated and back extracted with ether. The combined organic extracts were washed with brine, dried over $MgSO_4$ and filtered. Concentration of the filtrate in vacuo afforded the title compound which can be purified further by way of column chromatography ($SiO_2$, 90:10 (v:v) Hex:EtOAc→40:60 (v/v) Hex:EtOAc).

Step 6: tert-Butyl {2-chloro-5-[3-(dimethylamino) propyl]benzyl}cyclopropylcarbamate To a solution of tert-butyl [2-chloro-5-(3-(hydroxypropropyl)benzyl]cyclopropylcarbamate from the previous step (1 eq.) in dichloromethane (0.1 M) was added Dess-Martin periodinane (1.2 eq.). The resulting suspension was stirred at RT for 2 h. The reaction was then quenched with sat. aq. NaHSO$_3$ and extracted with dichloromethane. The combined organic extracts were washed with brine, dried over MgSO$_4$ and filtered. Concentration of the filtrate in vacuo afforded the crude aldehyde as a pale yellow oil. This was then taken up in MeOH (0.15 M) and added, sequentially, sodium cyanoborohydride (1.3 eq.), dimethylamine (2 M THF solution, 2.5 eq.) and acetic acid (2.5 eq.). After 18 h of stirring at RT, the reaction was concentrated in vacuo and partitioned between ether and sat. aq. NaHCO$_3$. The aqueous layer was separated and back extracted with ether. The combined organic extracts were washed with brine, dried over MgSO$_4$ and filtered. Concentration of the filtrate in vacuo afforded the crude product as a yellow oil. Further purification by way of column chromatography (SiO$_2$, 79:19:2 (v:v:v) Hex:EtOAc:NEt$_3$→98:2 (v/v) EtOAc:NEt$_3$) afforded the title compound as a pale yellow oil.

Step 7: Amine 14

To a solution of tert-butyl {2-chloro-5-[3-(dimethylamino)propyl]benzyl}cyclopropylcarbamate from the previous step (1 eq.) in dichloromethane (0.2 M) was added HCl (4 M dioxane solution, 8 eq.). The resulting mixture was stirred at RT for 18 h. The reaction was quenched with 1 N aq. NaOH and extracted with dichloromethane. The combined organic extracts were washed with brine, dried over MgSO$_4$ and filtered. Concentration of the filtrate in vacuo afforded the crude product as a pale yellow oil. Further purification by way of column chromatography (SiO$_2$, CH$_2$Cl$_2$→93:7 (v/v) CH$_2$Cl$_{2:2.0}$ M NH$_3$ in MeOH) afforded the title compound as a colorless oil.

Amine 15

N-[2,3-dichloro-5-(3-methoxypropyl)benzyl]cyclopropanamine

Step 1: 5-Bromo-2,3-dichlorobenzaldehyde

To a THF solution (0.2 M) of diisopropylamine (1.2 eq.) was added at 0° C. n-butyl lithium (2.3 M hexane solution, 1.2 eq.) dropwise over 10 min. The resulting pale yellow solution was stirred at 0° C. for 30 min before 1-bromo-3,4-chlorobenzene was added at −78° C. After 1 h of stirring at −78° C., DMF (5 eq.) was added and the resulting solution was stirred at −78° C. for another 2 h. The reaction then allowed to warm slowly to RT before it was quenched with sat. aq. NH$_4$Cl. The aqueous layer was separated and back extracted with ether. The combined organic extracts were washed with brine, dried over MgSO$_4$, filtered and the filtrate concentrated in vacuo. The crude product thus obtained was purified by way of column chromatography (SiO$_2$, Hex→95:5 (v/v) Hex:EtOAc) to afford the title compound as a white solid.

Step 2: N-(5-Bromo-2,3-dichlorobenzyl)cyclopropanamine

A mixture of 5-bromo-2,3-dichlorobenzaldehyde from the previous step (1 eq.), cyclopropylamine (1 eq.) and sodium cyanoborohydride (1.5 eq.) were combined in MeOH (0.2 M). At 0° C., acetic acid (3 eq.) was added dropwise and the reaction mixture was slowly warmed to RT over 16 h. The reaction mixture was then diluted with ether and quenched with 1N aq. NaHCO$_3$. The aqueous layer was separated and back-extracted with ether. The combined organic extracts were then washed with brine, dried over MgSO$_4$, filtered and the filtrate concentrated in vacuo. Purification of the crude product thus obtained by way of flash chromatography (SiO$_2$, Hex→80:20 (v/v) Hex:EtOAc) afforded the title compound as a colorless oil.

Step 3: tert-Butyl (5-bromo-2,3-dichlorobenzyl)cyclopropylcarbamate

A THF solution (0.3 M) of N-(5-bromo-2,3-dichlorobenzyl)cyclopropanamine from the previous step (1 eq.) was added at −78° C. potassium hexamethyldisilazide (0.5 M in toluene, 1.2 eq.). After 1 h of stirring at −78° C., di-tert-butyl dicarbonate was added and the resulting mixture was slowly warmed to RT over 2 h. The reaction was quenched with sat. aq. NH$_4$Cl and then extracted with ether. The combined organic extracts were washed with brine, dried over MgSO$_4$, filtered and the filtrate concentrated in vacuo. Further purification by way of column chromatography (SiO$_2$, Hex→95:5 (v/v) Hex:Et$_2$O) to reveal the title compound as a colorless oil.

Step 4: tert-Butyl (5-allyl-2,3-dichlorobenzyl)cyclopropylcarbamate

A THF solution (0.12 M) of tert-butyl (5-bromo-2,3-dichlorobenzyl)cyclopropylcarbamate from the previous step (1 eq.), Pd(PCy$_3$)$_2$ (0.05 eq.) and cesium fluoride (2.0 eq.) was added allyl tributylstannane (1.2 eq.). The resulting brown solution was heated at reflux for 8 h and then filtered through a pad of SiO$_2$. The insolubles were rinsed further with ether and the filtrate was concentrated in vacuo to afford a brown semisolid. Purification of the crude product thus obtained by way of column chromatography (SiO$_2$, Hex→90:10 (v/v) Hex:Et$_2$O) afforded the title compound as a pale yellow oil.

Step 5: tert-Butyl cyclopropyl[2,3-dichloro-5-(3-(hydroxypropropyl)benzyl]carbamate To a solution of tert-butyl (5-allyl-2,3-dichlorobenzyl)cyclopropylcarbamate from the previous step (1 eq.) in THF (0.16 M) was added dropwise at 0° C. BH$_3$.SMe$_2$ complex (1.2 eq.) over 20 min. The resulting solution was stirred at 0° C. for 1 h and then at RT for another 2 h. The reaction was then quenched at 0° C. with NaOH (1 N aqueous solution, 4 eq.) and H$_2$O$_2$ (30% w/w aqueous solution, 4 eq.). The biphasic mixture was slowly warmed to RT and stirred at RT for 2 h. The aqueous layer then was separated and back extracted with ether. The combined organic extracts were washed with brine, dried over MgSO$_4$ and filtered. Concentration of the filtrate in vacuo afforded the title compound which can be purified further by way of column chromatography (SiO$_2$, 80:20 (v:v) Hex:EtOAc→60:40 (v/v) Hex:EtOAc).

Step 6: tert-Butyl cyclopropyl[2,3-dichloro-5-methoxypropyl)benzyl]carbamate To a solution of tert-butyl cyclopropyl[2,3-dichloro-5-(3-(hydroxypropropyl)benzyl]carbamate from the previous step (1 eq.) in THF (0.2 M) was added sodium hydride (2 eq.). The resulting suspension was stirred at RT for 30 min and then added iodomethane (8 eq.). After 12 h of heating at reflux, the reaction mixture was cooled to RT and quenched with sat. aq. NH₄Cl. The aqueous layer was separated and extracted with ether. The combined organic extracts were washed with brine, dried over MgSO₄ and filtered. Concentration of the filtrate in vacuo afforded the crude product as a yellow oil. Further purification by way of column chromatography (SiO₂, Hex→80:20 (v/v) Hex:EtOAc) afforded the title compound as a pale yellow oil.

Step 7: Amine 15

To a solution of tert-butyl cyclopropyl[2,3-dichloro-5-methoxypropyl)benzyl]carbamate from the previous step (1 eq.) in dichloromethane (0.2 M) was added HCl (4 M dioxane solution, 8 eq.). The resulting mixture was stirred at RT for 18 h. The reaction was quenched with 1 N aq. NaOH and extracted with dichloromethane. The combined organic extracts were washed with brine, dried over MgSO₄ and filtered. Concentration of the filtrate in vacuo afforded the crude product as a pale yellow oil. Further purification by way of column chromatography (SiO₂, CH₂Cl₂→93:7 (v/v) CH₂Cl₂: 2.0 M NH₃ in MeOH) afforded the title compound as a colorless oil.

Amine 16

{8-Cyclopropylamino)methyl]quinoline-6-yl}acetonitrile

Step 1: (8-Formylquinolin-6-yl)acetonitrile

To a solution of (8-bromoquinolin-6-yl)acetonitrile (1 eq.) in anhydrous, deoxygenated DMF (0.08 M) was added freshly-dried sodium formate (1.5 eq.) and Pd(PPh₃)Cl₂ (2% loading). Through the resulting yellow suspension, was bubbled CO and then reaction was heated to 80° C. for 16 h. The now black reaction suspension was cooled to RT, diluted with water, and extracted with EtOAc. The combined organic extracts were washed with brine, dried over MgSO₄ and filtered. Concentration of the filtrate in vacuo afforded the title compound.

Step 2: Amine 16

Amine 16 was prepared according to the procedure described in Amine 3, but using instead (8-formylquinolin-6-yl)acetonitrile from the previous step as the starting material. The title compound was isolated as a yellow oil.

Amine 17

N-{[2-(3-Methoxypropyl)quinoline-4-yl]methyl}cyclopropanamine

Step 1: Methyl 2-hydroxyquinoline-4-carboxylate

To a solution of 2-hydroxyquinoline-4-carboxylic acid (1 eq.) in methanol (0.11 M) was added HCl (4 M dioxane solution, 1 eq.) and the resulting suspension was heated at reflux for 24 h. The reaction was quenched with sat. aq. NaHCO₃ and extracted with EtOAc. The combined organic extracts were washed with brine, dried over MgSO₄ and filtered. Concentration of the filtrate in vacuo afforded the title compound.

Step 2: Methyl 2-{[(trifluoromethyl)sulfonyl]oxy}quinoline-4-carboxylate

To a solution of methyl 2-hydroxyquinoline-4-carboxylate from the previous step (1 eq.) in dichloromethane (0.2 M) was added sequentially at 0° C. pyridine (1.4 eq.) and triflic anhydride (1.1 eq.). The reaction mixture was stirred at 0° C. for 1 h and then at RT for 2 h. The reaction mixture was quenched with water and extracted with EtOAc. The combined organic extracts were washed with water, sat. aq. NaHCO₃ and brine. Drying over MgSO₄, filtration and concentration of the filtrate in vacuo afforded the title compound.

Step 3: Propyl 2-[(1E)-3-methoxyprop-1-en-1-yl]quinoline-4-carboxylate

Methyl 2-{[(trifluoromethyl)sulfonyl]oxy}quinoline-4-carboxylate from the previous step (1 eq.) and 2-[(1E)-3-methoxyprop-1-en-1-yl]-4,4,5,5-tetramethyl-1,3,2-dioxaborolane (1 eq.) were combined in n-propanol (0.1 M). To this solution was then added palladium acetate (5% loading), triphenylphosphine (15% loading) and sodium carbonate (2 M aqueous solution, 4 eq.). The resulting suspension was heated at 80° C. for 2 h. The reaction mixture was quenched with water and extracted with EtOAc. The combined organic extracts were washed with water, sat. aq. NaHCO₃ and brine. Drying over MgSO₄, filtration and concentration of the filtrate in vacuo afforded the crude product as a brown tar. Purification by way of column chromatography (SiO₂, 10:1 (v/v) Hex:EtOAc→1:1 (v/v) Hex:EtOAc) afforded the title compound as a yellow oil.

Step 4: Propyl 2-(3-methoxypropyl]quinoline-4-carboxylate

To a solution of propyl 2-[(1E)-3-methoxyprop-1-en-1-yl]quinoline-4-carboxylate from the previous step (1 eq.) in toluene (0.06 M) was added at 80° C. benzenesulfonyl hydrazide (3×1 eq.) over 3 h. The reaction mixture was diluted with EtOAc and washed sequentially with water, sat. aq. NaHCO₃ and brine. Drying over MgSO₄, filtration and concentration of the filtrate in vacuo afforded the crude product as a yellow oil. Purification by way of column chromatography (SiO₂, 10:1 (v/v) Hex:EtOAc→1:1 (v/v) Hex:EtOAc) afforded the title compound as a yellow oil.

Step 5: [2-(3-Methoxypropyl)quinoline-4-yl]methanol

To a solution of propyl 2-(3-methoxypropyl]quinoline-4-carboxylate from the previous step (1 eq.) in toluene (0.1 M) was added at −78° C. DIBAL (1.5 M toluene solution, 2 eq.) dropwise over 10 min. The reaction mixture was stirred at −78° C. for 30 min and then at 0° C. for 2 h. The reaction mixture was quenched with sat. aq. Rochelle's salt and extracted with EtOAc. The combined organic extracts were washed sequentially with water, sat. aq. NaHCO₃ and brine. Drying over MgSO₄, filtration and concentration of the filtrate in vacuo afforded the crude product as a milky oil. Purification by way of column chromatography (SiO₂, 10:1 (v/v) Hex:EtOAc→EtOAc) afforded the title compound as a pale yellow oil.

Step 6: 2-(3-Methoxypropyl)quinoline-4-carbaldehyde

To a solution of [2-(3-methoxypropyl)quinoline-4-yl]methanol from the previous step (1 eq.) in CH₂Cl₂ (0.05 M)

was added Dess-Martin periodinane (1.1 eq.) portionwise. The resulting suspension was stirred at RT for 3 h. The reaction was quenched with MeOH and H$_2$O. The organic layer was separated and the aqueous layer was back-extracted with EtOAc. The combined organic extracts were washed sat. aq. NaHCO$_3$ and brine, dried over Na$_2$SO$_4$ and filtered. Concentration of the filtrate in vacuo afforded the title compound which was purified further by way of flash chromatography (SiO$_2$, 2:1 (v/v) Hex:EtOAc).

Step 7: Amine 17

To a solution of 2-(3-methoxypropyl)quinoline-4-carbaldehyde from the previous step (1 eq.) in THF (0.05 M) was added cyclopropylamine (2 eq.) and magnesium sulfate (1 eq.). The resulting mixture was stirred at RT for 3 h. The insolubles were then filtered off and the filtrate evaporated in vacuo. The resulting residue was taken up in methanol (0.05 M) and added sodium borohydride (2 eq.). After 2 h of stirring at RT, the reaction was quenched by the addition of 1 N aq. HCl. The volatiles were removed in vacuo and the resulting residue was partitioned between EtOAc and H$_2$O. The organic layer was separated and the aqueous layer was back extracted with EtOAc. The combined organic extracts were washed with brine, dried over Na$_2$SO$_4$ and filtered. Concentration of the filtrate in vacuo afforded the title compound as a pale yellow oil.

Amine 18

3-{4-Chloro-3-[(cyclopropylamino)methyl]phenyl}propanenitrile

Step 1: (2E)-3-[3-({[tert-Butyl(dimethyl)silyl]oxy}methyl)-4-chlorophenyl]acrylonitrile To a solution of diethyl cyanomethylphosphonate (1.1 eq.) in THF (0.14 M) was added at 0° C. potassium tert-butoxide (1 M THF solution, 1.1 eq.). The resulting yellow solution was stirred at 0° C. for 1 h before 3-({[tert-butyl(dimethyl)silyl]oxy}methyl)-4-chlorobenzaldehyde from step 3 of Amine 10 synthesis (1 eq.) in THF (0.14 M) was added. The resulting mixture was stirred at RT 3 h. The reaction was quenched by the addition of sat. aq. NH$_4$Cl and then extracted with EtOAc. The combined organic extracts were washed with sat. aq. NaHCO$_3$, dried over MgSO$_4$ and filtered. Concentration of the filtrate in vacuo afforded an orange oil. Purification of the crude product thus obtained by way of flash chromatography (SiO$_2$, Hex→2:1 (v/v) Hex:EtOAc) afforded the title compound.

Step 2: 3-[4-Chloro-3-(hydroxymethyl)phenyl]propanenitrile

To a solution of (2E)-3-[3-({[tert-butyl(dimethyl)silyl]oxy}methyl)-4-chlorophenyl]acrylonitrile from the previous step (1 eq.) in toluene (0.01 M) was added at 80° C. benzenesulfonyl hydrazide (3×1 eq.) over 3 h. The reaction mixture was diluted with EtOAc and washed sequentially with water, sat. aq. NaHCO$_3$ and brine. Drying over MgSO$_4$, filtration and concentration of the filtrate in vacuo afforded a yellow oil. The residue was taken up in THF (0.1 M) and added tetrabutylammonium fluoride (1.0 M THF solution, 1.1 eq.). The resulting reaction mixture was stirred at RT for 2 h. After quenching the reaction with sat. aq. NH$_4$Cl, the mixture was extracted with EtOAc. The combined organic extracts were washed with sat. aq. NaHCO$_3$ and brine, dried over MgSO$_4$ and filtered. Concentration of the filtrate in vacuo and purification of the crude product thus obtained by way of flash chromatography (SiO$_2$, Hex→1:1 (v/v) Hex:EtOAc) afforded the title compound as a pale yellow oil.

Step 3: 3-(4-Chloro-3-formylphenyl)propanenitrile

To a solution of 3-[4-chloro-3-(hydroxymethyl)phenyl]propanenitrile from the previous step (1 eq.) in CH$_2$Cl$_2$ (0.1 M) was added Dess-Martin periodinane (1.1 eq.) portionwise. The resulting suspension was stirred at RT for 2 h. The reaction was quenched with MeOH and H$_2$O. The organic layer was separated and the aqueous layer was back-extracted with EtOAc. The combined organic extracts were washed sat. aq. NaHCO$_3$ and brine, dried over Na$_2$SO$_4$ and filtered. Concentration of the filtrate in vacuo afforded the title compound as a pale yellow oil.

Step 4: Amine 18

To a solution of 3-(4-chloro-3-formylphenyl)propanenitrile from the previous step (1 eq.) in THF (0.1 M) was added cyclopropylamine (2 eq.) and MgSO$_4$ (1 eq.). The resulting suspension was stirred at RT for 3 h. The insolubles were then filtered off and the filtrate evaporated in vacuo. The resulting residue was taken up in methanol (0.1 M) and added sodium borohydride (2 eq.). After 2 h of stirring at RT, the reaction was quenched by the addition of 1 N aq. HCl. The volatiles were removed in vacuo and the resulting residue was partitioned between EtOAc and H$_2$O. The organic layer was separated and the aqueous layer was back extracted with EtOAc. The combined organic extracts were washed with brine, dried over Na$_2$SO$_4$ and filtered. Concentration of the filtrate in vacuo and purification of the crude product thus obtained by way of column chromatography (SiO$_2$, Hex→EtOAc) afforded the title compound as a pale yellow oil.

Amine 19

N-[5-(3-Methoxypropyl)-2-methylbenzyl]cyclopropanamine

Amine 19 was prepared according to the procedure described in Amine 14, but using instead 5-chloro-2-methylbenzoic acid from the previous step as the starting material in step 1 and [BrPdP$^t$Bu$_3$]$_2$ as the palladium source in step 4. The title compound was isolated as a pale yellow oil.

Amine 20

{4-Chloro-3-[(cyclopropylamino)methyl]phenyl}acetonitrile

Step 1: [3-({[tert-Butyl(dimethyl)silyl]oxy}methyl)-4-chlorophenyl]methanol

To a solution of 3-({[tert-butyl(dimethyl)silyl]oxy}methyl)-4-chlorobenzaldehyde from step 3 of Amine 10 synthesis (1 eq.) in methanol (0.14 M) was added sodium borohydride (5 eq.). The resulting mixture was stirred at RT 3 h. The reaction was quenched by the addition of sat. aq. NH$_4$Cl and then extracted with EtOAc. The combined organic extracts were washed with sat. aq. NaHCO$_3$, dried over MgSO$_4$ and filtered. Concentration of the filtrate in vacuo afforded an colorless oil. Purification of the crude product thus obtained by way of flash chromatography (SiO$_2$, Hex→1:1 (v/v) Hex:EtOAc) afforded the title compound.

Step 2: [3-({[tert-Butyl(dimethyl)silyl]oxy}methyl)-4-chlorophenyl]acetonitrile

To a solution of [3-({[tert-butyl(dimethyl)silyl]oxy}methyl)-4-chlorophenyl]methanol from the previous step (1 eq.) in dichloromethane (0.14 M) was added sequentially at 0° C. Hunig's base (1 eq.) and methanesulfonyl chloride (1.1 eq.). The reaction mixture was warmed to RT and stirred at RT for 3 h. The reaction was then quenched with water and extracted with EtOAc. The combined organic extracts were washed with brine, dried over MgSO$_4$, filtered and the filtrate concentrated in vacuo. The crude mesylate thus obtained was taken up in DMF (0.14 M) and added sodium cyanide (1.5 eq.). After 16 h of stirring at RT, the reaction mixture was partitioned between water and ether. The organic layer was separated and washed with sat. aq. NaHCO$_3$ and brine, dried over MgSO$_4$ and filtered. Concentration of the filtrate in vacuo and purification of the crude product thus obtained by way of flash chromatography (SiO$_2$, Hex→2:1 (v/v) Hex:EtOAc) afforded the title compound as a pale yellow oil.

Step 3: [4-Chloro-3-(hydroxymethyl)phenyl]acetonitrile

To a solution of 3-({[tert-butyl(dimethyl)silyl]oxy}methyl)-4-chlorophenyl]acetonitrile from the previous step (1 eq.) in THF (0.15 M) and added tetrabutylammonium fluoride (1.0 M THF solution, 1.2 eq.). The resulting reaction mixture was stirred at RT for 2 h. After quenching the reaction with water, the resulting mixture was extracted with EtOAc. The combined organic extracts were washed with sat. aq. NaHCO$_3$ and brine, dried over MgSO$_4$ and filtered. Concentration of the filtrate in vacuo and purification of the crude product thus obtained by way of flash chromatography (SiO$_2$, Hex→1:1 (v/v) Hex:EtOAc) afforded the title compound as a pale yellow oil.

Step 4: (4-Chloro-3-formylphenyl acetonitrile

To a solution of [4-chloro-3-(hydroxymethyl)phenyl]acetonitrile from the previous step (1 eq.) in CH$_2$Cl$_2$ (0.14 M) was added Dess-Martin periodinane (1.1 eq.) portionwise. The resulting suspension was stirred at RT for 3 h. The reaction was quenched with MeOH and H$_2$O. The organic layer was separated and the aqueous layer was back-extracted with EtOAc. The combined organic extracts were washed sat. aq. NaHCO$_3$ and brine, dried over Na$_2$SO$_4$ and filtered. Concentration of the filtrate in vacuo afforded the title compound as a pale yellow oil.

Step 5: Amine 20

To a solution of (4-chloro-3-formylphenyl)acetonitrile from the previous step (1 eq.) in THF (0.1 M) was added cyclopropylamine (2 eq.) and MgSO$_4$ (1 eq.). The resulting suspension was stirred at RT for 18 h. The insolubles were then filtered off and the filtrate evaporated in vacuo. The resulting residue was taken up in methanol (0.1 M) and added sodium borohydride (2 eq.). After 2 h of stirring at RT, the reaction was quenched by the addition of 1 N aq. HCl. The volatiles were removed in vacuo and the resulting residue was partitioned between EtOAc and H$_2$O. The organic layer was separated and the aqueous layer was back extracted with EtOAc. The combined organic extracts were washed with brine, dried over Na$_2$SO$_4$ and filtered. Concentration of the filtrate in vacuo and purification of the crude product thus obtained by way of column chromatography (SiO$_2$, Hex 4 EtOAc) afforded the title compound as a pale yellow oil.

Amine 21

N-[5-(2-Methoxyethyl)-2-methylbenzyl]cyclopropanamine

Step 1: tert-Butyl cyclopropyl[5-(2-hydroxyethyl)-2-methylbenzyl]carbamate

To a dichloromethane solution (0.33 M) of tert-butyl (5-allyl-2-methylbenzyl)cyclopropylcarbamate from step 4 of Amine 19 synthesis (1 eq) was bubbled, at −78° C., ozone until a persistent blue color was observed. At this time, the reaction mixture was diluted with an equivalent volume of ethanol and added sodium borohydride (2.5 eq.). The reaction was then allowed to slowly warm to RT overnight. The reaction was quenched by the addition of sat. aq. NH$_4$Cl before the volatiles were removed in vacuo. The resulting residue was extracted with ether. The combined organic extracts were washed with brine, dried over MgSO$_4$ and filtered. Concentration of the filtrate in vacuo and purification of the crude product thus obtained by way of flash chromatography (SiO$_2$, Hex→3:2 (v/v) Hex:EtOAc) afforded the title compound as a colorless oil.

Step 2: tert-Butyl cyclopropyl[5-(methoxyethyl)-2-methylbenzyl]carbamate

To a solution of tert-butyl cyclopropyl[5-(2-hydroxyethyl)-2-methylbenzyl]carbamate from the previous step (1 eq.) in THF (0.2 M) was added sodium hydride (2 eq.). The resulting suspension was stirred at RT for 30 min and then added iodomethane (8 eq.). After 12 h of heating at reflux, the reaction mixture was cooled to RT and quenched with sat. aq. NH$_4$Cl. The aqueous layer was separated and extracted with ether. The combined organic extracts were washed with brine, dried over MgSO$_4$ and filtered. Concentration of the filtrate in vacuo afforded the crude product as a colorless oil. Further purification by way of column chromatography (SiO$_2$, Hex→7:3 (v/v) Hex:EtOAc) afforded the title compound as a colorless oil.

Step 3: Amine 21

To a solution of tert-butyl cyclopropyl[5-(methoxyethyl)-2-methylbenzyl]carbamate from the previous step (1 eq.) in dichloromethane (0.2 M) was added HCl (4 M dioxane solution, 5 eq.). The resulting mixture was stirred at RT for 16 h. The reaction was quenched with 1 N aq. NaOH and extracted with dichloromethane. The combined organic extracts were washed with brine, dried over MgSO$_4$ and filtered. Concentration of the filtrate in vacuo afforded the crude product as a pale yellow oil. Further purification by way of column chromatography (SiO$_2$, Hex→3:2 (v/v) Hex:EtOAc) afforded the title compound as a pale yellow oil.

Amine 22

N-[2,5-Bis(trifluoromethyl)benzyl]cyclopropanamine

Amine 22 was prepared according to the reaction sequence described for Amine 3, but using instead 2,5-bis(trifluoromethyl)benzaldehyde as the starting material. The title compound was isolated as a colorless oil.

Amine 23

2-{8-[(Cyclopropylamino)methyl]quinoline-6-yl}-2-methylpropanenitrile

Amine 23 was prepared according to the procedure described in Amine 16, but using instead 2-(8-bromoquinolin-6-yl)-2-methylpropanenitrile acetonitrile as the starting material. The title compound was isolated as a yellow oil.

Amine 24

N-(1-Phenylethyl)cyclopropanamine

To a solution of 1-phenylethanone (1 eq.) in dichloromethane (0.17 M) was added cyclopropylamine (3 eq.) and magnesium sulfate (9 eq.). The resulting mixture was stirred at reflux for 2 days. The insolubles were then filtered off and the filtrate evaporated in vacuo. The resulting residue was taken up in methanol (0.2 M) and added sodium borohydride (1.5 eq.). The reaction mixture was then stirred at RT overnight. After quenching with 1 N aq. HCl, the volatiles were removed in vacuo. The resulting residue was partitioned between 1 N NaOH and extracted with ether. The combined organic extracts were washed with brine, dried over $MgSO_4$ and filtered. Concentration of the filtrate in vacuo afforded the title compound as a colorless oil.

Amine 25

N-Benzylcyclopropanamine

Amine 26 was prepared according to the procedure described in Amine 24, but using instead benzaldehyde as the starting material. The title compound was isolated as a colorless oil.

Amine 26

N-(2-Phenylethyl)cyclopropanamine

To a solution of cyclopropanamine (1 eq.) in dichloromethane (0.13 M) was added sequentially at 0° C. pyridine (1.5 eq.) and phenylacetyl chloride (9 eq.). The resulting mixture was slowly warmed to RT and stirred at RT for 3 h. After quenching with 1 N aq. HCl, the reaction mixture was extracted with EtOAc. The combined organic extracts were washed with sat. aq. $NaHCO_3$ and brine, dried over $MgSO_4$, filtered and the filtrate concentrated in vacuo. The crude amide thus obtained was taken up in THF (0.3 M) and added $BH_3.SMe_2$ complex (3 eq.). The reaction was heated to reflux and the volatiles were slowly distilled off. The resulting distillation residue was carefully quenched with 1 N aq. HCl and allowed to stir at 50° C. overnight. The reaction was cooled to 0° C. and the pH of the solution was brought to ~12 with 1 N aq. NaOH before it was extracted with ether. The combined organic extracts were washed with brine, dried over $MgSO_4$, filtered and the filtrate concentrated in vacuo. The crude product thus obtained could be further purified by way of column chromatography ($SiO_2$, 2:1 (v/v) Hex:EtOAc→EtOAc) afforded the title compound as a colorless oil.

Amine 27

N-(2,3-dichlorobenzyl)-2,2,2-trifluoroethanamine

Amine 27 was prepared according to the reaction sequence described for Amine 3, but using instead 2,3-dichlorobenzaldehyde as the starting aldehyde and 2,2,2-trifluoroethylamine as the starting amine. The title compound was isolated as a colorless oil.

Amine 28

N-methyl-2-phenylpropan-2-amine

To a solution of 2-phenylpropan-2-amine (1 eq.) in benzene (0.25 M) was added formaldehyde (37% w/w aqueous solution, 2 eq.). The vessel attached a Dean-Stark apparatus and heated at 80° C. for 36 h. The reaction mixture was cooled to RT, dried with $Na_2SO_4$ and filtered. Concentration of the filtrate in vacuo afforded the crude imine. This was then taken up in methanol (1.4 M) and added sodium borohydride (10 eq.). The resulting mixture was stirred at RT for 2 h and then quenched with 1 N aq. HCl. The volatiles were removed in vacuo and the pH of the resulting residue was carefully brought up to ~12 with 1 N aq. NaOH. The mixture was then extracted with EtOAc. The combined organic extracts were washed with brine, dried over $MgSO_4$, filtered and the filtrate concentrated in vacuo. Purification of the crude product thus obtained by way of column chromatography ($SiO_2$, 2:1 (v/v) Hex:EtOAc→EtOAc) afforded the title compound as a colorless oil.

Amine 29

1-[2-Chloro-5-(2-methoxyethyl)phenyl]-N-(cyclopropylmethyl)methanamine

To a solution of 2-chloro-5-(2-methoxyethyl)benzaldehyde from Amine 7, Step 6 (1 eq.) in methanol (0.8 M) was added 1-cyclopropylmethanamine (1.2 eq.) and sodium bicarbonate (1.5 eq). The vessel was sealed and heated at 70° C. for 2 h. The insolubles were removed via filtration and to the filtrate was then added sodium borohydride (1.5 eq.) at 0° C. The reaction mixture was allowed to warm slowly to RT overnight. The volatiles were removed in vacuo and the resulting residue was partitioned between 1 N aq. NaOH and ether. The aqueous layer was separated and back extracted with ether. The combined ethereal extracts were washed with brine, dried over $Na_2SO_4$ and filtered. Concentration of the filtrate in vacuo afforded the title compound.

Amine 30

1-[2-Chloro-5-(2-methoxyethyl)phenyl]-N-methyl-methanamine

Amine 30 was prepared according to the reaction sequence described for Amine 29, but using instead methylamine (2.0 M solution in methanol) as starting material. The title compound was isolated as a colorless oil.

Amine 31

1-[2-Chloro-5-(2-methoxyethyl)phenyl]-N-(cyclobutylmethyl)methanamine

Step 1: 1-Cyclobutylmethanamine

To a solution of cyclobutane carbonitrile (1 eq.) in ethanol (0.5 M) was added glacial acetic acid (1.05 eq.) and platinum oxide (5% loading). The resulting suspension was hydrogenated on a Parr apparatus at 52 psi for 18 h. The reaction suspension was then filtered and the filtrate concentrated in vacuo. The resulting residue was partitioned between 1 N aq. NaOH and ether. The aqueous layer was separated and back extracted with ether. The combined ethereal extracts were washed with brine, dried over $MgSO_4$ and filtered. Concentration of the filtrate in vacuo afforded the title compound.

Step 2: Amine 31

Amine 31 was prepared according to the procedure described in Amine 30, but using instead 1-cyclobutylmethanamine from the previous step as the starting material. The title compound was isolated as a colorless oil.

Amine 32

N-2-Chloro-5-(2-methoxyethyl)benzyl]propan-2-amine

Amine 32 was prepared according to the procedure described in Amine 30, but using instead isopropylamine as the starting material. The title compound was isolated as a colorless oil.

Amine 33

N-2-Chloro-5-(2-methoxyethyl)benzyl]prop-2-en-1-amine

Amine 33 was prepared according to the procedure described in Amine 30, but using instead allylamine as the starting material. The title compound was isolated as a colorless oil.

Amine 34

N-2-Chloro-5-(2-methoxyethyl)benzyl]cyclobutanamine

Amine 34 was prepared according to the procedure described in Amine 30, but using instead cyclobutylamine as the starting material. The title compound was isolated as a colorless oil.

Amine 35

N-[2-Chloro-5-(2-methoxyethyl)phenyl]-N-ethanamine

Amine 35 was prepared according to the reaction sequence described for Amine 29, but using instead ethylamine (2.0 M solution in methanol) as starting material. The title compound was isolated as a colorless oil.

Amine 36

N-[3-{[tert-Butyl(dimethyl)silyl]oxy}-5-(3-methoxypropyl)benzyl]cyclopropanamine

Step 1: 3-Bromo-5-hydroxybenzaldehyde

To a toluene solution (1.6 M) of n-butyl lithium (2.5 M hexane solution, 2.1 eq.) was added at $-10°$ C. n-butyl magnesium chloride (2.0 M THF solution, 0.6 eq.). The reaction mixture was stirred at $-10°$ C. for 30 min before a toluene solution (0.7 M) of 3,5-dibromophenol (1 eq.) was added dropwise at $-10°$ C. over a period of 35 min. After stirring at $-10°$ C. for a further 30 min, the reaction mixture was cooled to $-40°$ C. before DMF (20 eq.) was added dropwise over 20 min. The reaction mixture was then slowly warmed to RT and allowed to stir at RT for 1 h. The reaction was carefully quenched at $0°$ C. with 10% aq. HCl and extracted with ether. The combined organic extracts were washed with water and brine, dried over $MgSO_4$ and filtered. Concentration of the filtrate in vacuo afforded a yellow solid. Recrystallization of the crude product thus obtained from ether-hexane afforded the title compound as a beige powder.

Step 2: 3-Hydroxy-5-[(1E)-3-methoxyprop-1-en-1-yl]benzaldehyde

3-Bromo-5-hydroxybenzaldehyde from the previous step (1 eq.) and 2-[(1E)-3-methoxyprop-1-en-1-yl]-4,4,5,5-tetramethyl-1,3,2-dioxaborolane (1 eq.) were combined in DMF (0.05 M). To this solution was then added palladium acetate (10% loading), triphenylphosphine (20% loading) and sodium carbonate (2 M aqueous solution, 4 eq.). The resulting suspension was heated at $80°$ C. for 16 h. The reaction mixture was quenched with 10% aq. HCl and extracted with ether. The combined organic extracts were washed with water, sat. aq. $NaHCO_3$ and brine. Drying over $MgSO_4$, filtration and concentration of the filtrate in vacuo afforded the crude product as a brown tar. Purification by way of column chromatography ($SiO_2$, 4:1 (v/v) Hex:EtOAc→2:1 (v/v) Hex:EtOAc) afforded the title compound as a yellow oil.

Step 3: 3-{[tert-Butyl(dimethyl)silyl]oxy}-5-[(1E)-3-methoxyprop-1-en-1-yl]benzaldehyde 3-Hydroxy-5-[(1E)-3-methoxyprop-1-en-1-yl]benzaldehyde from the previous step (1 eq.) and tert-butylchlorodimethylsilane (1 eq.) were combined in DMF (0.5 M). To this solution was then added imidazole (1.5 eq.) and the reaction mixture was stirred at RT for 16 h. The resulting solution was quenched with water and extracted with 1:1 (v:v) ether:hexanes. The combined organic extracts were washed with brine, dried over $MgSO_4$ and filtered through a plug of $SiO_2$. Concentration of the filtrate in vacuo afforded the title compound as a pale yellow oil.

Step 4: N-{3-{[tert-Butyl(dimethyl)silyl]oxy}-5-[(1E)-3-methoxyprop-1-en-1-yl]benzyl}cyclopropanamine To a solution of 3-{[tert-butyl(dimethyl)silyl]oxy}-5-[(1E)-3-methoxyprop-1-en-1-yl]benzaldehyde from the previous step (1 eq.) in dichloromethane (0.5 M) was added cyclopropylamine (2 eq.) and magnesium sulfate (1.5 eq.).

The resulting suspension was stirred at RT for 12 h. The insolubles were removed via filtration. Concentration of the filtrate in vacuo afforded the crude imine as a yellow oil. This was then taken up in methanol (0.3 M) and then added at 0° C. sodium borohydride (1.5 eq.) portionwise over 5 min. The reaction mixture was slowly warmed to RT over 1 h and then stirred at RT for 2 h. After carefully quenching with sat. aq. NaHCO$_3$, the resulting mixture was extracted with ether. The combined organic extracts were washed with water and brine, dried over MgSO$_4$ and filtered. Concentration of the filtrate in vacuo afforded the title compound as a golden, yellow oil.

Step 5: Amine 36

To a solution of N-{3-{[tert-butyl(dimethyl)silyl]oxy}-5-[(1E)-3-methoxyprop-1-en-1-yl]benzyl}cyclopropanamine from the previous step (1 eq.) in EtOAc (0.04 M) was added palladium (10% w/w over activated carbon, 10% loading). The vessel was evacuated and back filled with hydrogen. The reaction suspension was then stirred under a balloon atmosphere of hydrogen for 1.5 h.

The reaction was quenched with dichloromethane and filtered through a bed of celite. The insolubles were washed further with EtOAc and methanol. Concentration of the filtrate in vacuo afforded the title compound as a colorless oil.

Amine 37

Ethyl 2-{[2-chloro-3-[(cyclopropylamino)methyl]-5-(3-methoxypropyl)phenoxy]methyl}cyclopropane carboxylate Step 1: 3-{[tert-Butyl(dimethyl)silyl]oxy}-5-(3-methoxypropyl)benzaldehyde To a solution of 3-{[tert-butyl(dimethyl)silyl]oxy}-5-[(1E)-3-methoxyprop-1-en-1-yl]benzaldehyde from Amine 36, Step 3 (1 eq.) in EtOAc (0.1 M) was added palladium (10% w/w over activated carbon, 10% loading). The vessel was evacuated and back filled with hydrogen. The reaction suspension was then stirred under a balloon atmosphere of hydrogen for 1 h. The reaction was quenched with dichloromethane and filtered through a bed of celite. The insolubles were washed further with EtOAc and methanol. Concentration of the filtrate in vacuo and purification of the crude product thus obtained by way of column chromatography (SiO$_2$, Hex→3:2 (v/v) Hex:EtOAc) afforded the title compound as a pale yellow oil.

Step 2: 3-Hydroxy-5-(3-methoxypropyl)benzaldehyde

To a solution of 3-{[tert-butyl(dimethyl)silyl]oxy}-5-(3-methoxypropyl)benzaldehyde from the previous step (1 eq.) in THF (0.2 M) was added tetrabutylammonium fluoride (1.0 M THF solution, 1.1 eq.). The resulting reaction mixture was then stirred at RT for 30 min. The reaction was quenched sat. aq. NH$_4$Cl and then extracted with ether. The combined organic extracts were washed with water and brine, dried over MgSO$_4$, filtered and the filtrate concentrated in vacuo. Further purification of the crude product thus obtained by way of column chromatography (SiO$_2$, Hex→3:2 (v/v) Hex:EtOAc) afforded the title compound as a pale yellow oil.

Step 3: 2-Chloro-3-hydroxy-5-(3-methoxypropyl)benzaldehyde

To a solution of 3-hydroxy-5-(3-methoxypropyl)benzaldehyde from the previous step (I eq.) in dichloromethane (0.2 M) was added sulfuryl chloride (1 eq.). The resulting reaction mixture was then stirred at RT for 18 h. The volatiles were removed in vacuo and purification of the crude product thus obtained by way of column chromatography (SiO$_2$, Hex→3:2 (v/v) Hex:EtOAc) afforded the title compound as a yellow oil.

Step 4: Ethyl 2-{[2-chloro-3-formyl-5-(3-methoxypropyl)phenoxy]methyl}cyclopropanecarboxylate To a solution of ethyl 2-(hydroxymethyl)cyclopropanecarboxylate from Experiment 86, Step 1 (1.2 eq.) in dichloromethane (0.15 M) was added at −78° C. Hunig's base (3 eq.) and methanesulfonyl chloride (1.5 eq.). The resulting solution was stirred at −78° C. for 15 min and then warmed to RT over 3 h. The reaction was quenched with sat. aq. NaHCO$_3$ and then extracted with ether. The combined organic extracts were washed with water and brine, dried over MgSO$_4$, filtered and the filtrate concentrated in vacuo to afford the crude mesylate as a pale yellow oil. This was then taken up in DMF (0.014 M) and added cesium carbonate (1.2 eq.) and 2-chloro-3-hydroxy-5-(3-methoxypropyl)benzaldehyde from the previous step (1 eq.). The resulting suspension was stirred at 50° C. for 3 h. The reaction was quenched with sat. aq. NH$_4$Cl and then extracted with ether. The combined organic extracts were washed with water and brine, dried over MgSO$_4$ and filtered. Concentration of the filtrate in vacuo and purification of the crude product thus obtained by way of column chromatography (SiO$_2$, Hex→7:3 (v/v) Hex:EtOAc) afforded the title compound.

Step 5: Amine 37

Amine 37 was prepared according to the procedure described in Amine 3, but using instead ethyl 2-{[2-chloro-3-formyl-5-(3-methoxypropyl)phenoxy]methyl}cyclopropanecarboxylate from the previous step as the starting material. The title compound was isolated as a white foam.

Amine 38

N-[3,5-Bis(2-methoxyethoxy)benzyl]cyclopropanamine

Step 1: 3,5-Bis(2-methoxyethoxy)benzaldehyde

To a solution of 3,5-dihydroxybenzaldehyde (1 eq.) in DMF (0.5 M) was added 2-bromoethyl methyl ether (3.5 eq.) and cesium carbonate (5 eq.). The resulting suspension was heated at 80° C. for 16 h. The reaction was quenched with sat. aq. NH$_4$Cl and then extracted with ether. The combined organic extracts were washed with water and brine, dried over Na$_2$SO$_4$, filtered and the filtrate concentrated in vacuo. Purification of the crude product thus obtained by way of column chromatography (SiO$_2$, Hex→3:1 (v/v) Hex:EtOAc) afforded the title compound as a yellow oil.

Step 2: Amine 38

To a solution of 3,5-bis(2-methoxyethoxy)benzaldehyde from the previous step (1 eq.) in dichloromethane (0.3 M) was added cyclopropylamine (2 eq.) and magnesium sulfate (1.5 eq.). The resulting suspension was stirred at RT for 12 h. The insolubles were removed via filtration. Concentration of the filtrate in vacuo afforded the crude imine as a yellow oil. This was then taken up in methanol (0.8 M) and then added at 0° C. sodium borohydride (1.5 eq.) portionwise over 5 min. The reaction mixture was slowly warmed to RT over 1 h and then stirred at RT for 1.5 h. The reaction was quenched with sat. aq. NaHCO$_3$ and then extracted with EtOAc. The combined organic extracts were washed with water and brine, dried over MgSO$_4$, filtered and the filtrate concentrated in vacuo. Purification of the crude product thus obtained by way of column chromatography (SiO$_2$, 95:5 (v/v) CH$_2$Cl$_2$:EtOH→90:10 (v/v) CH$_2$Cl$_2$:EtOH) afforded the title compound as a colorless oil.

Amine 39

N-[3,5-Bis(4,4,4-trifluorobutoxy)benzyl]cyclopropanamine

Amine 39 was prepared according to the reaction sequence described for Amine 38, but using instead 4,4,4-trifluorobutan-1-ol as starting material. The title compound was isolated as a colorless oil.

Amine 40

[5-Chloro-2-(3-methoxy-propyl)-pyridin-4-ylmethyl]-cyclopropyl-amine

Step 1: 2-Bromo-5-chloro-pyridine-4-carbaldehyde

To a stirred sol. of diisopropylamine (20.9 mL, 148 mmol) in dry THF (350 mL) at −5° C. was added dropwise BuLi (1.6M in hexane, 89.5 mL, 143 mmol), and the resulting sol. was stirred for 30 min at −5° C. The sol. was allowed to cool to −70° C., and a sol. of 2-bromo-5-chloropyridine (25.0 g, 130 mmol) in THF (100 mL) was added dropwise at −70° C. over 15 min, such that the internal temperature did not exceed −65° C. The mixture was stirred at −70° C. for 30 min. DMF (10.52 mL, 136 mmol) was added dropwise over 20 min such that the internal temperature did not exceed −70° C. The orange mixture was stirred at −70° C. for 40 min. The mixture was allowed to warm up to rt, and was poured onto a mixture of water (200 mL) and aq. 1 M NaOH (50 mL). The mixture was extracted with EtOAc (2×), and the combined org. extracts were washed back with aq. 1M NaOH (2×). The org. extracts were dried over MgSO$_4$, filtered, and the solvents were removed under reduced pressure. Purification of the crude by FC (EtOAc/heptane 1:9→1:8→1:6→1:4→1:2→1:1) yielded the title compound (21.55 g, 72%). LC-MS: t$_R$=0.74 min; ES+: 295.01.

Step 2: 2-Bromo-5-chloro-4-dimethoxymethyl-pyridine

To a sol. of 2-bromo-5-chloro-pyridine-4-carbaldehyde (43.9 g, 199 mmol) in MeOH (800 mL) were successively added at rt trimethyl orthoformate (65.3 mL, 597 mmol) and p-toluenesulfonic acid monohydrate (1.90 g, 10.0 mmol). This reaction mixture was then heated to reflux for 3 h. The mixture was allowed to cool to rt and was concentrated under reduced pressure. The residue was dissolved in CH$_2$Cl$_2$ and this mixture was washed with aq. 10% K$_2$CO$_3$. The org. layer was dried over MgSO$_4$, filtered, and the solvents were removed under reduced pressure. Drying under high vacuum yielded the title compound (51.7 g, 97%). LC-MS: t$_R$=0.92 min; ES+: 309.06.

Step 3: 5-Chloro-4-dimethoxymethyl-2-(3-methoxypropyl)-pyridine

To a suspension of Mg (911 mg, 37.5 mmol) and of iodine (one crystal) in dry THF (30 mL) was added dropwise 5% of the total amount of 1-bromo-3-methoxypropane (4.59 g, 30.0 mmol). The mixture was heated to reflux with the help of a heat gun until the Grignard formation had started. The rest of the 1-bromo-3-methoxypropane was added slowly, while an exothermic reaction proceeded. After the end of the addition, the reaction mixture was stirred under reflux for 20 min, and was allowed to cool to rt. This Grignard sol. (1M in THF, 23.5 mL, 23.5 mmol) was added dropwise to a mixture of 2-bromo-5-chloro-4-dimethoxymethyl-pyridine (2.50 g, 9.38 mmol) and Ni(dppp)Cl$_2$ (495 mg, 0.938 mmol) in THF (50 mL) at 0° C. The reaction mixture was stirred at rt for 30 min, and was then heated to reflux for 2 h. The mixture was allowed to cool to rt, and was dissolved with EtOAc. This mixture was washed with aq. sat. NaHCO$_3$. The org. layer was dried over MgSO$_4$, filtered, and the solvents were removed under reduced pressure. Purification of the residue by FC (heptane→EtOAc/heptane 1:1) yielded the title compound (1.51 g, 62%). LC-MS: t$_R$=0.80 min; ES+: 260.15.

Step 4: 5-Chloro-2-(3-methoxy-propyl)-pyridine-4-carbaldehyde

5-Chloro-4-dimethoxymethyl-2-(3-methoxy-propyl)-pyridine (25.5 g, 98.2 mmol) was dissolved in aq. 1M HCl (500 mL), and the mixture was heated to 80° C. for 2 h. The mixture was allowed to cool to rt, and EtOAc was added. The mixture was cooled to 0° C., and was basified with an aq. 2.5M NaOH until a pH=10 was reached. The layers were separated, and the org. layer was dried over MgSO$_4$, filtered, and concentrated under reduced pressure. Drying the residue under high vacuum yielded the crude title compound (98.1 mmol, 99%) that was used further without purification. LC-MS: t$_R$=0.62 min; ES+: 246.12.

Step 5: [5-Chloro-2-(3-methoxy-propyl)-pyridin-4-ylmethyl]-cyclopropyl-amine

A mixture of 5-chloro-2-(3-methoxy-propyl)-pyridine-4-carbaldehyde (21.0 g, 98.2 mmol) and cyclopropylamine (13.8 mL, 196 mmol) in MeOH (450 mL) was stirred at rt overnight. NaBH$_4$ (4.83 g, 128 mmol) was added at 0° C., and the mixture was stirred at rt overnight. Ice was added, and the mixture was concentrated under reduced pressure. The crude product was dissolved in EtOAc, and this mixture was washed with aq. 1 M NaOH. The aq. layer was extracted back with EtOAc. The combined org. extracts were dried over MgSO$_4$, filtered, and the solvents were removed under reduced pressure. Purification of the crude by FC (EtOAc/heptane 1:5→1:4→1:3→1:1→3:1→EtOAc) yielded the title compound (11.8 g) and [5-chloro-2-(3-methoxy-propyl)-pyridin-4-ylmethylene]-cyclopropyl-amine (10.7 g). This unreacted imine was dissolved in MeOH (20 mL), and this sol. was cooled to 0° C. NaBH$_4$ (3.20 g, 84.6 mmol) was added, and the mixture was stirred at rt overnight. NaBH$_4$ (3.20 g, 84.6 mmol) was added again, and the mixture was stirred for 3 days. Ice was added to the reaction mixture, and the mixture was concentrated under reduced pressure. The crude product was dissolved in EtOAc and the resulting mixture was washed with aq. 1M NaOH. The aq. phase was extracted back with EtOAc. The combined org. extracts were dried over MgSO$_4$, filtered, and the solvents were removed under reduced pressure. Purification of the crude by FC (EtOAc/heptane 1:3→1:2→1:1→EtOAc) yielded the title compound (9.4 g). The fractions of the title compound were mixed together (21.2 g, 85%). LC-MS: t$_R$=0.55 min; ES+: 296.16.

Amine 41

N-{[2-Methoxy-6-(3-methoxypropyl)pyridin-4-yl]methyl}cyclopropanamine

Step 1: 2,6-Dichloro-N-cyclopropylisonicotinamide

To a solution of 2,6-dichloroisonicotinic acid (1 eq.) in DMF (0.05 M) was added sequentially cyclopropylamine (1.05 eq.), Hunig's base (3 eq.) and O-(7-azabenzotriazol-1-yl)-N,N,N',N'-tetramethyluronium hexafluorophosphate (1.2 eq.). The resulting solution was stirred at RT for 4 h. The reaction was quenched with sat. aq. $NH_4Cl$ and extracted with EtOAc. The combined organic extracts were washed with brine, dried over $Na_2SO_4$, filtered and the filtrate concentrated in vacuo. Purification of the crude product thus obtained by way of flash chromatography ($SiO_2$, 10:1 (v/v) $CH_2Cl_2$:EtOAc) afforded the title compound as a white solid.

Step 2: 2-Chloro-N-cyclopropyl-6-methoxyisonicotinamide

To a solution of 2,6-dichloro-N-cyclopropylisonicotinamide from the previous step (1 eq.) in methanol (0.2 M) was added sodium methoxide (6 eq.). The reaction vessel was sealed and the resulting solution was heated in the microwave at 105° C. for 30 min. The volatiles were removed in vacuo and the resulting residue was partitioned between sat. aq. $NH_4Cl$ and EtOAc. The organic layer was separated and washed further with brine. Drying over $Na_2SO_4$, filtration and concentration of the filtrate in vacuo afforded the title compound as a white solid.

Step 3: N-Cyclopropyl-2-methoxy-6-[(1E)-3-methoxyprop-1-en-1-yl]isonicotinamide To a solution of 2-chloro-N-cyclopropyl-6-methoxyisonicotinamide from the previous step (1 eq.) in DMF (0.3 M) was added (2-[(1E)-3-methoxyprop-1-en-1-yl]-4,4,5,5-tetramethyl-1,3,2-dioxaborolane (1 eq.), palladium bromide (5% loading), triphenylphosphine (10% loading) and sodium carbonate (2 M aqueous solution, 3 eq.). The resulting suspension was heated at 100° C. for 7 h. The reaction mixture was quenched with water and extracted with ether. The combined organic extracts were washed with sat. aq. $NaHCO_3$ and brine. Drying over $Na_2SO_4$, filtration and concentration of the filtrate in vacuo afforded the crude product as a brown tar. Purification by way of column chromatography ($SiO_2$, 1:1 (v/v) Hex:EtOAc) followed by recrystallization from Hex:ether afforded the title compound as a white solid.

Step 4: N-Cyclopropyl-2-methoxy-6-(3-methoxypropyl)isonicotinamide

To a solution of N-cyclopropyl-2-methoxy-6-[(1E)-3-methoxyprop-1-en-1-yl]isonicotinamide from the previous step (1 eq.) in EtOAc (0.2 M) was added palladium (10% w/w over activated carbon, 15% loading). The reaction vessel was evacuated and back-filled with hydrogen. The reaction suspension was then stirred under a balloon atmosphere of hydrogen for 4 h. The reaction was quenched with $CH_2Cl_2$, filtered through celite and the insolubles washed further with EtOAc. Concentration of the filtrate in vacuo afforded the title compound as a white solid.

Step 5: Amine 41

To a solution of N-cyclopropyl-2-methoxy-6-(3-methoxypropyl)isonicotinamide from the previous step (1 eq.) in THF (0.2 M) was added lithium aluminum hydride (1.0 M THF solution, 5 eq.). The resulting solution was then heated at 70° C. for 1 h. The reaction was quenched carefully with sat. aq. $NaHCO_3$. The resulting gel was then diluted with EtOAc and sat. aq. Rochelle's salt and the biphasic mixture was stirred at RT for 3 h. The organic layer was separated, washed with brine, dried over $MgSO_4$ and filtered. Concentration of the filtrate in vacuo and purification of the crude product thus obtained by way of column chromatography ($SiO_2$, 90:9:1 (v/v/v) $CH_2Cl_2$:EtOH:conc. $NH_4OH$) afforded the title compound as a colorless oil.

Amine 42

N-{[2-{[tert-butyl(dimethyl)silyl]oxy}-6-(3-methoxypropyl)pyridin-4-yl]methyl}cyclopropanamine

Step 1: 4-[(Cyclopropylamin)methyl]-6-(3-methoxypropyl)pyridin-2-ol

To a solution of N-{[2-methoxy-6-(3-methoxypropyl)pyridin-4-yl]methyl}cyclopropanamine (1 eq.) in DMF (0.13 M) was added at 0° C. sodium hydride (60% w/w dispersion in mineral oil, 2.5 eq.) and ethanethiol (2.5 eq.). The resulting mixture was stirred at 150° C. for 1.5 h. The reaction was diluted with water and washed with EtOAc. The aqueous layer was then separated, saturated with $NH_4Cl$ and extracted with EtOAc. Concentration of the combined organic extracts in vacuo afforded the title compound as a white solid.

Step 2: Amine 42

To a solution of 4-[(cyclopropylamin)methyl]-6-(3-methoxypropyl)pyridin-2-ol from the previous step (1 eq.) in DMF (0.1 M) was added and tert-butylchlorodimethylsilane (1.1 eq.) and imidazole (1.1 eq.). The resulting reaction mixture was stirred at RT for 18 h. The reaction was quenched with water and extracted with ether. The combined organic extracts were washed with brine, dried over $MgSO_4$ and filtered. Concentration of the filtrate in vacuo and purification of the crude product thus obtained by way of column chromatography ($SiO_2$, 80:15:5 (v/v/v) Hex:EtOAc:triethylamine) afforded the title compound as a colorless oil.

Amine 43

N-{[2,6-bis(3-methoxypropyl)pyridin-4-yl]methyl}cyclopropanamine

Step 1: N-Cyclopropyl-2,6-bis[(1E)-3-methoxyprop-1-en-1-yl]isonicotinamide

To a solution of 2,6-dichloro-N-cyclopropylisonicotinamide from Amine 41, Step 1 (I eq.) in DMF (0.08 M) was added (2-[(1E)-3-methoxyprop-1-en-1-yl]-4,4,5,5-tetramethyl-1,3,2-dioxaborolane (2.7 eq.), palladium bromide (5% loading), triphenylphosphine (10% loading) and sodium carbonate (2 M aqueous solution, 5 eq.). The resulting suspension was heated at 100° C. for 8 h. The reaction mixture was quenched with water and extracted with ether. The combined organic extracts were washed with sat. aq. $NaHCO_3$ and brine. Drying over $Na_2SO_4$, filtration and concentration of the filtrate in vacuo afforded the crude product as a red oil. Purification by way of column chromatography ($SiO_2$, 1:1 (v/v) Hex:EtOAc) afforded the title compound as a yellow oil.

Step 2: N-Cyclopropyl-2,6-bis(3-methoxypropyl) isonicotinamide

To a solution of N-cyclopropyl-2,6-bis[(1E)-3-methoxyprop-1-en-1-yl]isonicotinamide from the previous step (1 eq.) in EtOAc (0.2 M) was added palladium (10% w/w over activated carbon, 40% loading). The reaction vessel was evacuated and back-filled with hydrogen. The reaction suspension was then stirred under a balloon atmosphere of hydrogen for 24 h. The reaction was quenched with $CH_2Cl_2$, filtered through celite and the insolubles washed further with EtOAc. Concentration of the filtrate in vacuo and purification of the crude product thus obtained by way of column chromatography ($SiO_2$, 1:1 (v/v) Hex:EtOAc→1:4 (v/v) Hex:EtOAc) afforded the title compound as a colorless oil.

Step 3: Amine 43

To a solution of N-cyclopropyl-2,6-bis(3-methoxypropyl) isonicotinamide from the previous step (1 eq.) in THF (0.1 M) was added lithium aluminum hydride (1.0 M THF solution, 6 eq.). The resulting solution was then heated at 70° C. for 2 h. The reaction was quenched carefully with sat. aq. $NaHCO_3$. The resulting gel was then diluted with EtOAc and sat. aq. Rochelle's salt and the biphasic mixture was stirred at RT for 3 h. The organic layer was separated, washed with brine, dried over $MgSO_4$ and filtered. Concentration of the filtrate in vacuo and purification of the crude product thus obtained by way of column chromatography ($SiO_2$, 95:5:1 (v/v/v) $CH_2Cl_2$:EtOH:conc. $NH_4OH$→90:10:1 (v/v/v) $CH_2Cl_2$:EtOH:conc. $NH_4OH$) afforded the title compound as a pale yellow oil.

Amine 44

N-({2-(3-methoxypropyl)-6-[(3-(methylthio)propoxy]pyridin-4-yl}methyl)cyclopropanamine Amine 44 was prepared according to the reaction sequence described for Amine 41, but using instead the sodium salt of 3-(methylthio)propan-1-ol as starting material and N-methyl-2-pyrrolidinone as solvent in Step 2. The title compound was isolated as a yellow oil.

Amine 45

N-{[2-(3-methoxypropyl)-6-(2-(morpholin-4-ylethoxy)pyridin-4-yl]methyl}cyclopropanamine Amine 45 was prepared according to the reaction sequence described for Amine 41, but using instead the sodium salt of 2-morpholine-4-ylethanol as starting material and N-methyl-2-pyrrolidinone as solvent in Step 2. The title compound was isolated as a colorless oil.

Amine 46

N-(Pyridin-4-ylmethyl)cyclopropanamine

Amine 46 was prepared according to the reaction sequence described for Amine 3, but using instead isonicotinaldehyde as the starting material. The title compound was isolated as a yellow oil.

Amine 47

N-(Pyridin-3-ylmethyl)cyclopropanamine

Amine 47 was prepared according to the reaction sequence described for Amine 3, but using instead nicotinaldehyde as the starting material. The title compound was isolated as a yellow oil.

Amine 48

N-(Pyridin-2-ylmethyl)cyclopropanamine

Amine 47 was prepared according to the reaction sequence described for Amine 3, but using instead pyridine-2-carbaldehyde as the starting material. The title compound was isolated as a yellow oil.

Amine 49

Ethyl (2-bromo-3[(cyclopropylamino)methyl]phenoxy)acetate

Step 1: Ethyl (2-bromo-3-formylphenoxy)acetate

To a solution of 2-bromo-3-hydroxybenzaldehyde (1 eq.) in DMF (0.4 M) was added cesium carbonate (1.2 eq.) and ethyl bromoacetate (1 eq.). The resulting suspension was stirred at RT for 16 h. The reaction mixture was quenched with water and extracted with EtOAc. The combined organic extracts were washed with water and brine. Drying over $MgSO_4$, filtration and concentration of the filtrate in vacuo afforded the crude product as a red oil. Purification by way of column chromatography ($SiO_2$, 5:1 (v/v) Hex:EtOAc→1:1 (v/v) Hex:EtOAc) afforded the title compound.

Step 2: Amine 49

Amine 47 was prepared according to the reaction procedure described in Amine 3, but using instead ethyl (2-bromo-3-formylphenoxy)acetate from the previous step as the starting material. The title compound was isolated as a pale yellow oil.

Amine 50

Ethyl 3-{2-bromo-3-[(cyclopropylamino)methyl]phenoxy}propanoate

Step 1: 3-(2-Bromo-3-formylphenoxy)propanoic acid

To a solution of 2-bromo-3-hydroxybenzaldehyde (1 eq.) in THF (1.2 M) was added sequentially potassium tert-butoxide (1.0 M THF solution, 0.8 eq.) and oxetan-2one at RT. The resulting yellow suspension was stirred at RT for 16 h. The reaction mixture was quenched with 10% aq. HCl and extracted with EtOAc. The combined organic extracts were washed with water and brine. Drying over $MgSO_4$, filtration and concentration of the filtrate in vacuo afforded the title compound as a white solid.

Step 2: Ethyl 3-(2-Bromo-3-formylphenoxy)propanoate

To a solution of 3-(2-bromo-3-formylphenoxy)propanoic acid from the previous step (I eq.) in EtOH (0.13 M) was added conc. sulfuric acid (0.8 eq.). The reaction was heated at reflux for 30 min. The reaction mixture was quenched with water and extracted with EtOAc. The combined organic extracts were washed with water and sat. aq. NaHCO$_3$. Drying over Na$_2$SO$_4$, filtration and concentration of the filtrate in vacuo afforded the title compound as a yellow oil.

Step 3: Amine 50

Amine 50 was prepared according to the reaction procedure described in Amine 3, but using instead ethyl 3-(2-bromo-3-formylphenoxy)propanoate from the previous step as the starting material. The title compound was isolated as a pale yellow oil.

Amine 51

Ethyl 5-{2-bromo-3-[(cyclopropylamino)methyl]phenoxy)pentanoate

Amine 51 was prepared according to the reaction sequence described for Amine 49, but using instead ethyl 5-{2-bromo-3-[(cyclopropylamino)methyl]phenoxy}pentanoate as the starting material. The title compound was isolated as a pale yellow oil.

The aldehyde building blocks in Table 2 were synthesized as follows.

TABLE 2

| Compound | Structure |
|---|---|
| Aldehyde 1 | Cl, Me, Cl substituted phenyl-O-CH$_2$CH$_2$-O-phenyl-CHO |
| Aldehyde 2 | F, Cl, F substituted phenyl-O-CH$_2$CH$_2$CH$_2$-phenyl-CHO |
| Aldehyde 3 | TBSO-CH$_2$CH$_2$CH$_2$-phenyl-CHO |
| Aldehyde 4 | Me, Cl, Cl substituted phenyl-O-CH$_2$CH$_2$-phenyl-CHO |
| Aldehyde 5 | TBSO-CH$_2$CH$_2$-O-phenyl-CHO |

Aldehyde 1

4-[2-(2,6-Dichloro-4-methylphenoxy)ethoxy]benzaldehyde

Step 1: 2-(2,6-Dichloro-4-methylphenoxy)ethanol 2,6-Dichloro-4-methylphenol (1 eq.), ethylene carbonate (1 eq.) and imidazole (0.5% loading) were combined and heated at 150° C. for 4 h to afford the title compound as a brown oil.

Step 2: Aldehyde 1

2-(2,6-Dichloro-4-methylphenoxy)ethanol from the previous step (1 eq.) and 4-hydroxybenzaldehyde (1 eq.) were taken up in freshly deoxygenated 3:1 (v/v) toluene:THF (0.3 M). To this solution was then added 1,1'-(azodicarbonyl)-dipiperidine (1.2 eq.) and finally tributylphosphine (1.2 eq.). The resulting orange solution was heated at 80° C. for 4 h. The reaction mixture was cooled to RT, diluted with ether, and washed with 1 N aq. NaOH. The aqueous wash was back extracted with ether and the combined organic extracts were dried over MgSO$_4$. Filtration and concentration of the filtrate in vacuo afforded a yellow semi-solid. Purification of the crude product thus obtained by way of flash chromatography (SiO$_2$, Hex→4:1 (v/v) Hex:EtOAc) afforded the title compound as white needles.

Aldehyde 2

4-[3-(2-Chloro-3,6-difluorophenoxy)propyl]benzaldehyde

Step 1: 3-(4-Bromophenyl)propan-1-ol

To a THF solution (0.5 M) of methyl (2E)-3-(4-bromophenyl)acrylate (1 eq.) was added, at 0° C., lithium aluminum hydride (1.0 M THF solution, 1 eq.) dropwise over a period of for 3 h. The reaction mixture was then warmed slowly to RT over 1 h. At 0° C., the reaction was carefully quenched with freshly-deoxygenated H$_2$O. The organic layer was separated and washed with cold 10% aq. HCl. The aqueous washes were combined and back-extracted with ether. The organic extracts were then washed further with sat. aq. NaHCO$_3$ and brine, dried over MgSO$_4$, filtered and the filtrate concentrated in vacuo to reveal a yellow oil. Purification by way of full vacuum distillation afforded the title compound as a colorless oil.

Step 2: 2-[3-(4-Bromophenyl)propoxy]-3-chloro-1,4-difluorobenzene 3-(4-Bromophenyl)propan-1-ol from the previous step (1 eq.) and 2-chloro-3,6-difluorophenol (1 eq.) were taken up in freshly deoxygenated toluene (0.3 M). To this solution was then added 1,1'-(azodicarbonyl)-dipiperidine (1.2 eq.) and finally tributylphosphine (1.2 eq.). The resulting yellow solution was heated at 80° C. for 2 h. The reaction mixture was cooled to RT, diluted with ether, and washed with 1 N aq. NaOH. The aqueous wash was back extracted with ether and the combined organic extracts were dried over MgSO$_4$. Filtration and concentration of the filtrate in vacuo afforded a yellow semi-solid. Purification of the crude product thus obtained by way of flash chromatography (SiO$_2$, Hex→15:1 (v/v) Hex:EtOAc) afforded the title compound as a colorless oil.

Step 3: Aldehyde 2

To a solution of 2-[3-(4-bromophenyl)propoxy]-3-chloro-1,4-difluorobenzene from the previous step (1 eq.) in anhydrous, deoxygenated DMF (0.5 M) was added freshly dried sodium formate (1.5 eq.) and Pd(PPh$_3$)Cl$_2$ (2% loading). The resulting yellow suspension was bubbled CO and then heated to 95° C. for 6 h. The now black reaction suspension was cooled to RT, diluted with water, and extracted with ether. The combined organic extracts were washed with brine, dried over MgSO$_4$ and filtered. Concentration of the filtrate in vacuo afforded a yellow oil. Purification of the crude product thus obtained by way of flash chromatography (SiO$_2$, Hex→4:1 (v/v) Hex:EtOAc) afforded the title compound as a colorless oil.

Aldehyde 3

4-{(3-[tert-Butyl(dimethyl)silyl]oxy}propyl)benzaldehyde

Step 1: [3-(4-Bromophenyl)propoxy](tert-butyl)dimethylsilane

To a solution of 3-(4-bromophenyl)propan-1-ol (1 eq.) in DMF (0.25 M) was added imidazole (1.2 eq.) and tert-butyldimethylsilyl chloride (1.1 eq.). The resulting solution was stirred at RT for 13 h. The reaction mixture was quenched with sat. aq. NH$_4$Cl and extracted with hexanes. The combined organic extracts were washed further with water and brine. Concentration of the organic extracts in vacuo afforded the title compound as a colorless oil.

Step 2: Aldehyde 3

To a solution of [3-(4-bromophenyl)propoxy](tert-butyl)dimethylsilane from the previous step (1 eq.) in anhydrous, deoxygenated DMF (1.2 M) was added freshly dried sodium formate (1.5 eq.) and Pd(PPh$_3$)Cl$_2$ (2% loading). The resulting yellow suspension was bubbled CO and then heated to 90° C. for 8 h. The now black reaction suspension was cooled to RT, diluted with water, and extracted with hexanes. The combined organic extracts were washed with brine, dried over MgSO$_4$ and filtered. Concentration of the filtrate in vacuo afforded a yellow oil. Purification of the crude product thus obtained by way of flash chromatography (SiO$_2$, Hex→4:1 (v/v) Hex:EtOAc) afforded the title compound as a colorless oil.

Aldehyde 4

4-[2-(2,6-dichloro-4-methylphenoxy)ethyl]benzaldehyde

Step 1: 2-[2-(4-Bromophenyl)ethoxy]-1,3-dichloro-5-methylbenzene 2-(4-Bromophenyl)ethanol (1 eq.) and 2,6-dichloro-4-methylphenol (1.5 eq.) were taken up in freshly deoxygenated toluene (0.1 M). To this solution was then added 1,1'-(azodicarbonyl)-dipiperidine (1.2 eq.) and finally tributylphosphine (1.2 eq.). The resulting yellow solution was heated at 80° C. for 2 h. The reaction mixture was cooled to RT, diluted with ether, and washed with 1 N aq. NaOH. The aqueous wash was back extracted with ether and the combined organic extracts were dried over MgSO$_4$. Filtration and concentration of the filtrate in vacuo afforded a yellow semi-solid. Purification of the crude product thus obtained by way of flash chromatography (SiO$_2$, Hex→10:1 (v/v) Hex:EtOAc) afforded the title compound as a colorless oil.

Step 2: Aldehyde 4

To a solution of 2-[2-(4-bromophenyl)ethoxy]-1,3-dichloro-5-methylbenzene from the previous step (1 eq.) in THF (0.08 M) was added, at −78° C., n-butyl lithium (2.5 M hexane solution, 1.1 eq) dropwise over 15 min. The reaction mixture was stirred at −78° C. for a further 30 min before DMF (2 eq.) was slowly added. The resulting solution was allowed to warm to RT over 3 h and then quenched with H$_2$O. The organic layer was separated and the aqueous layer was back extracted with ether. The combined organic extracts were washed with sat. aq. NaHCO$_3$ and brine, dried over MgSO$_4$ and filtered. Concentration of the filtrate in vacuo afforded the title compound as a yellow oil.

Aldehyde 5

4-(2-{[tert-Butyl(dimethyl)silyl]oxy}ethoxy)benzaldehyde

Step 1: 2-(4-Bromophenoxy)ethanol

4-Bromophenol (1 eq.), ethylene carbonate (1 eq.) and imidazole (0.5% loading) were combined and heated at 150° C. for 2 h to afford the title compound as a brown oil.

Step 2: 2-[(4-Bromophenoxy)ethoxy](tert-butyl)dimethylsilane

To a solution of 2-[(4-bromophenoxy)ethanol (1 eq.) in DMF (0.5 M) was added imidazole (1.2 eq.) and tert-butyldimethylsilyl chloride (1.1 eq.). The resulting solution was stirred at RT for 13 h. The reaction mixture was quenched with sat. aq. NH$_4$Cl and extracted with hexanes. The combined organic extracts were washed further with water and brine. Concentration of the organic extracts in vacuo afforded the title compound as a yellow oil.

Step 3: Aldehyde 5

To a solution of 2-(4-bromophenoxy)ethoxy](tert-butyl)dimethylsilane from the previous step (1 eq.) in THF (0.2 M) was added, at −78° C., n-butyl lithium (2.5 M hexane solution, 1.1 eq) dropwise over 15 min. The reaction mixture was stirred at −78° C. for a further 30 min before DMF (2 eq.) was slowly added. The resulting solution was allowed to warm to RT over 3 h and then quenched with H$_2$O. The organic layer was separated and the aqueous layer was back-extracted with ether. The combined organic extracts were washed with sat. aq. NaHCO$_3$ and brine, dried over MgSO$_4$ and filtered. Concentration of the filtrate in vacuo afforded the title compound as a yellow oil.

Compounds of the present invention were prepared according to the following methods.

Example 1

3-Amino-N-cyclopropyl-2-{4-[2-(2,6-dichloro-4-methylphenoxy)ethoxy]benzyl}-N-(2,3-dimethylbenzyl)propanamide

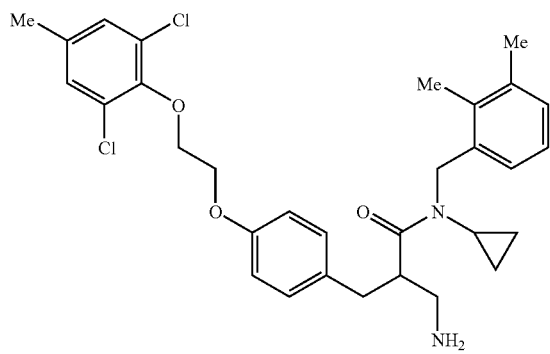

Step 1: 2-Cyano-N-cyclopropyl-N-(2,3-dimethylbenzyl)acetamide

To a DMF solution (0.6 M) of cyanoacetic acid (1 eq.), Hunig's base (3 eq.) and Amine 1 (1 eq.) was added portionwise O-(7-azabenzotriazol-1-yl)-N,N,N',N-tetramethyluronium hexafluorophosphate (1.2 eq.). The resulting reaction solution was stirred at RT for 16 h. The now reddish solution was diluted with ether and washed with $H_2O$ and 10% aq. HCl. The aqueous washes were back extracted with ether. The combined organic extracts were washed with brine, dried over $MgSO_4$, filtered and the filtrate concentrated in vacuo to afford a yellow semi-solid. Purification of the crude product thus obtained by way of flash chromatography ($SiO_2$, 10:1→1:1 (v/v) Hex:EtOAc) afforded the title compound as off-white crystalline plates.

Step 2: (2E)-2-Cyano-N-cyclopropyl-3-{4-[2-(2,6-dichloro-4-methylphenoxy)ethoxy]phenyl}-N-(2,3-dimethylbenzyl)acrylamide 2-Cyano-N-cyclopropyl-N-(2,3-dimethylbenzyl)acetamide from the previous step (1 eq.) and Aldehyde 1 (1 eq.) were combined in benzene (0.04 M). To this solution was then added a few drops of piperidine and a Dean-Stark apparatus was attached to the reaction vessel. The resulting pale yellow solution was heated at reflux for 48 h. The volatiles were removed in vacuo and the crude product thus obtained was purified by way of column chromatography ($SiO_2$, 10:1→1:1 (v/v) Hex:EtOAc). The title compound was isolated as a white foam.

Step 3: tert-Butyl (3-[cyclopropyl(2,3-dimethylbenzyl)amino]-2-{4-[2-(2,6-dichloro-4-methylphenoxy)ethoxy]benzyl}-3-oxopropyl)carbamate (2E)-2-Cyano-N-cyclopropyl-3-{4-[2-(2,6-dichloro-4-methylphenoxy)ethoxy]phenyl}-N-(2,3-dimethylbenzyl) acrylamide from the previous step (1 eq.) and cobalt(II) chloride hexahydrate (2 eq.) were combined in a 8:1 (v/v) MeOH:THF solution (0.02 M). To this mixture was then added sodium borohydride (10 eq.) slowly and portionwise. The resulting black suspension was stirred at RT for 8 h. The reaction mixture was then diluted with 95:5 (v/v) $CH_2Cl_2$:MeOH and quenched with 1 N aq. NaOH. The resulting emulsion was then filtered through a bed of celite and the insolubles were rinsed with 95:5 (v/v) $CH_2Cl_2$:MeOH. The organic layer was separated and washed further with 1 N aq. NaOH, $H_2O$ and brine. Drying over $MgSO_4$, filtration and concentration of the filtrate in vacuo afforded the crude amine as a golden oil. This residue was then taken up in $CH_2Cl_2$ (0.06 M) and added di-tert-butyl dicarbonate (1 eq.). Finally, sodium hydroxide (1.0 N aqueous solution, 3 eq.) was added and the resulting biphasic mixture was vigorously stirred for 4 h. Following careful acidification with 10% aq. HCl to a pH of ~2, the aqueous layer was separated and back extracted with ether. The combined organic extracts were then washed $H_2O$ and brine, dried over $MgSO_4$ and filtered. Concentration of the filtrate in vacuo afforded a yellow oil. Purification of the crude product thus obtained by way of column chromatography ($SiO_2$, Hex→1:1 (v/v) Hex:EtOAc) afforded the title compound as a white froth.

Step 4: 3-Amino-N-cyclopropyl-2-{4-[2-(2,6-dichloro-4-methylphenoxy)ethoxy]benzyl}-N-(2,3-dimethylbenzyl)propanamide To a $CH_2Cl_2$ solution (0.05 M) of tert-butyl(3-[cyclopropyl(2,3-dimethylbenzyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 30 eq.). The resulting solution was stirred at RT for 3 h. Following the removal of the volatiles in vacuo, the resulting residue was directly loaded onto a $SiO_2$ column packed with 97:3 (v/v) $CH_2Cl_2$: 2.0 M $NH_3$ in MeOH. Elution with the same solvent system furnished the title compound as a white froth. MS (ESI+): 555.0.

Example 2

3-Amino-N-cyclopropyl-}-N-(2,3-dichlorobenzyl)-2-{4-[2-(2,6-dichloro-4-methylphenoxy)ethoxy]benzyl}propanamide

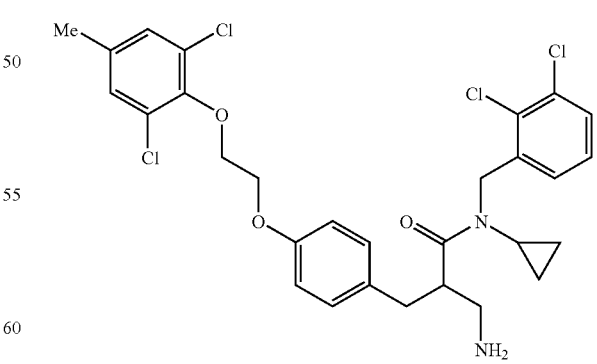

Prepared according to the procedure described in Example 1 but using instead Amine 2 as starting material. The title compound was obtained as a white froth. MS (ESI+): 595.0.

Example 3

3-Amino-N-cyclopropyl-2-{4-[2-(2,6-dichloro-4-methylphenoxy)ethoxy]benzyl}-N-(1,2,3,4-tetrahydroquinolin-8-ylmethyl)propanamide

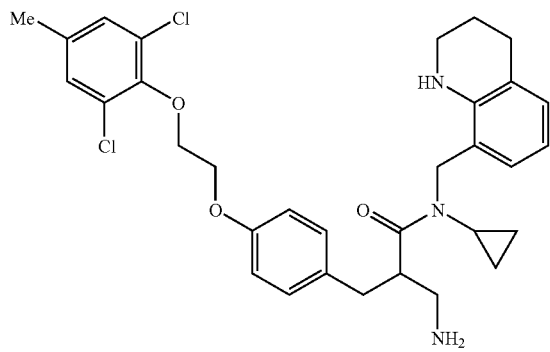

Prepared according to the procedure described in Example 1 but using instead Amine 4 as starting material. The title compound was obtained as a white froth. MS (ESI+): 582.2.

Example 4

3-Amino-N-cyclopropyl-2-{4-[2-(2,6-dichloro-4-methylphenoxy)ethoxy]benzyl}-N-[3-(3-methoxypropyl)benzyl]propanamide

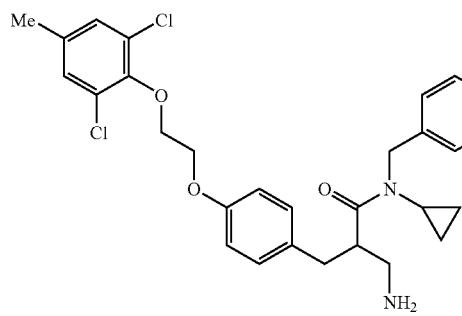

Prepared according to the procedure described in Example 1 but using instead Amine 5 as starting material. The title compound was obtained as a colorless oil. MS (ESI+): 599.5.

Example 5

3-Amino-2-{4-[3-(2-chloro-3,6-difluorophenoxy)propyl]benzyl}-N-cyclopropyl-N-[3-(3-methoxypropyl)benzyl]propanamide

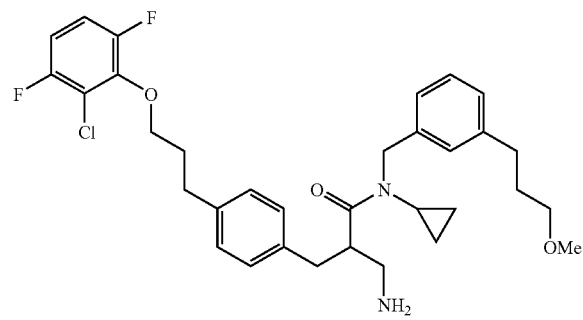

Prepared according to the procedure described in Example 1 but using instead Amine 5 and Aldehyde 2 as starting materials. The title compound was obtained as a colorless oil. MS (ESI+): 584.9.

Example 6

3-Amino-N-[2-chloro-5-(3-methoxypropyl)benzyl]-N-cyclopropyl-2-{4-[2-(2,6-dichloro-4-methylphenoxy)ethoxy]benzyl}propanamide

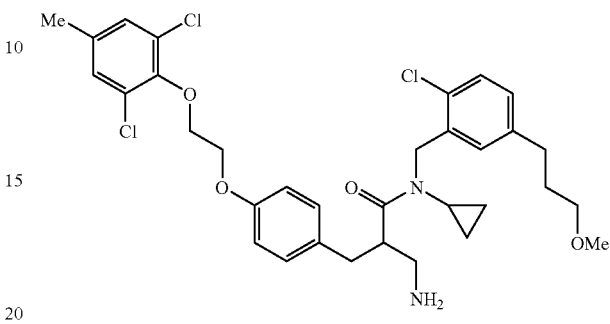

Prepared according to the procedure described in Example 1 but using instead Amine 6 as starting material. The title compound was obtained as a colorless oil. MS (ESI+): 633.0.

Example 7

3-Amino-2-{4-[3-(2-chloro-3,6-difluorophenoxy)propyl]benzyl}-N-[2-chloro-5-(3-methoxypropyl)benzyl]-N-cyclopropylpropanamide

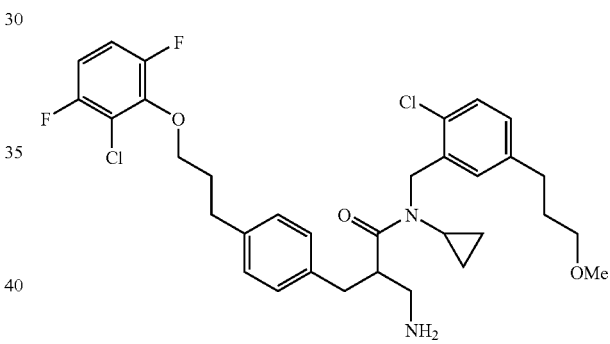

Prepared according to the procedure described in Example 1 but using instead Amine 6 and Aldehyde 2 as starting materials. The title compound was obtained as a colorless oil. MS (ESI+): 618.9.

Example 8

3-Amino-N-cyclopropyl-2-{4-[2-(2,6-dichloro-4-methylphenoxy)ethoxy]benzyl}-N-{3-[2-(methylsulfonyl)ethyl]benzyl}propanamide

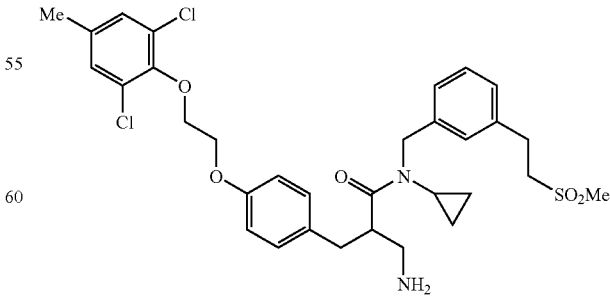

Prepared according to the procedure described in Example 1 but using instead Amine 8 as starting material. The title compound was obtained as a colorless oil. MS (ESI+): 633.1.

Example 9

3-Amino-N-cyclopropyl-2-{4-[2-(2,6-dichloro-4-methylphenoxy)ethoxy]benzyl}-N-(quinolin-4-ylmethyl)propanamide

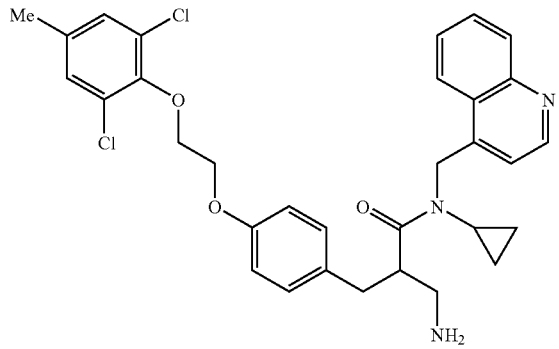

Step 1: Methyl (2E)-2-cyano-3-{4-[2-(2,6-dichloro-4-methylphenoxy)ethoxy]phenyl}acrylate Methyl cyanoacetate (1 eq.) and Aldehyde 1 (1 eq.) were combined in toluene (0.16 M). To this solution was then added a few drops of piperidine and a Dean-Stark apparatus was attached to the reaction vessel. The resulting pale yellow solution was heated at reflux for 3 h. The volatiles were removed in vacuo to afford the title compound was isolated as an off-white powder.

Step 2: Methyl 3-[(tert-butoxycarbonyl)amino]-2-{4-[2-(2,6-dichloro-4-methylphenoxy)ethoxy]benzyl}propanoate Methyl (2E)-2-cyano-3-{4-[2-(2,6-dichloro-4-methylphenoxy)ethoxy]phenyl}acrylate from the previous step (1 eq.) and cobalt(II) chloride hexahydrate (2 eq.) were combined in a 5:3 (v/v) THF:MeOH solution (0.016 M). To this mixture was then added sodium borohydride (10 eq.) slowly and portionwise. The resulting black suspension was stirred at RT for 2 h. The reaction mixture was then carefully quenched with 10% aq. HCl and extracted with ether. The combined organic extracts were washed further with $H_2O$ and brine. Drying over $MgSO_4$, filtration and concentration of the filtrate in vacuo afforded the crude amine as a golden oil. This residue was combined with di-tert-butyl dicarbonate (1 eq.), Hunig's base (1.5 eq.) and a few crystals of 4-(dimethylamino)pyridine in $CH_2Cl_2$ (0.06 M). The resulting yellow solution was stirred at RT for 8 h. The volatiles were then removed in vacuo to afford an orange residue which was partitioned between ether and 10% aq. HCl. The organic layer was separated and the aqueous layer was back extracted with ether. The combined organic extracts were then washed $H_2O$ and brine, dried over $MgSO_4$ and filtered. Concentration of the filtrate in vacuo afforded a yellow oil. Purification of the crude product thus obtained by way of column chromatography ($SiO_2$, Hex→1:1 (v/v) Hex:EtOAc) afforded the title compound as a pale yellow oil.

Step 3: 3-[tert-Butoxycarbonyl)amino]-2-{4-[2-(2,6-dichloro-4-methylphenoxy ethoxy]benzyl}propanoic acid Methyl 3-[(tert-butoxycarbonyl)amino]-2-{4-[2-(2,6-dichloro-4-methylphenoxy)ethoxy]benzyl}propanoate from the previous step (1 eq.) was dissolved in a 2:1 (v/v) THF: MeOH solution (0.056 M). To this was then added sodium hydroxide (1.0 M aqueous solution, 3 eq.) and the resulting solution was stirred at RT for 18 h. The volatiles were then removed in vacuo. Following careful acidification of the resulting mixture to pH ~1 with 10% aq. HCl, the solution was extracted with ether and EtOAc. The combined organic extracts were washed further with $H_2O$ and brine, dried over $MgSO_4$ and filtered. Concentration of the filtrate in vacuo afforded a yellow oil. Purification of the crude product thus obtained by way of column chromatography ($SiO_2$, 66:33:1 (v/v/v) Hex:EtOAc:AcOH) afforded the title compound as a white froth.

Step 4: tert-Butyl (3-[cyclopropyl(quinolin-4-ylmethyl)amino]-2-{4-[2-(2,6-dichloro-4-methylphenoxy)ethoxy]benzyl}-3-oxopropyl)carbamate 3-[tert-Butoxycarbonyl)amino]-2-{4-[2-(2,6-dichloro-4-methylphenoxy)ethoxy]benzyl}propanoic acid from the previous step (1 eq.) was combined with Hunig's base (3 eq.) and Amine 3 (1 eq.) in anhydrous DMF (0.6 M). To this was then added portionwise O-(7-azabenzotriazol-1-yl)-N,N,N',N'-tetramethyluronium hexafluorophosphate (1.2 eq.). The resulting yellow solution was stirred at RT for 18 h. The now reddish solution was diluted with ether and washed with $H_2O$. The aqueous washes were back extracted with ether. The combined organic extracts were washed with brine, dried over $MgSO_4$, filtered and the filtrate concentrated in vacuo to afford a yellow semi-solid. Purification of the crude product thus obtained by way of flash chromatography ($SiO_2$, 10:1 (v/v) Hex:EtOAc→EtOAc) afforded the title compound as a white froth.

Step 5: 3-Amino-N-cyclopropyl-2-{4-[2-(2,6-dichloro-4-methylphenoxy)ethoxy]benzyl}-N-(quinolin-4-ylmethyl)propanamide To a $CH_2Cl_2$ solution (0.05 M) of tert-butyl (3-[cyclopropyl(quinolin-4-ylmethyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 30 eq.). The resulting solution was stirred at RT for 3 h. Following the removal of the volatiles in vacuo, the resulting residue was directly loaded onto a $SiO_2$ column packed with 95:5 (v/v) $CH_2Cl_2$: 2.0 M $NH_3$ in MeOH. Elution with the same solvent system furnished the title compound as a white froth. MS (ESI+): 578.0.

Example 10

3-Amino-N-cyclopropyl-2-{4-[2-(2,6-dichloro-4-methylphenoxy)ethoxy]benzyl}-N-(quinolin-8-ylmethyl)propanamide

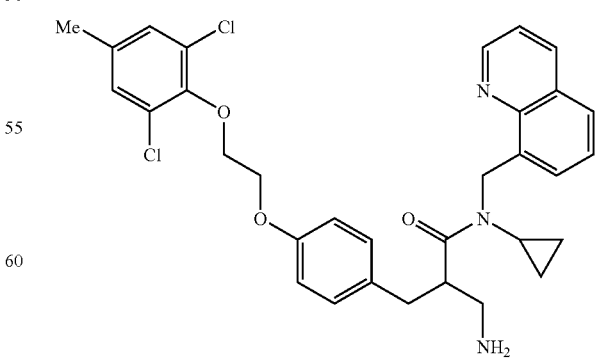

Prepared according to the procedure described in Example 9 but using instead Amine 4 as starting material. The title compound was obtained as a white froth. MS (ESI+): 578.1.

Example 11

3-Amino-N-[2-chloro-5-(2-methoxyethyl)benzyl]-N-cyclopropyl-2-{4-[2-(2,6-dichloro-4-methylphenoxy)ethoxy]benzyl}propanamide

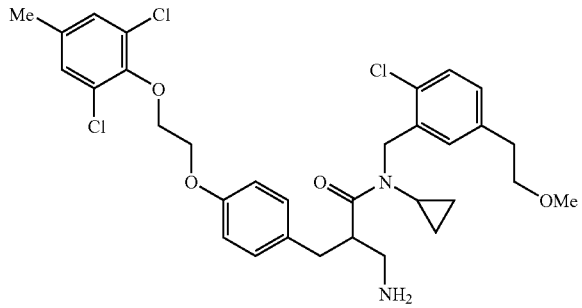

Prepared according to the procedure described in Example 9 but using instead Amine 6 as starting material. The title compound was obtained as a colorless oil. MS (ESI+): 619.3.

Example 12

N-(3-{[Acetyl(methyl)amino]methyl}benzyl)-3-amino-N-cyclopropyl-2-{4-[2-(2,6-dichloro-4-methylphenoxy)ethoxy]benzyl}propanamide

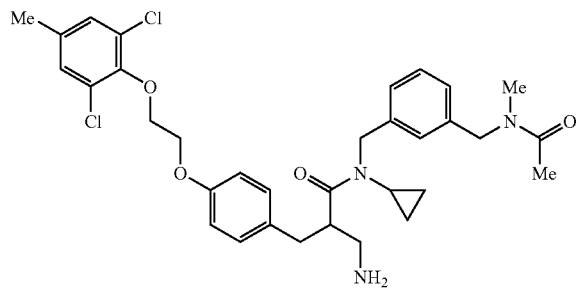

Prepared according to the procedure described in Example 9 but using instead Amine 9 as starting material. The title compound was obtained as a white froth. MS (ESI+): 612.2.

Example 13

N-(5-{[Acetyl(methyl)amino]methyl}-2-chlorobenzyl)-3-amino-N-cyclopropyl-2-{4-[2-(2,6-dichloro-4-methylphenoxy)ethoxy]benzyl}propanamide

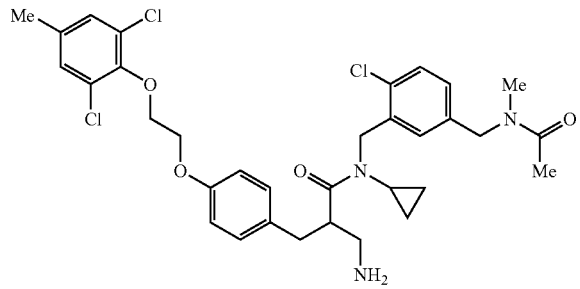

Prepared according to the procedure described in Example 9 but using instead Amine 10 as starting material. The title compound was obtained as a white froth. MS (ESI+): 646.1.

Example 14

3-Amino-N-cyclopropyl-N-(2,3-dichlorobenzyl)-2-{4-[3-(2,6-dichloro-4-methylphenoxy)propyl]benzyl}propanamide

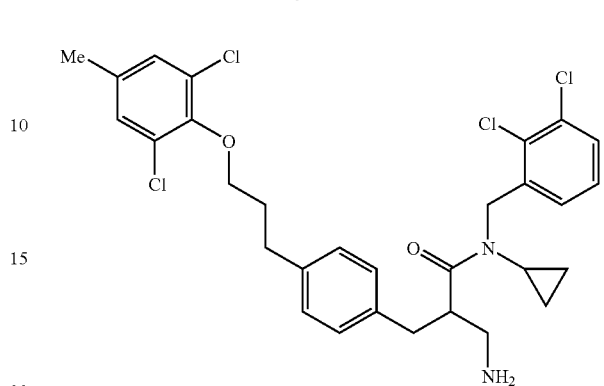

Step 1: [4-(3-{[tert-Butyl(dimethyl)silyl]oxy}propyl)phenyl]methanol

At 0° C., sodium borohydride (1.5 eq.) was added portionwise to a MeOH solution (0.2 M) of Aldehyde 3 (1 eq.). The resulting mixture was stirred at 0° C. for 15 min and then at RT for 30 min. Following the removal of the volatiles in vacuo, the resulting residue was partitioned between ether and 1 N aq. NaOH. The aqueous layer was separated and back extracted with ether. The combined organic extracts were washed with H$_2$O and brine, dried over MgSO$_4$ and filtered. Concentration of the filtrate in vacuo afforded the title compound as a colorless oil.

Step 2: tert-Butyl{3-[4-(iodomethyl)phenyl]propoxy}dimethylsilane

At 0° C., iodine (1.2 eq.) and imidazole (1.2 eq.) were added to a CH$_2$Cl$_2$ solution (0.12 M) of triphenylphosphine (1.2 eq.). The resulting yellow-orange suspension was stirred at 0° C. for 10 min and then at RT for 30 min. Finally, 4-(3-{[tert-butyl(dimethyl)silyl]oxy}propyl)phenyl]methanol from the previous step (1 eq.) was added. After another 5 h of stirring at RT, the volatiles were removed in vacuo. The resulting brown residue was partitioned between ether and H$_2$O. The aqueous layer was separated and back-extracted with ether. The combined organic extracts were washed with 1 M aq. Na$_2$S$_2$O$_3$ and brine, dried over MgSO$_4$ and filtered. The filtrate was added hexanes and passed through a plug of SiO$_2$. Removal of the volatiles in vacuo afforded the title compound as a pale pink oil.

Step 3: 3-[4-(3-{[tert-Butyl(dimethyl)silyl]oxy}propyl)phenyl]-2-cyano-N-cyclopropyl-N-(2,3-dichlorobenzyl)propanamide 2-Cyano-N-cyclopropyl-N-(2,3-dichlorobenzyl)acetamide (1 eq.), prepared from Amine 2 and cyanoacetic acid as detailed in Step 1 of Example 1, was dissolved in THF (0.1 M). At −78° C., potassium bis(trimethylsilyl)amide (15% w/w toluene solution, 1 eq.) was then added and the resulting yellow suspension was stirred at −78° C. for 15 min and at −40° C. for 15 min. tert-Butyl{3-[4-(iodomethyl)phenyl]propoxy}dimethylsilane from the previous step (1 eq.) was then added, at −78° C., as a 0.33 M THF solution over a period of 10 min. The resulting pale yellow mixture was allowed to warm slowly to RT over 5 h. The reaction was quenched with sat. aq. NH₄Cl and extracted with ether. The combined organic extracts were washed with H₂O and brine, dried over MgSO₄ and filtered. Concentration of the filtrate in vacuo afforded a viscous yellow oil. Purification of the crude product thus obtained by way of column chromatography (SiO₂, 10:1 (v/v) Hex:EtOAc→EtOAc) afforded the title compound as a colorless oil.

Step 4: 2-Cyano-N-cyclopropyl-N-(2,3-dichlorobenzyl)-3-[4-(3-hydroxypropyl)phenyl]propanamide To a solution of 3-[4-(3-{[tert-butyl(dimethyl)silyl]oxy}propyl)phenyl]-2-cyano-N-cyclopropyl-N-(2,3-dichlorobenzyl)propanamide from the previous step (1 eq.) in THF (0.1 M) was added tetrabutylammonium fluoride (1.0 M THF solution, 1.5 eq.). The resulting reaction mixture was stirred at RT for 3 h. After quenching the reaction with 10% aq. HCl, the mixture was extracted with ether. The combined organic extracts were washed with sat. aq. NaHCO₃ and brine, dried over MgSO₄ and filtered. Concentration of the filtrate in vacuo afforded a pale yellow oil. Purification of the crude product thus obtained by way of flash chromatography (SiO₂, 10:1 (v/v) Hex:EtOAc→EtOAc) afforded the title compound as a colorless oil.

Step 5: 2-Cyano-N-cyclopropyl-N-(2,3-dichlorobenzyl)-3-{4-[(3-(2,6-dichloro-4-methylphenoxy)propyl]phenyl}propanamide 2-Cyano-N-cyclopropyl-N-(2,3-dichlorobenzyl)-3-[4-(3-hydroxypropyl)phenyl]propanamide from the previous step (1 eq.) and 2,6-dichloro-4-methylphenol (2 eq.) were taken up in freshly-deoxygenated toluene (0.1 M). To this solution was then added 1,1'-(azodicarbonyl)-dipiperidine (2 eq.) and finally tributylphosphine (2 eq.). The resulting yellow solution was heated at 80° C. for 2 h. The reaction mixture was cooled to RT, diluted with ether, and washed with 1 N aq. NaOH. The aqueous wash was back extracted with ether and the combined organic extracts were dried over MgSO₄. Filtration and concentration of the filtrate in vacuo afforded a yellow semi-solid. Purification of the crude product thus obtained by way of flash chromatography (SiO₂, 10:1 (v/v) Hex:EtOAc→EtOAc) afforded the title compound as a colorless oil.

Step 6: 3-Amino-N-cyclopropyl-N-(2,3-dichlorobenzyl)-2-{4-[3-(2,6-dichloro-4-methylphenoxy)propyl]benzyl}propanamide 2-Cyano-N-cyclopropyl-N-(2,3-dichlorobenzyl)-3-{4-[(3-(2,6-dichloro-4-methylphenoxy)propyl]phenyl}propanamide from the previous step (1 eq.) and palladium (10% w/w over carbon, 50% loading) were suspended in freshly deoxygenated MeOH (0.03 M). Then, HCl (4.0 M dioxane solution, 20 eq) was added and the resulting suspension was stirred under a static atmosphere of H₂ for 16 h. The reaction mixture was basified with ammonia (2.0 M MeOH solution), diluted with CH₂Cl₂ and filtered through a bed of celite. The insolubles were washed further with EtOAc. The combined filtrates were concentrated in vacuo and the crude product thus obtained was purified by way of flash chromatography (SiO₂, 97:3→95:5 (v/v) CH₂Cl₂: 2.0 M NH₃ in MeOH) to furnish the title compound as a colorless oil. MS (ESI+): 593.0.

Example 15

3-Amino-2-{4-[3-(2-chloro-3,6-difluorophenoxy)propyl]benzyl}-N-cyclopropyl-N-(2,3-dichlorobenzyl)propanamide

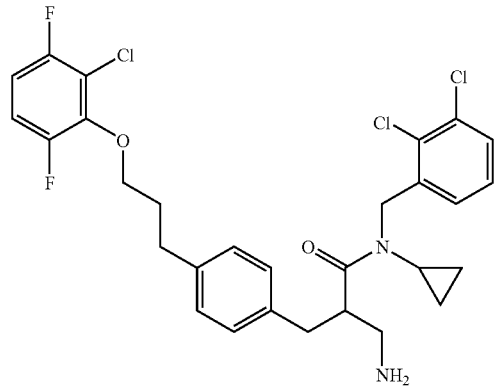

Prepared according to the procedure described in Example 14 but using 2-chloro-3,6-difluorphenol instead of 2,6-dichloro-4-methylphenol in Step 5. The title compound was obtained as a colorless oil. MS (ESI+): 580.9.

Example 16

3-Amino-2-{4-[3-(2-chloro-3,6-difluorophenoxy)propyl]benzyl}-N-cyclopropyl-N-(2,3-dichlorobenzyl)-2-methylpropanamide

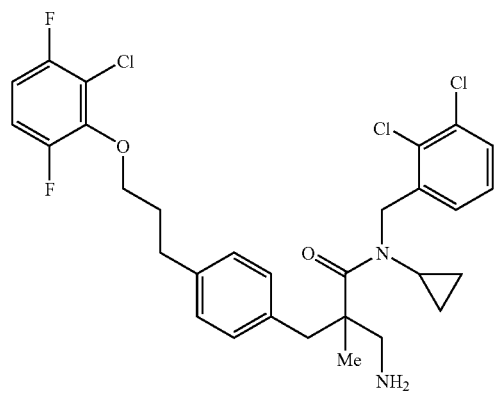

Step 1: 3-[4-(3-{[tert-Butyl(dimethyl)silyl]oxy}propyl)phenyl]-2-cyano-N-cyclopropyl-N-(2,3-dichlorobenzyl)-2-methylpropanamide To a solution of 3-[4-(3-{[tert-butyl(dimethyl)silyl]oxy}propyl)phenyl]-2-cyano-N-cyclopropyl-N-(2,3-dichlorobenzyl)propanamide (prepared as detailed in Example 14, 1 eq.) in THF (0.1 M) was added, at −78° C., potassium bis(trimethylsilyl)amide (15% w/w toluene solution, 1 eq.).

The resulting yellow suspension was stirred at −78° C. for 15 min and at −40° C. for 15 min. Iodomethane (1 eq.) was then added and the reaction mixture was slowly warmed to RT over 14 h. The reaction was quenched with sat. aq. NH$_4$Cl and extracted with ether. The combined organic extracts were washed with H$_2$O and brine, dried over MgSO$_4$ and filtered. Concentration of the filtrate in vacuo afforded a pale yellow oil. Purification of the crude product thus obtained by way of column chromatography (SiO$_2$, 10:1→1:1 (v/v) Hex:EtOAc) afforded the title compound as a colorless oil.

Step 2: 2-Cyano-N-cyclopropyl-N-(2,3-dichlorobenzyl)-3-[4-(3-hydroxypropyl)phenyl]-2-methylpropanamide To a solution of 3-[4-(3-{[tert-butyl(dimethyl)silyl]oxy}propyl)phenyl]-2-cyano-N-cyclopropyl-N-(2,3-dichlorobenzyl)-2-methylpropanamide from the previous step (1 eq.) in THF (0.2 M) was added tetrabutylammonium fluoride (1.0 M THF solution, 8 eq.). The resulting reaction mixture was stirred at RT for 4 h. After quenching the reaction with 10% aq. HCl, the mixture was extracted with ether. The combined organic extracts were washed with sat. aq. NaHCO$_3$ and brine, dried over MgSO$_4$ and filtered. Concentration of the filtrate in vacuo afforded a pale yellow oil. Purification of the crude product thus obtained by way of flash chromatography (SiO$_2$, 10:1 (v/v) Hex:EtOAc→EtOAc) afforded the title compound as a colorless oil.

Step 3: 3-{4-[3-(2-Chloro-3,6-difluorophenoxy)propyl]phenyl}-2-cyano-N-cyclopropyl-N-(2,3-dichlorobenzyl)-2-methylpropanamide 2-Cyano-N-cyclopropyl-N-(2,3-dichlorobenzyl)-3-[4-(3-hydroxypropyl)phenyl]-2-methylpropanamide from the previous step (1 eq.) and 2-chloro-3,6-difluorphenol (4 eq.) were taken up in freshly deoxygenated toluene (0.05 M). To this solution was then added 1,1'-(azodicarbonyl)-dipiperidine (4 eq.) and finally tributylphosphine (4 eq.). The resulting yellow solution was heated at 80° C. for 3 h. The reaction mixture was cooled to RT, diluted with ether, and washed with 1 N aq. NaOH. The aqueous wash was back extracted with ether and the combined organic extracts were dried over MgSO$_4$. Filtration and concentration of the filtrate in vacuo afforded a yellow semi-solid. Purification of the crude product thus obtained by way of flash chromatography (SiO$_2$, Hex→3:2 (v/v) Hex:EtOAc) afforded the title compound as a colorless oil.

Step 4: 3-Amino-2-{4-[3-(2-chloro-3,6-difluorophenoxy)propyl]benzyl}-N-cyclopropyl-N-(2,3-dichlorobenzyl)-2-methylpropanamide 3-{4-[3-(2-Chloro-3,6-difluorophenoxy)propyl]phenyl}-2-cyano-N-cyclopropyl-N-(2,3-dichlorobenzyl)-2-methylpropanamide from the previous step (1 eq.) and cobalt(II) chloride hexahydrate (2 eq.) were combined in MeOH (0.1 M). To this mixture was then added sodium borohydride (10 eq.) slowly and portionwise. The resulting black suspension was stirred at RT for 1 h. The volatiles were then removed in vacuo. The resulting black tar was partitioned between EtOAc and 1 N aq. NaOH. The aqueous layer was separated and back-extracted with EtOAc. The combined organic extracts were washed further with H$_2$O and brine, dried over MgSO$_4$ and filtered. Concentration of the filtrate in vacuo revealed a brown oil. Purification of the crude product thus obtained by way of column chromatography (SiO$_2$, CH$_2$Cl$_2$→95:5 (v/v) CH$_2$Cl$_2$: 2.0 M NH$_3$ in MeOH) afforded the title compound as a colorless oil. MS (ESI+): 595.0.

Example 17

Ethyl 2-{[(3-[cyclopropyl(2,3-dichlorobenzyl)amino]-2-{4-[2-[2-(2,6-dichloro-4-methylphenoxy)ethoxy]benzyl}-3-oxopropyl)amino]methyl}cyclopropanecarboxylate

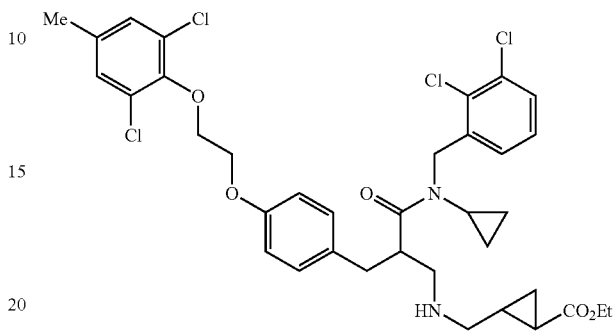

A mixture of 3-amino-N-cyclopropyl-N-(2,3-dichlorobenzyl)-2-{4-[2-(2,6-dichloro-4-methylphenoxy)ethoxy]benzyl}propanamide (Example 2, 1 eq.), trans-ethyl 2-formyl-1-cyclopropanecarboxylate (1 eq.) and sodium cyanoborohydride (1.5 eq.) were combined in MeOH (0.02 M). At 0° C., acetic acid (3 eq.) was added dropwise and the reaction mixture was slowly warmed to RT over 2 h. The reaction mixture was then diluted with ether and quenched with 1 N aq. NaOH. The aqueous layer was separated and back extracted with ether. The combined organic extracts were then washed with water and brine, dried over MgSO$_4$ and filtered. Concentration of the filtrate in vacuo afforded a purple residue. Purification of the crude product thus obtained by way of flash chromatography (SiO$_2$, 96:4 (v/v) CH$_2$Cl$_2$:MeOH) afforded the title compound as a colorless oil. MS (ESI+): 721.1.

Example 18

3-(Benzylamino)-2-{4-[3-(2-chloro-3,6-difluorophenoxy)propyl]benzyl}-N-cyclopropyl-N-(2,3-dichlorobenzyl)propanamide

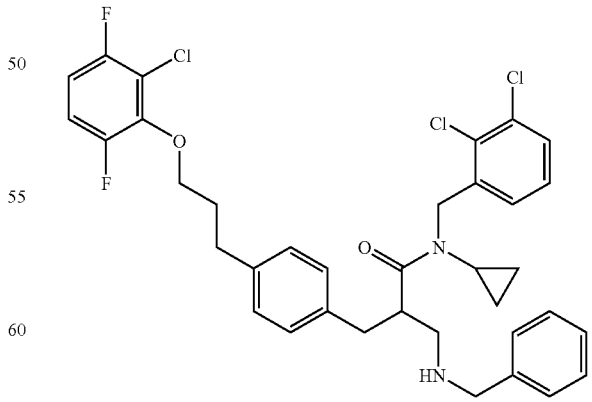

Prepared according to the procedure described in Example 17 but using instead 3-amino-2-{4-[3-(2-chloro-3,6-difluorophenoxy)propyl]benzyl}-N-cyclopropyl-N-(2,3-dichlo-

Example 19

Methyl 5-[(3-[cyclopropyl(2,3-dichlorobenzyl)amino]-2-{4-[2-(2,6-dichloro-4-methylphenoxy)ethoxy]benzyl}-3-oxopropyl)amino]pentanoate

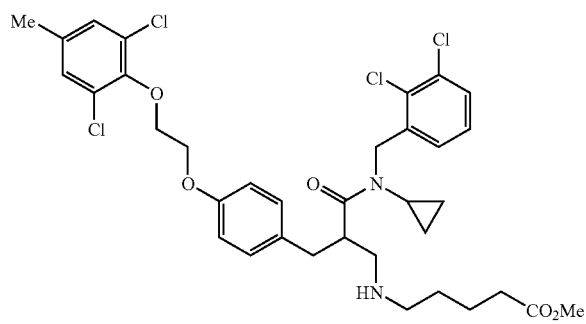

In a vessel equipped with a Dean-Stark apparatus, a benzene solution (0.01 M) of 3-amino-N-cyclopropyl-N-(2,3-dichlorobenzyl)-2-{4-[2-(2,6-dichloro-4-methylphenoxy)ethoxy]benzyl}propanamide (Example 2, 1 eq.) and methyl 5-oxopentanoate was heated at reflux for 8 h. The now yellow solution was cooled to RT and then concentrated in vacuo. The resulting residue was taken up in a 7:2 (v/v) MeOH:THF solution (0.01 M) and then added sodium borohydride (10 eq.) portionwise. After stirring at RT for 24 h, the mixture was diluted with ether and quenched with 1 N aq. NaOH. The aqueous phase was separated and back extracted with ether. The combined organic extracts were then washed with water and brine, dried over $MgSO_4$ and filtered. Concentration of the filtrate in vacuo afforded a yellow oil. Purification of the crude product thus obtained by way of flash chromatography ($SiO_2$, 97:3 (v/v) $CH_2Cl_2$: 2.0 M $NH_3$ in MeOH) afforded the title compound as a colorless oil. MS (ESI+): 709.0.

Example 20

Methyl 6-[(3-[cyclopropyl(2,3-dichlorobenzyl)amino]-2-{4-[2-(2,6-dichloro-4-methylphenoxy)ethoxy]benzyl}-3-oxopropyl)amino]hexanoate

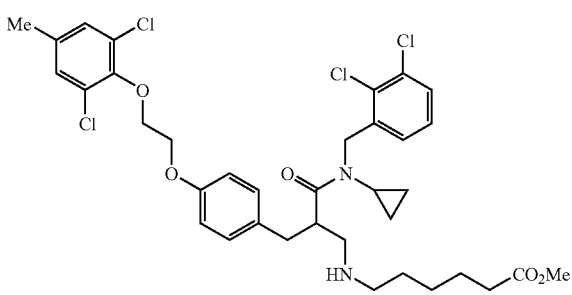

Prepared according to the procedure described in Example 19 but using instead methyl 6-oxohexanoate. The title compound was obtained as a colorless oil. MS (ESI+): 723.2.

Example 21

N-Cyclopropyl-N-(2,3-dichlorobenzyl)-2-{4-[2-(2,6-dichloro-4-methylphenoxy)ethoxy]benzyl}-3-[(2,2,2-trifluoroethyl)amino]propanamide

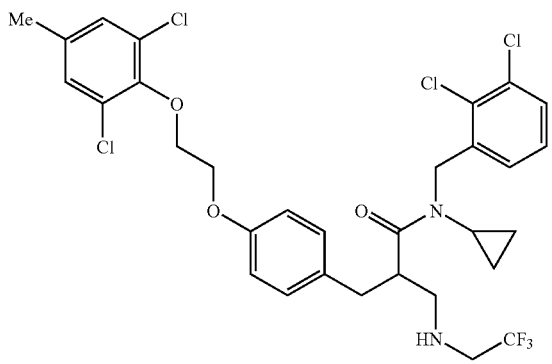

Prepared according to the procedure described in Example 19 but using instead 2,2,2-trifluoro-1-methoxyethanol. The title compound was obtained as a colorless oil. MS (ESI+): 677.0.

Example 22

2-{4-[3-(2-Chloro-3,6-difluorophenoxy)propyl]benzyl}-N-cyclopropyl-N-(2,3-dichlorobenzyl)-3-(methylamino)propanamide

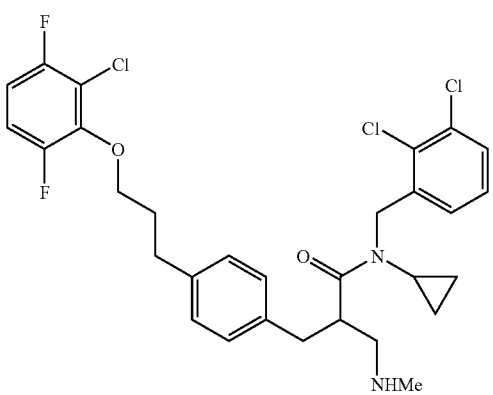

Prepared according to the procedure described in Example 19 but using instead 3-amino-2-{4-[3-(2-chloro-3,6-difluorophenoxy)propyl]benzyl}-N-cyclopropyl-N-(2,3-dichlorobenzyl)propanamide (Example 15) and paraformaldehyde. The title compound was obtained as a colorless oil. MS (ESI+): 595.3.

Example 23

6-[(3-[Cyclopropyl(2,3-dichlorobenzyl)amino]-2-{4-[2-(2,6-dichloro-4-methylphenoxy)ethoxy]benzyl}-3-oxopropyl)amino]hexanoic acid

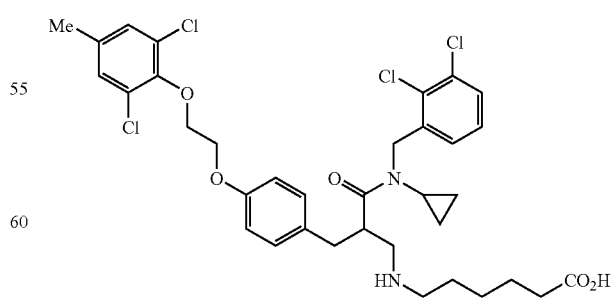

Methyl 6-[(3-[cyclopropyl(2,3-dichlorobenzyl)amino]-2-{4-[2-(2,6-dichloro-4-methylphenoxy)ethoxy]benzyl}-3-oxopropyl)amino]hexanoate (Example 20, 1 eq.) was dissolved in a 2:1 (v/v) THF:MeOH solution (0.01 M). To this

Example 24

2-{[(3-[cyclopropyl(2,3-dichlorobenzyl)amino]-2-{4-[2-[2-(2,6-dichloro-4-methylphenoxy)ethoxy]benzyl}-3-oxopropyl)amino]methyl}cyclopropanecarboxylic acid

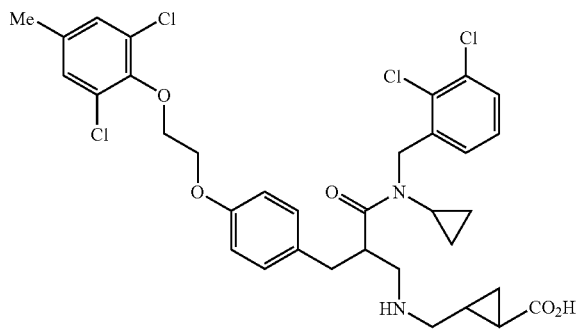

To an ethanol solution (0.04 M) of ethyl 2-{[(3-[cyclopropyl(2,3-dichlorobenzyl)amino]-2-{4-[2-[2-(2,6-dichloro-4-methylphenoxy)ethoxy]benzyl}-3-oxopropyl)amino]methyl}cyclopropanecarboxylate (Example 17, 1 eq.) was added sodium hydroxide (1.0 M aqueous solution, 4 eq.). The resulting solution was then heated at 80° C. for 18 h. The volatiles were then removed in vacuo. Following careful acidification of the resulting residue to a pH of ~4 with 10% aq. HCl, the mixture was saturated with sodium chloride and extracted with EtOAc. The combined organic extracts were dried over activated Na$_2$SO$_4$ and filtered. Concentration of the filtrate in vacuo afforded the title compound as a white solid. MS (ESI+): 693.1.

Example 25

3-Amino-N-cyclopropyl-N-(2,3-dichlorobenzyl)-2-{4-[2-(2,6-dichloro-4-methylphenoxy)ethyl]benzyl}propanamide

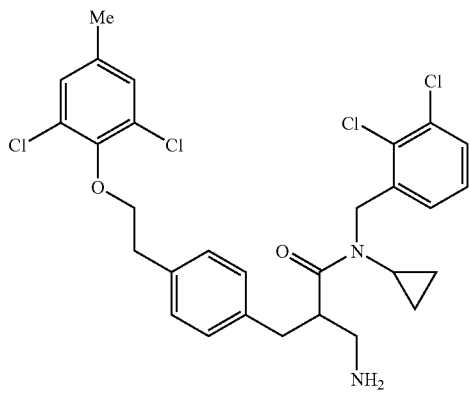

Step 1: {4-[2-(2,6-Dichloro-4-methylphenoxy)ethyl]phenyl}methanol

At 0° C., sodium borohydride (1.5 eq.) was added portionwise to a MeOH solution (0.2 M) of Aldehyde 4 (1 eq.). The resulting mixture was stirred at 0° C. for 15 min and then at RT for 30 min. Following the removal of the volatiles in vacuo, the resulting residue was partitioned between ether and 1 N aq. NaOH. The aqueous layer was separated and back extracted with ether. The combined organic extracts were washed with H$_2$O and brine, dried over MgSO$_4$ and filtered. Concentration of the filtrate in vacuo afforded the title compound as a colorless oil.

Step 2: 2-{2-[4-(Bromomethyl)phenyl]ethoxy}-1,3-dichloro-5-methylbenzene

To a solution of triphenylphosphine dibromide (1.2 eq.) and Hunig's base (2 eq.) in dichloromethane (0.09 M) was added, dropwise over 5 min, {4-[2-(2,6-dichloro-4-methylphenoxy)ethyl]phenyl}methanol prepared in the previous step (1 eq.). The resulting mixture was stirred at RT for 2 h and then concentrated in vacuo. The residue was suspended in a 10:1 (v/v) Hex:ether solution and filtered through a pad of SiO$_2$. The filtrate was concentrated in vacuo to afford the title compound as a white solid.

Step 3: 2-Cyano-N-cyclopropyl-N-(2,3-dichlorobenzyl)-3-{4-[2,6-dichloro-4-methylphenoxy)ethyl]phenyl}propanamide 2-Cyano-N-cyclopropyl-N-(2,3-dichlorobenzyl)acetamide (1 eq.), prepared from Amine 2 and cyanoacetic acid as detailed in Step 1 of Example 1, was dissolved in THF (0.1 M). At −78° C., potassium bis(trimethylsilyl)amide (15% w/w toluene solution, 1.2 eq.) was then added and the resulting yellow suspension was stirred at −78° C. for 15 min and at −40° C. for 15 min. 2-{2-[4-(bromomethyl)phenyl]ethoxy}-1,3-dichloro-5-methylbenzene from the previous step (1 eq.) was then added, at −78° C., as a 0.6 M THF solution over a period of 10 min. Finally, tetrabutylammonium iodide (10% loading) was added. The resulting pale yellow mixture was allowed to warm slowly to RT over 15 h. The reaction was quenched with sat. aq. NH$_4$Cl and extracted with ether. The combined organic extracts were washed with H$_2$O and brine, dried over MgSO$_4$ and filtered. Concentration of the filtrate in vacuo afforded a viscous yellow oil. Purification of the crude product thus obtained by way of column chromatography (SiO$_2$, Hex→1:1 (v/v) Hex:EtOAc) afforded the title compound as a colorless oil.

Step 4: tert-Butyl (3-[cyclopropyl(2,3-dichlorobenzyl)amino]-2-{4-[2-(2,6-dichloro-4-methylphenoxy)ethyl]benzyl}-3-oxopropyl)carbamate 2-Cyano-N-cyclopropyl-N-(2,3-dichlorobenzyl)-3-{4-[2,6-dichloro-4-methylphenoxy)ethyl]phenyl}propanamide from the previous step (1 eq.) and cobalt(II) chloride hexahydrate (2 eq.) were combined in MeOH (0.07 M). To this mixture was then added sodium borohydride (10 eq.) slowly and portionwise. The resulting black suspension was stirred at RT for 2 h. The reaction mixture was then diluted with EtOAc and quenched with 1 N aq. NaOH. The resulting emulsion was then filtered through a bed of celite and the insolubles were rinsed with EtOAc and CH$_2$Cl$_2$. The organic layer was separated and washed further with 1 N aq. NaOH, H$_2$O and brine. Drying over MgSO$_4$, filtration and concen- (cont. from previous column at top)
was then added sodium hydroxide (1.0 M aqueous solution, 3 eq.) and the resulting solution was stirred at RT for 18 h. The volatiles were then removed in vacuo. Following careful acidification of the resulting residue to a pH of ~4 with 10% aq. HCl, the mixture was saturated with sodium chloride and extracted with EtOAc. The combined organic extracts were concentrated in vacuo. The resulting solid residue was then azeotroped with toluene to give the title compound as a white solid. MS (ESI+): 709.1.

tration of the filtrate in vacuo afforded the crude amine as a golden oil. This residue was then taken up in $CH_2Cl_2$ (0.06 M). To this solution was added Hunig's base (4.7 eq.) and di-tert-butyl dicarbonate (2 eq.). The resulting reaction mixture was stirred at RT for 16 h. Following careful acidification with 10% aq. HCl to a pH of 2, the aqueous layer was separated and back extracted with EtOAc. The combined organic extracts were then washed $H_2O$ and brine, dried over $MgSO_4$ and filtered. Concentration of the filtrate in vacuo afforded a yellow oil. Purification of the crude product thus obtained by way of column chromatography ($SiO_2$, Hex→1:1 (v/v) Hex:EtOAc) afforded the title compound as a white froth.

Step 5: 3-Amino-N-cyclopropyl-N-(2,3-dichlorobenzyl)-2-{4-[2-(2,6-dichloro-4-methylphenoxy)ethyl]benzyl}propanamide To a $CH_2Cl_2$ solution (0.06 M) of tert-butyl (3-[cyclopropyl(2,3-dichlorobenzyl)amino]-2-{4-[2-(2,6-dichloro-4-methylphenoxy)ethyl]benzyl}-3-oxopropyl)carbamate (1 eq.) from the previous step was added HCl (4.0 M dioxane solution, 14 eq.). The resulting solution was stirred at RT for 3 h. Following the removal of the volatiles in vacuo, the resulting residue was directly loaded onto a $SiO_2$ column packed with 97:3 (v/v) $CH_2Cl_2$: 2.0 M $NH_3$ in MeOH. Elution with the same solvent system furnished the title compound as a white froth. MS (ESI+): 578.9.

Example 26

4-Amino-N-cyclopropyl-N-(2,3-dichlorobenzyl)-2-{4-[2-(2,6-dichloro-4-methylphenoxy)ethoxy]benzyl}butanamide

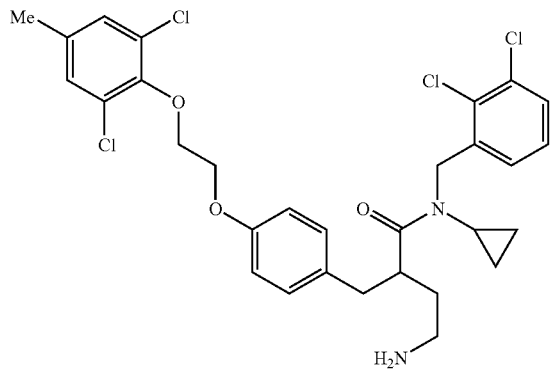

Step 1: [4-(2-{[tert-Butyl(dimethyl)silyl]oxy}ethoxy)phenyl]methanol

At 0° C., sodium borohydride (1.5 eq.) was added portionwise to a MeOH solution (0.5 M) of Aldehyde 5 (1 eq.). The resulting mixture was stirred at 0° C. for 30 min and then at RT for 30 min. Following the removal of the volatiles in vacuo, the resulting residue was partitioned between ether and 1 N aq. NaOH. The aqueous layer was separated and back extracted with ether. The combined organic extracts were washed with $H_2O$ and brine, dried over $MgSO_4$ and filtered. Concentration of the filtrate in vacuo afforded the title compound as a colorless oil.

Step 2: tert-Butyl{2-[4-(iodomethyl)phenoxy]ethoxy}dimethylsilane

At 0° C., iodine (1.2 eq.) and imidazole (1.2 eq.) were added to a $CH_2Cl_2$ solution (0.05 M) of triphenylphosphine (1.2 eq.). The resulting yellow-orange suspension was stirred at 0° C. for 10 min and then at RT for 15 min. Finally, [4-(2-{[tert-butyl(dimethyl)silyl]oxy}ethoxy)phenyl]methanol from the previous step (1 eq.) was added over 30 min as a 0.2 M $CH_2Cl_2$ solution. After another 10 h of stirring at RT, the volatiles were removed in vacuo. The resulting brown residue was suspended in ether and rapidly passed through a plug of $SiO_2$. Removal of the volatiles in vacuo afforded the title compound as a pink oil.

Step 3: Ethyl 2-[4-(2-{[tert-butyl(dimethyl)silyl]oxy}ethoxy)benzyl]pent-4-enoate To a solution of diisopropylamine (1.1 eq.) in THF (0.12 M) was added, at −78° C., n-butyllithium (1.6 M hexane solution, 1.1 eq.) over a period of 5 min. The resulting mixture was stirred at −78° C. for 15 min and then warmed at RT for 10 min. With the reaction mixture re-cooled to −78° C., ethyl pent-4-enoate (1.1 eq.) was added dropwise as a 1.6 M THF solution. The resulting solution was stirred for 30 min at −78° C. Finally, tert-butyl{2-[4-(iodomethyl)phenoxy]ethoxy}dimethylsilane (1 eq.) was added dropwise as a 1.5 M THF solution. The reaction mixture was allowed to warm slowly to RT over 12 h. After the reaction was carefully quenched with the addition of a sat. aq. $NH_4Cl$ solution, the reaction mixture was extracted with ether. The combined organic extracts were washed with brine, dried over $MgSO_4$, filtered and the filtrate concentrated in vacuo. Purification of the crude product thus obtained by way of column chromatography ($SiO_2$, 10:1 (v/v) Hex:ether) afforded the title compound as a colorless oil.

Step 4: Ethyl 2-[4-(2-hydroxyethoxy)benzyl]pent-4-enoate

To a solution of ethyl 2-[4-(2-{[tert-butyl(dimethyl)silyl]oxy}ethoxy)benzyl]pent-4-enoate from the previous step (1 eq.) in THF (0.2 M) was added tetrabutylammonium fluoride (1.0 M THF solution, 2 eq.). The resulting reaction mixture was stirred at RT for 2 h. After quenching the reaction with sat. aq. $NH_4Cl$, the mixture was extracted with ether. The combined organic extracts were washed with water and brine, dried over $MgSO_4$, filtered and the filtrate concentrated in vacuo. Purification of the crude product thus obtained by way of flash chromatography ($SiO_2$, 10:1 (v/v) Hex:EtOAc→EtOAc) afforded the title compound as a colorless oil.

Step 5: Ethyl 2-(4-{2-[(2,6-dichloro-4-methylphenoxy)ethoxy]benzyl}pent-4-enoate Ethyl 2-[4-(2-hydroxyethoxy)benzyl]pent-4-enoate from the previous step (1 eq.) and 2,6-dichloro-4-methylphenol (2 eq.) were taken up in freshly deoxygenated toluene (0.1 M). To this solution was then added 1,1'-(azodicarbonyl)-dipiperidine (3 eq.) and finally tributylphosphine (3 eq.). The resulting yellow solution was heated at 80° C. for 2 h. The reaction mixture was cooled to RT, quenched with 1 N aq. NaOH and extracted with ether. The combined organic extracts were dried over $MgSO_4$, filtered and the filtrate concentrated in vacuo. Purification of the crude product thus obtained by way of flash chromatography ($SiO_2$, Hex→7:3 (v/v) Hex:EtOAc) afforded the title compound as a colorless oil.

Step 6: 2-{4-[2-(2,6-Dichloro-4-methylphenoxy)ethoxy]benzyl}pent-4-enoic acid Ethyl 2-(4-{2-[(2,6-dichloro-4-methylphenoxy)ethoxy]benzyl}pent-4-enoate from the previous step (1 eq.) was dissolved in a 2:1 (v/v) THF:MeOH solution (0.06 M). To this was then added lithium hydroxide (1.0 M aqueous solution, 3.4 eq.) and the resulting solution was stirred at 50° C. for 12 h. The volatiles were then removed in vacuo. Following careful acidification of the resulting residue with 10% aq. HCl, the mixture was extracted with EtOAc. The combined organic extracts were washed with $H_2O$ and brine, dried over $MgSO_4$ and filtered. Concentration of the filtrate in vacuo afforded the title compound as a viscous oil.

Step 7: N-Cyclopropyl-N-(2,3-dichlorobenzyl)-2-{4-[2-(2,6-dichloro-4-methylphenoxy)ethoxy]benzyl}pent-4-enamide 2-{4-[2-(2,6-Dichloro-4-methylphenoxy)ethoxy]benzyl}pent-4-enoic acid from the previous step (1 eq.) was combined with Hunig's base (3 eq.) and Amine 2 (1.1 eq.) in anhydrous DMF (0.2 M). To this was then added portionwise O-(7-azabenzotriazol-1-yl)-N,N,N',N'-tetramethyluronium hexafluorophosphate (1.2 eq.). The resulting yellow solution was stirred at RT for 12 h. The reaction was quenched with 1 N aq. HCl and extracted with ether and EtOAc. The combined organic extracts were washed with $H_2O$ and brine, dried over $MgSO_4$, filtered and the filtrate concentrated in vacuo. Purification of the crude product thus obtained by way of flash chromatography ($SiO_2$, Hex→1:1 (v/v) Hex:EtOAc) afforded the title compound as a viscous oil.

Step 8: N-Cyclopropyl-N-(2,3-dichlorobenzyl)-2-{4-[2-(2,6-dichloro-4-methylphenoxy)ethoxy]benzyl}-4-hydroxybutanamide At −78° C., a 1:1 (v/v) THF:MeOH solution (0.02 M) of N-cyclopropyl-N-(2,3-dichlorobenzyl)-2-{4-[2-(2,6-dichloro-4-methylphenoxy)ethoxy]benzyl}pent-4-enamide from the previous step (1 eq.) was bubbled ozone for 20 min. The resulting solution was purged of excess ozone by bubbling with nitrogen. Sodium borohydride (4 eq.) was then added and the reaction mixture was warm to RT over 16 h. The resulting mixture was concentrated in vacuo, diluted with 1 N aq. NaOH and extracted with EtOAc. The combined organic extracts were washed with brine, dried over $MgSO_4$, filtered and the filtrate concentrated in vacuo. Purification of the crude product thus obtained by way of column chromatography ($SiO_2$, 10:1 (v/v) Hex:EtOAc→EtOAc) afforded the title compound as a viscous oil.

Step 9: 4-Azido-N-cyclopropyl-N-(2,3-dichlorobenzyl)-2-{4-[2-(2,6-dichloro-4-methylphenoxy)ethoxy]benzyl}butanamide N-Cyclopropyl-N-(2,3-dichlorobenzyl)-2-{4-[2-(2,6-dichloro-4-methylphenoxy)ethoxy]benzyl}-4-hydroxybutanamide from the previous step (1 eq.) and Hunig's base (3.5 eq.) were combined in $CH_2Cl_2$ (0.024 M). At −78° C., methanesulfonyl chloride (1.5 eq) was added and the reaction mixture was stirred at −78° C. for 10 min and at 0° C. for 10 min. The resulting mixture was quenched with sat. aq. $NaHCO_3$ and extracted with $CH_2Cl_2$. The combined organic extracts were dried over MgSO4, filtered and the filtrate concentrated in vacuo. The resulting residue was taken up in DMF (0.06 M) and added sodium azide (5 eq). This mixture was then allowed to stir at RT for 24 h. The resulting mixture was poured into water and extracted with ether. The combined organic extracts were washed with water and brine, dried over $MgSO_4$, filtered and the filtrate concentrated in vacuo. Purification of the crude product thus obtained by way of column chromatography ($SiO_2$, Hex→1:1 (v/v) Hex:EtOAc) afforded the title compound as a viscous oil.

Step 10: 4-Amino-N-cyclopropyl-N-(2,3-dichlorobenzyl)-2-{4-[2-(2,6-dichloro-4-methylphenoxy)ethoxy]benzylbutanamide To a THF solution (0.036 M) of 4-azido-N-cyclopropyl-N-(2,3-dichlorobenzyl)-2-{4-[2-(2,6-dichloro-4-methylphenoxy)ethoxy]benzyl}butanamide from the previous step (1 eq.) was added triphenylphosphine (1.1 eq) and $H_2O$ (1.6 eq.). The resulting solution was stirred at RT for 24 h. The volatiles were then removed in vacuo. Purification of the crude product thus obtained by way of column chromatography ($SiO_2$, 97:3 (v/v) $CH_2Cl_2$: 2.0 M $NH_3$ in MeOH) afforded the title compound as a colorless oil. MS (ESI+): 608.7.

Example 27

4-Amino-N-cyclopropyl-N-(2,3-dichlorobenzyl)-2-{4-[3-(2,6-dichloro-4-methylphenoxy)propyl]benzyl}butanamide

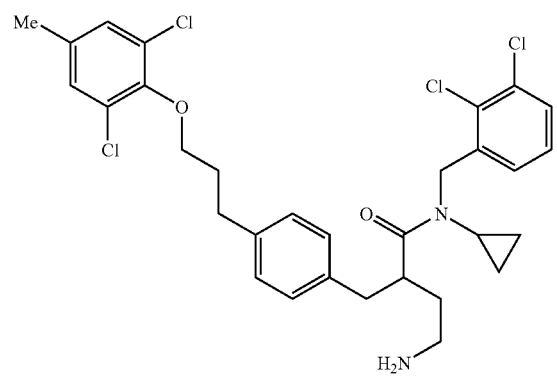

Prepared according to the procedure described in Example 26 but using instead Aldehyde 3. The title compound was obtained as a colorless oil. MS (ESI+): 607.0.

Example 28

N-Cyclopropyl-N-(2,3-dichlorobenzyl)-O-[2-(2,6-dichloro-4-methylphenoxy)ethyl]tyrosinamide

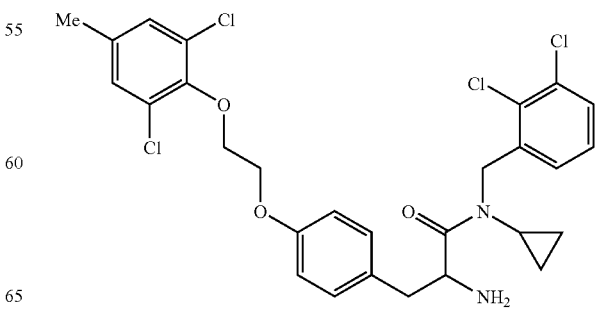

Step 1: Methyl N-(tert-butoxycarbonyl)-O-[2-(2,6-dichloro-4-methylphenoxy)ethyl]tyrosinate Methyl N-(tert-butoxycarbonyl)tyrosinate (1 eq.) and 2-(2,4-dichloro-4-methylphenoxy)ethanol (1 eq.) were taken up in freshly-deoxygenated toluene (0.18 M). To this solution was then added 1,1'-(azodicarbonyl)-dipiperidine (1.1 eq.) and finally tributylphosphine (3 eq.). The resulting yellow solution was heated at 80° C. for 3 h. The reaction mixture was cooled to RT, diluted with $H_2O$ and extracted with EtOAc. The combined organic extracts were washed with sat. aq. $NaHCO_3$ and brine, dried over $MgSO_4$ and filtered. Concentration of the filtrate in vacuo afforded the title compound.

Step 2: N-(tert-Butoxycarbonyl)-O-[2-(2,6-dichloro-4-methylphenoxy)ethyl]tyrosine Methyl N-(tert-butoxycarbonyl)-O-[2-(2,6-dichloro-4-methylphenoxy)ethyl]tyrosinate from the previous step (1 eq.) was dissolved in a 2:1 (v/v) THF:MeOH solution (0.07 M). To this was then added lithium hydroxide (1.0 M aqueous solution, 5 eq.) and the resulting solution was stirred at RT for 16 h. The volatiles were then removed in vacuo. Following careful acidification of the resulting residue with 10% aq. HCl, the mixture was extracted with EtOAc. The combined organic extracts were washed with $H_2O$ and brine, dried over $MgSO_4$ and filtered. Concentration of the filtrate in vacuo afforded the title compound.

Step 3: N-(tert-Butoxycarbonyl)-N-cyclopropyl-N-(2,3-dichlorobenzyl)-O-[2-(2,6-dichloro-4-methylphenoxy)ethyl]tyrosinamide N-(tert-Butoxycarbonyl)-O-[2-(2,6-dichloro-4-methylphenoxy)ethyl]tyrosine from the previous step (1 eq.) was combined with Hunig's base (3 eq.) and Amine 2 (1.2 eq.) in anhydrous DMF (0.04 M). To this was then added portionwise O-(7-azabenzotriazol-1-yl)-N,N,N',N'-tetramethyluronium hexafluorophosphate (1.5 eq.). The resulting solution was stirred at RT for 16 h. The reaction was quenched with 1 N aq. HCl and extracted with EtOAc. The combined organic extracts were washed with sat. aq. $NaHCO_3$ and brine, dried over $MgSO_4$, filtered and the filtrate concentrated in vacuo. Purification of the crude product thus obtained by way of flash chromatography ($SiO_2$, 10:1 (v/v) Hex:EtOAc→EtOAc) afforded the title compound as a viscous oil.

Step 4: N-Cyclopropyl-N-(2,3-dichlorobenzyl)-O-[2-(2,6-dichloro-4-methylphenoxy)ethyl]tyrosinamide To a $CH_2Cl_2$ solution (0.03 M) of N-(tert-butoxycarbonyl)-N-cyclopropyl-N-(2,3-dichlorobenzyl)-O-[2-(2,6-dichloro-4-methylphenoxy)ethyl]tyrosinamide from the previous step (1 eq.) was added HCl (4.0 M dioxane solution, 10 eq.). The resulting solution was stirred at RT for 5 h. Following the removal of the volatiles in vacuo, the resulting residue was directly loaded onto a $SiO_2$ column packed with 95:5 (v/v) $CH_2Cl_2$: 2.0 M $NH_3$ in MeOH. Elution with the same solvent system furnished the title compound as a white froth. MS (ESI+): 581.3.

Example 29

Methyl (2R)-2-{2-[(3-[cyclopropyl(2,3-dichlorobenzyl)amino]-2-{4-[2-[2-(2,6-dichloro-4-methylphenoxy)ethoxy]benzyl}-3-oxopropyl)amino]ethyl}-3-methylbutanoate

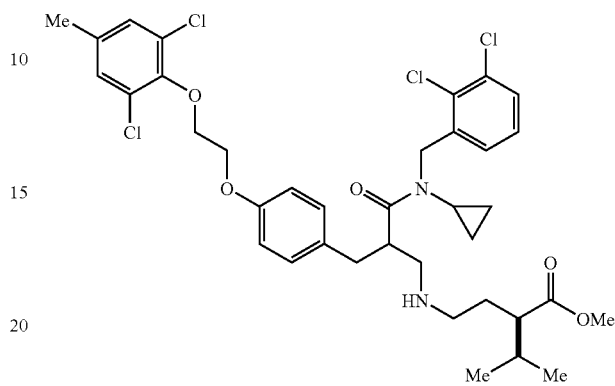

A mixture of 3-amino-N-cyclopropyl-N-(2,3-dichlorobenzyl)-2-{4-[2-(2,6-dichloro-4-methylphenoxy)ethoxy]benzyl}propanamide (Example 2, 1 eq.) and methyl (2R)-3-methyl-2-(2-oxoethyl)butanoate (1.2 eq.) were combined in toluene (0.1 M). To this was then added a few crystals of p-toluenesulfonic acid monohydrate and the resulting solution was azeotroped for 3 h. The reaction mixture was then cooled to RT and added sodium cyanoborohydride (1.2 eq.) was added portionwise. After 1 h of stirring, the reaction mixture was quenched with 10% aq. $Na_2CO_3$ and extracted with EtOAc. The combined organic extracts were then washed with brine, dried over $MgSO_4$ and filtered. Concentration of the filtrate in vacuo afforded a brown residue. Purification of the crude product thus obtained by way of flash chromatography ($SiO_2$, 97:3:1 (v/v/v) $CH_2Cl_2$:Acetone:2.0 M $NH_3$ in MeOH) afforded the title compound as a colorless oil. MS (ESI+): 739.1.

Example 30

N-Cyclopropyl-N-(2,3-dichlorobenzyl)-2-{4-[2-(2,6-dichloro-4-methylphenoxy)ethoxy]benzyl}-3-[(3R)-3-isopropyl-2-oxopyrrolidin-1-yl]propanamide

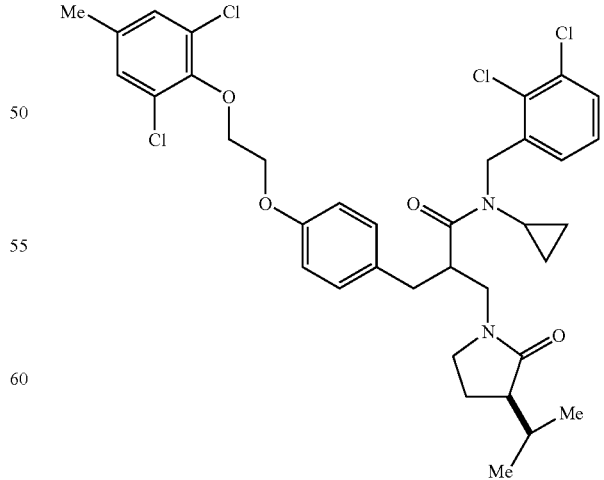

To a solution of methyl (2R)-2-{2-[(3-[cyclopropyl(2,3-dichlorobenzyl)amino]-2-{4-[2-[2-(2,6-dichloro-4-methylphenoxy)ethoxy]benzyl}-3-oxopropyl)amino]ethyl}-3- methylbutanoate (Example 29, 1 eq.) in MeOH (0.1 M) was added KOH (8.0 M aq. solution, 2 eq.). The resulting solution was then stirred at RT for 2 h. Removal of the volatiles in vacuo and purification of the crude product thus obtained by way of flash chromatography (SiO₂, 3:2 (v/v) Hex:EtOAc) afforded the title compound as a colorless oil. MS (ESI+): 707.2.

Example 31

Methyl (2S)-2-{2-[(3-[cyclopropyl(2,3-dichlorobenzyl)amino]-2-{4-[2-[2-(2,6-dichloro-4-methylphenoxy)ethoxy]benzyl}-3-oxopropyl)amino]ethyl}-3-methylbutanoate

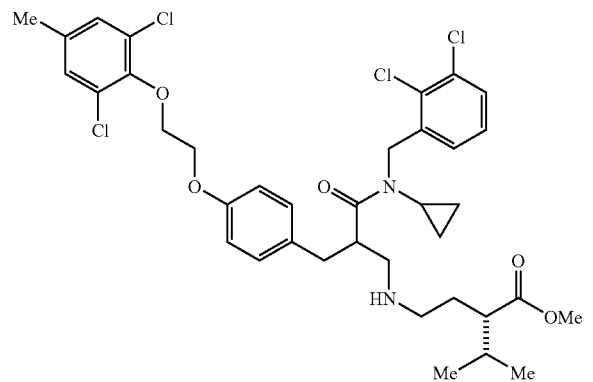

A mixture of 3-amino-N-cyclopropyl-N-(2,3-dichlorobenzyl)-2-{4-[2-(2,6-dichloro-4-methylphenoxy)ethoxy]benzyl}propanamide (Example 2, 1 eq.) and methyl (2S)-3-methyl-2-(2-oxoethyl)butanoate (1.3 eq.) were combined in toluene (0.2 M). To this was then added a few crystals of p-toluenesulfonic acid monohydrate and the resulting solution was azeotroped for 3 h. The reaction mixture was then cooled to RT, concentrated in vacuo and the resulting residue taken up in THF (0.2 M). At 0° C., sodium borohydride (1.3 eq.) was added. After O/N of stirring, the reaction mixture was quenched with 10% aq. NH₄Cl and extracted with EtOAc. The combined organic extracts were then washed with brine, dried over MgSO₄ and filtered. Concentration of the filtrate in vacuo and purification of the crude product thus obtained by way of flash chromatography (SiO₂, 95:4:1 (v/v/v) CH₂Cl₂:Acetone:2.0 M NH₃ in MeOH) afforded the title compound as a colorless oil. MS (ESI+): 739.2.

Example 32

N-Cyclopropyl-N-(2,3-dichlorobenzyl)-2-{4-[2-(2,6-dichloro-4-methylphenoxy)ethoxy]benzyl}-3-{[2-(2-napthyl)ethyl]amino}propanamide

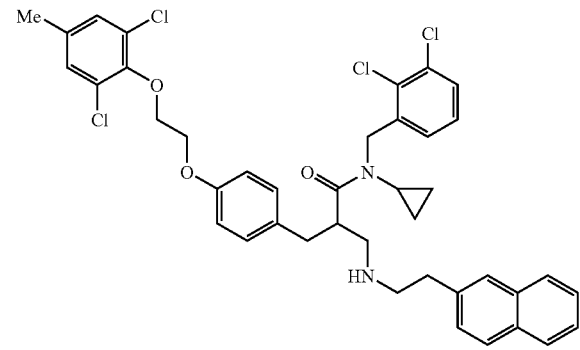

A mixture of 3-amino-N-cyclopropyl-N-(2,3-dichlorobenzyl)-2-{4-[2-(2,6-dichloro-4-methylphenoxy)ethoxy]benzyl}propanamide (Example 2, 1 eq.), 2-(2-bromoethyl)naphthalene (1 eq.) and sodium hydride (60% w/w dispersion in oil, 1 eq.) were combined at 0° C. in DMF (0.2 M). The cooling bath was removed and the reaction mixture was allowed to stir at RT O/N. The resulting cloudy suspension was diluted with EtOAc and quenched with 10% aq. NH₄Cl. The organic layer was separated, washed further with water and brine, dried over MgSO₄ and filtered. Concentration of the filtrate in vacuo and purification of the crude product thus obtained by way of flash chromatography (SiO₂, 97:3 (v/v) CH₂Cl₂: 2.0 M NH₃ in MeOH) afforded the title compound as a pale yellow oil. MS (ESI+): 750.1.

Example 33

2-(Aminomethyl)-N-cyclopropyl-3-{4-[2-(2,6-dichloro-4-methylphenoxy)ethoxy]phenyl}-N-(2,3-dimethylbenzyl)-4-pyridin-2-ylbutanamide

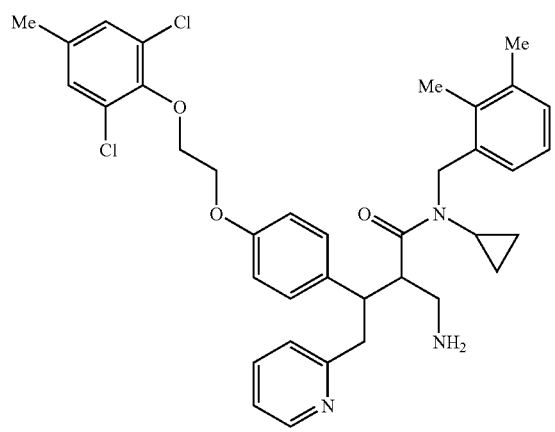

Step 1: 2-Cyano-N-cyclopropyl-3-{4-[2-(2,6-dichloro-4-methylphenoxy)ethoxy]phenyl}-N-(2,3-dimethylbenzyl)-4-pyridin-2-ylbutanamide To a THF solution (0.5 M) of 2-bromopyridine (2.8 eq.) was added, at –78° C., n-butyl lithium (1.6 M hexane solution, 2.8 eq.) dropwise over 15 min. The resulting yellow suspension was stirred at –78° C. for a further 15 min before an ether solution (0.5 M) of cuprous iodide (1.4 eq.) and dibutyl sulfide (2.8 eq.) was added over 15 min. The resulting reaction mixture was allowed to stir at –78° C. for 15 min and then at 0° C. for 15 min. Finally, to this was added dropwise at 0° C., a THF solution (0.1 M) of (2E)-2-cyano-N-cyclopropyl-3-{4-[2-(2,6-dichloro-4-methylphenoxy)ethoxy]phenyl}-N-(2,3-dimethylbenzyl)acrylamide (Example 1, Step 2, 1 eq.). The resulting emerald green suspension was stirred at 0° C. for 15 min and then at RT for 2 h. The reaction was quenched with 3:1 (v:v) sat. aq. NH₄Cl:conc. aq. NH₄OH solution and extracted with ether. The combined organic extracts were washed with brine, dried over MgSO₄, filtered and the filtrate concentrated in vacuo. The crude product thus obtained was purified by way of column chromatography (SiO₂, 10:1→1:1 (v/v) Hex:EtOAc). The title compound was isolated as a mixture of diastereomers.

Step 2: tert-Butyl (2-{[cyclopropyl(2,3-dimethylbenzyl)amino]carbonyl}-3-{4-[2-(2,6-dichloro-4-methylphenoxy)ethoxy]phenyl}-4-pyridin-2-ylbutyl)carbamate 2-Cyano-N-cyclopropyl-3-{4-[2-(2,6-dichloro-4-methylphenoxy)ethoxy]phenyl}-N-(2,3-dimethylbenzyl)-4-pyridin-2-ylbutanamide from the previous step (1 eq.) and cobalt (II) chloride hexahydrate (1 eq.) were combined in MeOH (0.06 M). To this mixture was then added sodium borohydride (3 eq.) slowly and portionwise. The resulting black suspension was stirred at RT for 1 h. The reaction mixture was then diluted with 95:5 (v/v) CH₂Cl₂:MeOH and quenched with 1 N aq. NaOH. The resulting emulsion was then filtered through a bed of celite and the insolubles were rinsed with 95:5 (v/v) CH₂Cl₂:MeOH. The organic layer was separated and washed further with 1 N aq. NaOH, H₂O and brine. Drying over MgSO₄, filtration and concentration of the filtrate in vacuo afforded the crude amine as a white froth. This residue was then taken up in CH₂Cl₂ (0.03 M) and added di-tert-butyl dicarbonate (1 eq.). Finally, sodium hydroxide (1.0 N aqueous solution, 3 eq.) was added and the resulting biphasic mixture was vigorously stirred for 4 h. The aqueous layer was separated and back extracted with ether. The combined organic extracts were then washed H₂O and brine, dried over MgSO₄ and filtered. Concentration of the filtrate in vacuo afforded a yellow oil. Purification of the crude product thus obtained by way of column chromatography (SiO₂, 10:1 (v/v) Hex:EtOAc→EtOAc) afforded the title compound as a mixture of diastereomers.

Step 3: 2-(Aminomethyl)-N-cyclopropyl-3-{4-[2-(2,6-dichloro-4-methylphenoxy)ethoxy]phenyl}-N-(2,3-dimethylbenzyl)-4-pyridin-2-ylbutanamide To a CH₂Cl₂ solution (0.03 M) of tert-butyl (2-{[cyclopropyl(2,3-dimethylbenzyl)amino]carbonyl}-3-{4-[2-(2,6-dichloro-4-methylphenoxy)ethoxy]phenyl}-4-pyridin-2-ylbutyl)carbamate from the previous step (1 eq.) was added HCl (4.0 M dioxane solution, 30 eq.). The resulting solution was stirred at RT for 4 h. Following the removal of the volatiles in vacuo, the resulting residue was directly loaded onto a SiO₂ column packed with 95:5 (v/v) CH₂Cl₂:2.0 M NH₃ in MeOH. Elution with the same solvent system furnished the title compound as a white froth. Diastereomer A: MS (ESI+): 646.0. Diastereomer B: MS (ESI+): 646.0.

Example 34

3-Amino-N-[2-chloro-5-(2-methoxyethyl)benzyl]-N-cyclopropyl-2-{4-[2-(2,6-dichloro-4-methylphenoxy)ethoxy]benzyl}butanamide

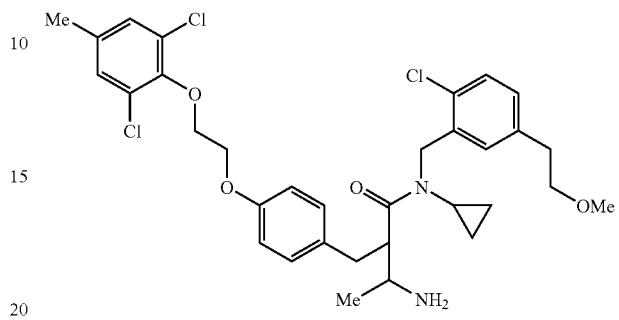

Step 1: {4-[2-(2,6-Dichloro-4-methylphenoxy)ethoxy]phenyl}methanol

At 0° C., sodium borohydride (1.5 eq.) was added portionwise to a MeOH solution (0.2 M) of Aldehyde 1 (1 eq.). The resulting mixture was stirred at 0° C. for 15 min and then at RT for 30 min. Following the removal of the volatiles in vacuo, the resulting residue was partitioned between ether and 1 N aq. NaOH. The aqueous layer was separated and back extracted with ether. The combined organic extracts were washed with H₂O and brine, dried over MgSO₄ and filtered. Concentration of the filtrate in vacuo afforded the title compound as a colorless oil.

Step 2: 1,3-Dichloro-2-{2-[4-(iodomethyl)phenoxy]ethoxy}-5-methylbenzene

To a solution of triphenylphosphine (1.2 eq.) in dichloromethane (0.09 M) was added iodine (1.2 eq.) and the resulting reddish-orange mixture was stirred at RT for 15 min. At 0° C., a dichloromethane solution (0.1 M) of {4-[2-(2,6-dichloro-4-methylphenoxy)ethyoxy]phenyl}methanol prepared in the previous step (1 eq.) and imidazole (3 eq.) was then added dropwise over 15 min. The resulting orange-yellow suspension was stirred at 0° C. for 1 h and then at RT for 15 min. The reaction was quenched with 10% (w/w) aq. NaHSO₃ and extracted with ether. The organic extracts were combined, washed with brine, dried over MgSO₄, filtered and the filtrate concentrated in vacuo. The resulting residue was triturated in a 10:1 (v/v) Hex:ether solution and filtered through a pad of SiO₂. The filtrate was concentrated in vacuo to afford the title compound as a white solid.

Step 3: Methyl 2-{4-[2,6-dichloro-4-methylphenoxy)ethoxy]benzyl}-3-oxobutanoate

Methyl 3-oxobutanoate (1.2 eq.) in THF (0.1 M) was added, at −78° C., potassium bis(trimethylsilyl)amide (15% w/w toluene solution, 1.2 eq.). The resulting yellow suspension was stirred at −78° C. for 15 min and at −40° C. for 15 min. 1,3-Dichloro-2-{2-[4-(iodomethyl)phenoxy]ethoxy}-5-methylbenzene from the previous step (1 eq.) was then added, at −78° C., as a 0.6 M THF solution over a period of 15 min. The resulting pale yellow mixture was allowed to warm slowly to RT over 15 h. The reaction was quenched with sat.

aq. NH₄Cl and extracted with ether. The combined organic extracts were washed with H₂O and brine, dried over MgSO₄ and filtered. Concentration of the filtrate in vacuo afforded a viscous yellow oil. Purification of the crude product thus obtained by way of column chromatography (SiO₂, Hex→1:1 (v/v) Hex:EtOAc) afforded the title compound as a colorless oil.

Step 4: Methyl 2-{4-[2-(2,6-dichloro-4-methylphenoxy)ethoxy]benzyl}-3-hydroxybutanoate Methyl 2-{4-[2,6-dichloro-4-methylphenoxy)ethoxy]benzyl}-3-oxobutanoate from the previous step (1 eq.) in 2:1 (v:v) THF:MeOH (0.1 M) was added sodium borohydride (1.2 eq.) in one rapid portion. After 30 min of stirring at RT, the volatiles were removed in vacuo and the resulting residue partitioned ether and 1 N aq. NaOH. The aqueous layer was separated and back extracted with ether. The combined ethereal extracts were then washed further with water and brine, dried over MgSO₄ and filtered. Concentration of the filtrate in vacuo afforded a pale yellow oil. Purification of the crude product thus obtained by way of column chromatography (SiO₂, Hex→1:1 (v/v) Hex:EtOAc) afforded the title compound as a colorless oil.

Step 5: 2-{4-[2-(2,6-Dichloro-4-methylphenoxy)ethoxy]benzyl}-3-hydroxybutanoic acid Methyl 2-{4-[2,6-dichloro-4-methylphenoxy)ethoxy]benzyl}-3-hydroxybutanoate from the previous step (1 eq.) in 1:1 (v:v) THF:MeOH (0.1 M) was added lithium hydroxide (1.0 M aqueous solution, 2 eq.). The resulting solution was stirred at RT for 12 h. Following the removal of the volatiles in vacuo, the resulting residue was carefully acidified to pH ~2 with 1 N aq. HCl and extracted with EtOAc. The combined organic extracts were washed further with water and brine, dried over MgSO₄, filtered and the filtrate concentrated in vacuo to afford the title compound as a a white froth.

Step 6: N-[2-Chloro-5-(2-methoxyethyl)benzyl]-N-cyclopropyl-2-{4-[2-(2,6-dichloro-4-methylphenoxy)ethoxy]benzyl}-3-hydroxybutanamide 2-{4-[2-(2,6-Dichloro-4-methylphenoxy)ethoxy]benzyl}-3-hydroxybutanoic acid from the previous step (1 eq.) was combined with Hunig's base (3 eq.) and Amine 7 (1.2 eq.) in anhydrous DMF (0.06 M). To this was then added portionwise O-(7-azabenzotriazol-1-yl)-N,N,N',N'-tetramethyluronium hexafluorophosphate (1.2 eq.). The resulting solution was stirred at RT for 18 h. The reaction was quenched with 1 N aq. HCl and extracted with EtOAc. The combined organic extracts were washed with brine, dried over MgSO₄, filtered and the filtrate concentrated in vacuo. Purification of the crude product thus obtained by way of flash chromatography (SiO₂, 10:1 (v/v) Hex:EtOAc→EtOAc) afforded the title compound as a viscous oil.

Step 7: N-[2-Chloro-5-(2-methoxyethyl)benzyl]-N-cyclopropyl-2-{4-[2-(2,6-dichloro-4-methylphenoxy)ethoxy]benzyl}-3-oxobutanamide N-[2-Chloro-5-(2-methoxyethyl)benzyl]-N-cyclopropyl-2-{4-[2-(2,6-dichloro-4-methylphenoxy)ethoxy]benzyl}-3-hydroxybutanamide from the previous step (1 eq.) in dichloromethane (0.05 M) was added at 0° C. Dess-Martin periodinane (1.2 eq.). The resulting solution was allowed to warm to RT over 2 h before the reaction was quenched with methanol and diluted with ether. This was then washed sequentially with sat. aq. NaHCO₃, water and brine. Drying of the organic layer over MgSO₄, filtration and concentration of the filtrate in vacuo afforded the crude product as a colorless oil. Further purification by way of flash chromatography (SiO₂, Hex→10:1 (v/v) Hex:EtOAc) afforded the title compound as a viscous oil.

Step 8: 3-Amino-N-[2-chloro-5-(2-methoxyethyl)benzyl]-N-cyclopropyl-2-{4-[2-(2,6-dichloro-4-methylphenoxy)ethoxy]benzyl}butanamide N-[2-Chloro-5-(2-methoxyethyl)benzyl]-N-cyclopropyl-2-{4-[2-(2,6-dichloro-4-methylphenoxy)ethoxy]benzyl}-3-oxobutanamide from the previous step (1 eq.) and ammonium acetate (10 eq.) were combined in MeOH (0.06 M). After the addition of sodium cyanoborohydride (1.2 eq.), the resulting reaction mixture was heated at reflux for 2 h. The volatiles were then removed in vacuo and the resulting residue partitioned between EtOAc and 1 N aq. NaOH. The aqueous wash was separated and back extracted with EtOAc. The combined organic extracts were then washed further with water and brine, dried over MgSO₄, filtered and the filtrate concentrated in vacuo. The crude product thus obtained was purified further by way of flash chromatography (SiO₂, 96:4 (v/v) CH₂Cl₂: 2.0 M NH₃ in MeOH) to reveal the title compound as a white froth. MS (ESI+): 635.3.

Example 35

3-Amino-N-[2-chloro-5-(3-hydroxypropyl)benzyl]-N-cyclopropyl-2-{4-[2-(2,6-dichloro-4-methylphenoxy)ethoxy]benzyl}propanamide

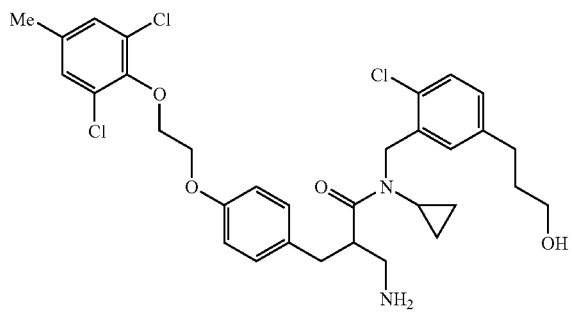

Prepared according to the procedure described in Example 9 but using instead Amine 11 as starting material. The title compound was obtained as a colorless oil. MS (ESI+): 620.8.

Example 36

3-Amino-N-[2-chloro-5-(2-methoxyethoxy)benzyl]-N-cyclopropyl-2-{4-[2-(2,6-dichloro-4-methylphenoxy)ethoxy]benzyl}propanamide

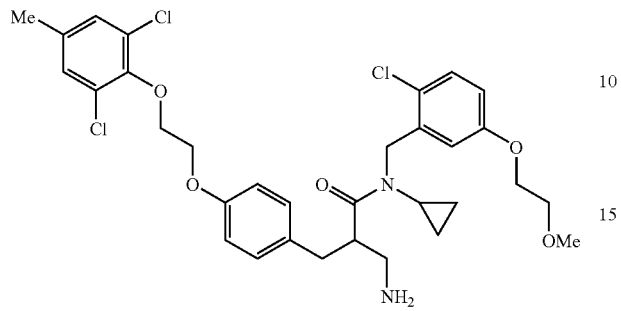

Prepared according to the procedure described in Example 9 but using instead Amine 12 as starting material. The title compound was obtained as a colorless oil. MS (ESI+): 635.

Example 37

3-Amino-N-cyclopropyl-2-{4-[2-(2,6-dichloro-4-methylphenoxy)ethoxy]benzyl}-N-{[6-(pyridin-4-ylmethyl)quinoline-8-yl]methyl}propanamide

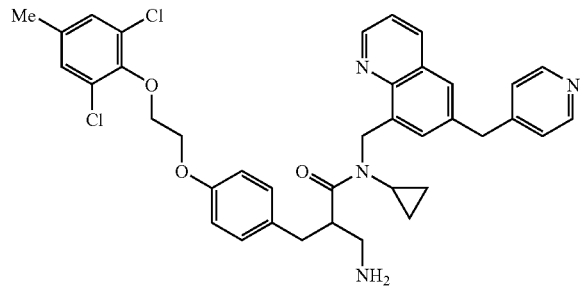

Prepared according to the procedure described in Example 9 but using instead Amine 13 as starting material. The title compound was obtained as a pale yellow oil. MS (ESI+): 669.2.

Example 38

3-Amino-N-[2-chloro-5-(3-methoxypropyl)benzyl]-N-cyclopropyl-2-{4-[2-(2,6-dichloro-4-methylphenoxy)ethyl]benzyl}propanamide

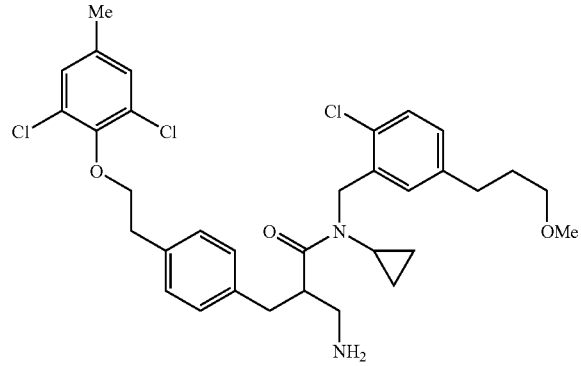

Prepared according to the procedure described in Example 9 but using instead Aldehyde 4 as starting material in step 1 and Amine 6 as starting material in step 4. The title compound was obtained as a pale yellow oil. MS (ESI+): 617.1.

Example 39

3-Amino-N-[2-chloro-5-(2-methoxyethyl)benzyl]-N-cyclopropyl-2-{4-[2-(2,6-dichloro-4-methylphenoxy)ethyl]benzyl}propanamide

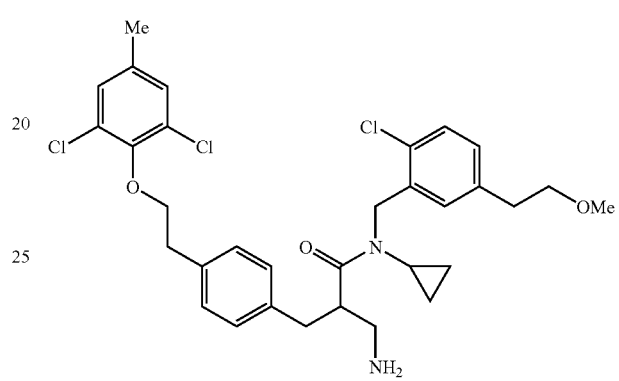

Prepared according to the procedure described in Example 9 but using instead Aldehyde 4 as starting material in step 1 and Amine 7 as starting material in step 4. The title compound was obtained as a pale yellow oil. MS (ESI+): 603.2.

Example 40

3-Amino-N-{2-chloro-5-[3-(dimethylamino)propyl)benzyl}-N-cyclopropyl-2-{4-[2-(2,6-dichloro-4-methylphenoxy)ethoxy]benzyl}propanamide

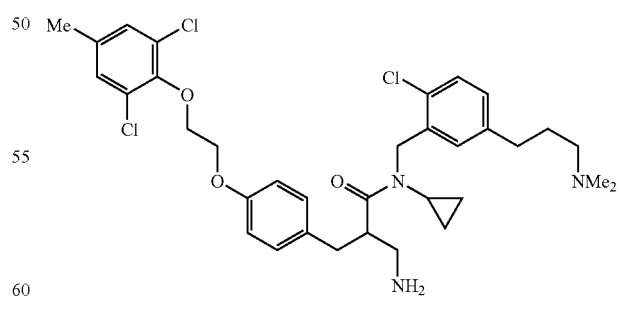

Prepared according to the procedure described in Example 9 but using instead Amine 14 as starting material. The title compound was obtained as a colorless oil. MS (ESI+): 646.1.

Example 41

3-Amino-N-cyclopropyl-N-[2,3-dichloro-5-[3-methoxypropyl)benzyl]-2-{4-[2-(2,6-dichloro-4-methylphenoxy)ethoxy]benzyl}propanamide

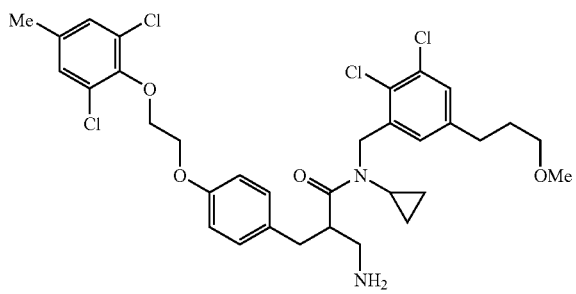

Prepared according to the procedure described in Example 9 but using instead Amine 15 as starting material. The title compound was obtained as a colorless oil. MS (ESI+): 667.0.

Example 42

3-Amino-N-cyclopropyl-N-[2,3-dichloro-5-[3-methoxypropyl)benzyl]-2-{4-[2-(2,6-dichloro-4-methylphenoxy)ethyl]benzyl}propanamide

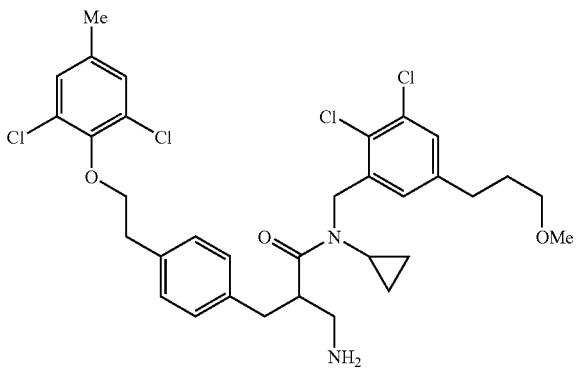

Prepared according to the procedure described in Example 9 but using instead Aldehyde 4 as starting material in step 1 and Amine 15 as starting material in step 4. The title compound was obtained as a colorless oil. MS (ESI+): 652.2.

Example 43

3-Amino-N-{[6-(cyanomethyl)quinoline-8-yl]methyl}-N-cyclopropyl]-2-{4-[2-(2,6-dichloro-4-methylphenoxy)ethoxy]benzyl}propanamide

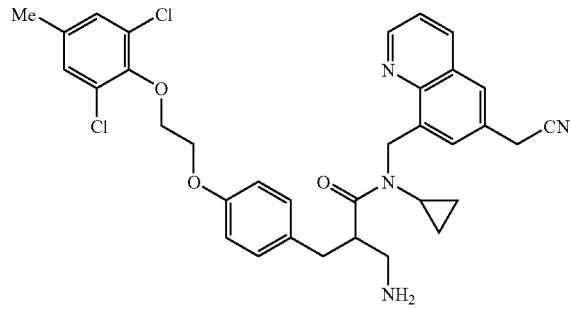

Prepared according to the procedure described in Example 9 but using instead Amine 16 as starting material. The title compound was obtained as a colorless oil. MS (ESI+): 617.1.

Example 44

3-Amino-N-cyclopropyl-2-{4-[2-(2,6-dichloro-4-methylphenoxy)ethoxy]benzyl}-N-{[2-(3-methoxypropyl)quinoline-4-yl]methyl}propanamide

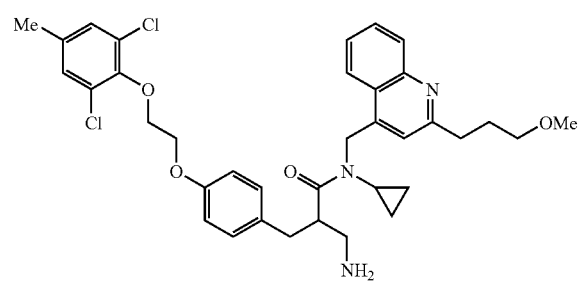

Prepared according to the procedure described in Example 9 but using instead Amine 17 as starting material. The title compound was obtained as a colorless oil. MS (ESI+): 650.2.

Example 45

3-Amino-N-[2-chloro-5-(2-cyanoethyl)benzyl]-N-cyclopropyl-2-{4-[2-(2,6-dichloro-4-methylphenoxy)ethoxy]benzyl}propanamide

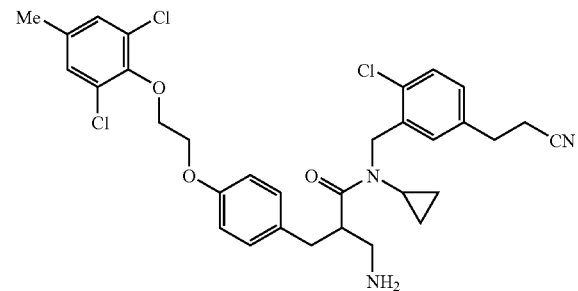

Prepared according to the procedure described in Example 9 but using instead Amine 18 as starting material. The title compound was obtained as a colorless oil. MS (ESI+): 616.1.

Example 46

3-Amino-N-cyclopropyl-2-{4-[2-(2,6-dichloro-4-methylphenoxy)ethoxy]benzyl}-N-[5-(3-methoxypropyl)-2-methylbenzyl]propanamide

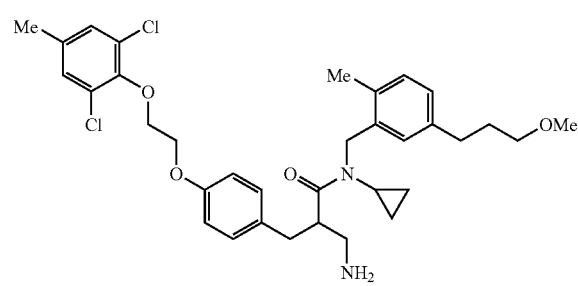

Prepared according to the procedure described in Example 9 but using instead Amine 19 as starting material. The title compound was obtained as a colorless oil. MS (ESI+): 613.0.

Example 47

3-Amino-N-[2-chloro-5-(2-cyanomethyl)benzyl]-N-cyclopropyl-2-{4-[2-(2,6-dichloro-4-methylphenoxy)ethoxy]benzyl}propanamide

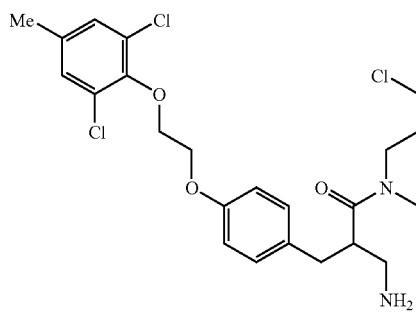

Prepared according to the procedure described in Example 9 but using instead Amine 20 as starting material. The title compound was obtained as a colorless oil. MS (ESI+): 601.4.

Example 48

3-Amino-N-cyclopropyl-2-{4-[2-(2,6-dichloro-4-methylphenoxy)ethoxy]benzyl}-N-[5-(3-methoxyethyl)-2-methylbenzyl]propanamide

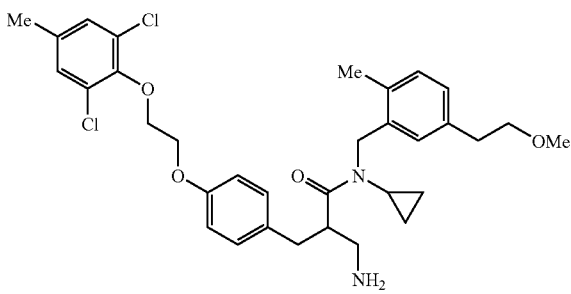

Prepared according to the procedure described in Example 9 but using instead Amine 21 as starting material. The title compound was obtained as a colorless oil. MS (ESI+): 599.1

Example 49

3-Amino-N-[2,5-bis(trifluoromethyl)benzyl]-N-cyclopropyl-2-{4-[2-(2,6-dichloro-4-methylphenoxy)ethoxy]benzyl}propanamide

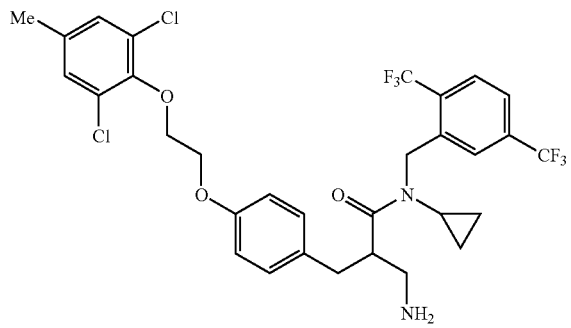

Prepared according to the procedure described in Example 9 but using instead Amine 22 as starting material. The title compound was obtained as a colorless oil. MS (ESI+): 702.3.

Example 50

3-Amino-N-{[6-(1-cyano-1-methylethyl)quinoline-8-yl]methyl}-N-cyclopropyl-2-{4-[2-(2,6-dichloro-4-methylphenoxy)ethoxy]benzyl}propanamide

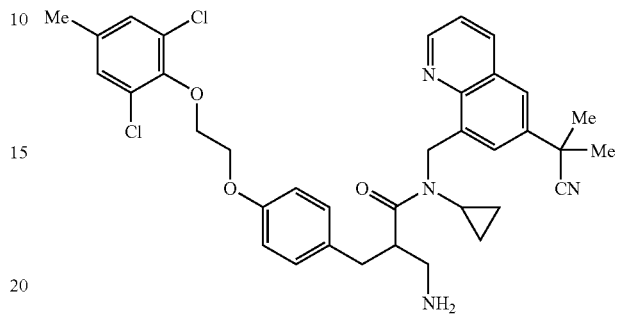

Prepared according to the procedure described in Example 9 but using instead Amine 23 as starting material. The title compound was obtained as a colorless oil. MS (ESI+): 645.2.

Example 51

3-Amino-N-cyclopropyl-2-{4-[2-(2,6-dichloro-4-methylphenoxy)ethoxy]benzyl}-N-(1-phenylethyl)propanamide

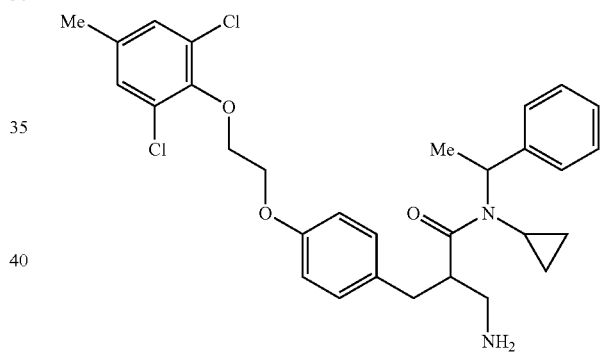

Prepared according to the procedure described in Example 9 but using instead Amine 24 as starting material. The title compound was obtained as a colorless oil. MS (ESI+): 541.3.

Example 52

3-Amino-N-benzyl-2-{4-[2-(2,6-dichloro-4-methylphenoxy)ethoxy]benzyl}-N-methylpropanamide

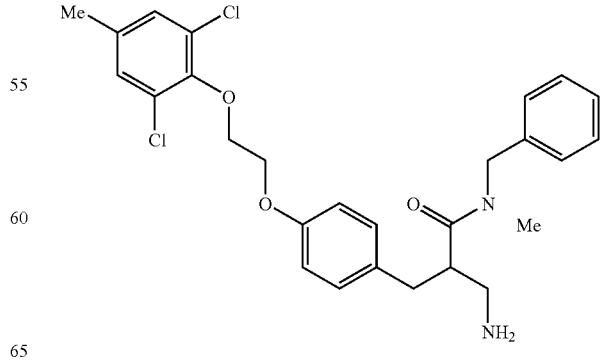

Prepared according to the procedure described in Example 9 but using instead N-methyl-1-phenylmethanamine as start ing material. The title compound was obtained as a colorless oil. MS (ESI+): 501.4.

Example 53

3-Amino-N-benzyl-N-cyclopropyl-2-{4-[2-(2,6-dichloro-4-methylphenoxy)ethoxy]benzyl}propanamide

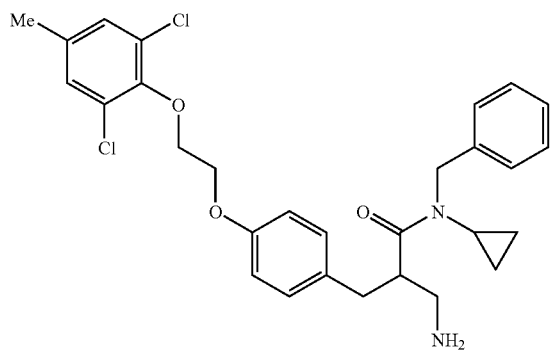

Prepared according to the procedure described in Example 9 but using instead Amine 25 as starting material. The title compound was obtained as a colorless oil. MS (ESI+): 527.1.

Example 54

3-Amino-N-benzyl-N-cyclopropyl-2-{4-[2-(2,6-dichloro-4-methylphenoxy)ethoxy]benzyl}-N-(2-phenylethyl)propanamide

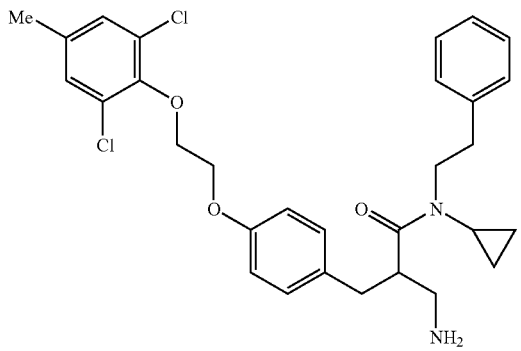

Prepared according to the procedure described in Example 9 but using instead Amine 26 as starting material. The title compound was obtained as a colorless oil. MS (ESI+): 541.4.

Example 55

3-Amino-2-{4-[2-(2,6-dichloro-4-methylphenoxy)ethoxy]benzyl}-N-methyl-N-(2-phenylethyl)propanamide

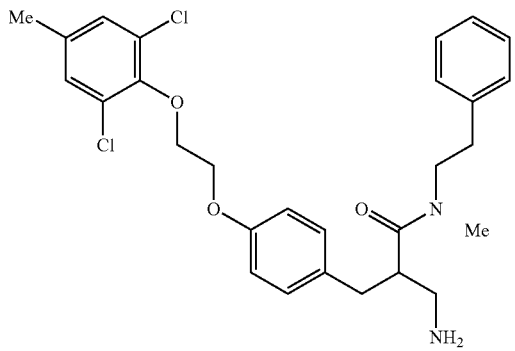

Prepared according to the procedure described in Example 9 but using instead N-methyl-2-phenylethanamine as starting material. The title compound was obtained as a colorless oil. MS (ESI+): 515.1.

Example 56

3-Amino-2-{4-[2-(2,6-dichloro-4-methylphenoxy)ethoxy]benzyl}-A-methyl-N-(1-phenylethyl)propanamide

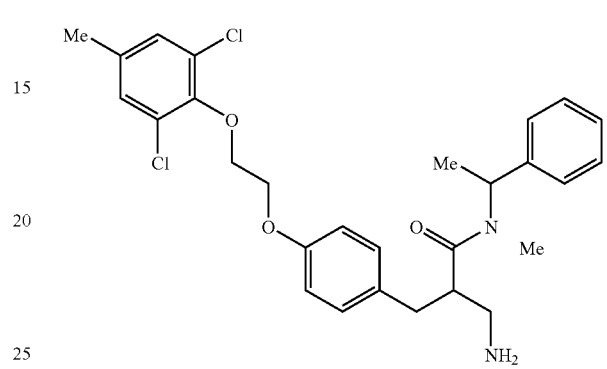

Prepared according to the procedure described in Example 9 but using instead N-methyl-1-phenylethanamine as starting material. The title compound was obtained as a colorless oil. MS (ESI+): 515.2.

Example 57

3-Amino-N-(2,3-dichlorobenzyl)-2-{4-[2-(2,6-dichloro-4-methylphenoxy)ethoxy]benzyl}-N-(2,2,2-trifluoroethyl)propanamide

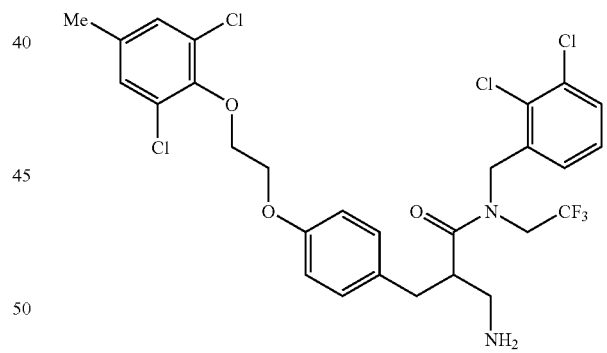

Step 1: (2E)-2-Cyano-3-{4-[2-(2,6-dichloro-4-methylphenoxy)ethoxy]phenyl}acrylic acid To a 2:1 (v/v) THF:MeOH solution (0.1 M) of methyl (2E)-2-cyano-3-{4-[2-(2,6-dichloro-4-methylphenoxy)ethoxy]phenyl}acrylate from Example 9, Step 1 (1 eq.) was added sodium hydroxide (1.0 M aq. solution, 3 eq.). The resulting solution was stirred at RT for 18 h before the volatiles were removed in vacuo. Following careful acidification of the resulting mixture to pH ~1 with 10% aq. HCl, the solution was extracted with EtOAc. The combined organic extracts were washed further with water and brine, dried over MgSO$_4$ and filtered. Concentration of the filtrate in vacuo afforded the title compound as a yellow semi-solid.

Step 2: (2E)-2-Cyano-N-(2,3-dichlorobenzyl)-3-{4-[2-(2,6-dichloro-4-methylphenoxy)ethoxy]phenyl}-N-(2,2,2-trifluoroethyl)acrylamide To a solution of (2E)-2-cyano-3-{4-[2-(2,6-dichloro-4-methylphenoxy)ethoxy]phenyl}acrylic acid from the previous step (1 eq.) in dichloromethane (0.02 M) was added oxalyl chloride (1.2 eq.). Then, several drops of neat DMF were added dropwise. After no further gaseous evolution could be discerned, the crude reaction mixture was diluted with toluene and the volatiles were removed in vacuo. The resulting residue was taken up in dichloromethane (0.02 M) and added sequentially Amine 27 (2 eq.), triethylamine (2 eq.) and a few crystals of DMAP. After 16 h of stirring at RT, the reaction was quenched with sat. aq. NH$_4$Cl and then extracted with EtOAc. The combined organic extracts were washed with water and brine, dried over MgSO$_4$, filtered and the filtrate concentrated in vacuo. Purification of the crude product thus obtained by way of column chromatography (SiO$_2$, Hex→7:3 (v/v) Hex:EtOAc) afforded the title compound as a white foam.

Step 3: tert-Butyl (3-[(2,3-dichlorobenzyl)(2,2,2-trifluoroethyl)amino]-2-{4-[2-(2,6-dichloro-4-methylphenoxy)ethoxy]benzyl}-3-oxopropyl)carbamate (2E)-2-Cyano-N-(2,3-dichlorobenzyl)-3-{4-[2-(2,6-dichloro-4-methylphenoxy)ethoxy]phenyl}-N-(2,2,2-trifluoroethyl)acrylamide from the previous step (1 eq.) and cobalt(II) chloride hexahydrate (2 eq.) were combined in a 7:3 (v/v) THF:MeOH solution (0.003 M). To this mixture was then added sodium borohydride (10 eq.) slowly and portionwise. The resulting black suspension was stirred at RT for 2 h. The reaction mixture was then carefully quenched with 10% aq. HCl and extracted with ether. The combined organic extracts were washed further with H$_2$O and brine. Drying over MgSO$_4$, filtration and concentration of the filtrate in vacuo afforded the crude amine. This residue was combined with di-tert-butyl dicarbonate (1 eq.), Hunig's base (1.5 eq.) and a few crystals of 4-(dimethylamino)pyridine in CH$_2$Cl$_2$ (0.06 M). The resulting solution was stirred at RT for 3 h. The volatiles were then removed in vacuo and purification of the crude product thus obtained by way of column chromatography (SiO$_2$, Hex→7:3 (v/v) Hex:EtOAc) afforded the title compound as a pale yellow oil.

Step 4: 3-Amino-N-(2,3-dichlorobenzyl)-2-{4-[2-(2,6-dichloro-4-methylphenoxy)ethoxy]benzyl}-N-(2,2,2-trifluoroethyl)propanamide To a CH$_2$Cl$_2$ solution (0.05 M) of tert-butyl (3-[(2,3-dichlorobenzyl)(2,2,2-trifluoroethyl)amino]-2-{4-[2-(2,6-dichloro-4-methylphenoxy)ethoxy]benzyl}-3-oxopropyl)carbamate from the previous step (1 eq.) was added HCl (4 M dioxane solution, 20 eq.). The resulting solution was stirred at RT for 13 h. Following the removal of the volatiles in vacuo, the resulting residue was directly loaded onto a SiO$_2$ column packed with 95:5 (v/v) CH$_2$Cl$_2$: 2.0 M NH$_3$ in MeOH. Elution with the same solvent system furnished the title compound as a colorless oil. MS (ESI+): 638.2.

Example 58

3-Amino-2-{4-[2-(2,6-dichloro-4-methylphenoxy)ethoxy]benzyl}-N-methyl-N-(1-methyl-1-phenylethyl)propanamide

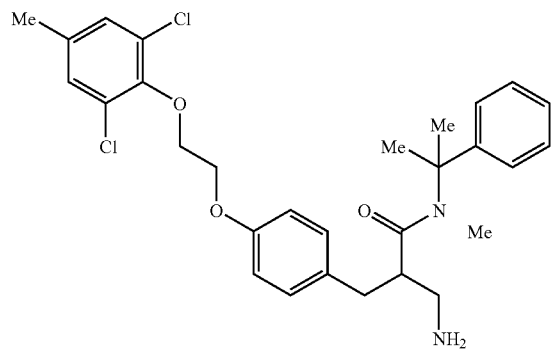

Prepared according to the procedure described in Example 9 but using instead Amine 28 as starting material. The title compound was obtained as a colorless oil. MS (ESI+): 529.1.

Example 59

3-Amino-N-[2-chloro-5-(2-methoxyethyl)benzyl]-N-(cyclopropyl)methyl)-2-{4-[2-(2,6-dichloro-4-methylphenoxy)ethoxy]benzyl}propanamide

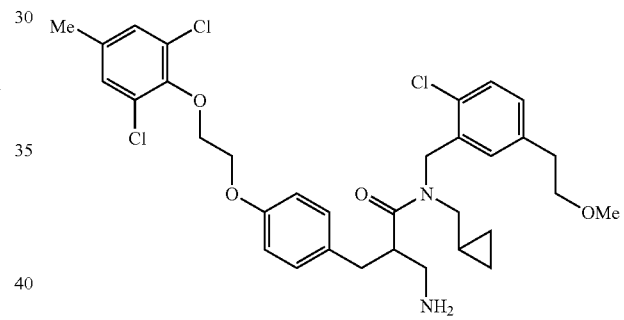

Prepared according to the procedure described in Example 9 but using instead Amine 29 as starting material. The title compound was obtained as a colorless oil. MS (ESI+): 633.2.

Example 60

3-Amino-N-[2-chloro-5-(2-methoxyethyl)benzyl]-2-{4-[2-(2,6-dichloro-4-methylphenoxy)ethoxy]benzyl}-N-methylpropanamide

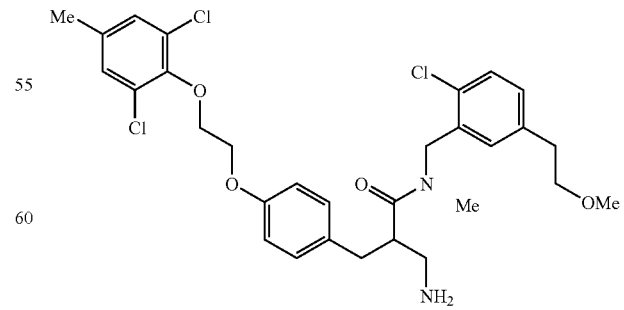

Prepared according to the procedure described in Example 9 but using instead Amine 30 as starting material. The title compound was obtained as a colorless oil. MS (ESI+): 593.2.

Example 61

3-Amino-N-[2-chloro-5-(2-methoxyethyl)benzyl]-N-(cyclobutylmethyl)-2-{4-[2-(2,6-dichloro-4-methylphenoxy)ethoxy]benzyl}propanamide

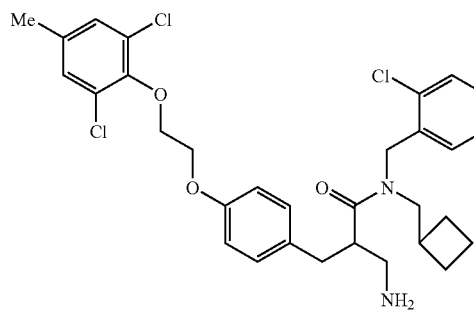

Prepared according to the procedure described in Example 9 but using instead Amine 31 as starting material. The title compound was obtained as a colorless oil. MS (ESI+): 647.3.

Example 62

3-Amino-N-[2-chloro-5-(2-methoxyethyl)benzyl]-2-{4-[2-(2,6-dichloro-4-methylphenoxy)ethoxy]benzyl}-N-isopropylpropanamide

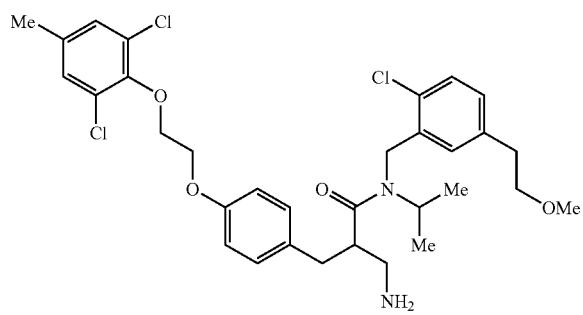

Prepared according to the procedure described in Example 9 but using instead Amine 32 as starting material. The title compound was obtained as a colorless oil. MS (ESI+): 621.1.

Example 63

N-Allyl-3-amino-N-[2-chloro-5-(2-methoxyethyl)benzyl]-2-{4-[2-(2,6-dichloro-4-methylphenoxy)ethoxy]benzyl}propanamide

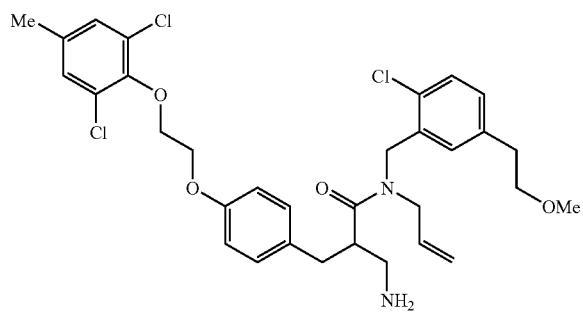

Prepared according to the procedure described in Example 9 but using instead Amine 33 as starting material. The title compound was obtained as a colorless oil. MS (ESI+): 619.2.

Example 64

3-Amino-N-[2-chloro-5-(2-methoxyethyl)benzyl]-N-cyclobutyl-2-{4-[2-(2,6-dichloro-4-methylphenoxy)ethoxy]benzyl}propanamide

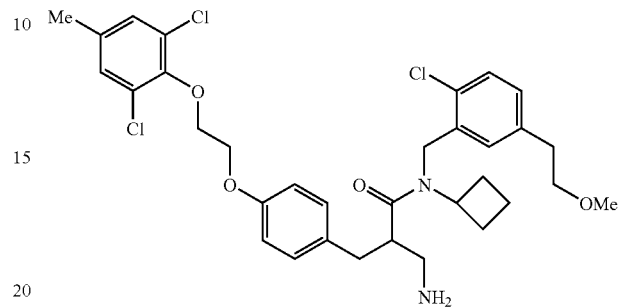

Prepared according to the procedure described in Example 9 but using instead Amine 34 as starting material. The title compound was obtained as a colorless oil. MS (ESI+): 633.2

Example 65

3-Amino-N-[2-chloro-5-(2-methoxyethyl)benzyl]-2-{4-[2-(2,6-dichloro-4-methylphenoxy)ethoxy]benzyl}-N-ethylpropanamide

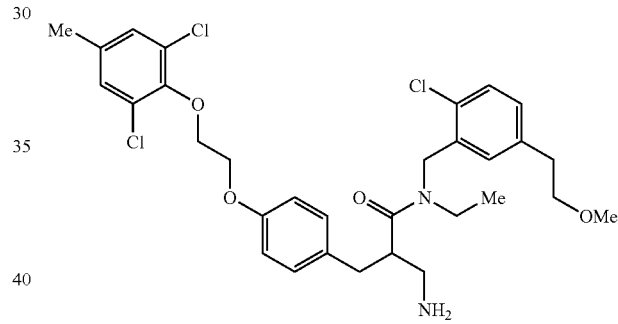

Prepared according to the procedure described in Example 9 but using instead Amine 35 as starting material. The title compound was obtained as a colorless oil. MS (ESI+): 607.2

Example 66

3-{[Amino(imino)methyl]amino}-N-[2-chloro-5-(3-methoxypropyl)benzyl]-N-cyclopropyl-2-{4-[2-(2,6-dichloro-4-methylphenoxy)ethoxy]benzyl}propanamide

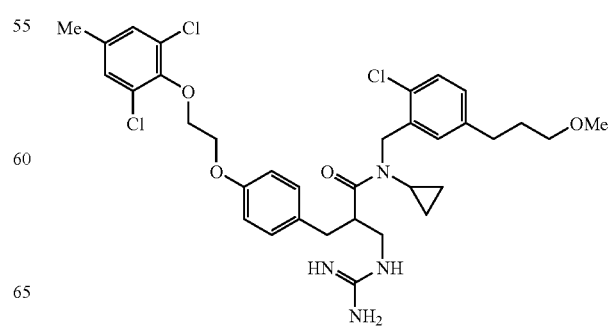

Step 1: Di-tert-butyl{(Z)-[(3-{[2-chloro-5-(3-methoxypropyl)benzyl](cyclopropyl)amino]-N-2-{4-[2-(2,6-dichloro-4-methylphenoxy)ethoxy]benzyl}-3-oxopropyl)amino]methylylidene)biscarbamate To a solution of 3-amino-N-[2-chloro-5-(3-methoxypropyl)benzyl]-N-cyclopropyl-2-{4-[2-(2,6-dichloro-4-methylphenoxy)ethoxy]benzyl}propanamide (Example 6, 1 eq.) in DMF (0.04 M) was added sequentially O,O-di-tert-butyl diimidothiocarbonate (1.2 eq.), triethylamine (2.2 eq.) and EDCI (1.2 eq.), sodium hydroxide (1.0 M aq. solution, 3 eq.). The resulting solution was stirred at RT for 18 h. The reaction mixture was diluted with water and then extracted with ether. The combined organic extracts were washed further with water and brine, dried over MgSO₄, filtered and the filtrate concentrated in vacuo. Purification of the crude product thus obtained by way of column chromatography (SiO₂, Hex→EtOAc) afforded the title compound.

Step 2: 3-{[Amino(imino)methyl]amino}-N-[2-chloro-5-(3-methoxypropyl)benzyl]-N-cyclopropyl-2-{4-[2-(2,6-dichloro-4-methylphenoxy)ethoxy]benzyl}propanamide To a CH₂Cl₂ solution (0.04 M) of di-tert-butyl{(Z)-[(3-[[2-chloro-5-(3-methoxypropyl)benzyl](cyclopropyl)amino]-N-2-{4-[2-(2,6-dichloro-4-methylphenoxy)ethoxy]benzyl}-3-oxopropyl)amino]methylylidene)biscarbamate from the previous step (1 eq.) was added trifluoroacetic acid (190 eq.). The resulting solution was stirred at RT for 3 h. Following the removal of the volatiles in vacuo, the resulting residue was directly loaded onto a SiO₂ column packed with 90:10 (v/v) CH₂Cl₂: 2.0 M NH₃ in MeOH. Elution with the same solvent system furnished the title compound as a white solid. MS (ESI+): 675.3.

Example 67

2-{[Amino(imino)methyl]amino}-N-cyclopropyl-N-(2,3-dichlorobenzyl)-3-{4-[2-(2,6-dichloro-4-methylphenoxy)ethoxy]benzyl}propanamide

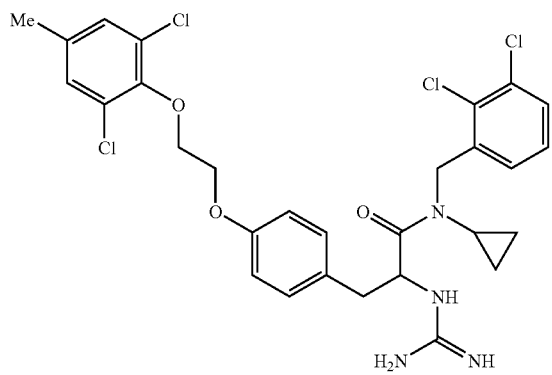

Prepared according to the procedure described in Example 66 but using instead N-cyclopropyl-N-(2,3-dichlorobenzyl)-O-[2-(2,6-dichloro-4-methylphenoxy)ethyl]tyrosinamide (Example 28) as starting material. The title compound was obtained as a colorless oil. MS (ESI+): 625.0.

Example 68

2-Amino-N-[2-chloro-5-(3-methoxypropyl)benzyl]-N-cyclopropyl-3-{4-[2-(2,6-dichloro-4-methylphenoxy)ethoxy]benzyl}propanamide

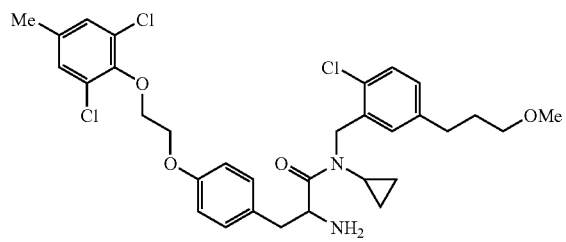

Prepared according to the procedure described in Example 28 but using instead Amine 6 as starting material. The title compound was obtained as a colorless oil. MS (ESI+): 619.5.

Example 69

2-{[Amino(imino)methyl]amino}-N-[2-chloro-5-(3-methoxypropyl)benzyl]-N-cyclopropyl-3-{4-[2-(2,6-dichloro-4-methylphenoxy)ethoxy]benzyl}propanamide

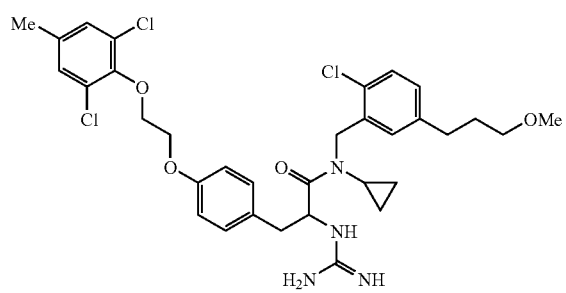

Prepared according to the procedure described in Example 66 but using instead 2-amino-N-[2-chloro-5-(3-methoxypropyl)benzyl]-N-cyclopropyl-3-{4-[2-(2,6-dichloro-4-methylphenoxy)ethoxy]benzyl}propanamide (Example 68) as starting material. The title compound was obtained as a colorless oil. MS (ESI+): 661.1.

Example 70

3-Amino-N-cyclopropyl-2-{4-[2-(2,6-dichloro-4-methylphenoxy)ethoxy]benzyl}-N-[3-hydroxy-5-(3-methoxypropyl)benzyl]propanamide

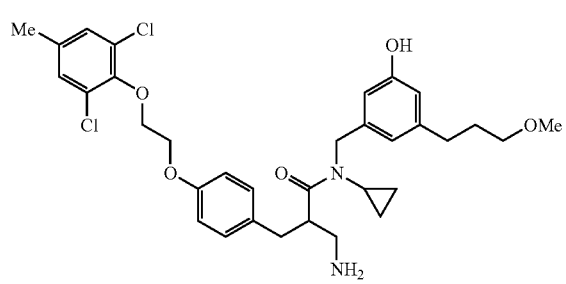

Step 1: tert-Butyl (3-[[3-{[tert-butyl(dimethyl)silyl]oxy}-5-(3-methoxypropyl)benzyl](cyclopropyl)amino]-2-{4-[2-(2,6-dichloro-4-methylphenoxy)ethoxy]benzyl}-3-oxopropyl)carbamate 3-[tert-Butoxycarbonyl)amino]-2-{4-[2-(2,6-dichloro-4-methylphenoxy)ethoxy]benzyl}propanoic acid from Example 9, Step 3 (1 eq.) was combined with Hunig's base (3 eq.) and Amine 36 (1 eq.) in anhydrous DMF (0.5 M). To this was then added portionwise O-(7-azabenzotriazol-1-yl)-N,N,N',N'-tetramethyluronium hexafluorophosphate (1.2 eq.). The resulting yellow solution was stirred at RT for 18 h. The now reddish solution was diluted with ether and washed with H$_2$O. The aqueous washes were back extracted with ether. The combined organic extracts were washed with brine, dried over MgSO$_4$, filtered and the filtrate concentrated in vacuo. Purification of the crude product thus obtained by way of flash chromatography (SiO$_2$, 3:1 (v/v) Hex:EtOAc) afforded the title compound as a colorless oil.

Step 2: tert-Butyl (3-{cyclopropyl[3-hydroxy-5-(3-methoxypropyl)benzyl](cyclopropyl)amino}-2-{4-[2-(2,6-dichloro-4-methylphenoxy)ethoxy]benzyl}-3-oxopropyl)carbamate To a solution of tert-butyl (3-[[3-{[tert-butyl(dimethyl)silyl]oxy}-5-(3-methoxypropyl)benzyl] (cyclopropyl)amino]-2-{4-[2-(2,6-dichloro-4-methylphenoxy)ethoxy]benzyl}-3-oxopropyl)carbamate from the previous step (1 eq.) in THF (0.05 M) was added tetrabutylammonium fluoride (1.0 M THF solution, 1.5 eq.). The resulting golden yellow solution was stirred at RT for 8 h. The reaction mixture was quenched with sat. aq. NH$_4$Cl and then extracted with ether. The combined organic extracts were washed with brine, dried over MgSO$_4$, filtered and the filtrate concentrated in vacuo. Purification of the crude product thus obtained by way of flash chromatography (SiO$_2$, 2:1 (v/v) Hex:EtOAc→1:1 (v/v) Hex:EtOAc) afforded the title compound as a white semisolid.

Step 3: 3-Amino-N-cyclopropyl-2-{4-[2-(2,6-dichloro-4-methylphenoxy)ethoxy]benzyl}-N-[3-hydroxy-5-(3-methoxypropyl)benzyl]propanamide To a CH$_2$Cl$_2$ solution (0.08 M) of tert-butyl (3-{cyclopropyl[3-hydroxy-5-(3-methoxypropyl)benzyl] (cyclopropyl)amino}-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.). The resulting solution was stirred at RT for 3 h. Following the removal of the volatiles in vacuo, the resulting residue was directly loaded onto a SiO$_2$ column packed with 92:8 (v/v) CH$_2$Cl$_2$: 2.0 M NH$_3$ in MeOH. Elution with the same solvent system furnished the title compound as a white froth. MS (ESI+): 615.0.

Example 71

3-Amino-N-cyclopropyl-2-{4-[2-(2,6-dichloro-4-methylphenoxy)ethoxy]benzyl}-N-[3-(3-methoxypropyl)-5-(2-pyrrolidin-1-ylethoxy)benzyl]propanamide

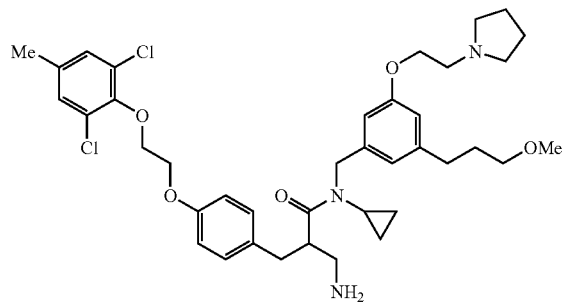

Step 1: tert-Butyl (3-{cyclopropyl[3-(3-methoxypropyl)-5-(2-pyrrolidin-1-ylethoxy)benzyl]amino}-2-{4-[2-(2,6-dichloro-4-methylphenoxy)ethoxy]benzyl}-3-oxopropyl)carbamate To a solution of tert-butyl (3-{cyclopropyl[3-hydroxy-5-(3-methoxypropyl)benzyl](cyclopropyl)amino}-2-{4-[2-(2,6-dichloro-4-methylphenoxy)ethoxy]benzyl}-3-oxopropyl)carbamate from Example 70, Step 2 (1 eq.) in DMF (0.05 M) was added 1-(2-chloroethyl)pyrrolidine (1.2 eq.) and cesium carbonate (1.3 eq.). The resulting suspension was heated at 60° C. for 5 h. The reaction mixture was quenched sat. aq. NaHCO$_3$ and then extracted with ether. The combined organic extracts were washed with water and brine, dried over MgSO$_4$, filtered and the filtrate concentrated in vacuo. Purification of the crude product thus obtained by way of flash chromatography (SiO$_2$, CH$_2$Cl$_2$→95:5 (v/v) CH$_2$Cl$_2$: 2.0 M NH$_3$ in MeOH) afforded the title compound as a colorless oil.

Step 2: 3-Amino-N-cyclopropyl-2-{4-[2-(2,6-dichloro-4-methylphenoxy)ethoxy]benzyl}-N-[3-(3-methoxypropyl)-5-(2-pyrrolidin-1-ylethoxy)benzyl]propanamide To a CH$_2$Cl$_2$ solution (0.03 M) of tert-butyl (3-{cyclopropyl[3-(3-methoxypropyl)-5-(2-pyrrolidin-1-ylethoxy)benzyl]amino}-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.). The resulting solution was stirred at RT for 3 h. Following the removal of the volatiles in vacuo, the resulting residue was directly subjected to column chromatography (SiO$_2$, CH$_2$Cl$_2$→90:10 (v/v) CH$_2$Cl$_2$:2.0 M NH$_3$ in MeOH) to afford the title compound. MS (ESI+): 712.2.

Example 72

3-Amino-N-cyclopropyl-2-{4-[2-(2,6-dichloro-4-methylphenoxy)ethoxy]benzyl}-N-[3-(3-methoxypropyl)-5-(pyridin-2-ylmethoxy)benzyl]propanamide

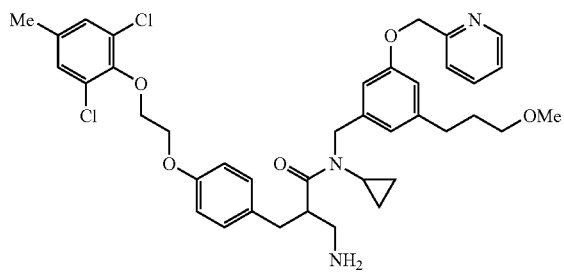

Prepared according to the procedure described in Example 71 but using instead 2-(chloromethyl)pyridine as starting material. The title compound was obtained as a colorless oil. MS (ESI+): 706.4.

Example 73

3-Amino-N-cyclopropyl-2-{4-[2-(2,6-dichloro-4-methylphenoxy)ethoxy]benzyl}-N-[3-(2-methoxyethoxy)-5-(3-methoxypropyl)benzyl]propanamide

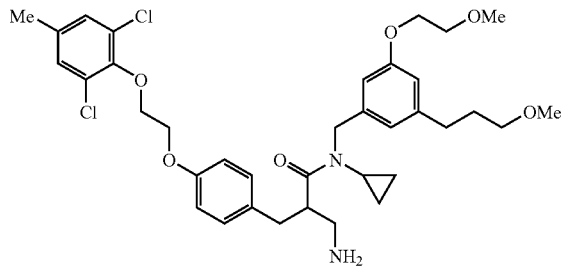

Prepared according to the procedure described in Example 71 but using instead 2-bromoethyl methyl ether as starting material. The title compound was obtained as a colorless oil. MS (ESI+): 673.2.

Example 74

3-Amino-N-[3-(3-cyanopropoxy)-5-(3-methoxypropyl)benzyl]-N-cyclopropyl-2-{4-[2-(2,6-dichloro-4-methylphenoxy)ethoxy]benzyl}propanamide

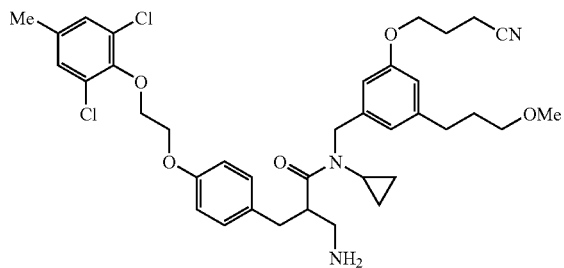

Prepared according to the procedure described in Example 71 but using instead 4-bromobutanenitrile as starting material. The title compound was obtained as a colorless oil. MS (ESI+): 682.2.

Example 75

3-Amino-N-cyclopropyl-2-{4-[2-(2,6-dichloro-4-methylphenoxy)ethoxy]benzyl}-N-{3-(3-methoxypropyl)-5-[(3-methylthio)propoxy]benzyl}propanamide

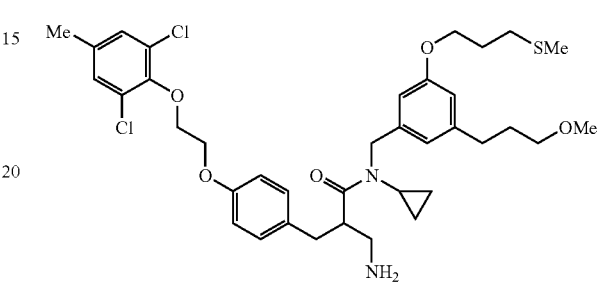

Step 1: 3-(Methylthio)propyl methanesulfonate

To a solution of 3-(methylthio)propan-1-ol in dichloromethane (0.2 M) was added sequentially at −78° C. Hunig's base (1.3 eq.) and methanesulfonyl chloride (1.3 eq.). The resulting reaction mixture was stirred at −78° C. for 1 h and then warmed slowly to RT. The reaction was quenched with sat. aq. NH$_4$Cl and then extracted with ether. The combined organic extracts were washed with water and brine, dried over MgSO$_4$, and filtered. Concentrated of the filtrate in vacuo afforded the title compound as a yellow oil.

Step 2: tert-Butyl (3-{cyclopropyl{3-(3-methoxypropyl)-5-[3-(methylthio)propoxy]benzyl}amino)-2-{4-[2-(2,6-dichloro-4-methylphenoxy)ethoxy]benzyl}-3-oxopropyl)carbamate To a solution of tert-butyl (3-{cyclopropyl[3-hydroxy-5-(3-methoxypropyl)benzyl](cyclopropyl)amino}-2-{4-[2-(2,6-dichloro-4-methylphenoxy)ethoxy]benzyl}-3-oxopropyl)carbamate from Example 70, Step 2 (1 eq.) in DMF (0.05 M) was added 3-(methylthio)propyl methanesulfonate from the previous step (1.4 eq.) and cesium carbonate (1.4 eq.). The resulting suspension was heated at 60° C. for 12 h. The reaction mixture was quenched sat. aq. NaHCO$_3$ and then extracted with ether. The combined organic extracts were washed with water and brine, dried over MgSO$_4$, filtered and the filtrate concentrated in vacuo. Purification of the crude product thus obtained by way of flash chromatography (SiO$_2$, 3:2 (v/v) Hex:EtOAc→2:3 (v/v) Hex:EtOAc) afforded the title compound as a colorless oil.

Step 3: 3-Amino-N-cyclopropyl-2-{4-[2-(2,6-dichloro-4-methylphenoxy)ethoxy]benzyl}-N-{3-(3-methoxypropyl)-5-[(3-methylthio)propoxy]benzyl}propanamide To a CH$_2$Cl$_2$ solution (0.08 M) of tert-butyl (3-{cyclopropyl{3-(3-methoxypropyl)-5-[3-(methylthio)propoxy]benzyl}amino)-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.). The resulting solution was stirred at RT for 3 h. Following the removal of the volatiles in vacuo, the resulting residue was directly subjected to column chromatography (SiO$_2$, CH$_2$Cl$_2$→95:5 (v/v) CH$_2$Cl$_2$:2.0 M NH$_3$ in MeOH) to afford the title compound. MS (ESI+): 703.0.

Example 76

3-Amino-N-cyclopropyl-2-{4-[2-(2,6-dichloro-4-methylphenoxy)ethoxy]benzyl}-N-{3-(3-methoxypropyl)-5-[(3-methylsulfonyl)propoxy]benzyl}propanamide

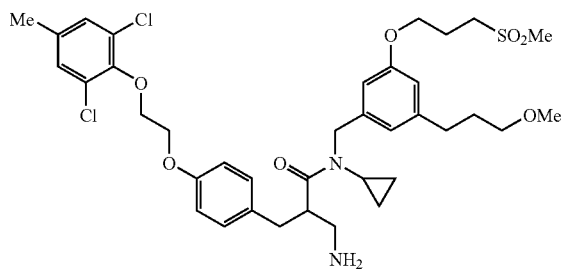

Step 1: tert-Butyl (3-{cyclopropyl{3-(3-methoxypropyl)-5-[3-(methyl sulfonyl)propoxy]benzyl}amino)-2-{4-[2-(2,6-dichloro-4-methylphenoxy)ethoxy]benzyl}-3-oxopropyl)carbamate To tert-butyl (3-{cyclopropyl{3-(3-methoxypropyl)-5-[3-(methylthio)propoxy]benzyl}amino)-2-{4-[2-(2,6-dichloro-4-methylphenoxy)ethoxy]benzyl}-3-oxopropyl)carbamate from Example 75, Step 2 (1 eq.) in a 1:1 (v/v) methanol:water solution (0.05 M) was added Oxone™ (2.5 eq.) and sodium bicarbonate (10 eq.). The reaction mixture was stirred at RT for 1 h. The volatiles were then removed in vacuo and the result residue was extracted with ether. The combined organic extracts were washed with water and brine, dried over MgSO$_4$, filtered and the filtrate concentrated in vacuo. Purification of the crude product thus obtained by way of flash chromatography (SiO$_2$, 3:2 (v/v) Hex:EtOAc→1:3 (v/v) Hex:EtOAc) afforded the title compound as a colorless oil.

Step 2: 3-Amino-N-cyclopropyl-2-{4-[2-(2,6-dichloro-4-methylphenoxy)ethoxy]benzyl}-N-{3-(3-methoxypropyl)-5-[(3-methylsulfonyl)propoxy]benzyl}propanamide To a CH$_2$Cl$_2$ solution (0.08 M) of tert-butyl (3-{cyclopropyl{3-(3-methoxypropyl)-5-[3-(methylsulfonyl)propoxy]benzyl}amino)-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.). The resulting solution was stirred at RT for 4 h. Following the removal of the volatiles in vacuo, the resulting residue was directly subjected to column chromatography (SiO$_2$, CH$_2$Cl$_2$→92:8 (v/v) CH$_2$Cl$_2$:2.0 M NH$_3$ in MeOH) to afford the title compound. MS (ESI+): 734.8.

Example 77

3-Amino-N-cyclopropyl-2-{4-[2-(2,6-dichloro-4-methylphenoxy)ethoxy]benzyl}-N-[3-(3-methoxypropyl)-5-(pyridin-3-ylmethoxy)benzyl]propanamide

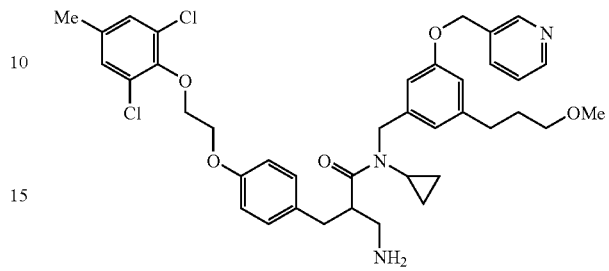

Prepared according to the procedure described in Example 71 but using instead 3-(chloromethyl)pyridine as starting material. The title compound was obtained as a pale yellow oil. MS (ESI+): 706.4.

Example 78

3-Amino-N-cyclopropyl-2-{4-[2-(2,6-dichloro-4-methylphenoxy)ethoxy]benzyl}-N-[3-(3-methoxypropyl)-5-(pyridin-4-ylmethoxy)benzyl]propanamide

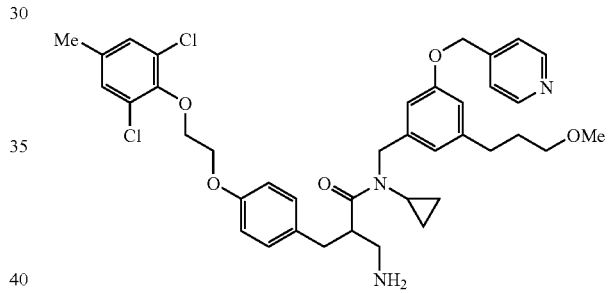

Prepared according to the procedure described in Example 71 but using instead 4-(chloromethyl)pyridine as starting material. The title compound was obtained as a pale yellow oil. MS (ESI+): 706.4.

Example 79

3-Amino-N-cyclopropyl-2-{4-[2-(2,6-dichloro-4-methylphenoxy)ethoxy]benzyl}-N-{3-(3-methoxypropyl)-5-[(1-oxidopyridin-2-yl)methoxy]benzyl}propanamide

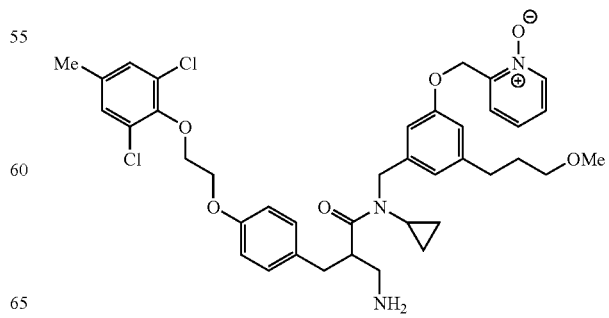

Step 1: tert-Butyl (3-(cyclopropyl{3-(3-methoxypropyl)-5-[(1-oxidopyridin-2-yl)methoxy]benzyl}amino)-2-{4-[2-(2,6-dichloro-4-methylphenoxy)ethoxy]benzyl}-3-oxopropyl)carbamate To a solution of tert-butyl (3-{cyclopropyl[3-(3-methoxypropyl)-5-(pyridin-2-ylmethoxy)benzyl]amino}-2-{4-[2-(2,6-dichloro-4-methylphenoxy)ethoxy]benzyl}-3-oxopropyl)carbamate from Example 72, Step 1 (1 eq.) in dichloromethane (0.02 M) was added 3-chloroperoxybenzoic acid (2 eq.). The reaction mixture was stirred at RT for 1 h. The reaction was quenched with sat. aq. NaHCO$_3$ and then extracted with ether. The combined organic extracts were washed with water and brine, dried over MgSO$_4$, filtered and the filtrate concentrated in vacuo. Purification of the crude product thus obtained by way of flash chromatography (SiO$_2$, CH$_2$Cl$_2$→97:3 (v/v) CH$_2$Cl$_2$: 2.0 M NH$_3$ in MeOH) afforded the title compound.

Step 2: 3-Amino-N-cyclopropyl-2-{4-[2-(2,6-dichloro-4-methylphenoxy)ethoxy]benzyl}-N-{3-(3-methoxypropyl)-5-[(1-oxidopyridin-2-yl)methoxy]benzyl}propanamide To a CH$_2$Cl$_2$ solution (0.03 M) of tert-butyl (3-(cyclopropyl{3-(3-methoxypropyl)-5-[(1-oxidopyridin-2-yl)methoxy]benzyl}amino)-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.).

The resulting solution was stirred at RT for 24 h. Following the removal of the volatiles in vacuo, the resulting residue was directly subjected to column chromatography (SiO$_2$, 98:2 (v/v) CH$_2$Cl$_2$: 2.0 M NH$_3$ in MeOH→90:10 (v/v) CH$_2$Cl$_2$: 2.0 M NH$_3$ in MeOH) to afford the title compound. MS (ESI+): 721.8.

Example 80

3-Amino-N-cyclopropyl-2-{4-[2-(2,6-dichloro-4-methylphenoxy)ethoxy]benzyl}-N-{3-(3-methoxypropyl)-5-[(1-oxidopyridin-3-yl)methoxy]benzyl}propanamide

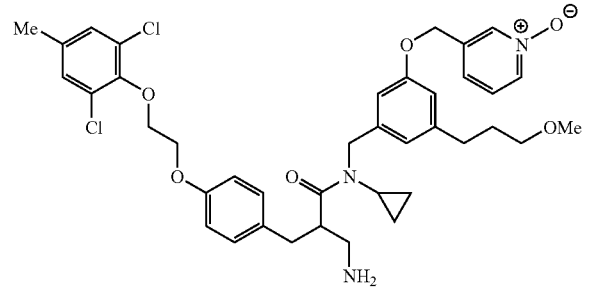

Prepared according to the procedure described in Example 79 but using instead tert-butyl (3-{cyclopropyl[3-(3-methoxypropyl)-5-(pyridin-3-ylmethoxy)benzyl]amino}-2-{4-[2-(2,6-dichloro-4-methylphenoxy)ethoxy]benzyl}-3-oxopropyl)carbamate from Example 77, Step 1 as starting material. The title compound was obtained as a colorless oil. MS (ESI+): 721.8.

Example 81

3-Amino-N-cyclopropyl-2-{4-[2-(2,6-dichloro-4-methylphenoxy)ethoxy]benzyl}-N-{3-(3-methoxypropyl)-5-[(1-oxidopyridin-4-yl)methoxy]benzyl}propanamide

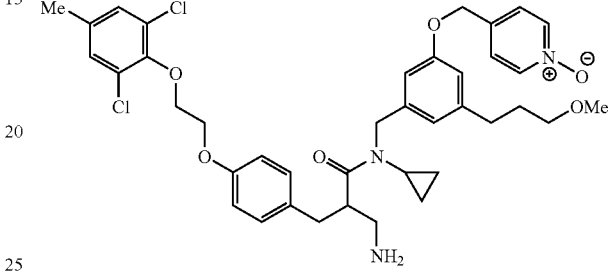

Prepared according to the procedure described in Example 79 but using instead tert-butyl (3-{cyclopropyl[3-(3-methoxypropyl)-5-(pyridin-4-ylmethoxy)benzyl]amino}-2-{4-[2-(2,6-dichloro-4-methylphenoxy)ethoxy]benzyl}-3-oxopropyl)carbamate from Example 78, Step 1 as starting material. The title compound was obtained as a colorless oil. MS (ESI+): 721.8.

Example 82

3-Amino-N-cyclopropyl-2-{4-[2-(2,6-dichloro-4-methylphenoxy)ethoxy]benzyl}-A-[3-(3-methoxypropyl)-5-(2-pyridin-2-ylethoxy)benzyl]propanamide

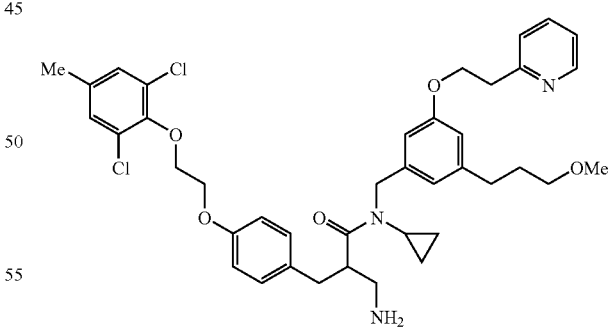

Step 1: tert-Butyl (3-{cyclopropyl[3-(3-methoxypropyl)-5-(2-pyridin-2-ylethoxy)benzyl]amino}-2-{4-[2-(2,6-dichloro-4-methylphenoxy)ethoxy]benzyl}-3-oxopropyl)carbamate To a solution of tert-butyl (3-{cyclopropyl[3-hydroxy-5-(3-methoxypropyl)benzyl] (cyclopropyl)amino}-2-{4-[2-(2, 6-dichloro-4-methylphenoxy)ethoxy]benzyl}-3-oxopropyl) carbamate from Example 70, Step 2 (1 eq.) in toluene (0.1 M) was added 2-pyridin-2-ylethanol (1.2 eq.) and 1,1'-(azodicarbonyl)-dipiperidine (1.2 eq.). The resulting orange solution was deoxygenated before tributylphosphine (1.2 eq.) was added. The now yellow-orange solution was heated at 100° C. for 14 h. The reaction mixture was cooled to RT, diluted with ether, and washed with 1 N aq. NaOH. The aqueous wash was back extracted with ether and the combined organic extracts were dried over MgSO$_4$. Filtration and concentration of the filtrate in vacuo afforded a red oil. Purification of the crude product thus obtained by way of flash chromatography (SiO$_2$, 4:1 (v/v) Hex:EtOAc→EtOAc) afforded the title compound as a pale yellow oil.

Step 2: 3-Amino-N-cyclopropyl-2-{4-[2-(2,6-dichloro-4-methylphenoxy)ethoxy]benzyl}-N-[3-(3-methoxypropyl)-5-(2-pyridin-2-ylethoxy)benzyl] propanamide To a CH$_2$Cl$_2$ solution (0.03 M) of tert-butyl (3-{cyclopropyl[3-(3-methoxypropyl)-5-(2-pyridin-2-ylethoxy)benzyl] amino}-2-{4-[2-(2,6-dichloro-4-methylphenoxy)ethoxy] benzyl}-3-oxopropyl)carbamate from the previous step (1 eq.) was added HCl (4.0 M dioxane solution, 30 eq.). The resulting solution was stirred at RT for 12 h. Following the removal of the volatiles in vacuo, the resulting residue was directly subjected to column chromatography (SiO$_2$, 90:10 (v/v) CH$_2$Cl$_2$: 2.0 M NH$_3$ in MeOH) to afford the title compound as a white froth. MS (ESI+): 720.0.

Example 83

3-Amino-N-cyclopropyl-2-{4-[2-(2,6-dichloro-4-methylphenoxy)ethoxy]benzyl}-N-{3-(3-methoxypropyl)-5-[2-(1-oxidopyridin-2-yl)ethoxy] benzyl}propanamide

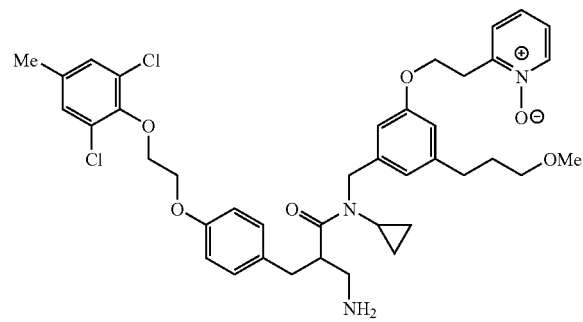

Prepared according to the procedure described in Example 79 but using instead tert-butyl (3-{cyclopropyl[3-(3-methoxypropyl)-5-(2-pyridin-2-ylethoxy)benzyl]amino}-2-{4-[2-(2,6-dichloro-4-methylphenoxy)ethoxy]benzyl}-3-oxopropyl)carbamate from Example 82, Step 1 as starting material. The title compound was obtained as a white froth. MS (ESI+): 735.9.

Example 84

3-Amino-N-cyclopropyl-2-{4-[2-(2,6-dichloro-4-methylphenoxy)ethoxy]benzyl}-N-[3-(3-methoxypropyl)-5-(2-morpholin-4-ylmethoxy)benzyl]propanamide

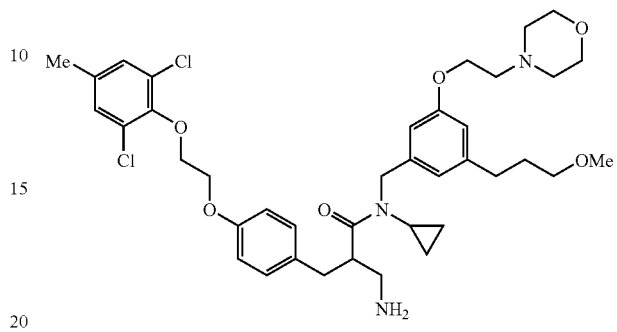

Prepared according to the procedure described in Example 71 but using instead 4-(2-chloroethyl)morpholine as starting material. The title compound was obtained as a colorless oil. MS (ESI+): 728.0.

Example 85

3-Amino-N-cyclopropyl-2-{4-[2-(2,6-dichloro-4-methylphenoxy)ethoxy]benzyl}-N-[3-(3-methoxypropyl)-5-{[4-(methylsulfonyl)benzyl]oxy}benzyl) propanamide

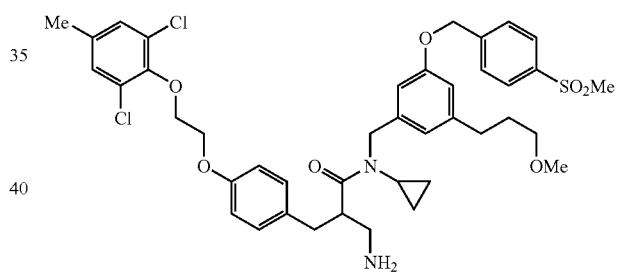

Prepared according to the procedure described in Example 71 but using instead 4-(chloromethyl)phenyl methyl sulfone as starting material. The title compound was obtained as a colorless oil. MS (ESI+): 782.8.

Example 86

Ethyl 2-{[3-{[(3-amino-2-{4-[2-(2,6-dichloro-4-methylphenoxy)ethoxy]benzyl}propanoyl) (cyclopropyl)amino]methyl}-5-(3-methoxypropyl)phenoxy]methyl}cyclopropanecarboxylate

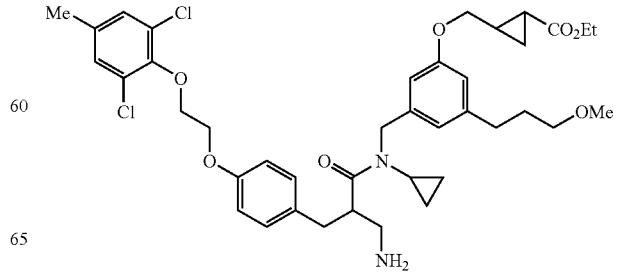

Step 1: Ethyl 2-(hydroxymethyl)cyclopropanecarboxylate

To a solution of ethyl 2-formylcyclopropanecarboxylate in methanol (0.7 M) was added at −0° C. sodium borohydride portionwise. The resulting reaction mixture was stirred at 0° C. for 30 min and then at RT for 1.5 h. The reaction was quenched with sat. aq. $NH_4Cl$ and then extracted with ether. The combined organic extracts were washed with water and brine, dried over $MgSO_4$, and filtered. Concentrated of the filtrate in vacuo afforded the title compound as a colorless oil.

Step 2: Ethyl 2-{[3-{[(3-[tert-butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenoxy]methyl}cyclopropanecarboxylate To a solution of tert-butyl (3-{cyclopropyl[3-hydroxy-5-(3-methoxypropyl)benzyl](cyclopropyl)amino}-2-{4-[2-(2,6-dichloro-4-methylphenoxy)ethoxy]benzyl}-3-oxopropyl)carbamate from Example 70, Step 2 (1 eq.) in toluene (0.06 M) was added ethyl 2-(hydroxymethyl)cyclopropanecarboxylate from the previous step (2 eq.) and 1,1'-(azodicarbonyl)-dipiperidine (2.4 eq.). The resulting orange solution was deoxygenated before tributylphosphine (2.4 eq.) was added. The now yellow-orange solution was heated at 80° C. for 24 h. The reaction mixture was cooled to RT, quenched with water and diluted with EtOAc. The biphasic mixture was vigorously stirred at RT for 16 h. The organic layer was then separated and washed sequentially with water, 5% aq. HCl, sat. aq. $NaHCO_3$ and brine. The organic layer was dried over $MgSO_4$, filtered and the filtrate concentrated in vacuo. Purification of the crude product thus obtained by way of flash chromatography ($SiO_2$, 10:1 (v/v) toluene:acetone) afforded the title compound as a colorless oil.

Step 3: Ethyl 2-{[3-{[(3-amino-2-{4-[2-(2,6-dichloro-4-methylphenoxy)ethoxy]benzyl}propanoyl) (cyclopropyl)amino]methyl}-5-(3-methoxypropyl)phenoxy]methyl}cyclopropanecarboxylate To a $CH_2Cl_2$ solution (0.03 M) of ethyl 2-{[3-{[(3-[tert-butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenoxy]methyl}cyclopropanecarboxylate from the previous step (1 eq.) was added HCl (4.0 M dioxane solution, 25 eq.). The resulting solution was stirred at RT for 3 h. Following the removal of the volatiles in vacuo, the resulting residue was directly subjected to column chromatography ($SiO_2$, 95:5 (v/v) $CH_2Cl_2$: 2.0 M $NH_3$ in MeOH) to afford the title compound as a colorless oil. MS (ESI+): 741. $^1$H NMR (acetone-$d_6$): 0.31 (m, 1H), 0.65-0.69 (m, 2H), 0.88 (m, 1H), 1.05 (m, 1H), 1.18 (m, 1H), 1.24 (t, J=6.9 Hz, 3H), 1.74 (m, 1H), 1.75-1.9 (m, 3H), 2.33 (s, 3H), 2.41 (m, 1H), 2.61 (t, J=7.5 Hz, 2H), 2.74-2.83 (m, 4H), 2.90 (t, J=10.7 Hz, 1H), 3.28 (s, 3H), 3.30-3.34 (m, 2H), 3.59 (t, J=10.6 Hz, 1H), 3.83 (t, J=7.4 Hz, 1H), 3.95-4.07 (m, 2H), 4.09-4.12 (m, 2H), 4.26 (d, J=14.9 Hz, 1H), 4.37-4.40 (m, 4H), 4.67 (d, J=14.9 Hz, 1H), 6.65 (br s, 3H), 6.86 (d, J=7.1 Hz, 2H), 7.16 (d, J=7.1 Hz, 2H), 7.27 (s, 2H).

Example 87

Sodium 2-{[3-{[(3-amino-2-{4-[2-(2,6-dichloro-4-methylphenoxy)ethoxy]benzyl}propanoyl) (cyclopropyl)amino]methyl}-5-(3-methoxypropyl)phenoxy]methyl}cyclopropanecarboxylate

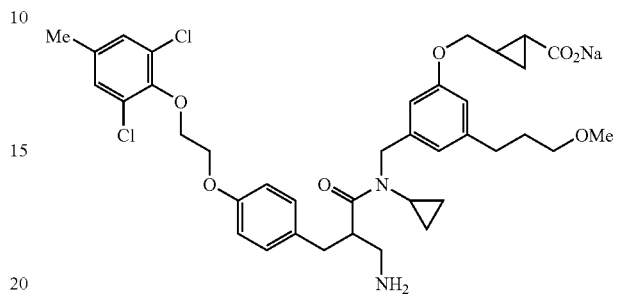

To a ethanol solution (0.03 M) of ethyl 2-{[3-{[(3-amino-2-{4-[2-(2,6-dichloro-4-methylphenoxy)ethoxy]benzyl}propanoyl) (cyclopropyl)amino]methyl}-5-(3-methoxypropyl)phenoxy]methyl}cyclopropanecarboxylate from Example 86 was added sodium hydroxide (1 N aqueous solution, 2.2 eq.). The resulting solution was stirred at 80° C. for 18 h. The volatiles were removed in vacuo and the resulting solid residue was suspended in dichloromethane. The insolubles were then filtered off and the filtrate was concentrated in vacuo to afford the title compound as a white solid. MS for the corresponding free acid (ESI+): 713.2. $^1$H NMR (methanol-$d_4$): 0.41 (m, 1H), 0.70-0.83 (m, 4H), 1.11 (m, 1H), 1.52 (m, 1H), 1.72 (m, 1H), 1.80-1.87 (m, 2H), 2.24 (m, 1H), 2.31 (s, 3H), 2.59-2.62 (m, 2H), 2.75-2.80 (m, 2H), 2.84 (dd, J=13.2, 9.5 Hz, 1H), 2.95 (dd, J=12.7, 7.5 Hz, 1H), 3.31 (s, 3H), 3.37 (t, J=6.4 Hz, 2H), 3.73 (7l, 1H), 3.85 (d, J=6.7 Hz, 2H), 4.22-4.45 (m, 4H), 4.48 (d, J=14.6 Hz, 1H), 4.58 (d, J=14.8 Hz, 1H), 6.58 (s, 1H), 6.62 (s, 1H), 6.65 (s, 1H), 6.78 (d, J=8.6 Hz, 2H), 7.08 (d, J=8.5 Hz, 2H), 7.22 (s, 2H).

Example 88

Ethyl 2-{[3-{[(3-amino-2-{4-[2-(2,6-dichloro-4-methylphenoxy)ethoxy]benzyl}propanoyl) (cyclopropyl)amino]methyl}-2-chloro-5-(3-methoxypropyl)phenoxy]methyl}cyclopropanecarboxylate

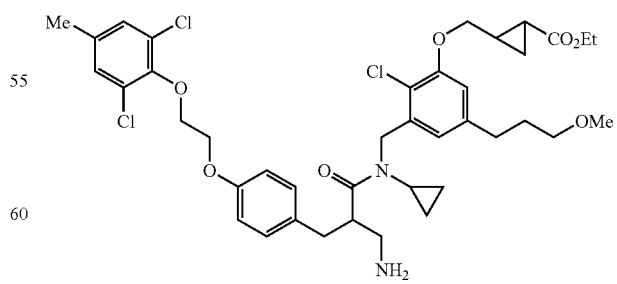

Prepared according to the procedure described in Example 9 but using instead Amine 37 as starting material. The title compound was obtained as a colorless oil. MS (ESI+): 777.2.

Example 89

Sodium 2-{[3-{[(3-amino-2-{-4-[2-(2,6-dichloro-4-methylphenoxy)ethoxy]benzyl}propanoyl)(cyclopropyl)amino]methyl}-2-chloro-5-(3-methoxypropyl)phenoxy]methyl}cyclopropanecarboxylate

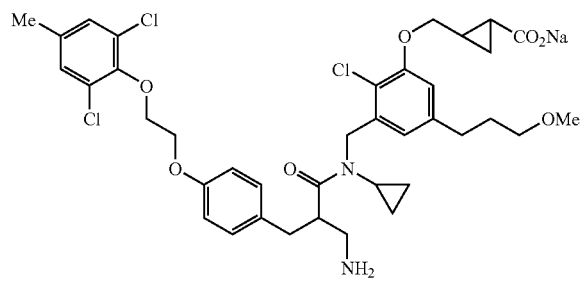

Prepared according to the procedure described in Example 87 but using instead ethyl 2-{[3-{[(3-amino-2-{4-[2-(2,6-dichloro-4-methylphenoxy)ethoxy]benzyl}propanoyl)(cyclopropyl)amino]methyl}-2-chloro-5-(3-methoxypropyl)phenoxy]methyl}cyclopropanecarboxylate from Example 88 as starting material. The title compound was obtained as a white solid. MS for the corresponding free acid (ESI+): 747.3.

Example 90

Ethyl 2-[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]-2-methylpropanoate

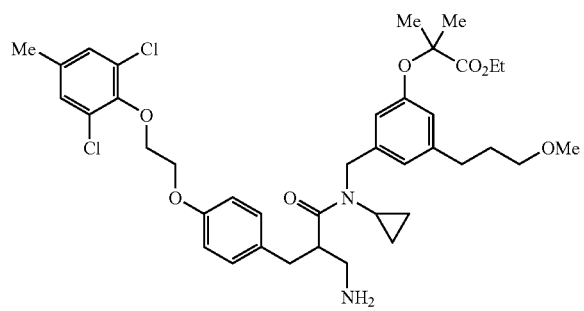

Prepared according to the procedure described in Example 71 but using instead ethyl 2-bromo-2-methylpropanoate as starting material. The title compound was obtained as a colorless oil. MS (ESI+): 729.

Example 91

Sodium 2-[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]-2-methylpropanoate

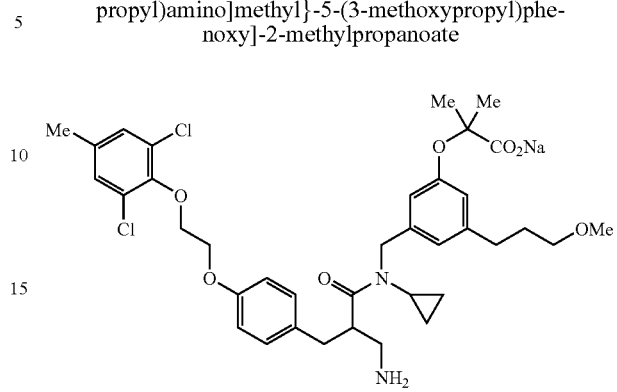

Prepared according to the procedure described in Example 87 but using instead ethyl 2-[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]-2-methylpropanoate from Example 90 as starting material. The title compound was obtained as a white foam. MS for the corresponding free acid (ESI+): 700.

Example 92

3-Amino-N-[3,5-bis(2-methoxyethoxy)benzyl]-N-cyclopropyl-2-{4-[2-(2,6-dichloro-4-methylphenoxy)ethoxy]benzyl}propanamide

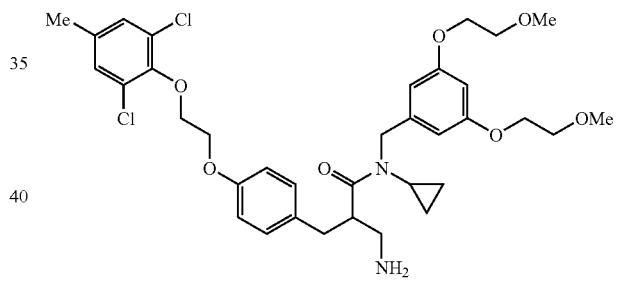

Prepared according to the procedure described in Example 9 but using instead Amine 38 as starting material. The title compound was obtained as a colorless oil. MS (ESI+): 672.0.

Example 93

3-Amino-N-[3,5-bis(4,4,4-trifluorobutoxy)benzyl]-N-cyclopropyl-2-{4-[2-(2,6-dichloro-4-methylphenoxy)ethoxy]benzyl}propanamide

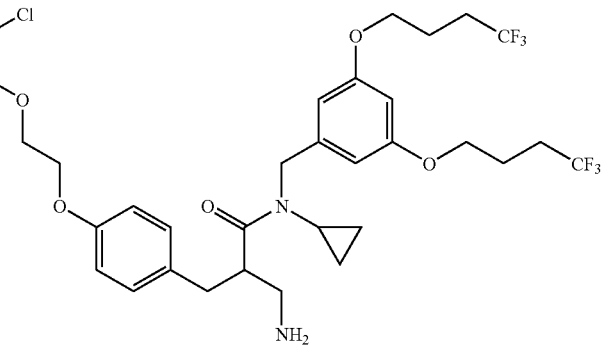

Prepared according to the procedure described in Example 9 but using instead Amine 39 as starting material. The title compound was obtained as a pale yellow oil. MS (ESI+): 779.1.

Example 94

3-Amino-N-cyclopropyl-2-{4-[2-(2,6-dichloro-4-methylphenoxy)ethoxy]benzyl}-N-{3-(3-methoxypropyl)-5-[3-(1H-tetrazol-5-yl)propoxy]benzyl}propanamide

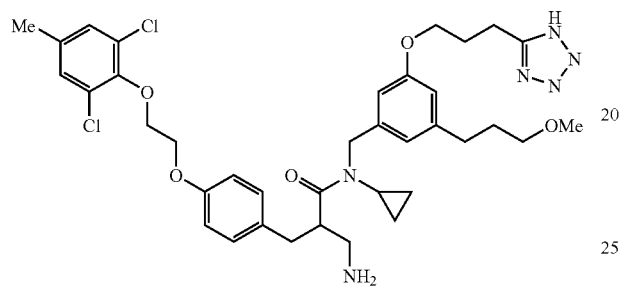

To a solution of tert-butyl (3-[[3-(3-cyanopropoxy)-5-(3-methoxypropyl)benzyl](cyclopropyl)amino]-2-{4-[2-(2,6-dichloro-4-methylphenoxy)ethoxy]benzyl}-3-oxopropyl)carbamate from Example 74 in dichlorobenzene (0.08 M) was added azidotributyltin (2 eq.). The resulting mixture was heated to 150° C. for 22 h. The reaction was quenched with glacial acetic acid (6 eq.) and directly loaded onto a silica gel column packed with 85:15 (v/v) CH$_2$Cl$_2$: 2.0 M NH$_3$ in MeOH. Elution with the same solvent system afforded the title compound as a yellow oil. MS (ESI+): 725.4.

Example 95

3-Amino-N-{[5-chloro-2-(3-methoxypropyl)pyridin-4-yl]methyl}-N-cyclopropyl-2-{4-[2-(2,6-dichloro-4-methylphenoxy)ethoxy]benzyl}propanamide

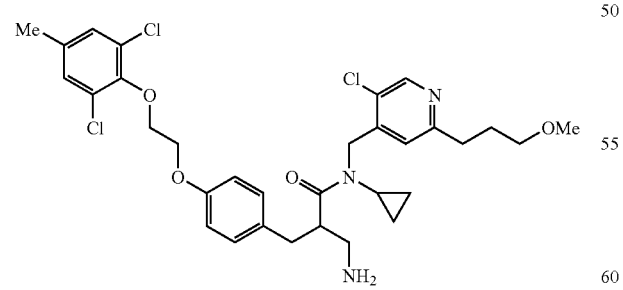

Prepared according to the procedure described in Example 9 but using instead Amine 40 as starting material. The title compound was obtained as a pale yellow oil. MS (ESI+): 779.1.

Example 96

3-Amino-N-{[5-chloro-2-(3-methoxypropyl)-1-oxidopyridin-4-yl]methyl}-A-cyclopropyl-2-{4-[2-(2,6-dichloro-4-methylphenoxy)ethoxy]benzyl}propanamide

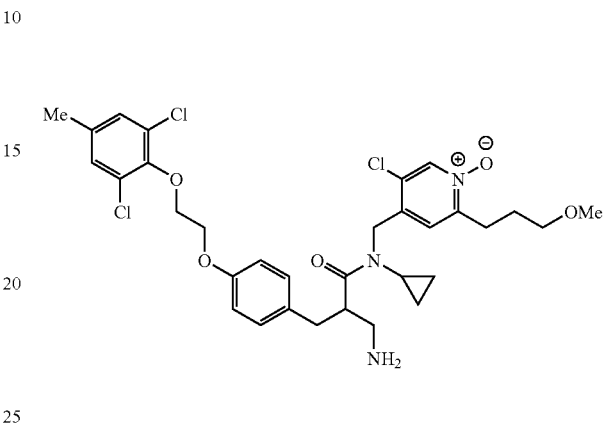

Step 1: tert-Butyl (3-[{[5-chloro-2-(methoxypropyl)-1-oxidopyridin-4-yl]methyl}(cyclopropyl)amino]-2-{4-[2-(2,6-dichloro-4-methylphenoxy)ethoxy]benzyl}-3-oxopropyl)carbamate To a solution of tert-butyl (3-[{[5-chloro-2-(methoxypropyl)pyridin-4-yl]methyl}(cyclopropyl)amino]-2-{4-[2-(2,6-dichloro-4-methylphenoxy)ethoxy]benzyl}-3-oxopropyl)carbamate from Experiment 94, Step 4 in dichloromethane (0.03 M) was added 3-chloroperoxybenzoic acid. The reaction mixture was stirred at RT for 16 h. The reaction was quenched with water and then extracted with EtOAc. The combined organic extracts were washed with 10% aq. HCl and brine, dried over MgSO$_4$, filtered and the filtrate concentrated in vacuo. Purification of the crude product thus obtained by way of flash chromatography (SiO$_2$, 1:1 (v/v) Hex:EtOAc 4 EtOAc) afforded the title compound.

Step 2: 3-Amino-N-{[5-chloro-2-(methoxypropyl)-1-oxidopyridin-4-yl]methyl}-N-cyclopropyl-2-{4-[2-(2,6-dichloro-4-methylphenoxy)ethoxy]benzyl}propanamide To a CH$_2$Cl$_2$ solution (0.07 M) of tert-butyl (3-[{[5-chloro-2-(methoxypropyl)-1-oxidopyridin-4-yl]methyl}(cyclopropyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 30 eq.). The resulting solution was stirred at RT for 16 h. Following the removal of the volatiles in vacuo, the resulting residue was directly subjected to column chromatography (SiO$_2$, 95:5 (v/v) CH$_2$Cl$_2$: 2.0 M NH$_3$ in MeOH) to afford the title compound as an oil. MS (ESI+): 651.

Example 97

3-Amino-N-cyclopropyl-2-{4-[2-(2,6-dichloro-4-methylphenoxy)ethoxy]benzyl}-N-{[2-methoxy-6-(3-methoxypropyl)pyridin-4-yl]methyl}propanamide

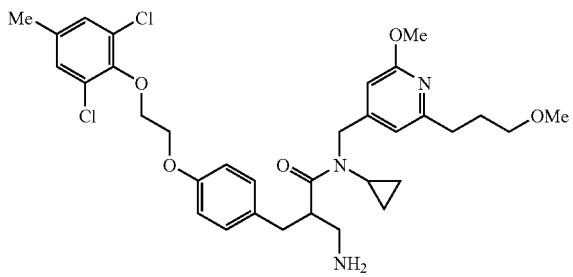

Prepared according to the procedure described in Example 9 but using instead Amine 41 as starting material. The title compound was obtained as a pale yellow oil. MS (ESI+): 630.0.

Example 98

3-Amino-N-cyclopropyl-2-{4-[2-(2,6-dichloro-4-methylphenoxy)ethoxy]benzyl}-N-{[2-hydroxy-6-(3-methoxypropyl)pyridin-4-yl]methyl}propanamide

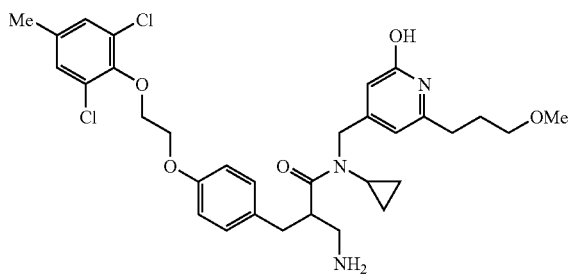

Step 1: tert-Butyl (3-[{[2-{[tert-butyl(dimethyl)silyl]oxy}-6-(3-methoxypropyl)pyridin-4-yl]methyl}(cyclopropyl)amino]-2-{4-[2-(2,6-dichloro-4-methylphenoxy)ethoxy]benzyl}-3-oxopropyl)carbamate 3-[tert-Butoxycarbonyl)amino]-2-{4-[2-(2,6-dichloro-4-methylphenoxy)ethoxy]benzyl}propanoic acid from Example 9, Step 3 (1 eq.) was combined with Hunig's base (3 eq.) and Amine 42 (1.2 eq.) in anhydrous DMF (0.5 M). To this was then added portionwise O-(7-azabenzotriazol-1-yl)-N,N,N',N'-tetramethyluronium hexafluorophosphate (1.2 eq.). The resulting yellow solution was stirred at RT for 48 h. The now reddish solution was diluted with ether and washed with H₂O. The aqueous washes were back extracted with ether. The combined organic extracts were washed with brine, dried over MgSO₄, filtered and the filtrate concentrated in vacuo. Purification of the crude product thus obtained by way of flash chromatography (SiO₂, 3:1 (v/v) Hex: EtOAc→EtOAc) afforded the title compound as a colorless oil.

Step 2: 3-Amino-N-cyclopropyl-2-{4-[2-(2,6-dichloro-4-methylphenoxy)ethoxy]benzyl}-N-{[2-hydroxy-6-(3-methoxypropyl)pyridin-4-yl]methyl}propanamide To a CH₂Cl₂ solution (0.03 M) of tert-butyl (3-[{[2-{[tert-butyl(dimethyl)silyl]oxy}-6-(3-methoxypropyl)pyridin-4-yl]methyl}(cyclopropyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 60 eq.). The resulting solution was stirred at RT for 3 h and the volatiles were removed in vacuo. The resulting residue was recrystallized from ether-dichloromethane to afford the title compound as a white solid. MS (ESI+): 616.1.

Example 99

3-Amino-N-{[2,6-bis(3-methoxypropyl)pyridin-4-yl]methyl}-N-cyclopropyl-2-{4-[2-(2,6-dichloro-4-methylphenoxy)ethoxy]benzyl}propanamide

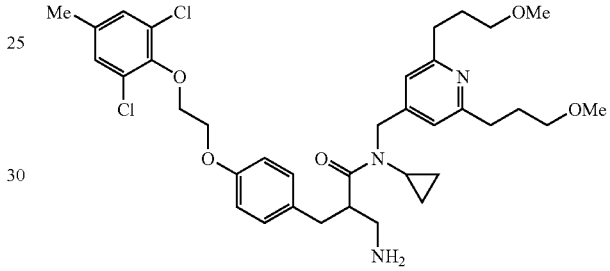

Prepared according to the procedure described in Example 9 but using instead Amine 43 as starting material. The title compound was obtained as a pale yellow oil. MS (ESI+): 672.

Example 100

3-Amino-N-cyclopropyl-2-{4-[2-(2,6-dichloro-4-methylphenoxy)ethoxy]benzyl}-N-({2-(3-methoxypropyl)-6-[3-(methylthio)propoxy]pyridin-4-yl}methyl)propanamide

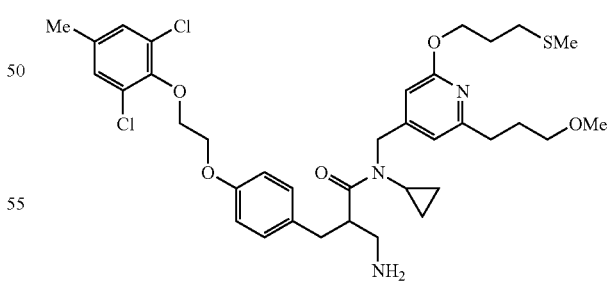

Step 1: tert-Butyl (3-[cyclopropyl({2-(3-methoxypropyl)-6-[3-(methylthio)propoxy]pyridin-4-yl]methyl)amino]-2-{4-[2-(2,6-dichloro-4-methylphenoxy)ethoxy]benzyl}-3-oxopropyl)carbamate 3-[tert-Butoxycarbonyl)amino]-2-{4-[2-(2,6-dichloro-4-methylphenoxy)ethoxy]benzyl}propanoic acid from Example 9, Step 3 (1 eq.) was combined with Hunig's base (3 eq.) and Amine 44 (1.1 eq.) in anhydrous DMF (0.15 M). To this was then added portionwise O-(7-azabenzotriazol-1-yl)-N,N,N',N'-tetramethyluronium hexafluorophosphate (1.2 eq.). The resulting yellow solution was stirred at RT for 18 h. The now reddish solution was diluted with EtOAc and washed with $H_2O$. The aqueous washes were back extracted with EtOAc. The combined organic extracts were washed with brine, dried over $Na_7SO_4$ filtered and the filtrate concentrated in vacuo. Purification of the crude product thus obtained by way of flash chromatography ($SiO_2$, 7:3 (v/v) Hex:EtOAc→1:1 (v/v) Hex:EtOAc) afforded the title compound as a colorless oil.

Step 2: 3-Amino-N-cyclopropyl-2-{4-[2-(2,6-dichloro-4-methylphenoxy)ethoxy]benzyl}-N-({2-(3-methoxypropyl)-6-[3-(methylthio)propoxy]pyridin-4-yl}methyl)propanamide To a $CH_2Cl_2$ solution (0.04 M) of tert-butyl (3-[cyclopropyl({2-(3-methoxypropyl)-6-[3-(methylthio)propoxy]pyridin-4-yl]methyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 30 eq.). The resulting solution was stirred at RT for 1 h and the volatiles were removed in vacuo. Purification of the crude product thus obtained by way of column chromatography ($SiO_2$, 94:6 (v/v) $CH_2Cl_2$: 2.0 M $NH_3$ in MeOH) afforded the title compound as an oil. MS (ESI+): 704.

Example 101

3-Amino-N-cyclopropyl-2-{4-[2-(2,6-dichloro-4-methylphenoxy)ethoxy]benzyl}-N-({2-(3-methoxypropyl)-6-[3-(methylsulfonyl)propoxy]pyridin-4-yl}methyl)propanamide

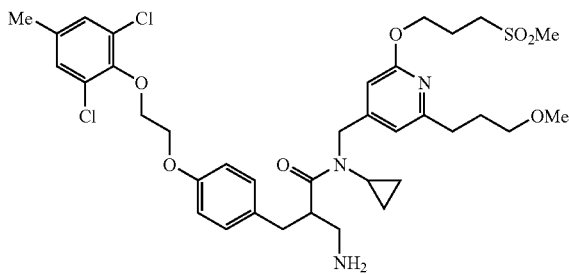

Step 1: tert-Butyl (3-[cyclopropyl({2-(3-methoxypropyl)-6-[3-(methylsulfonyl)propoxy]pyridin-4-yl]methyl)amino]-2-{4-[2-(2,6-dichloro-4-methylphenoxy)ethoxy]benzyl}-3-oxopropyl)carbamate To a 2:1:1 (v/v/v) THF:MeOH:water solution (0.1 M) of tert-butyl (3-[cyclopropyl({2-(3-methoxypropyl)-6-[3-(methylthio)propoxy]pyridin-4-yl]methyl)amino]-2-{4-[2-(2,6-dichloro-4-methylphenoxy)ethoxy]benzyl}-3-oxopropyl)carbamate from Example 100, Step 1 (1 eq.) was added Oxone™ (2.2 eq.) The resulting solution was stirred at RT for 2 h. The reaction was quenched with sat. aq. $NaHCO_3$ and then extracted with EtOAc. The combined organic extracts were washed with brine, dried over $Na_2SO_4$, filtered and the filtrate concentrated in vacuo. Purification of the crude product thus obtained by way of flash chromatography ($SiO_2$, 95:5 (v/v) $CH_2Cl_2$:EtOH) afforded the title compound as a colorless oil.

Step 2: 3-Amino-N-cyclopropyl-2-{4-[2-(2,6-dichloro-4-methylphenoxy)ethoxy]benzyl}-N-({2-(3-methoxypropyl)-6-[3-(methylsulfonyl)propoxy]pyridin-4-yl}methyl)propanamide To a $CH_2Cl_2$ solution (0.04 M) of tert-butyl (3-[cyclopropyl({2-(3-methoxypropyl)-6-[3-(methylsulfonyl)propoxy]pyridin-4-yl]methyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 30 eq.). The resulting solution was stirred at RT for 1.5 h and the volatiles were removed in vacuo. Purification of the crude product thus obtained by way of column chromatography ($SiO_2$, 94:6 (v/v) $CH_2Cl_2$: 2.0 M $NH_3$ in MeOH→90:10 (v/v) $CH_2Cl_2$: 2.0 M $NH_3$ in MeOH) afforded the title compound as an oil. MS (ESI+): 736.

Example 102

3-Amino-N-cyclopropyl-2-{4-[2-(2,6-dichloro-4-methylphenoxy)ethoxy]benzyl}-N-({2-(3-methoxypropyl)-6-[3-(methylsulfonyl)propoxy]-1-oxidopyridin-4-yl}methyl)propanamide

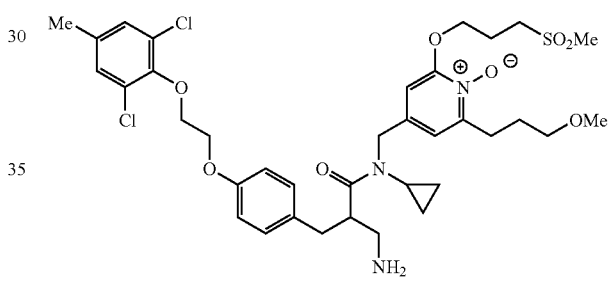

Step 1: tert-Butyl (3-[cyclopropyl[(2-(3-methoxypropyl)-6-[3-(methylsulfonyl)propoxy]-1-oxidopyridin-4-yl]methyl)amino]-2-{4-[2-(2,6-dichloro-4-methylphenoxy)ethoxy]benzyl}-3-oxopropyl)carbamate To a dichloromethane solution (0.06 M) of tert-butyl (3-[cyclopropyl({2-(3-methoxypropyl)-6-[3-(methylsulfonyl)propoxy]pyridin-4-yl]methyl)amino]-2-{4-[2-(2,6-dichloro-4-methylphenoxy)ethoxy]benzyl}-3-oxopropyl)carbamate from Example 101, Step 1 (1 eq.) was added 3-chloroperoxybenzoic acid (3.6 eq.). The resulting solution was stirred at RT for 18 h. The reaction was quenched with sat. aq. $NaHCO_3$ and then extracted with EtOAc. The combined organic extracts were washed with brine, dried over $Na_2SO_4$, filtered and the filtrate concentrated in vacuo. Purification of the crude product thus obtained by way of flash chromatography ($SiO_2$, 90:10 (v/v) $CH_2Cl_2$:EtOH→85:15 (v/v) $CH_2Cl_2$:EtOH) afforded the title compound.

Step 2: 3-Amino-N-cyclopropyl-2-{4-[2-(2,6-dichloro-4-methylphenoxy)ethoxy]benzyl}-N-({2-(3-methoxypropyl)-6-[3-(methylsulfonyl)propoxy]-1-oxidopyridin-4-yl}methyl)propanamide To a $CH_2Cl_2$ solution (0.04 M) of tert-butyl (3-[cyclopropyl(2-(3-methoxypropyl)-6-[3-(methylsulfonyl)propoxy]-1- oxidopyridin-4-yl]methyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 20 eq.). The resulting solution was stirred at RT for 1 h and the volatiles were removed in vacuo. Purification of the crude product thus obtained by way of column chromatography (SiO$_2$, 95:5 (v/v) CH$_2$Cl$_2$:2.0 M NH$_3$ in MeOH→90:10 (v/v) CH$_2$Cl$_2$: 2.0 M NH$_3$ in MeOH) afforded the title compound as an oil. MS (ESI+): 752.

Example 103

3-Amino-N-cyclopropyl-2-{4-[2-(2,6-dichloro-4-methylphenoxy)ethoxy]benzyl}-N-{[2-(3-methoxypropyl)-6-(2-morpholin-4-ylethoxy)pyridin-4-yl]methyl}propanamide

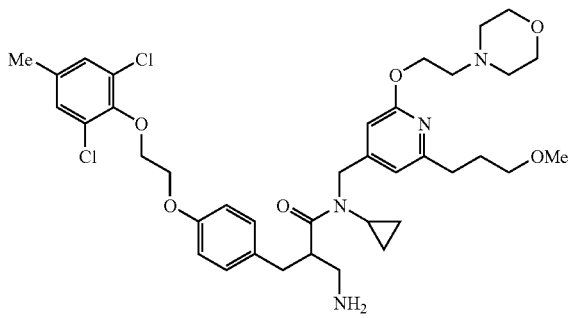

Prepared according to the procedure described in Example 9 but using instead Amine 45 as starting material. The title compound was obtained as a pale yellow oil. MS (ESI+): 729.2.

Example 104

3-Amino-N-[3-(2-amino-2-oxoethoxy)-5-(3-methoxypropyl)benzyl]-N-cyclopropyl-2-{4-[2-(2,6-dichloro-4-methylphenoxy)ethoxy]benzyl}propanamide

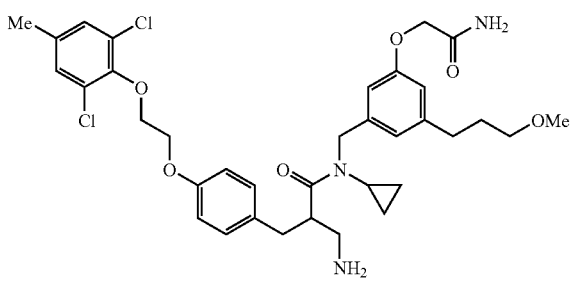

Prepared according to the procedure described in Example 71 but using instead 2-bromoacetamide as starting material. The title compound was obtained as an off-white solid. MS (ESI+): 672.

Example 105

3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl ethylcarbamate

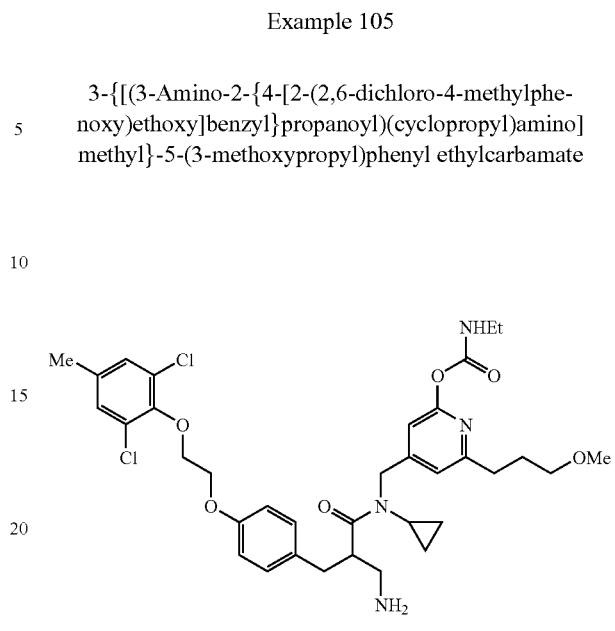

Step 1: 3-{[(3-[(tert-Butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenyl ethylcarbamate To a solution of tert-butyl (3-{cyclopropyl[3-hydroxy-5-(3-methoxypropyl)benzyl] (cyclopropyl)amino}-2-{4-[2-(2,6-dichloro-4-methylphenoxy)ethoxy]benzyl}-3-oxopropyl)carbamate from Example 70, Step 2 (1 eq.) in dichloromethane (0.08 M) was added ethyl isocyanate (3 eq.), triethylamine (3 eq.) and a few crystals of DMAP. The resulting solution was stirred at RT for 1.5 h. The reaction mixture was concentrated in vacuo and directly subjected to purification by way of column chromatography (SiO$_2$, 3:2 (v/v) Hex:EtOAc→2:3 (v/v) Hex:EtOAc). The title compound was isolated as a colorless oil.

Step 2: 3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl ethylcarbamate To a CH$_2$Cl$_2$ solution (0.07 M) of 3-{[(3-[(tert-butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenyl ethylcarbamate from the previous step (1 eq.) was added HCl (4.0 M dioxane solution, 35 eq.). The resulting solution was stirred at RT for 3 h. Following the removal of the volatiles in vacuo, the resulting residue was directly subjected to column chromatography (SiO$_2$, 94:6 (v/v) CH$_2$Cl$_2$:2.0 M NH$_3$ in MeOH) to afford the title compound. MS (ESI+): 686.

Example 106

3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl morpholine-4-carboxylate

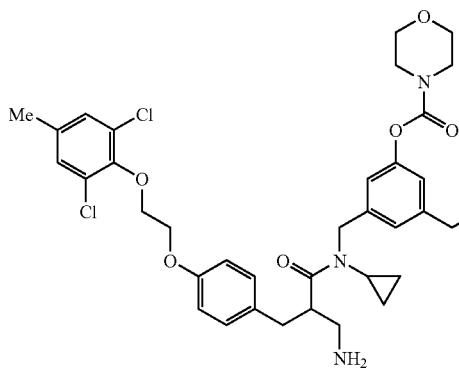

Prepared according to the procedure described in Example 105 but using instead morpholine-4-carbonyl chloride as starting material. The title compound was obtained as colorless oil. MS (APCI+): 728.

Example 107

3-{[(3-Amino-2-{4-[2-(2,6-dichloro-4-methylphenoxy)ethoxy]benzyl}propanoyl)(cyclopropyl)amino]methyl}-5-(3-methoxypropyl)pheny 4-methylpiperazine-1-carboxylate

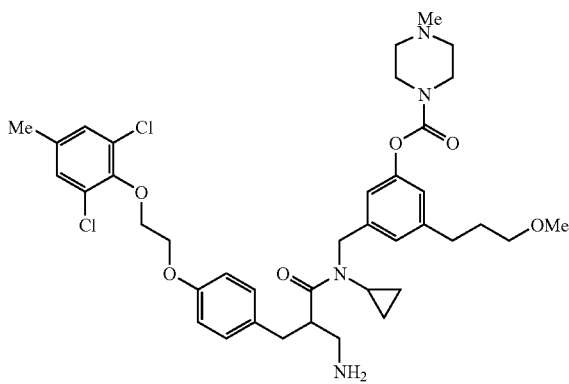

Prepared according to the procedure described in Example 105 but using instead 4-methylpiperazine-1-carbonyl chloride as starting material. The title compound was obtained as colorless oil. MS (APCI+): 741.

Example 108

3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl (3-amino-2,2-dimethyl-3-oxopropyl)carbamate

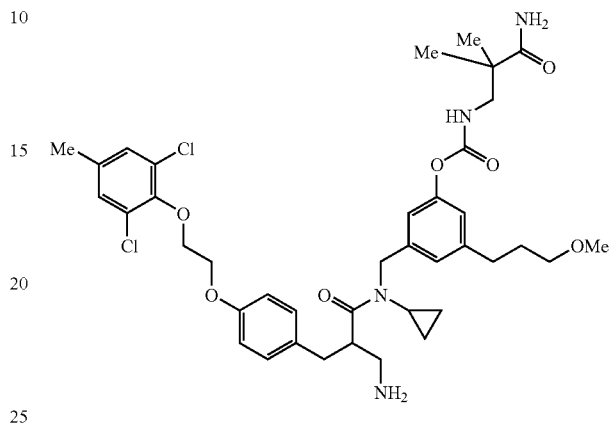

Step 1: 3-{[(3-[(tert-Butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenyl (3-amino-2,2-dimethyl-3-oxopropyl)carbamate To a solution of tert-butyl (3-{cyclopropyl[3-hydroxy-5-(3-methoxypropyl)benzyl] (cyclopropyl)amino}-2-{4-[2-(2,6-dichloro-4-methylphenoxy)ethoxy]benzyl}-3-oxopropyl)carbamate from Example 70, Step 2 (1 eq.) in dichloromethane (0.13 M) was added triphosgene (0.3 eq.) and then sodium hydroxide (1 M aq. solution, 3 eq.). The resulting mixture was stirred at RT for 2 h. The reaction was quenched with brine. The organic phase was separated and then added 3-amino-2,2-dimethylpropanamide (4 eq.). The resulting suspension was allowed to stir at RT for 16 h. The reaction was quenched with water and then extracted with EtOAc. The combined organic extracts were washed with brine, dried over MgSO$_4$, filtered, and the filtrate concentrated in vacuo. The crude product thus obtained was purified further by way of column chromatography (SiO$_2$, 1:1 (v/v) Hex:EtOAc→EtOAc) to afford the title compound as a colorless oil.

Step 2: 3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl (3-amino-2,2-dimethyl-3-oxopropyl)carbamate To a CH$_2$Cl$_2$ solution (0.07 M) of 3-{[(3-[(tert-butoxycarbonyl)amino]-2-{4-[2-(2,6-dichloro-4-methylphenoxy)ethoxy]benzyl}propanoyl)(cyclopropyl)amino]methyl}-5-(3-methoxypropyl)phenyl ethylcarbamate from the previous step (1 eq.) was added HCl (4.0 M dioxane solution, 35 eq.). The resulting solution was stirred at RT for 3 h. Following the removal of the volatiles in vacuo, the resulting residue was directly subjected to column chromatography (SiO$_2$, 95:5 (v/v) CH$_2$Cl$_2$: 2.0 M NH$_3$ in MeOH→90:10 (v/v) CH$_2$Cl$_2$:2.0 M NH$_3$ in MeOH) to afford the title compound as a white solid. MS (ESI+): 757.

Example 109

3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl (2-hydroxypropyl)carbamate

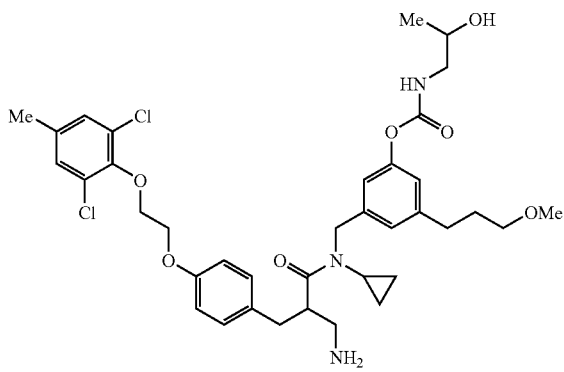

Prepared according to the procedure described in Example 108 but using instead 1-aminopropan-2-ol as starting material. The title compound was obtained as colorless oil. MS (ESI+): 716.

Example 110

3-Amino-N-cyclopropyl-2-{4-[2-(2,6-dichloro-4-methylphenoxy)ethoxy]benzyl}-N-(pyridin-4-ylmethyl)propanamide

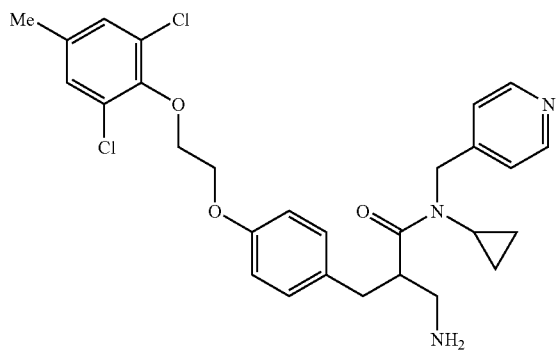

Step 1: tert-Butyl (3-[cyclopropyl(pyridin-4-ylmethyl)amino]-2-{4-[2-(2,6-dichloro-4-methylphenoxy)ethoxy]benzyl}-3-oxopropyl)carbamate 3-[tert-Butoxycarbonyl)amino]-2-{4-[2-(2,6-dichloro-4-methylphenoxy)ethoxy]benzyl}propanoic acid from Example 9, Step 3 (1 eq.) was combined with 1-hydroxybenzotriazole hydrate (1.5 eq.) and N-(3-dimethylaminopropyl)-N'-ethylcarbodiimide HCl salt (1.5 eq.) in chloroform (0.08 M). To this yellow solution was then added Amine 46 (4 eq.) and triethylamine (1.5 eq.). The resulting brown solution was stirred at RT for 48 h. The reaction solution was diluted with EtOAc and washed with H₂O. The aqueous washes were back extracted with EtOAc. The combined organic extracts were washed with brine, dried over MgSO₄, filtered and the filtrate concentrated in vacuo. Purification of the crude product thus obtained by way of flash chromatography (SiO₂, 2:3 (v/v) Hex:EtOAc→EtOAc) afforded the title compound.

Step 1: 3-Amino-N-cyclopropyl-2-{4-[2-(2,6-dichloro-4-methylphenoxy)ethoxy]benzyl}-N-(pyridin-4-ylmethyl)propanamide To a CH₂Cl₂ solution (0.09 M) of tert-butyl (3-[cyclopropyl(pyridin-4-ylmethyl)amino]-2-{4-[2-(2,6-dichloro-4-methylphenoxy)ethoxy]benzyl}-3-oxopropyl)carbamate from the previous step (1 eq.) was added HCl (4.0 M dioxane solution, 46 eq.). The resulting solution was stirred at RT for 5 h. The reaction was quenched with 2.0 M NH₃ in MeOH and concentrated in vacuo. The resulting residue was directly loaded onto a SiO₂ column packed with 90:9:1 (v/v) CH₂Cl₂:MeOH:conc. NH₄OH. Elution with the same solvent system furnished the title compound. MS (ESI+): 527.9.

Example 111

3-Amino-N-cyclopropyl-2-{4-[2-(2,6-dichloro-4-methylphenoxy)ethoxy]benzyl}-N-(pyridin-3-ylmethyl)propanamide

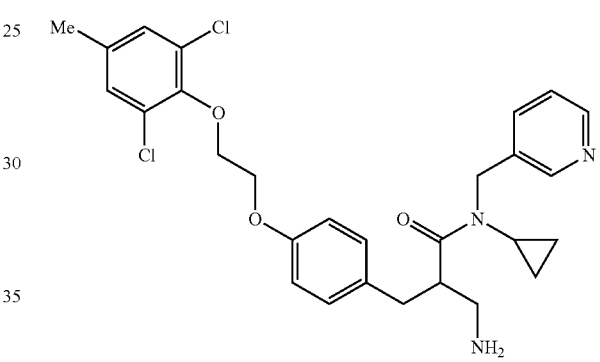

Prepared according to the procedure described in Example 110 but using instead Amine 47 as starting material. The title compound was obtained as colorless oil. MS (ESI+): 527.9.

Example 112

3-Amino-N-cyclopropyl-2-{4-[2-(2,6-dichloro-4-methylphenoxy)ethoxy]benzyl}-N-(pyridin-2-ylmethyl)propanamide

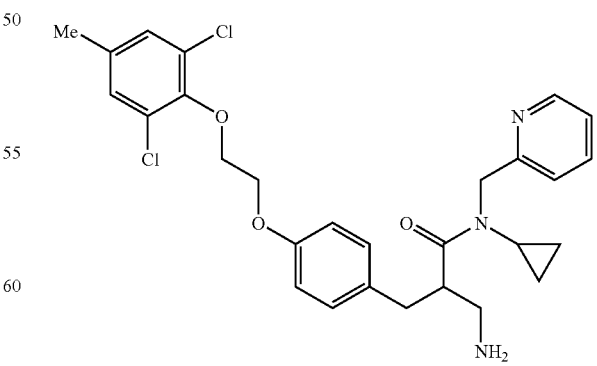

Prepared according to the procedure described in Example 110 but using instead Amine 48 as starting material. The title compound was obtained as colorless oil. MS (ESI+): 527.9.

Example 113

3-Amino-N-cyclopropyl-2-{4-[2-(2,6-dichloro-4-methylphenoxy)ethoxy]benzyl}-N-[(1-oxidopyridin-4-yl)methyl]propanamide

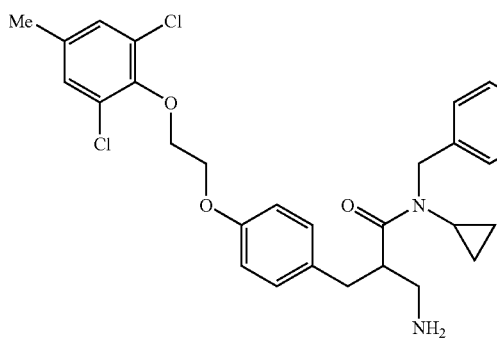

Step 1: tert-Butyl (3-{cyclopropyl[(1-oxidopyridin-4-yl)methyl]amino}-2-{4-[2-(2,6-dichloro-4-methylphenoxy)ethoxy]benzyl}-3-oxopropyl)carbamate To a solution of tert-butyl (3-[cyclopropyl(pyridin-4-ylmethyl)amino]-2-{4-[2-(2,6-dichloro-4-methylphenoxy)ethoxy]benzyl}-3-oxopropyl)carbamate from Example 110, Step 1 (1 eq.) in dichloromethane (0.12 M) was added 3-chloroperoxybenzoic acid (1.3 eq.). The reaction mixture was stirred at RT for 1.5 h. The reaction was then quenched with 10% aq. $Na_2S_2O_3$ and sat. aq. $NaHCO_3$. The organic layer was separated and the aqueous layer were back extracted with ether. The combined organic extracts were washed with water, dried over $Na_2SO_4$, filtered and the filtrate concentrated in vacuo. Purification of the crude product thus obtained by way of flash chromatography ($SiO_2$, EtOAc→4:1 (v/v) EtOAc:MeOH) afforded the title compound.

Step 1: 3-Amino-N-cyclopropyl-2-{4-[2-(2,6-dichloro-4-methylphenoxy)ethoxy]benzyl}-N-[(1-oxidopyridin-4-yl)methyl]propanamide To a $CH_2Cl_2$ solution (0.1 M) tert-butyl (3-{cyclopropyl[(1-oxidopyridin-4-yl)methyl]amino}-2-{4-[2-(2,6-dichloro-4-methylphenoxy)ethoxy]benzyl}-3-oxopropyl)carbamate from the previous step (1 eq.) was added HCl (4.0 M dioxane solution, 40 eq.). The resulting solution was stirred at RT for 5 h. The reaction was quenched with 2.0 M $NH_3$ in MeOH and concentrated in vacuo. The resulting residue was directly loaded onto a $SiO_2$ column packed with 86:13:1 (v/v) $CH_2Cl_2$:MeOH:conc. $NH_4OH$. Elution with the same solvent system furnished the title compound. MS (ESI+): 543.9.

Example 114

3-Amino-N-cyclopropyl-2-{4-[2-(2,6-dichloro-4-methylphenoxy)ethoxy]benzyl}-N-[(1-oxidopyridin-3-yl)methyl]propanamide

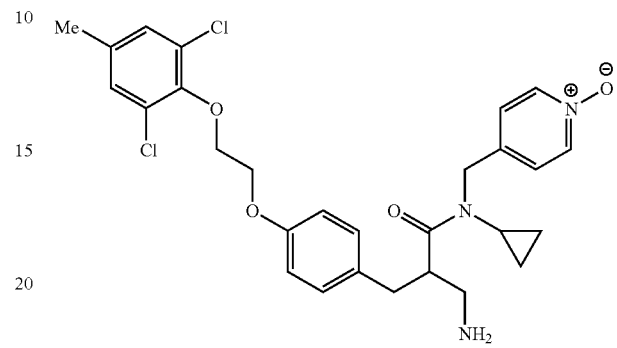

Prepared according to the procedure described in Example 113 but using instead tert-butyl (3-[cyclopropyl(pyridin-3-ylmethyl)amino]-2-{4-[2-(2,6-dichloro-4-methylphenoxy)ethoxy]benzyl}-3-oxopropyl)carbamate from Example 111, Step 1 as starting material.

The title compound was obtained as colorless oil. MS (ESI+): 543.9.

Example 115

3-Amino-N-cyclopropyl-2-{4-[2-(2,6-dichloro-4-methylphenoxy)ethoxy]benzyl}-N-[(1-oxidopyridin-2-yl)methyl]propanamide

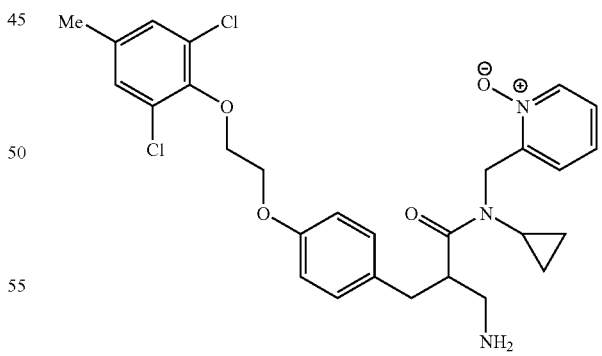

Prepared according to the procedure described in Example 113 but using instead tert-butyl (3-[cyclopropyl(pyridin-2-ylmethyl)amino]-2-{4-[2-(2,6-dichloro-4-methylphenoxy)ethoxy]benzyl}-3-oxopropyl)carbamate from Example 112, Step 1 as starting material. The title compound was obtained as colorless oil. MS (ESI+): 543.9.

Example 116

Ethyl 3-{[(3-amino-2-{4-[2-(2,6-dichloro-4-methylphenoxy)ethoxy]benzyl}propanoyl)(cyclopropyl)amino]methyl}-2-bromophenoxy)acetate

Example 117

Ethyl 3-(3-{[(3-amino-2-{4-[2-(2,6-dichloro-4-methylphenoxy)ethoxy]benzyl}propanoyl)(cyclopropyl)amino]methyl}-2-bromophenoxy)propanoate

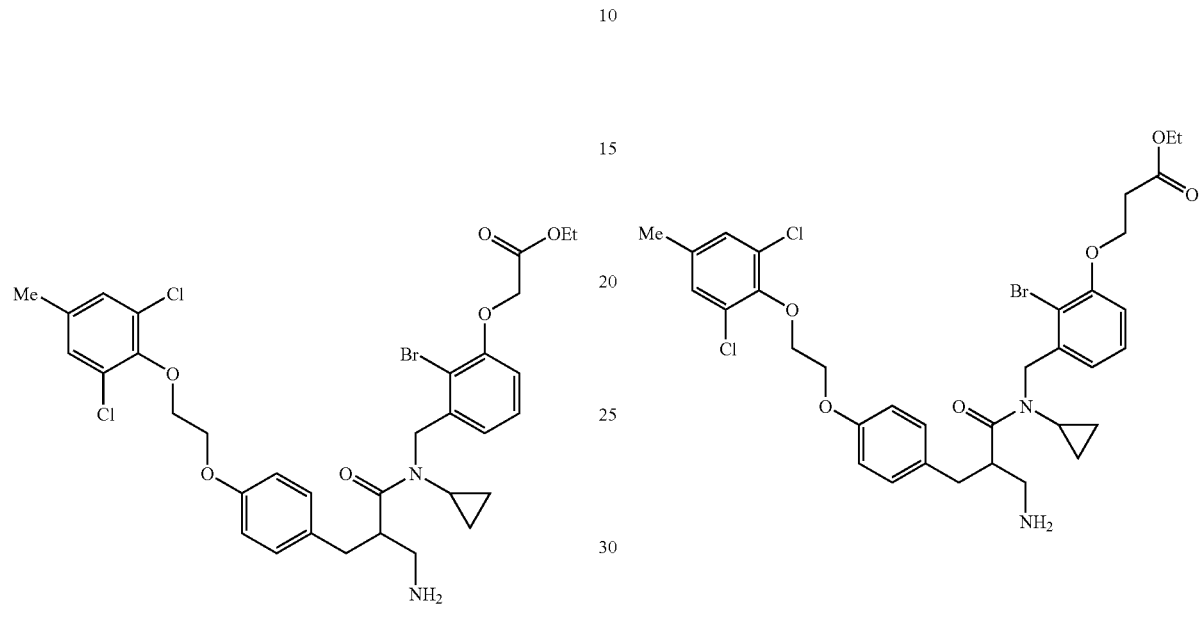

Prepared according to the procedure described in Example 9 but using instead Amine 49 as starting material. The title compound was obtained as colorless oil. MS (ESI+): 708.9.

Prepared according to the procedure described in Example 9 but using instead Amine 50 as starting material. The title compound was obtained as colorless oil. MS (ESI+): 722.9.

Example 118

Ethyl 5-(3-{[(3-amino-2-{4-[2-(2,6-dichloro-4-methylphenoxy)ethoxy]benzyl}propanoyl)(cyclopropyl)amino]methyl}-2-bromophenoxy)pentanoate Prepared according to the procedure described in Example 9 but using instead Amine 51 as starting material. The title compound was obtained as colorless oil. MS (ESI+): 750.9.

Example 119

Sodium 3-{[(3-amino-2-{4-[2-(2,6-dichloro-4-methylphenoxy)ethoxy]benzyl}propanoyl)(cyclopropyl)amino]methyl}-2-bromophenoxy)acetate

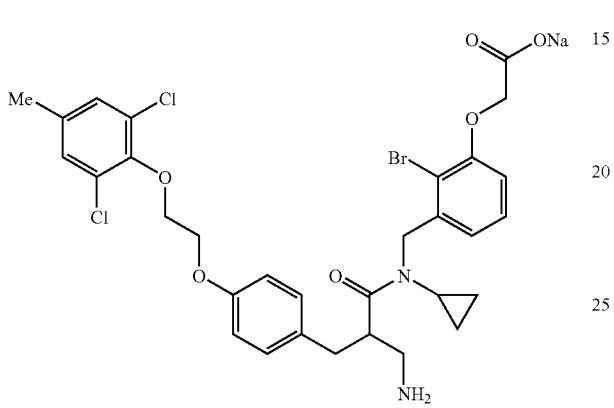

Prepared according to the procedure described in Example 87 but using instead ethyl (3-{[(3-amino-2-{4-[2-(2,6-dichloro-4-methylphenoxy)ethoxy]benzyl}propanoyl)(cyclopropyl)amino]methyl}-2-bromophenoxy)acetate from Example 116 as starting material. The title compound was obtained as colorless oil. MS for the corresponding free acid (ESI+): 681.3.

Example 120

Sodium 5-(3-{[(3-amino-2-{4-[2-(2,6-dichloro-4-methylphenoxy)ethoxy]benzyl}propanoyl)(cyclopropyl)amino]methyl}-2-bromophenoxy)pentanoate Prepared according to the procedure described in Example 87 but using instead ethyl 3-(3-{[(3-amino-2-{4-[2-(2,6-dichloro-4-methylphenoxy)ethoxy]benzyl}propanoyl)(cyclopropyl)amino]methyl}-2-bromophenoxy)pentanoate from Example 118 as starting material. The title compound was obtained as colorless oil. MS (ESI+): 723.2.

Example 121

3-Amino-N-cyclopropyl-2-{4-[2-(2,6-dichloro-4-methylphenoxy)ethoxy]benzyl}-N-[3-(3-methoxypropyl)-5-(2-morpholin-4-yl-2-oxoethoxy)benzyl]propanamide

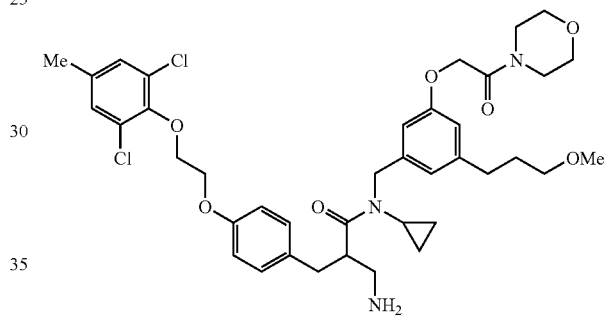

Prepared according to the procedure described in Example 71 but using instead 4-(chloroacetyl)morpholine as starting material. The title compound was obtained as an off-white solid. MS (ESI+): 742.3.

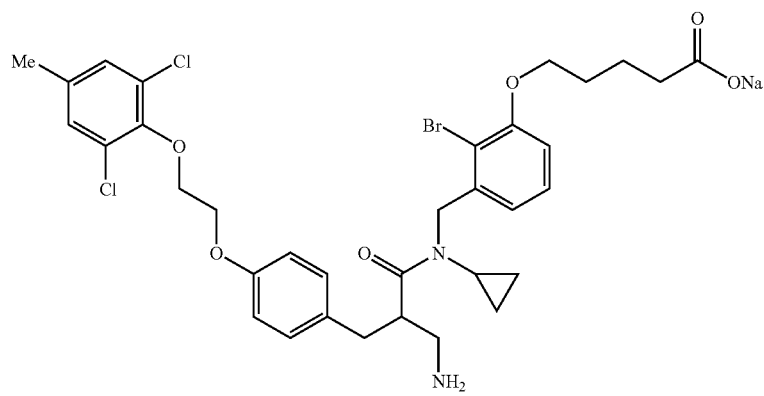

Example 122

2-{4-[2-(4-Allyl-2,6-dichlorophenoxy)ethoxy]benzyl}-3-amino-N-[2-chloro-5-(3-methoxypropyl)benzyl]-N-cyclopropanamide

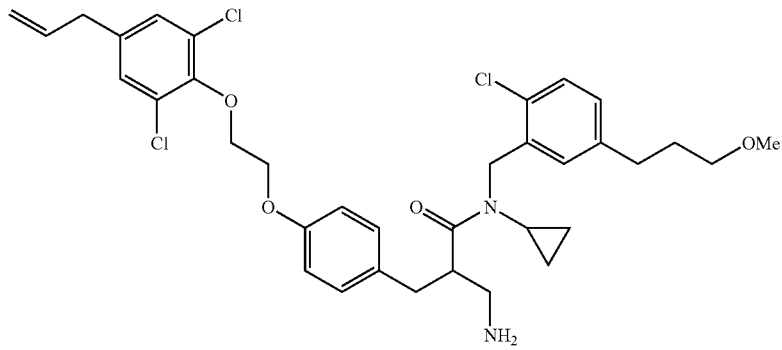

Step 1: Ethyl 2-cyano-3-[4-(hydroxyethoxy)phenyl]acrylate

Ethyl cyanoacetate (1.1 eq.) and 4-(2-hydroxyethoxy)benzaldehyde (1 eq.) were combined in ethanol (1.2 M). The reaction mixture was stirred at RT for 48. To this was then added an equal volume of hexane and the title compound was isolated by filtration as a pale yellow solid.

Step 2: Ethyl 3-[(tert-butoxycarbonyl)amino]-2-[4-(2-hydroxyethoxy)benzyl]propanoate Ethyl 2-cyano-3-[4-(hydroxyethoxy)phenyl]acrylate was combined with di-tert-butyl dicarbonate (1.2 eq.) and platinum(IV) oxide (20% loading) were combined in EtOH (0.18 M). The resulting suspension was shaken on a Parr apparatus under 50 psi of hydrogen gas for one week. The mixture was diluted with dichloromethane and filtered through a bed of celite. The filtrate was concentrated in vacuo to afford a viscous pale yellow oil.

Step 3: 3-[(tert-Butoxycarbonyl)amino]-2-[4-(2-hydroxyethoxy)benzyl]propanoic acid To a 5:3 (v/v) solution of EtOH and THF (0.2 M) of ethyl 3-[(tert-butoxycarbonyl)amino]-2-[4-(2-hydroxyethoxy)benzyl]propanoate from the previous step (1 eq.) was added LiOH (1 M aqueous solution, 2 eq.). The resulting mixture was stirred at RT for 48 h. Following the removal of the volatiles in vacuo, the resulting residue was partitioned between ether and 1 N aq. NaOH. The aqueous layer was separated and washed further with ether. The aqueous layer was then acidified to pH ~2 with conc. HCl and the resulting suspension extracted with dichloromethane. The combined dichloromethane extracts was concentrated in vacuo. The crude product thus obtained was recrystallized from EtOAc-hexane to afford the title compound as a white solid.

Step 4: tert-Butyl {(3-[[2-chloro-5-(3-methoxypropyl)benzyl](cyclopropyl)amino]-2-[4-(2-hydroxyethoxy)benzyl]-3-oxopropyl)carbamate 3-[(tert-Butoxycarbonyl)amino]-2-[4-(2-hydroxyethoxy)benzyl]propanoic acid from the previous step (1 eq.) was combined with Hunig's base (3 eq.) and Amine 6 (1 eq.) in anhydrous DMF (0.7 M). To this was then added portionwise O-(7-azabenzotriazol-1-yl)-N,N,N',N'-tetramethyluronium hexafluorophosphate (1.2 eq.). The resulting yellow solution was stirred at RT for 18 h. The reaction solution was diluted with ether and washed with water. The aqueous washes were back extracted with ether. The combined organic extracts were washed with brine, dried over $MgSO_4$, filtered and the filtrate concentrated in vacuo. Purification of the crude product thus obtained by way of flash chromatography ($SiO_2$, 5:1 (v/v) Hex:EtOAc→EtOAc) afforded the title compound pale yellow oil.

Step 5: tert-Butyl {2-{4-[2-(4-allyl-2,6-dichlorophenoxy)ethoxy]benzyl}-3-[[2-chloro-5-(3-methoxypropyl)benzyl](cyclopropyl)amino]-3-oxopropyl)carbamate To a solution of 2,6-dichlorophenol (1.2 eq.) in acetone (1.4 M) was added allyl bromide (1.2 eq.) and potassium carbonate (1.4 eq). The resulting suspension was heated to reflux for 4 h. The insolubles were removed via filtration and the filtrate was concentrated in vacuo. The resulting residue was heated at 160° C. for 17 h. This was then taken up in toluene (0.13 M) and added tert-butyl {(3-[[2-chloro-5-(3-methoxypropyl)benzyl] (cyclopropyl)amino]-2-[4-(2-hydroxyethoxy)benzyl]-3-oxopropyl)carbamate from the previous step (1 eq.) and 1,1'-(azodicarbonyl)dipiperidine (1.2 eq.). The resulting reaction mixture was deoxygenated and then added tributylphosphine (3 eq.). After 3 h of heating at 80° C., the reaction was quenched with 1 N NaOH and diluted with EtOAc. The aqueous layer was separated and back extracted with EtOAc. The combined organic extracts were washed further with 1 N aq. HCl, water and brine, dried over $Na_2SO_4$ and filtered. Concentration of the filtrate in vacuo afforded a brown oil that, following flash chromatography ($SiO_2$, 5:1 (v/v) Hex:EtOAc→1:1 (v/v) Hex:EtOAc), revealed the title compound as a pale yellow oil.

Step 6: 2-{4-[2-(4-Allyl-2,6-dichlorophenoxy)ethoxy]benzyl}-3-amino-N-[2-chloro-5-(3-methoxypropyl)benzyl]-N-cyclopropanamide To a $CH_2Cl_2$ solution (0.1 M) of tert-butyl {2-{4-[2-(4-allyl-2,6-dichlorophenoxy)ethoxy]benzyl}-3-[[2-chloro-5-(3-methoxypropyl)benzyl](cyclopropyl)amino]-3-oxopropyl)carbamate from the previous step (1 eq.) was added HCl (4.0 M dioxane solution, 35 eq.). The resulting solution was stirred at RT for 4 h. Removal of the volatiles in vacuo afforded the title compound. MS (ESI+): 661.8.

Example 123

3-Amino-N-[2-chloro-5-(3-methoxypropyl)benzyl]-N-cyclopropyl-2-(4-{2-[2,6-dichloro-4-(3-hydroxypropyl)phenoxy]ethoxy}benzyl}propanamide

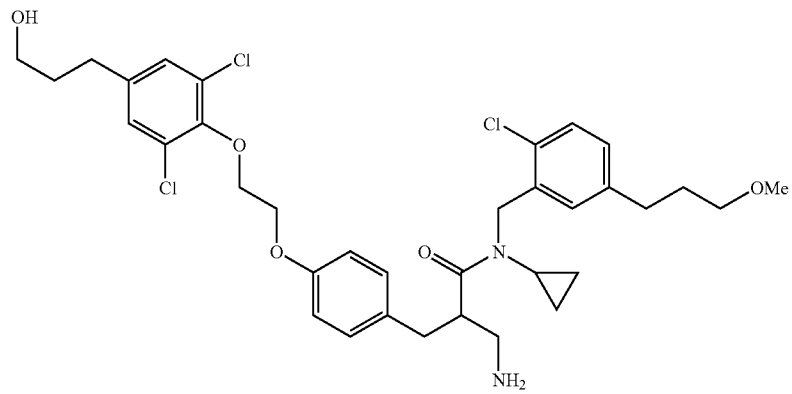

Step 1: tert-Butyl [3-[[2-chloro-5-(3-methoxypropyl)benzyl](cyclopropyl)amino]-2-(4-{2-[2,6-dichloro-4-(3-hydroxypropyl)phenoxy]ethoxy}benzyl}-3-oxopropyl]carbamate To a THF solution (0.04 M) of tert-butyl {2-{4-[2-(4-allyl-2,6-dichlorophenoxy)ethoxy]benzyl}-3-[[2-chloro-5-(3-methoxypropyl)benzyl](cyclopropyl)amino]-3-oxopropyl}carbamate from Example 122, Step 5 (1 eq.) was added 9-borabicyclo[3.3.1]nonane (0.5 M THF solution, 2.6 eq.) dropwise at 0° C. The resulting solution was warmed slowly to RT over 16 h. The reaction was quenched at 0° C. with the dropwise addition of ethanol. Then, NaOH (1 N aqueous solution, 4 eq.) and H$_2$O$_2$ (30% w/w aqueous solution, 12 eq.) were added. After 1 h of stirring at 0° C. and another 4 h of stirring at RT, the reaction mixture was diluted with EtOAc. The organic layer was separated, washed with water, dried over Na$_2$SO$_4$ and filtered. Concentration of the filtrate in vacuo and purification of the crude product thus obtained by way of flash chromatography (SiO$_2$, 3:1 (v/v) Hex:EtOAc→EtOAc), revealed the title compound.

Step 2: 3-Amino-N-[2-chloro-5-(3-methoxypropyl)benzyl]-N-cyclopropyl-2-(4-{2-[2,6-dichloro-4-(3-hydroxypropyl)phenoxy]ethoxy}benzyl}propanamide To a CH$_2$Cl$_2$ solution (0.1 M) of tert-butyl [3-[[2-chloro-5-(3-methoxypropyl)benzyl](cyclopropyl)amino]-2-(4-{2-[2,6-dichloro-4-(3-hydroxypropyl)phenoxy]ethoxy}benzyl}-3-oxopropyl]carbamate from the previous step (1 eq.) was added HCl (4.0 M dioxane solution, 35 eq.). The resulting solution was stirred at RT for 4 h. The reaction was quenched with 2.0 M NH$_3$ in MeOH and concentrated in vacuo. The resulting residue was directly loaded onto a SiO$_2$ column packed with 90:9:1 (v/v) CH$_2$Cl$_2$:MeOH:conc. NH$_4$OH. Elution with the same solvent system furnished the title compound. MS (ESI+): 677.2.

What is claimed is:

1. A compound of formula I, or a pharmaceutically acceptable salt thereof, or an optical isomer thereof, having the formula I

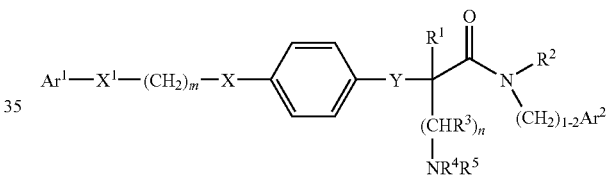

wherein, m is 1 or 2;

n, in each instance in which it occurs, is independently 0, 1 or 2;

p, in each instance in which it occurs, is independently 0, 1 or 2;

X and X$^1$ are each independently selected from the group consisting of CH$_2$, O, and S(O)$_p$, provided that when both X and X$^1$ are each independently O or S(O)$_p$, m is 2;

Y is selected from the group consisting of N(R$^a$), CH(R$^a$), O, and S(O)$_p$;

R$^1$, R$^3$, and R$^a$ are each independently selected from the group consisting of H, C$_1$-C$_6$alkyl and C$_2$-C$_6$alkenyl, wherein the alkyl and alkenyl group is unsubstituted or substituted with one, two, three or four substituents independently selected from:
1) OH,
2) CN,
3) CF$_3$,
4) COOH,
5) C$_1$-C$_6$alkoxy,
6) C(O)R$^b$,
7) C(O)N(R$^c$)$_2$,
8) S(O)$_p$C$_1$-C$_6$alkyl,
9) SO$_2$N(R$^c$)$_2$,
10) N(R$^c$)$_2$,
11) NHC(O)R$^b$, 12) NHC(O)NHR$^d$,
13) NHC(S)NHR$^d$, and
14) NH(NR$^c$)NHR$^c$;

R$^4$ is selected from the group consisting of H, C$_1$-C$_6$alkyl and C$_2$-C$_6$alkenyl, wherein the alkyl and alkenyl group is unsubstituted or substituted with one, two, three or four substituents independently selected from:
1) OH,
2) CN,
3) CF$_3$,
4) COOH,
5) C$_1$-C$_6$alkoxy,
6) C(O)R$^b$,
7) C(O)N(R$^c$)$_2$,
8) S(O)$_p$C$_1$-C$_6$alkyl,
9) SO$_2$N(R$^c$)$_2$,
10) N(R$^c$)$_2$,
11) NHC(O)R$^b$,
12) NHC(O)NHR$^d$,
13) NHC(S)NHR$^d$, and
14) NH(NR$^c$)NHR$^c$;

R$^5$ is selected from the group consisting of hydrogen and —C(NH(NH$_2$));

R$^2$ and R$^b$ are independently selected from the group consisting of H, C$_1$-C$_6$alkyl, C$_2$-C$_6$alkenyl, C$_1$-C$_6$alkoxy, CF$_3$ and CH$_2$CF$_3$;

R$^c$ is selected from the group consisting of H, C$_1$-C$_6$alkyl and CH$_2$CF$_3$;

R$^d$ is selected from the group consisting of H and C$_1$-C$_6$alkyl, wherein the alkyl group is unsubstituted or substituted with one, two, three or four substituents selected from the group consisting of:
1) OH,
2) CN,
3) CF$_3$,
4) COOH, and
5) C(O)NHR$^c$;

Ar$^1$ is an unsubstituted or substituted aryl ring wherein the substituted aryl ring is substituted with one, two three or four substituents independently selected from the group consisting of:
1) OH,
2) CN,
3) halogen,
4) N$_3$,
5) NO$_2$,
6) COOH,
7) OCF$_2$H,
8) CF$_3$,
9) C$_1$-C$_6$alkyl,
10) C$_2$-C$_6$alkenyl,
11) C$_1$-C$_6$alkoxy,
12) C(O)C$_1$-C$_6$alkyl, and
13) S(O)$_p$C$_1$-C$_6$alkyl,
wherein substituents (9)-(13) are unsubstituted or substituted with one, two three or four substituents independently selected from the group consisting of:
a) OH,
b) COOH,
c) CN,
d) CF$_3$,
e) C$_1$-C$_6$alkoxy,
f) S(O)$_p$C$_1$-C$_6$alkyl; and Ar$^2$ is independently selected from the group consisting of Ar$^1$ and a 9- or 10-membered fused bicyclic aryl, wherein the fused bicyclic aryl is unsubstituted or substituted with one, two, three or four substituents independently selected from the group consisting of:
1) OH,
2) CN,
3) halogen,
4) N$_3$,
5) NO$_2$,
6) COOH,
7) OCF$_2$H,
8) CF$_3$,
9) C$_1$-C$_6$alkyl,
10) C$_1$-C$_6$alkyl,
11) C$_2$-C$_6$alkenyl,
12) C$_1$-C$_6$alkoxy,
13) C(O)C$_1$-C$_6$alkyl,
14) S(O)$_p$C$_1$-C$_6$alkyl,
15) —OC(O)NH(C$_1$-C$_6$alkylene)C(O)NH$_2$, and
16) —OC(O)NH(C$_1$-C$_6$alkylene)(OH)R$^d$;
wherein substituents (10)-(14) are unsubstituted or substituted with one, two three or four substituents independently selected from the group consisting of:
a) OH,
b) COOR$^d$,
c) CN,
d) CF$_3$,
e) C$_1$-C$_6$alkoxy,
f) S(O)$_p$C$_1$-C$_6$alkyl,
g) —C(O)NH$_2$,
h) —COONa,
i) —NR$^d$R$^d$, and
j) —NR$^d$C(O)R$^d$.

2. A compound of claim 1, or a pharmaceutically acceptable salt thereof, wherein Y is CH(R$^a$) and R$^1$ is H.

3. A compound of claim 2, or a pharmaceutically acceptable salt thereof, wherein Y is CH(R$^a$), R$^1$ is H, and n is 1.

4. A compound of claim 3, or a pharmaceutically acceptable salt thereof, wherein Y is CH$_2$ and R$^2$ is C$_1$-C$_6$ alkyl or C$_2$-C$_6$ alkenyl.

5. A compound of claim 1, or a pharmaceutically acceptable salt thereof, wherein R$_2$ is C$_1$-C$_6$ alkyl or C$_2$-C$_6$ alkenyl.

6. A compound of claim 5, or a pharmaceutically acceptable salt thereof, wherein R$^2$ is C$_3$-C$_6$cycloalkyl.

7. A compound or a pharmaceutically acceptable salt thereof, selected from the group consisting of:
N-{3-[(Acetyl-methyl-amino)-methyl]-benzyl}-2-aminomethyl-N-cyclopropyl-3-{4-[2-(2,6-dichloro-4-methyl-phenoxy)-ethoxy]-phenyl}-propionamide,
3-Amino-N-cyclopropyl-2-{4-[2-(2,6-dichloro-4-methyl-phenoxy)-ethoxy]-benzyl}-N-(2,3-dimethyl-benzyl)-propionamide,
2-Aminomethyl-N-cyclopropyl-3-{4-[2-(2,6-dichloro-4-methyl-phenoxy)-ethoxy]-phenyl}-N-[3-(2-methanesulfonyl-ethyl)-benzyl]-propionamide,
5-(2-[Cyclopropyl-(2,3-dichloro-benzyl)-carbamoyl]-3-{4-[2-(2,6-dichloro-4-methyl-phenoxy)-ethoxy]-phenyl}-propylamino)-pentanoic acid methyl ester,
6-(2-[Cyclopropyl-(2,3-dichloro-benzyl)-carbamoyl]-3-{4-[2-(2,6-dichloro-4-methyl-phenoxy)-ethoxy]-phenyl}-propylamino)-hexanoic acid,
6-(2-[Cyclopropyl-(2,3-dichloro-benzyl)-carbamoyl]-3-{4-[2-(2,6-dichloro-4-methyl-phenoxy)-ethoxy]-phenyl}-propylamino)-hexanoic acid methyl ester,
N-Cyclopropyl-N-(2,3-dichloro-benzyl)-3-{4-[2-(2,6-dichloro-4-methyl-phenoxy)-ethoxy]-phenyl}-2-[(2,2,2-trifluoro-ethylamino)-methyl]-propionamide, 2-Aminomethyl-N-cyclopropyl-3-{4-[2-(2,6-dichloro-4-methyl-phenoxy)-ethoxy]-phenyl}-N-[3-(3-methoxypropyl)-benzyl]-propionamide,
2-Aminomethyl-N-[2-chloro-5-(3-methoxy-propyl)-benzyl]-N-cyclopropyl-3-{4-[2-(2,6-dichloro-4-methyl-phenoxy)-ethoxy]-phenyl}-propionamide,
2-[(2-[Cyclopropyl-(2,3-dichloro-benzyl)-carbamoyl]-3-{4-[2-(2,6-dichloro-4-methyl-phenoxy)-ethoxy]-phenyl}-propylamino)-methyl]-cyclopropanecarboxylic acid,
2-[(2-[Cyclopropyl-(2,3-dichloro-benzyl)-carbamoyl]-3-{4-[2-(2,6-dichloro-4-methyl-phenoxy)-ethoxy]-phenyl}-propylamino)-methyl]-cyclopropanecarboxylic acid ethyl ester,
2-Aminomethyl-3-{4-[3-(2-chloro-3,6-difluoro-phenoxy)-propyl]-phenyl}-N-cyclopropyl-N-[3-(3-methoxy-propyl)-benzyl]-propionamide,
2-Aminomethyl-3-{4-[3-(2-chloro-3,6-difluoro-phenoxy)-propyl]-phenyl}-N-[2-chloro-5-(3-methoxy-propyl)-benzyl]-N-cyclopropyl-propionamide,
3-Amino-N-cyclopropyl-N-(2,3-dichloro-benzyl)-2-{4-[2-(2,6-dichloro-4-methyl-phenoxy)-ethyl]-benzyl}-propionamide,
2-Aminomethyl-3-{4-[3-(2-chloro-3,6-difluoro-phenoxy)-propyl]-phenyl}-N-cyclopropyl-N-(2,3-dichloro-benzyl)-2-methyl-propionamide,
3-Amino-N-cyclopropyl-N-(2,3-dichloro-benzyl)-2-{4-[2-(2,6-dichloro-4-methyl-phenoxy)-ethoxy]-benzyl}-propionamide,
2-Aminomethyl-N-cyclopropyl-N-(2,3-dichloro-benzyl)-3-{4-[3-(2,6-dichloro-4-methyl-phenoxy)-propyl]-phenyl}-propionamide,
3-{4-[3-(2-Chloro-3,6-difluoro-phenoxy)-propyl]-phenyl}-N-cyclopropyl-N-(2,3-dichloro-benzyl)-2-methylaminomethyl-propionamide,
2-(Benzylamino-methyl)-3-{4-[3-(2-chloro-3,6-difluoro-phenoxy)-propyl]-phenyl}-N-cyclopropyl-N-(2,3-dichloro-benzyl)-propionamide,
2-Aminomethyl-3-{4-[3-(2-chloro-3,6-difluoro-phenoxy)-propyl]-phenyl}-N-cyclopropyl-N-(2,3-dichloro-benzyl)-propionamide,
2-Aminomethyl-N-[2-chloro-5-(2-methoxy-ethyl)-benzyl]-N-cyclopropyl-3-{4-[2-(2,6-dichloro-4-methyl-phenoxy)-ethoxy]-phenyl}-propionamide,
Methyl (2R)-2-{2-[(3-[cyclopropyl(2,3-dichlorobenzyl)amino]-2-{4-[2-(2,6-dichloro-4-methylphenoxy)ethoxy]benzyl}-3-oxopropyl)amino]ethyl}-3-methylbutanoate,
Methyl (2S)-2-{2-[(3-[cyclopropyl(2,3-dichlorobenzyl)amino]-2-{4-[2-(2,6-dichloro-4-methylphenoxy)ethoxy]benzyl}-3-oxopropyl)amino]ethyl}-3-methylbutanoate,
N-Cyclopropyl-N-(2,3-dichlorobenzyl)-2-{4-[2-(2,6-dichloro-4-methylphenoxy)ethoxy]benzyl}-3-{[2-(2-napthyl)ethyl]amino}propanamide,
3-Amino-N-[2-chloro-5-(2-methoxyethyl)benzyl]-N-cyclopropyl-2-{4-[2-(2,6-dichloro-4-methylphenoxy)ethoxy]benzyl}butanamide,
3-Amino-N-[2-chloro-5-(3-hydroxypropyl)benzyl]-N-cyclopropyl-2-{4-[2-(2,6-dichloro-4-methylphenoxy)ethoxy]benzyl}propanamide,
3-Amino-N-[2-chloro-5-(2-methoxyethoxy)benzyl]-N-cyclopropyl-2-{4-[2-(2,6-dichloro-4-methylphenoxy)ethoxy]benzyl}propanamide,
3-Amino-N-[2-chloro-5-(3-methoxypropyl)benzyl]-N-cyclopropyl-2-{4-[2-(2,6-dichloro-4-methylphenoxy)ethyl]benzyl}propanamide,
3-Amino-N-[2-chloro-5-(2-methoxyethyl)benzyl]-N-cyclopropyl-2-{4-[2-(2,6-dichloro-4-methylphenoxy)ethyl]benzyl}propanamide,
3-Amino-N-{2-chloro-5-[3-(dimethylamino)propyl]benzyl}-N-cyclopropyl-2-{4-[2-(2,6-dichloro-4-methylphenoxy)ethoxy]benzyl}propanamide,
3-Amino-N-cyclopropyl-N-[2,3-dichloro-5-[3-methoxypropyl)benzyl}-2-{4-[2-(2,6-dichloro-4-methylphenoxy)ethoxy]benzyl}propanamide,
3-Amino-N-cyclopropyl-N-[2,3-dichloro-5-[3-methoxypropyl)benzyl}-2-{4-[2-(2,6-dichloro-4-methylphenoxy)ethyl]benzyl}propanamide,
3-Amino-N-[2-chloro-5-(2-cyanoethyl)benzyl]-N-cyclopropyl-2-{4-[2-(2,6-dichloro-4-methylphenoxy)ethoxy]benzyl}propanamide,
3-Amino-N-cyclopropyl-2-{4-[2-(2,6-dichloro-4-methylphenoxy)ethoxy]benzyl}-N-[5-(3-methoxypropyl)-2-methylbenzyl]propanamide,
3-Amino-N-[2-chloro-5-(2-cyanomethyl)benzyl]-N-cyclopropyl-2-{4-[2-(2,6-dichloro-4-methylphenoxy)ethoxy]benzyl}propanamide,
3-Amino-N-cyclopropyl-2-{4-[2-(2,6-dichloro-4-methylphenoxy)ethoxy]benzyl}-N-[5-(3-methoxyethyl)-2-methylbenzyl]propanamide,
3-Amino-N-[2,5-bis(trifluoromethyl)benzyl]-N-cyclopropyl-2-{4-[2-(2,6-dichloro-4-methylphenoxy)ethoxy]benzyl}propanamide,
3-Amino-N-cyclopropyl-2-{4-[2-(2,6-dichloro-4-methylphenoxy)ethoxy]benzyl}-N-(1-phenylethyl)propanamide,
3-Amino-N-benzyl-2-{4-[2-(2,6-dichloro-4-methylphenoxy)ethoxy]benzyl}-N-methylpropanamide,
3-Amino-N-benzyl-N-cyclopropyl-2-{4-[2-(2,6-dichloro-4-methylphenoxy)ethoxy]benzyl}propanamide,
3-Amino-N-benzyl-N-cyclopropyl-2-{4-[2-(2,6-dichloro-4-methylphenoxy)ethoxy]benzyl}-N-(2-phenylethyl)propanamide,
3-Amino-2-{4-[2-(2,6-dichloro-4-methylphenoxy)ethoxy]benzyl}-N-methyl-N-(2-phenylethyl)propanamide,
3-Amino-2-{4-[2-(2,6-dichloro-4-methylphenoxy)ethoxy]benzyl}-N-methyl-N-(1-phenylethyl)propanamide,
3-Amino-N-(2,3-dichlorobenzyl)-2-{4-[2-(2,6-dichloro-4-methylphenoxy)ethoxy]benzyl}-N-(2,2,2-trifluoroethyl)propanamide,
3-Amino-2-{4-[2-(2,6-dichloro-4-methylphenoxy)ethoxy]benzyl}-N-methyl-N-(1-methyl-1-phenylethyl)propanamide,
3-Amino-N-[2-chloro-5-(2-methoxyethyl)benzyl]-N-(cyclopropyl)methyl)-2-{4-[2-(2,6-dichloro-4-methylphenoxy)ethoxy]benzyl}propanamide,
3-Amino-N-[2-chloro-5-(2-methoxyethyl)benzyl]-2-{4-[2-(2,6-dichloro-4-methylphenoxy)ethoxy]benzyl}-N-methylpropanamide,
3-Amino-N-[2-chloro-5-(2-methoxyethyl)benzyl]-N-(cyclobutylmethyl)-2-{4-[2-(2,6-dichloro-4-methylphenoxy)ethoxy]benzyl}propanamide,
3-Amino-N-[2-chloro-5-(2-methoxyethyl)benzyl]-2-{4-[2-(2,6-dichloro-4-methylphenoxy)ethoxy]benzyl}-N-isopropylpropanamide,
N-Allyl-3-amino-N-[2-chloro-5-(2-methoxyethyl)benzyl]-2-{4-[2-(2,6-dichloro-4-methylphenoxy)ethoxy]benzyl}propanamide, 3-Amino-N-[2-chloro-5-(2-methoxyethyl)benzyl]-N-cyclobutyl-2-{4-[2-(2,6-dichloro-4-methylphenoxy)ethoxy]benzyl}propanamide, 3-Amino-N-[2-chloro-5-(2-methoxyethyl)benzyl]-2-{4-[2-(2,6-dichloro-4-methylphenoxy)ethoxy]benzyl}-N-ethylpropanamide, 3-{[Amino(imino)methyl]amino}-N-[2-chloro-5-(3-methoxypropyl)benzyl]-N-cyclopropyl-2-{4-[2-(2,6-dichloro-4-methylphenoxy)ethoxy]benzyl}propanamide, 2-{[Amino(imino)methyl]amino}-N-cyclopropyl-N-(2,3-dichlorobenzyl)-3-{4-[2-(2,6-dichloro-4-methylphenoxy)ethoxy]benzyl}propanamide, 2-Amino-N-[2-chloro-5-(3-methoxypropyl)benzyl]-N-cyclopropyl-3-{4-[2-(2,6-dichloro-4-methylphenoxy)ethoxy]benzyl}propanamide, 2-{[Amino(imino)methyl]amino}-N-[2-chloro-5-(3-methoxypropyl)benzyl]-N-cyclopropyl-3-{4-[2-(2,6-dichloro-4-methylphenoxy)ethoxy]benzyl}propanamide, 3-Amino-N-cyclopropyl-2-{4-[2-(2,6-dichloro-4-methylphenoxy)ethoxy]benzyl}-N-[3-hydroxy-5-(3-methoxypropyl)benzyl]propanamide, 3-Amino-N-cyclopropyl-2-{4-[2-(2,6-dichloro-4-methylphenoxy)ethoxy]benzyl}-N-[3-(2-methoxyethoxy)-5-(3-methoxypropyl)benzyl]propanamide, 3-Amino-N-[3-(3-cyanopropoxy)-5-(3-methoxypropyl)benzyl]-N-cyclopropyl-2-{4-[2-(2,6-dichloro-4-methylphenoxy)ethoxy]benzyl}propanamide, 3-Amino-N-cyclopropyl-2-{4-[2-(2,6-dichloro-4-methylphenoxy)ethoxy]benzyl}-N-{3-(3-methoxypropyl)-5-[(3-methylthio)propoxy]benzyl}propanamide, 3-Amino-N-cyclopropyl-2-{4-[2-(2,6-dichloro-4-methylphenoxy)ethoxy]benzyl}-N-{3-(3-methoxypropyl)-5-[(3-methylsulfonyl)propoxy]benzyl}propanamide, 3-Amino-N-cyclopropyl-2-{4-[2-(2,6-dichloro-4-methylphenoxy)ethoxy]benzyl}-N-[3-(3-methoxypropyl)-5-{[4-(methylsulfonyl)benzyl]oxy}benzyl)propanamide, Ethyl 2-{[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]methyl}cyclopropanecarboxylate, Sodium 2-{[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]methyl}cyclopropanecarboxylate, Ethyl 2-{[3-{[(3-amino-2-{4-[2-(2,6-dichloro-4-methylphenoxy)ethoxy]benzyl}propanoyl)(cyclopropyl)amino]methyl}-2-chloro-5-(3-methoxypropyl)phenoxy]methyl}cyclopropanecarboxylate, Sodium 2-{[3-{[(3-amino-2-{4-[2-(2,6-dichloro-4-methylphenoxy)ethoxy]benzyl}propanoyl)(cyclopropyl)amino]methyl}-2-chloro-5-(3-methoxypropyl)phenoxy]methyl}cyclopropanecarboxylate, Ethyl 2-[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]-2-methylpropanoate, Sodium 2-[3-{[(3-amino-2-{4-[2-(2,6-dichloro-4-methylphenoxy)ethoxy]benzyl}propanoyl)(cyclopropyl)amino]methyl}-5-(3-methoxypropyl)phenoxy]-2-methylpropanoate, 3-Amino-N-[3,5-bis(2-methoxyethoxy)benzyl]-N-cyclopropyl-2-{4-[2-(2,6-dichloro-4-methylphenoxy)ethoxy]benzyl}propanamide, 3-Amino-N-[3,5-bis(4,4,4-trifluorobutoxy)benzyl]-N-cyclopropyl-2-{4-[2-(2,6-dichloro-4-methylphenoxy)ethoxy]benzyl}propanamide, 3-Amino-N-[3-(2-amino-2-oxoethoxy)-5-(3-methoxypropyl)benzyl]-N-cyclopropyl-2-{4-[2-(2,6-dichloro-4-methylphenoxy)ethoxy]benzyl}propanamide, 3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl ethylcarbamate, 3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl(3-amino-2,2-dimethyl-3-oxopropyl)carbamate, 3-{[(3-Amino-2-{4-[2-(2,6-dichloro-4-methylphenoxy)ethoxy]benzyl}propanoyl)(cyclopropyl)amino]methyl}-5-(3-methoxypropyl)phenyl (2-hydroxypropyl)carbamate, Ethyl 3-{[(3-amino-2-{4-[2-(2,6-dichloro-4-methylphenoxy)ethoxy]benzyl}propanoyl)(cyclopropyl)amino]methyl}-2-bromophenoxy)acetate, Ethyl 3-(3-{[(3-amino-2-{4-[2-(2,6-dichloro-4-methylphenoxy)ethoxy]benzyl}propanoyl)(cyclopropyl)amino]methyl}-2-bromophenoxy)propanoate, Ethyl 5-(3-{[(3-amino-2-{4-[2-(2,6-dichloro-4-methylphenoxy)ethoxy]benzyl}propanoyl)(cyclopropyl)amino]methyl}-2-bromophenoxy)pentanoate, Sodium 3-{[(3-amino-2-{4-[2-(2,6-dichloro-4-methylphenoxy)ethoxy]benzyl}propanoyl)(cyclopropyl)amino]methyl}-2-bromophenoxy)acetate, Sodium 5-(3-{[(3-amino-2-{4-[2-(2,6-dichloro-4-methylphenoxy)ethoxy]benzyl}propanoyl)(cyclopropyl)amino]methyl}-2-bromophenoxy)pentanoate, 2-{4-[2-(4-Allyl-2,6-dichlorophenoxy)ethoxy]benzyl}-3-amino-N-[2-chloro-5-(3-methoxypropyl)benzyl]-N-cyclopropanamide, 3-Amino-N-[2-chloro-5-(3-methoxypropyl)benzyl]-N-cyclopropyl-2-(4-{2-[2,6-dichloro-4-(3-hydroxypropyl)phenoxy]ethoxy}benzyl)propanamide, N-(5-{[Acetyl(methyl)amino]methyl}-2-chlorobenzyl)-3-amino-N-cyclopropyl-2-{4-[2-(2,6-dichloro-4-methylphenoxy)ethoxy]benzyl}propanamide, 4-Amino-N-cyclopropyl-N-(2,3-dichlorobenzyl)-2-{4-[2-(2,6-dichloro-4-methylphenoxy)ethoxy]benzyl}butanamide, 4-Amino-N-cyclopropyl-N-(2,3-dichlorobenzyl)-2-{4-[3-(2,6-dichloro-4-methylphenoxy)propyl]benzyl}butanamide, and N-Cyclopropyl-N-(2,3-dichlorobenzyl)-O-[2-(2,6-dichloro-4-methylphenoxy)ethyl]tyrosinamide.

8. A pharmaceutical composition comprising an effective amount of a compound according to claim 1, or a pharmaceutically acceptable salt thereof, and a pharmaceutically acceptable carrier.

* * * * *